US012578318B2

(12) United States Patent

Hartwell et al.

(10) Patent No.: US 12,578,318 B2

(45) Date of Patent: Mar. 17, 2026

(54) PH AND MOISTURE INDICATOR DEVICES AND FORMULATIONS

(71) Applicant: Smith & Nephew PLC, Watford (GB)

(72) Inventors: Edward Yerbury Hartwell, Hull (GB); John Kenneth Hicks, Pocklington (GB)

(73) Assignee: Smith & Nephew PLC, Watford (GB)

( * ) Notice: Subject to any disclaimer, the term of this patent is extended or adjusted under 35 U.S.C. 154(b) by 886 days.

(21) Appl. No.: 17/321,270

(22) Filed: May 14, 2021

(65) Prior Publication Data

US 2021/0372975 A1    Dec. 2, 2021

Related U.S. Application Data

(63) Continuation of application No. 16/241,736, filed on Jan. 7, 2019, now abandoned, which is a (Continued)

(30) Foreign Application Priority Data

Jan. 11, 2013    (GB) ..................................... 1300470
May 24, 2013    (GB) ..................................... 1309369
(Continued)

(51) Int. Cl.
*G01N 31/22*        (2006.01)
*A61B 5/00*        (2006.01)
(Continued)

(52) U.S. Cl.
CPC ......... *G01N 31/221* (2013.01); *A61B 5/0077* (2013.01); *A61B 5/14539* (2013.01);
(Continued)

(58) Field of Classification Search
CPC .... G01N 31/221; G01N 31/222; G01N 21/80; A61B 5/0077; A61B 5/14539;
(Continued)

(56) References Cited

U.S. PATENT DOCUMENTS 2,249,867 A    7/1941    Snelling
2,806,023 A    9/1957    Henry et al.
(Continued)

FOREIGN PATENT DOCUMENTS

AU      2003204827 B2    5/2006
CN         1114748 A    1/1996
(Continued)

OTHER PUBLICATIONS

Advantec MFS, Inc., "Membrane Filters" (catalog), retrieved from http://www.advantecmfs.com/catalog/filt/membrane.pdf, on Jan. 29, 2016, Copyright 2001-2011, 17 pages.
(Continued)

*Primary Examiner* — Robert J Eom
(74) *Attorney, Agent, or Firm* — Knobbe, Martens, Olson & Bear, LLP

(57) ABSTRACT

Disclosed herein are devices, wound dressings and methods for determining the pH of fluid or a wound exudate at a wound. Example devices include a device comprising a surface configured to contact the fluid or wound and a pH indicator covalently bound thereto or applied to the surface, wherein the pH indicator has a first colour prior to contact with the fluid or the wound exudate and changes colour as a function of the pH of the fluid or wound exudate. Example devices include a device which indicates wound exudate loading within a wound dressing and wound dressing comprising an absorbent layer and a moisture indicator which indicates would exudate loading within the dressing, wherein the visibility of the moisture indictor changes as a
(Continued)

result of a physical transformation of a first material within the dressing. Systems, devices, and methods are provided for monitoring wound status and progression by measuring pH levels indicated by pH-sensitive wound dressings. In some implementations, a wound is monitored by capturing an image of the pH-sensitive wound dressing and processing the captured image to determine the color of a pH indicator included on the wound dressing. The color of the indicator is determined in terms of RGB values from the image, and a pH value for the wound dressing is calculated from the dressing RGB values. The calculated pH value is then relayed to a user to be used as an indicator of wound status or health.

10 Claims, 57 Drawing Sheets

Related U.S. Application Data continuation-in-part of application No. 15/804,748, filed on Nov. 6, 2017, now Pat. No. 10,288,590, which is a continuation of application No. 14/650,547, filed as application No. PCT/EP2014/071520 on Oct. 8, 2014, now Pat. No. 9,829,471, said application No. 16/241,736 is a continuation-in-part of application No. 14/650,531, filed as application No. PCT/EP2014/071510 on Oct. 8, 2014, now abandoned, and a continuation-in-part of application No. 14/893,361, filed as application No. PCT/GB2014/051574 on May 22, 2014, now abandoned, and a continuation-in-part of application No. 14/759,786, filed as application No. PCT/GB2014/050048 on Jan. 9, 2014, now abandoned, and a continuation-in-part of application No. 15/113,775, filed as application No. PCT/EP2015/050964 on Jan. 20, 2015, now abandoned.

(30) Foreign Application Priority Data

| Oct. 8, 2013 | (GB) | ...................................... | 1317742 |
| Oct. 8, 2013 | (GB) | ...................................... | 1317746 |
| Jan. 23, 2014 | (GB) | ...................................... | 1401112 |

(51) Int. Cl.

| *A61B 5/145* | (2006.01) |
| *A61B 5/1495* | (2006.01) |
| *A61F 13/42* | (2006.01) |
| *G01N 21/80* | (2006.01) |
| *G01N 27/416* | (2006.01) |

(52) U.S. Cl.
CPC ............ *A61B 5/445* (2013.01); *A61B 5/6833* (2013.01); *A61F 13/42* (2013.01); *G01N 21/80* (2013.01); *G01N 31/222* (2013.01); *A61B 5/0013* (2013.01); *A61B 5/1495* (2013.01); *A61F 2013/427* (2013.01); *G01N 27/4165* (2013.01)

(58) Field of Classification Search
CPC ..... A61B 5/445; A61B 5/6833; A61B 5/0013; A61B 5/1495; A61F 3/42; A61F 2012/427; H01N 27/4165
See application file for complete search history.

(56) References Cited

U.S. PATENT DOCUMENTS

| 3,596,657 | A |  | 8/1971 | Eidus |
| 3,675,654 | A |  | 7/1972 | Baker et al. |
| 3,759,261 | A |  | 9/1973 | Wang |
| 3,896,802 | A |  | 7/1975 | Williams |
| 3,972,328 | A |  | 8/1976 | Chen |
| 4,022,211 | A |  | 5/1977 | Timmons et al. |
| 4,029,598 | A |  | 6/1977 | Neisius et al. |
| 4,192,311 | A |  | 3/1980 | Felfoldi |
| 4,382,380 | A |  | 5/1983 | Martin |
| 4,705,513 | A |  | 11/1987 | Sheldon et al. |
| 4,728,499 | A |  | 3/1988 | Fehder |
| 4,813,942 | A | * | 3/1989 | Alvarez ........... A61F 13/00063 |
|  |  |  |  | 602/56 |
| 4,885,077 | A |  | 12/1989 | Karakelle et al. |
| 4,999,306 | A |  | 3/1991 | Yafuso et al. |
| 5,056,510 | A |  | 10/1991 | Gilman |
| 5,104,660 | A |  | 4/1992 | Chvapil et al. |
| 5,181,905 | A |  | 1/1993 | Flam |
| 5,194,389 | A |  | 3/1993 | Rittersdorf et al. |
| 5,238,732 | A |  | 8/1993 | Krishnan |
| 5,277,872 | A |  | 1/1994 | Bankert et al. |
| 5,536,783 | A |  | 7/1996 | Olstein et al. |
| 5,549,584 | A |  | 8/1996 | Gross |
| 5,571,684 | A |  | 11/1996 | Lawrence et al. |
| 5,678,448 | A |  | 10/1997 | Fullen et al. |
| 5,690,610 | A | * | 11/1997 | Ito ...................... A61F 13/0203 |
|  |  |  |  | 602/56 |
| 5,690,624 | A |  | 11/1997 | Sasaki et al. |
| 5,707,499 | A |  | 1/1998 | Joshi et al. |
| 5,759,570 | A |  | 6/1998 | Arnold |
| 5,766,212 | A |  | 6/1998 | Jitoe et al. |
| 5,788,687 | A |  | 8/1998 | Batich et al. |
| 5,846,836 | A |  | 12/1998 | Mallow |
| 5,852,126 | A |  | 12/1998 | Barnard et al. |
| 5,853,669 | A |  | 12/1998 | Wolfbeis |
| 5,897,516 | A |  | 4/1999 | Kadash et al. |
| 6,071,267 | A |  | 6/2000 | Zamierowski |
| 6,095,992 | A |  | 8/2000 | Augustine |
| 6,120,904 | A |  | 9/2000 | Hostettler et al. |
| 6,178,342 | B1 |  | 1/2001 | Borgos et al. |
| 6,208,423 | B1 |  | 3/2001 | Voipio et al. |
| 6,284,942 | B1 |  | 9/2001 | Rabin |
| 6,333,093 | B1 |  | 12/2001 | Burrell et al. |
| 6,381,482 | B1 |  | 4/2002 | Jayaraman et al. |
| 6,388,043 | B1 |  | 5/2002 | Langer et al. |
| 6,482,491 | B1 |  | 11/2002 | Samuelsen et al. |
| 6,517,484 | B1 |  | 2/2003 | Wilk et al. |
| 6,551,252 | B2 |  | 4/2003 | Sackner et al. |
| 6,617,488 | B1 |  | 9/2003 | Springer et al. |
| 6,626,891 | B2 |  | 9/2003 | Ohmstede |
| 6,685,681 | B2 |  | 2/2004 | Lockwood et al. |
| 6,688,525 | B1 |  | 2/2004 | Nelson et al. |
| 6,696,240 | B1 |  | 2/2004 | Kloepfer et al. |
| 6,731,987 | B1 |  | 5/2004 | McAdams et al. |
| 6,747,185 | B2 |  | 6/2004 | Inoue et al. |
| 6,752,794 | B2 |  | 6/2004 | Lockwood et al. |
| 6,772,708 | B2 |  | 8/2004 | Klofta et al. |
| 6,815,207 | B2 |  | 11/2004 | Yabuki et al. |
| 6,936,037 | B2 |  | 8/2005 | Bubb et al. |
| 6,951,553 | B2 |  | 10/2005 | Bubb et al. |
| 6,979,324 | B2 |  | 12/2005 | Bybordi et al. |
| 7,004,915 | B2 |  | 2/2006 | Boynton et al. |
| 7,070,584 | B2 |  | 7/2006 | Johnson et al. |
| 7,077,832 | B2 |  | 7/2006 | Fleischmann |
| 7,108,683 | B2 |  | 9/2006 | Zamierowski |
| 7,159,532 | B2 |  | 1/2007 | Klofta et al. |
| 7,201,063 | B2 |  | 4/2007 | Taylor |
| 7,206,623 | B2 |  | 4/2007 | Blank et al. |
| 7,216,651 | B2 |  | 5/2007 | Argenta et al. |
| 7,316,652 | B2 |  | 1/2008 | Dalgaard et al. |
| 7,332,642 | B2 |  | 2/2008 | Liu |
| 7,361,184 | B2 |  | 4/2008 | Joshi |
| 7,381,859 | B2 |  | 6/2008 | Hunt et al. |
| 7,429,255 | B2 |  | 9/2008 | Thompson |
| 7,520,875 | B2 |  | 4/2009 | Bernabei |
| 7,521,292 | B2 |  | 4/2009 | Rogers et al. |
| 7,569,742 | B2 |  | 8/2009 | Haggstrom et al. |
| 7,605,298 | B2 |  | 10/2009 | Bechert et al. |
| 7,615,036 | B2 |  | 11/2009 | Joshi et al. |
| 7,622,629 | B2 |  | 11/2009 | Aali |
| 7,625,362 | B2 |  | 12/2009 | Boehringer et al. |

(56) References Cited

U.S. PATENT DOCUMENTS

| | | | |
|---|---|---|---|
| 7,687,678 B2 | 3/2010 | Jacobs | |
| 7,699,823 B2 | 4/2010 | Haggstrom et al. | |
| 7,708,724 B2 | 5/2010 | Weston | |
| 7,722,582 B2 | 5/2010 | Lina et al. | |
| 7,749,531 B2 | 7/2010 | Booher | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,777,092 B2 | 8/2010 | Lykke et al. | |
| 7,779,625 B2 | 8/2010 | Joshi et al. | |
| 7,811,269 B2 | 10/2010 | Boynton et al. | |
| 7,838,717 B2 | 11/2010 | Haggstrom et al. | |
| 7,846,141 B2 | 12/2010 | Weston | |
| 7,873,141 B2 | 1/2011 | Imai et al. | |
| 7,877,866 B1 | 2/2011 | Greenberg et al. | |
| 7,884,258 B2 | 2/2011 | Boehringer et al. | |
| 7,892,639 B2 | 2/2011 | Mess et al. | |
| 7,904,133 B2 | 3/2011 | Gehman et al. | |
| 7,910,791 B2 | 3/2011 | Coffey | |
| 7,922,703 B2 | 4/2011 | Riesinger | |
| 7,945,302 B2 | 5/2011 | McAdams | |
| 7,959,624 B2 | 6/2011 | Riesinger | |
| 7,964,766 B2 | 6/2011 | Blott et al. | |
| 7,976,519 B2 | 7/2011 | Bubb et al. | |
| 8,019,401 B1 | 9/2011 | Smith et al. | |
| 8,032,210 B2 | 10/2011 | Finneran et al. | |
| 8,034,037 B2 | 10/2011 | Adams et al. | |
| 8,060,174 B2 | 11/2011 | Simpson et al. | |
| 8,062,272 B2 | 11/2011 | Weston | |
| 8,062,331 B2 | 11/2011 | Zamierowski | |
| 8,079,247 B2 | 12/2011 | Russell et al. | |
| 8,080,702 B2 | 12/2011 | Blott et al. | |
| 8,111,165 B2 | 2/2012 | Ortega et al. | |
| 8,116,841 B2 | 2/2012 | Bly et al. | |
| 8,118,794 B2 | 2/2012 | Weston | |
| 8,152,785 B2 | 4/2012 | Vitaris | |
| 8,162,907 B2 | 4/2012 | Heagle | |
| 8,207,392 B2 | 6/2012 | Haggstrom et al. | |
| 8,238,996 B2 | 8/2012 | Burnes et al. | |
| 8,241,231 B2 | 8/2012 | Bausewein et al. | |
| 8,241,261 B2 | 8/2012 | Randolph et al. | |
| 8,282,611 B2 | 10/2012 | Weston | |
| 8,303,552 B2 | 11/2012 | Weston | |
| 8,332,053 B1 | 12/2012 | Patterson et al. | |
| 8,333,874 B2 | 12/2012 | Currie | |
| 8,366,692 B2 | 2/2013 | Weston et al. | |
| 8,372,049 B2 | 2/2013 | Jaeb et al. | |
| 8,372,050 B2 | 2/2013 | Jaeb et al. | |
| 8,425,478 B2 | 4/2013 | Olson | |
| 8,425,996 B2 | 4/2013 | Gorski et al. | |
| 8,444,612 B2 | 5/2013 | Patel et al. | |
| 8,460,255 B2 | 6/2013 | Joshi et al. | |
| 8,480,641 B2 | 7/2013 | Jacobs | |
| 8,545,466 B2 | 10/2013 | Andresen et al. | |
| 8,568,386 B2 | 10/2013 | Malhi | |
| 8,628,505 B2 | 1/2014 | Weston | |
| 8,641,691 B2 | 2/2014 | Fink et al. | |
| 8,663,106 B2 | 3/2014 | Stivoric et al. | |
| 8,663,198 B2 | 3/2014 | Buan et al. | |
| 8,682,442 B2 | 3/2014 | McAdams | |
| 8,715,256 B2 | 5/2014 | Greener | |
| 8,764,732 B2 | 7/2014 | Hartwell | |
| 8,783,948 B2 | 7/2014 | Panda et al. | |
| 8,788,009 B2 | 7/2014 | Greene et al. | |
| 8,791,315 B2 | 7/2014 | Lattimore et al. | |
| 8,795,243 B2 | 8/2014 | Weston | |
| 8,795,257 B2 | 8/2014 | Coulthard et al. | |
| 8,800,386 B2 | 8/2014 | Taylor | |
| 8,808,274 B2 | 8/2014 | Hartwell | |
| 8,818,478 B2 | 8/2014 | Scheffler et al. | |
| 8,829,263 B2 | 9/2014 | Haggstrom et al. | |
| 8,834,451 B2 | 9/2014 | Blott et al. | |
| 8,894,590 B2 | 11/2014 | Lamoise et al. | |
| 8,896,706 B2 | 11/2014 | Van Den Hengel et al. | |
| 8,925,392 B2 | 1/2015 | Esposito et al. | |
| 8,927,801 B2 | 1/2015 | Klofta | |
| 8,934,957 B2 | 1/2015 | Dias et al. | |
| 8,934,965 B2 | 1/2015 | Rogers et al. | |
| 8,943,897 B2 | 2/2015 | Beauvais et al. | |
| 8,948,839 B1 | 2/2015 | Longinotti-Buitoni et al. | |
| 8,956,336 B2 | 2/2015 | Haggstrom et al. | |
| 8,974,428 B2 | 3/2015 | Freedman et al. | |
| 8,986,940 B2 | 3/2015 | McNulty et al. | |
| 8,997,588 B2 | 4/2015 | Taylor | |
| 8,997,682 B1 | 4/2015 | Ashcroft | |
| 9,000,251 B2 | 4/2015 | Murphy et al. | |
| 9,012,714 B2 | 4/2015 | Fleischmann | |
| 9,061,095 B2 | 6/2015 | Adie et al. | |
| 9,127,665 B2 | 9/2015 | Locke et al. | |
| 9,192,531 B2 | 11/2015 | Wu | |
| 9,192,700 B2 | 11/2015 | Weston et al. | |
| 9,199,012 B2 | 12/2015 | Vitaris et al. | |
| 9,204,806 B2 | 12/2015 | Stivoric et al. | |
| 9,220,455 B2 | 12/2015 | Sarrafzadeh et al. | |
| 9,220,822 B2 | 12/2015 | Hartwell | |
| 9,226,402 B2 | 12/2015 | Hsu | |
| 9,282,897 B2 | 3/2016 | Ross, Jr. et al. | |
| 9,283,118 B2 | 3/2016 | Locke et al. | |
| 9,302,033 B2 | 4/2016 | Riesinger | |
| 9,311,520 B2 | 4/2016 | Burg et al. | |
| 9,314,175 B2 | 4/2016 | Jacofsky et al. | |
| 9,320,473 B2 | 4/2016 | Shuler | |
| 9,372,123 B2 | 6/2016 | Li et al. | |
| 9,375,353 B2 | 6/2016 | Vitaris et al. | |
| 9,375,521 B2 | 6/2016 | Hudspeth et al. | |
| 9,378,450 B1 | 6/2016 | Mei et al. | |
| 9,381,283 B2 | 7/2016 | Adams et al. | |
| 9,402,988 B2 | 8/2016 | Buchanan et al. | |
| 9,408,573 B2 | 8/2016 | Welch et al. | |
| 9,421,309 B2 | 8/2016 | Robinson et al. | |
| 9,427,179 B2 | 8/2016 | Mestrovic et al. | |
| 9,439,599 B2 | 9/2016 | Thompson et al. | |
| 9,445,749 B2 | 9/2016 | Erickson et al. | |
| 9,446,178 B2 | 9/2016 | Blott et al. | |
| 9,483,726 B2 | 11/2016 | Mei et al. | |
| 9,494,474 B2 | 11/2016 | Servati et al. | |
| 9,504,421 B2 | 11/2016 | Greener | |
| 9,511,215 B2 | 12/2016 | Skiba | |
| 9,516,758 B2 | 12/2016 | Arora et al. | |
| 9,526,439 B2 | 12/2016 | Connelly et al. | |
| 9,554,484 B2 | 1/2017 | Rogers et al. | |
| 9,572,507 B2 | 2/2017 | Moore et al. | |
| 9,582,072 B2 | 2/2017 | Connor | |
| 9,585,620 B2 | 3/2017 | Paquet et al. | |
| 9,587,991 B2 | 3/2017 | Padiy | |
| 9,592,007 B2 | 3/2017 | Nuovo et al. | |
| 9,603,560 B2 | 3/2017 | Monty et al. | |
| 9,610,388 B2 | 4/2017 | Aceto et al. | |
| 9,613,911 B2 | 4/2017 | Rogers et al. | |
| 9,629,584 B2 | 4/2017 | Macia et al. | |
| 9,629,986 B2 | 4/2017 | Patel et al. | |
| 9,681,993 B2 | 6/2017 | Wu et al. | |
| 9,687,195 B2 | 6/2017 | Sims et al. | |
| 9,956,312 B2 | 5/2018 | Klofta et al. | |
| 9,999,711 B2 | 6/2018 | Weston et al. | |
| 10,004,643 B2 | 6/2018 | Luckemeyer et al. | |
| 10,046,096 B2 | 8/2018 | Askem et al. | |
| 2002/0062114 A1 | 5/2002 | Murai et al. | |
| 2002/0091347 A1 | 7/2002 | Eakin | |
| 2003/0033032 A1 | 2/2003 | Lind et al. | |
| 2003/0210810 A1 | 11/2003 | Gee, Jr. et al. | |
| 2004/0044299 A1 | 3/2004 | Utsugi | |
| 2004/0133090 A1 | 7/2004 | Dostoinov et al. | |
| 2004/0230132 A1 | 11/2004 | Shehada | |
| 2005/0105789 A1 | 5/2005 | Isaacs et al. | |
| 2005/0124947 A1* | 6/2005 | Fernfors ................ A61F 13/42 604/361 | |
| 2005/0187146 A1 | 8/2005 | Helmus et al. | |
| 2005/0199055 A1 | 9/2005 | Browne | |
| 2005/0280531 A1 | 12/2005 | Fadem et al. | |
| 2006/0009744 A1 | 1/2006 | Erdman et al. | |
| 2006/0052678 A1 | 3/2006 | Drinan et al. | |
| 2006/0079852 A1 | 4/2006 | Bubb et al. | |
| 2006/0140999 A1 | 6/2006 | Lendlein et al. | |

(56)     References Cited

U.S. PATENT DOCUMENTS

| | | | | |
|---|---|---|---|---|
| 2007/0003606 A1 | 1/2007 | Booher | | |
| 2007/0048224 A1 | 3/2007 | Howell et al. | | |
| 2007/0055209 A1 | 3/2007 | Patel et al. | | |
| 2007/0129784 A1 | 6/2007 | Lendlein et al. | | |
| 2007/0142762 A1 | 6/2007 | Kaplan et al. | | |
| 2007/0161937 A1 | 7/2007 | Aali | | |
| 2007/0173892 A1 | 7/2007 | Fleischer et al. | | |
| 2007/0188759 A1 | 8/2007 | Mehendale et al. | | |
| 2007/0191754 A1* | 8/2007 | Aali | A61F 15/008 | 602/41 |
| 2007/0203442 A1 | 8/2007 | Bechert et al. | | |
| 2007/0225663 A1 | 9/2007 | Watt et al. | | |
| 2007/0270774 A1 | 11/2007 | Bergman et al. | | |
| 2007/0276207 A1 | 11/2007 | Eagland et al. | | |
| 2008/0021166 A1 | 1/2008 | Tong et al. | | |
| 2008/0132821 A1 | 6/2008 | Propp et al. | | |
| 2008/0167535 A1 | 7/2008 | Stivoric et al. | | |
| 2008/0208151 A1* | 8/2008 | Zacharias | A61F 13/42 | 604/361 |
| 2008/0258717 A1 | 10/2008 | Igney et al. | | |
| 2008/0281244 A1 | 11/2008 | Jacobs | | |
| 2008/0306456 A1 | 12/2008 | Riesinger | | |
| 2008/0319283 A1 | 12/2008 | Cotton et al. | | |
| 2009/0062757 A1 | 3/2009 | Long et al. | | |
| 2009/0125004 A1 | 5/2009 | Shen et al. | | |
| 2009/0157024 A1* | 6/2009 | Song | G01N 21/80 | 436/163 |
| 2009/0177051 A1 | 7/2009 | Arons et al. | | |
| 2009/0190135 A1 | 7/2009 | Clarizia et al. | | |
| 2009/0198167 A1 | 8/2009 | Ambrosio | | |
| 2009/0216168 A1 | 8/2009 | Eckstein | | |
| 2009/0221977 A1 | 9/2009 | Blott et al. | | |
| 2009/0227969 A1 | 9/2009 | Jaeb et al. | | |
| 2009/0234206 A1 | 9/2009 | Gaspard et al. | | |
| 2009/0234306 A1 | 9/2009 | Vitaris | | |
| 2009/0245601 A1 | 10/2009 | Cohen et al. | | |
| 2009/0299251 A1 | 12/2009 | Buan | | |
| 2009/0299306 A1 | 12/2009 | Buan | | |
| 2010/0022990 A1 | 1/2010 | Karpowicz et al. | | |
| 2010/0025831 A1 | 2/2010 | Yamazaki et al. | | |
| 2010/0041968 A1 | 2/2010 | Meschisen et al. | | |
| 2010/0069838 A1 | 3/2010 | Weber et al. | | |
| 2010/0112680 A1 | 5/2010 | Brockwell et al. | | |
| 2010/0125258 A1 | 5/2010 | Coulthard et al. | | |
| 2010/0166252 A1 | 7/2010 | Ahmed et al. | | |
| 2010/0168695 A1 | 7/2010 | Robles et al. | | |
| 2010/0168700 A1 | 7/2010 | Schmidt et al. | | |
| 2010/0168727 A1 | 7/2010 | Hancock et al. | | |
| 2010/0178203 A1 | 7/2010 | Kane et al. | | |
| 2010/0262090 A1 | 10/2010 | Riesinger | | |
| 2010/0268111 A1 | 10/2010 | Drinan et al. | | |
| 2010/0305473 A1 | 12/2010 | Yuzhakov | | |
| 2010/0305526 A1 | 12/2010 | Robinson et al. | | |
| 2010/0318052 A1 | 12/2010 | Ha et al. | | |
| 2010/0324510 A1 | 12/2010 | Andresen et al. | | |
| 2011/0004088 A1 | 1/2011 | Grossman | | |
| 2011/0004172 A1 | 1/2011 | Eckstein et al. | | |
| 2011/0054283 A1 | 3/2011 | Shuler | | |
| 2011/0092958 A1 | 4/2011 | Jacobs | | |
| 2011/0118683 A1 | 5/2011 | Weston | | |
| 2011/0218757 A1 | 9/2011 | Callsen et al. | | |
| 2011/0224631 A1 | 9/2011 | Simmons et al. | | |
| 2011/0245682 A1 | 10/2011 | Robinson et al. | | |
| 2011/0274593 A1 | 11/2011 | Gorski et al. | | |
| 2011/0301441 A1 | 12/2011 | Bandic et al. | | |
| 2012/0016322 A1 | 1/2012 | Coulthard et al. | | |
| 2012/0029306 A1 | 2/2012 | Paquet et al. | | |
| 2012/0029307 A1 | 2/2012 | Paquet et al. | | |
| 2012/0029410 A1 | 2/2012 | Koenig et al. | | |
| 2012/0041399 A1 | 2/2012 | Blott et al. | | |
| 2012/0095380 A1 | 4/2012 | Gergely et al. | | |
| 2012/0123220 A1 | 5/2012 | Iyer et al. | | |
| 2012/0165717 A1 | 6/2012 | Al Khaburi | | |
| 2012/0190956 A1 | 7/2012 | Connolly | | |
| 2012/0190989 A1 | 7/2012 | Kaiser et al. | | |
| 2012/0201437 A1 | 8/2012 | Ohnemus | | |
| 2012/0215190 A1 | 8/2012 | Kawashima | | |
| 2012/0256750 A1 | 10/2012 | Novak | | |
| 2012/0264163 A1 | 10/2012 | Booher | | |
| 2012/0271265 A1 | 10/2012 | Langdon | | |
| 2012/0277559 A1 | 11/2012 | Kohl-Bareis et al. | | |
| 2012/0279101 A1 | 11/2012 | Pretsch et al. | | |
| 2012/0316538 A1 | 12/2012 | Heiser et al. | | |
| 2012/0323274 A1 | 12/2012 | Lendlein et al. | | |
| 2012/0330252 A1 | 12/2012 | Stokes et al. | | |
| 2013/0041235 A1 | 2/2013 | Rogers et al. | | |
| 2013/0064772 A1 | 3/2013 | Swiss et al. | | |
| 2013/0066285 A1 | 3/2013 | Locke et al. | | |
| 2013/0066289 A1 | 3/2013 | Song et al. | | |
| 2013/0087298 A1 | 4/2013 | Phillips et al. | | |
| 2013/0090616 A1 | 4/2013 | Neubauer | | |
| 2013/0116635 A1 | 5/2013 | Fleischmann | | |
| 2013/0121544 A1 | 5/2013 | Sarrafzadeh et al. | | |
| 2013/0123722 A1 | 5/2013 | Pratt et al. | | |
| 2013/0131621 A1 | 5/2013 | Van Holten et al. | | |
| 2013/0138054 A1 | 5/2013 | Fleischmann | | |
| 2013/0144230 A1 | 6/2013 | Wu et al. | | |
| 2013/0150814 A1 | 6/2013 | Buan | | |
| 2013/0151223 A1 | 6/2013 | Zamierowski et al. | | |
| 2013/0165878 A1 | 6/2013 | Heagle | | |
| 2013/0200268 A1 | 8/2013 | Rafferty et al. | | |
| 2013/0261409 A1 | 10/2013 | Pathak et al. | | |
| 2013/0274629 A1 | 10/2013 | Duesterhoft et al. | | |
| 2013/0274688 A1 | 10/2013 | Weston | | |
| 2013/0303865 A1 | 11/2013 | Rebec et al. | | |
| 2013/0317367 A1 | 11/2013 | Shuler | | |
| 2013/0331822 A1 | 12/2013 | Patel et al. | | |
| 2014/0005618 A1 | 1/2014 | Locke et al. | | |
| 2014/0012108 A1 | 1/2014 | McPeak | | |
| 2014/0031663 A1 | 1/2014 | Gallego et al. | | |
| 2014/0072190 A1 | 3/2014 | Wu et al. | | |
| 2014/0098209 A1 | 4/2014 | Neff | | |
| 2014/0107495 A1 | 4/2014 | Marinelli et al. | | |
| 2014/0114268 A1 | 4/2014 | Auguste et al. | | |
| 2014/0121487 A1 | 5/2014 | Faybishenko et al. | | |
| 2014/0138441 A1 | 5/2014 | Davalos et al. | | |
| 2014/0147611 A1 | 5/2014 | Ackerman, Jr. | | |
| 2014/0154789 A1 | 6/2014 | Polwart et al. | | |
| 2014/0203797 A1 | 7/2014 | Stivoric et al. | | |
| 2014/0206947 A1 | 7/2014 | Isserow et al. | | |
| 2014/0228791 A1 | 8/2014 | Hartwell | | |
| 2014/0232516 A1 | 8/2014 | Stivoric et al. | | |
| 2014/0235166 A1 | 8/2014 | Molettiere et al. | | |
| 2014/0243709 A1 | 8/2014 | Gibson et al. | | |
| 2014/0296749 A1 | 10/2014 | Reid, Jr. et al. | | |
| 2014/0296808 A1 | 10/2014 | Curran et al. | | |
| 2014/0298927 A1 | 10/2014 | Allin et al. | | |
| 2014/0316359 A1 | 10/2014 | Collinson et al. | | |
| 2014/0340857 A1 | 11/2014 | Hsu et al. | | |
| 2014/0350882 A1 | 11/2014 | Everett et al. | | |
| 2015/0025343 A1 | 1/2015 | Gareau et al. | | |
| 2015/0032035 A1 | 1/2015 | Banwell et al. | | |
| 2015/0055134 A1 | 2/2015 | Papautsky et al. | | |
| 2015/0065965 A1 | 3/2015 | Haggstrom et al. | | |
| 2015/0080685 A1 | 3/2015 | Markle et al. | | |
| 2015/0138330 A1 | 5/2015 | Krishnamoorthi | | |
| 2015/0141767 A1 | 5/2015 | Rogers et al. | | |
| 2015/0182166 A1 | 7/2015 | Evans et al. | | |
| 2015/0211987 A1 | 7/2015 | Burg et al. | | |
| 2015/0223716 A1 | 8/2015 | Korkala et al. | | |
| 2015/0257644 A1 | 9/2015 | Cao | | |
| 2015/0265191 A1 | 9/2015 | Harding et al. | | |
| 2015/0265743 A1 | 9/2015 | Hanson et al. | | |
| 2015/0292968 A1 | 10/2015 | Vogt et al. | | |
| 2015/0313476 A1 | 11/2015 | Pisani et al. | | |
| 2015/0313533 A1 | 11/2015 | Rapp et al. | | |
| 2015/0327777 A1 | 11/2015 | Kostic et al. | | |
| 2015/0335254 A1 | 11/2015 | Fastert et al. | | |
| 2015/0335288 A1 | 11/2015 | Toth et al. | | |
| 2015/0351970 A1 | 12/2015 | Dagger et al. | | |
| 2015/0359458 A1 | 12/2015 | Erickson et al. | | |
| 2015/0359485 A1 | 12/2015 | Berg et al. | | |
| 2016/0015962 A1 | 1/2016 | Shokoueinejad Maragheh et al. | | |
| 2016/0022223 A1 | 1/2016 | Grundfest et al. | | |

(56) References Cited

U.S. PATENT DOCUMENTS

| | | |
|---|---|---|
| 2016/0029900 A1 | 2/2016 | LaPlante et al. |
| 2016/0030132 A1 | 2/2016 | Cheung et al. |
| 2016/0038064 A1 | 2/2016 | Johnson |
| 2016/0038083 A1 | 2/2016 | Ding et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1 | 3/2016 | Bergelin et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0143534 A1 | 5/2016 | Hyde et al. |
| 2016/0144084 A1 | 5/2016 | Collinson et al. |
| 2016/0157779 A1 | 6/2016 | Baxi et al. |
| 2016/0166438 A1 | 6/2016 | Rovaniemi |
| 2016/0232807 A1 | 8/2016 | Ghaffari et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0287177 A1 | 10/2016 | Huppert et al. |
| 2016/0298620 A1 | 10/2016 | Cordoba et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367406 A1 | 12/2016 | Barnett |
| 2017/0000407 A1 | 1/2017 | Saxby et al. |
| 2017/0027498 A1 | 2/2017 | Larson et al. |
| 2017/0079740 A1 | 3/2017 | Hufnagel et al. |
| 2017/0086519 A1 | 3/2017 | Vigano'et al. |
| 2017/0086709 A1 | 3/2017 | Khine et al. |
| 2017/0095208 A1 | 4/2017 | Oberleitner et al. |
| 2017/0161893 A1 | 6/2017 | Carnes et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0183705 A1 | 6/2017 | Hicks et al. |
| 2017/0234802 A1 | 8/2017 | Hicks et al. |
| 2017/0326004 A1 | 11/2017 | Long et al. |
| 2018/0008177 A1 | 1/2018 | Shimuta et al. |
| 2018/0196021 A1 | 7/2018 | Hammond et al. |
| 2018/0200414 A1 | 7/2018 | Askem et al. |
| 2019/0134280 A1 | 5/2019 | Toth |
| 2019/0212311 A1 | 7/2019 | Hammond et al. |
| 2019/0358089 A1 | 11/2019 | Dagger et al. |

FOREIGN PATENT DOCUMENTS

| | | |
|---|---|---|
| CN | 1250350 A | 4/2000 |
| CN | 1539515 A | 10/2004 |
| CN | 1625379 A | 6/2005 |
| CN | 1890563 A | 1/2007 |
| CN | 101297197 A | 10/2008 |
| CN | 100484501 C | 5/2009 |
| CN | 101453969 A | 6/2009 |
| CN | 101490556 A | 7/2009 |
| CN | 201414880 Y | 3/2010 |
| CN | 101894212 A | 11/2010 |
| CN | 102519959 A | 6/2012 |
| CN | 102634156 A | 8/2012 |
| CN | 102641187 A | 8/2012 |
| CN | 102879393 A | 1/2013 |
| CN | 103210304 A | 7/2013 |
| CN | 103217503 A | 7/2013 |
| CN | 105395184 A | 3/2016 |
| DE | 3443101 A1 | 5/1986 |
| DE | 202004017052 U1 | 6/2005 |
| DE | 102013013013 A1 | 2/2015 |
| EP | 0257916 A1 | 3/1988 |
| EP | 0340018 A2 | 11/1989 |
| EP | 0430608 A1 | 6/1991 |
| EP | 1476217 B1 | 3/2008 |
| EP | 2021046 B1 | 3/2012 |
| EP | 2454990 A2 | 5/2012 |
| EP | 2462908 A1 | 6/2012 |
| EP | 2574275 A2 | 4/2013 |
| EP | 1854342 B1 | 6/2014 |
| EP | 1734858 B1 | 7/2014 |
| EP | 2544642 B1 | 1/2015 |
| EP | 2648668 A4 | 1/2015 |
| EP | 2451349 B1 | 4/2016 |
| EP | 2941195 B1 | 12/2016 |
| FR | 1163907 A | 10/1958 |
| GB | 905040 A | 9/1962 |
| GB | 1255395 A | 12/1971 |
| GB | 2408330 A | 5/2005 |
| JP | S54176283 U | 12/1979 |
| JP | S57162304 U | 10/1982 |
| JP | H0755788 A | 3/1995 |
| JP | 2002165757 A | 6/2002 |
| JP | 2003210522 A | 7/2003 |
| JP | 2004239682 A | 8/2004 |
| JP | 2005123101 A | 5/2005 |
| JP | 2006338521 A | 12/2006 |
| JP | 2007163350 A | 6/2007 |
| JP | 2012157438 A | 8/2012 |
| KR | 20060133139 A | 12/2006 |
| KR | 20120059006 A | 6/2012 |
| RU | 114854 U1 | 4/2012 |
| WO | WO-8300742 A1 | 3/1983 |
| WO | WO-9529959 A1 | 11/1995 |
| WO | WO-9605873 A1 | 2/1996 |
| WO | WO-9812996 A1 | 4/1998 |
| WO | WO-9912581 A2 | 3/1999 |
| WO | WO-0247737 A1 | 6/2002 |
| WO | WO-2005025447 A2 | 3/2005 |
| WO | WO-2005052572 A1 | 6/2005 |
| WO | WO-2005123170 A1 | 12/2005 |
| WO | WO-2006042871 A1 | 4/2006 |
| WO | WO-2006052839 A2 | 5/2006 |
| WO | WO-2006110502 A1 | 10/2006 |
| WO | WO-2006133430 A2 | 12/2006 |
| WO | WO-2007030379 A2 | 3/2007 |
| WO | WO-2008003920 A1 | 1/2008 |
| WO | WO-2008006150 A1 | 1/2008 |
| WO | WO-2008010604 A1 | 1/2008 |
| WO | WO-2008125995 A1 | 10/2008 |
| WO | WO-2009066105 A1 | 5/2009 |
| WO | WO-2009124100 A1 | 10/2009 |
| WO | WO-2009141777 A1 | 11/2009 |
| WO | WO-2009158128 A2 | 12/2009 |
| WO | WO-2010020919 A1 | 2/2010 |
| WO | WO-2010105053 A2 | 9/2010 |
| WO | WO-2010142959 A2 | 12/2010 |
| WO | WO-2011098575 A2 | 8/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012074509 A1 | 6/2012 |
| WO | WO-2012131237 A1 | 10/2012 |
| WO | WO-2012131386 A1 | 10/2012 |
| WO | WO-2012140378 A1 | 10/2012 |
| WO | WO-2012141999 A1 | 10/2012 |
| WO | WO-2012143665 A1 | 10/2012 |
| WO | WO-2012171922 A1 | 12/2012 |
| WO | WO-2013010907 A1 | 1/2013 |
| WO | WO-2013026999 A1 | 2/2013 |
| WO | WO-2013044226 A2 | 3/2013 |
| WO | WO-2013074509 A1 | 5/2013 |
| WO | WO-2013083800 A1 | 6/2013 |
| WO | WO-2013090810 A1 | 6/2013 |
| WO | WO-2013136181 A2 | 9/2013 |
| WO | WO-2013149078 A1 | 10/2013 |
| WO | WO-2013155193 A1 | 10/2013 |
| WO | WO-2014008348 A2 | 1/2014 |
| WO | WO-2014016759 A1 | 1/2014 |
| WO | WO-2014020440 A1 | 2/2014 |
| WO | WO-2014020443 A2 | 2/2014 |
| WO | WO-2014025415 A2 | 2/2014 |
| WO | WO-2014036577 A1 | 3/2014 |

(56) References Cited

FOREIGN PATENT DOCUMENTS

| | | | |
|---|---|---|---|
| WO | WO-2014066913 A2 | 5/2014 | |
| WO | WO-2014108476 A1 | 7/2014 | |
| WO | WO-2014113253 A1 | 7/2014 | |
| WO | WO-2014113770 A1 | 7/2014 | |
| WO | WO-2014188200 A1 | 11/2014 | |
| WO | WO-2015022334 A1 | 2/2015 | |
| WO | WO-2015022340 A1 | 2/2015 | |
| WO | WO-2015031216 A1 | 3/2015 | |
| WO | WO-2015052219 A1 | 4/2015 | |
| WO | WO-2015052225 A1 | 4/2015 | |
| WO | WO-2015110411 A1 | 7/2015 | |
| WO | WO-2015112095 A1 | 7/2015 | |
| WO | WO-2015168720 A1 | 11/2015 | |
| WO | WO-2016005288 A1 | 1/2016 | |
| WO | WO-2016012219 A2 | 1/2016 | |
| WO | WO-2016025438 A1 | 2/2016 | |
| WO | WO-2016030752 A1 | 3/2016 | |
| WO | WO-2016058032 A1 | 4/2016 | |
| WO | WO-2016100218 A1 | 6/2016 | |
| WO | WO-2016109744 A1 | 7/2016 | |
| WO | WO-2016110564 A1 | 7/2016 | |

OTHER PUBLICATIONS

Aubakir B ., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

Carofiglio T., et al., "Optical Sensor Arrays: One-Pot, Multiparallel Synthesis and Cellulose Immobilization of pH and Metal Ion Sensitive Azo-Dyes," Tetrahedron, vol. 62, Dec. 2005, pp. 1502-1507.

Chen C.Y., et al., "A PNIPAM-Based Fluorescent Nanothermometer with Ratiometric Readout," Chemical Communications, vol. 47 (3), Nov. 26, 2010, pp. 994-996.

Cho S.M., et al., "Thermo-Sensitive Hydrogels Based on Interpenetrating Polymer Networks Made of Poly(N-isopropylacrylamide) and Polyurethane," Journal of Biomaterials Science, vol. 21 (8-9), 2010, pp. 1051-1068.

Convatec Ltd., "DuoDERM Signal Dressing—Time to Change," Retrieved from https://marketingworld.convatec.com/MarketPortCore/MediaFile/DownloadByApplication?applicationToken=dc038e44b0b0ee4d8616f7b6880b24551bfecf237645a04fb5b76ab792a36858&itemId=aea404fa-f437-423a-a70b-bc96c5971e2dmediaFileId=8531d794-0edf-45d4-b495-79ac8b21efcaforceDownload=true , Apr. 2009, 2 pages.

Dargaville T.R., et al., "Sensors and Imaging for Wound Healing: A Review," Biosensors and Bioelectronics, vol. 41, 2013, pp. 30-42.

Farooqui M.F., et al., "Low Cost Inkjet Printed Smart Bandage for Wireless Monitoring of Chronic Wounds," Scientific Reports, vol. 6, Jun. 29, 2016, 14 pages.

International Preliminary Report on Patentability for Application No. PCT/EP2014/071510, mailed on Apr. 21, 2016, 12 pages.

International Preliminary Report on Patentability for Application No. PCT/EP2014/071520, mailed on Apr. 21, 2016, 8 pages.

International Preliminary Report on Patentability for Application No. PCT/EP2015/050964, mailed on Aug. 4, 2016, 9 pages.

International Preliminary Report on Patentability for Application No. PCT/GB2014/050048, mailed on Jul. 23, 2015, 7 pages.

International Preliminary Report on Patentability for Application No. PCT/GB2014/051574, mailed on Dec. 3, 2015, 8 pages.

International Search Report and Written Opinion for Application No. PCT/EP2014/071520, mailed on Feb. 5, 2015, 12 pages.

International Search Report and Written Opinion for Application No. PCT/EP2015/050964, mailed on Apr. 2, 2015, 11 pages.

International Search Report and Written Opinion for Application No. PCT/GB2014/050048, mailed on Sep. 10, 2014, 8 pages.

International Search Report for Application No. PCT/EP2014/071510, mailed on Feb. 5, 2015, 7 pages.

International Search Report for Application No. PCT/GB2014/051574, mailed on Aug. 14, 2014, 3 pages.

Kendall ULTEC Hydrocolloid Dressing (4x4"), Product Ordering Page, web page downloaded on Jul. 13, 2014, 1 page.

Loh B.Y., et al., "Automated Mobile pH Reader on a Camera Phone," Iaeng International Journal of Computer Science, vol. 38, No. 3, Aug. 24, 2011, 7 pages.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Meier R. J., "Luminescent Single and Dual Sensors for In Vivo Imaging of pH and pO2," Doctoral Thesis, Submitted to University of Regensburg, Jun. 2011, 187 pages.

Meier R. J., et al., "Simultaneous Photographing of Oxygen and pH In Vivo Using Sensor Films," Angewandte Chemie, International Edition, vol. 50 (46), Nov. 2011, 17 pages.

Mohr G.J., et al., "Design of Acidochromic Dyes for Facile Preparation of pH Sensor Layers," Analytical and Bioanalytical Chemistry, vol. 392, 2008, pp. 1411-1418.

Mohr G.J., et al., "Optical Sensors for a Wide pH Range Based on Azo Dyes Immobilized on a Novel Support," Analytica Chimica Acta, vol. 292, No. 1-2, Jan. 2002, pp. 41-48.

Mohr G.J., et al., "Synthesis of Reactive Vinylsulphonyl Azo Dyes for Application in Optical pH Sensing," Dyes and Pigments, vol. 24, No. 3, Aug. 2001, pp. 223-240.

Protz K., "Modern Wound Dressings Support the Healing Process," Wound care: Indications and Application, Geriatrie Journal, Apr. 2005, pp. 3333-3339 (17 pages with English translation).

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Reddy T.T., et al., "Synthesis and Characterization of Semi-Interpenetrating Polymer Networks Based on Polyurethane and N-Isopropylacrylamide for Wound Dressing," Journal of Biomedical Materials Research Part B: Applied Biomaterials, vol. 88B (1), Sep. 8, 2008, pp. 32-40.

Smith & Nephew, "PICO Single Use Negative Pressure Wound Therapy System," Spiral Booklet, Mar. 2011, 7 pages.

Trupp S., et al., "Development of pH-Sensitive Indicator Dyes for the Preparation of Micro-Patterned Optical Sensor Layers," Sensors and Actuators B, vol. 150, Jul. 15, 2010, pp. 206-210.

Uchiyama S., et al., "Fluorescent Molecular Thermometers Based on Polymers Showing Temperature-induced Phase Transitions and Labeled With Polarity-responsive Benzofurazans," Analytical Chemistry, Amercian Chemical Society, vol. 75 (21), 2003, pp. 5926-5935.

Written Opinion for Application No. PCT/EP2014/071510, mailed on Feb. 5, 2015, 10 pages.

Written Opinion for Application No. PCT/GB2014/051574, mailed on Aug. 14, 2014, 6 pages.

Jingrui B., et al., "Cosmetic Formulation Design and Application Examples," China Petrochemical Press, Oct. 31, 2001, pp. 141-145.

Litmus test (chemistry), Retrieved on Mar. 10, 2025, 2 pages, Retrieved from Internet URL https://www.chemeurope.com/en/encyclopedia/Litmus_test/028chemistry%29.html.

\* cited by examiner

| 5 | 5.5 | 6 | 6.5 | 7 | 7.5 | 8 | 8.5 | 9 | 9.5 |
|---|-----|---|-----|---|-----|---|-----|---|-----|
| | | | | | | | | | |

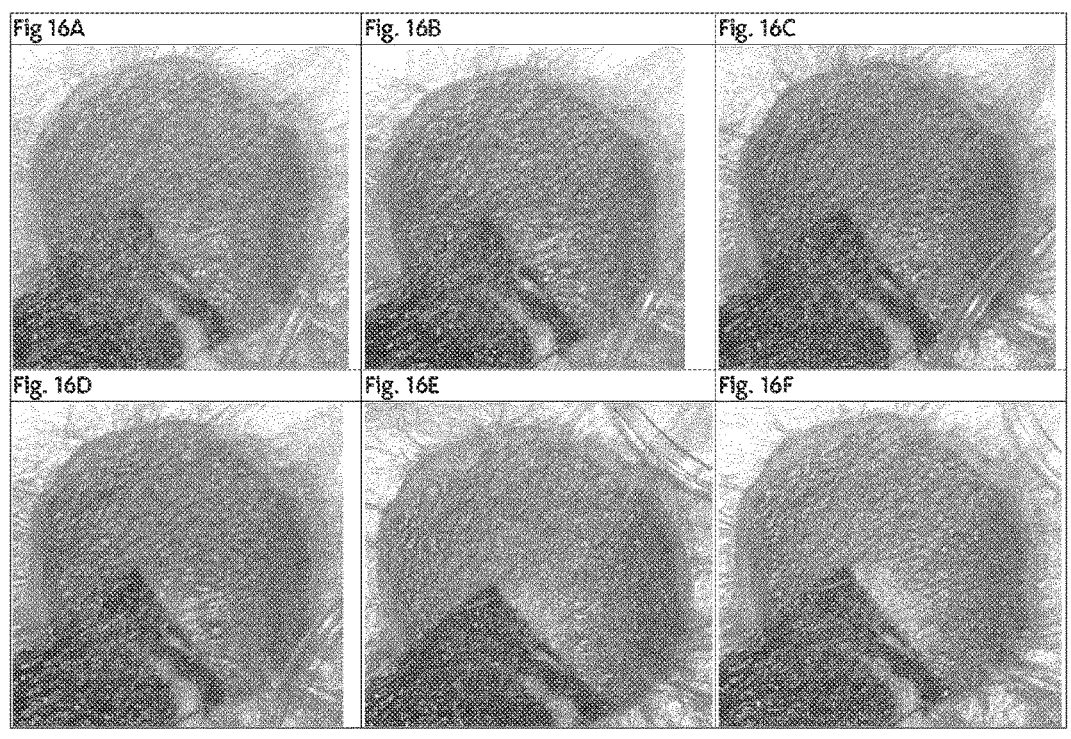
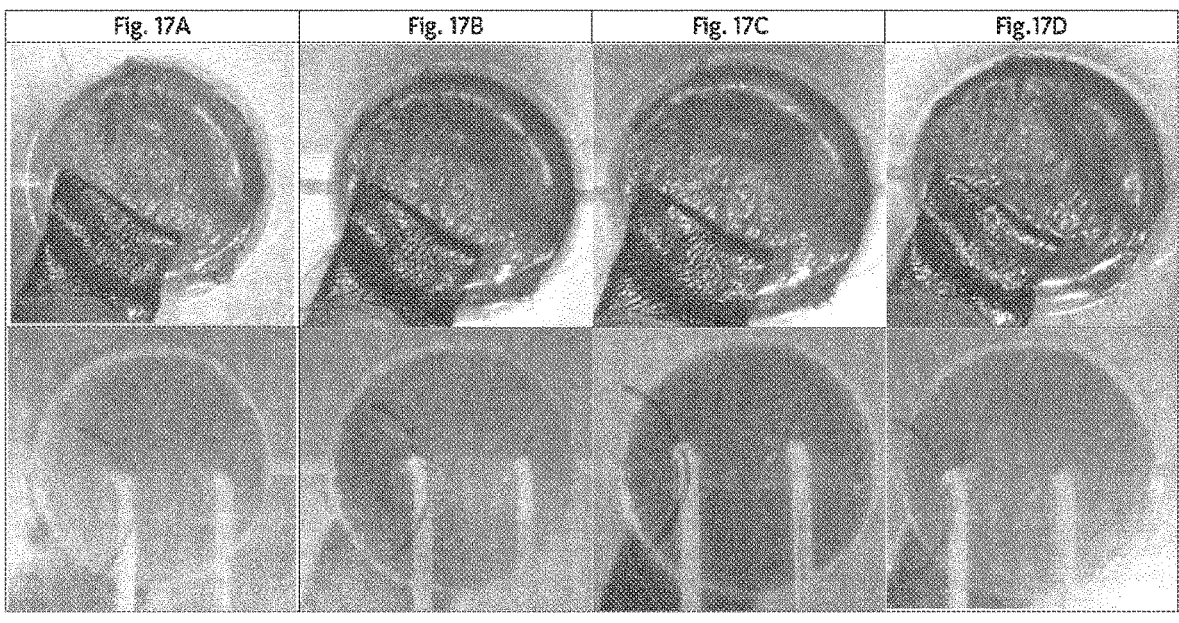

FIG. 21
FIG. 21A
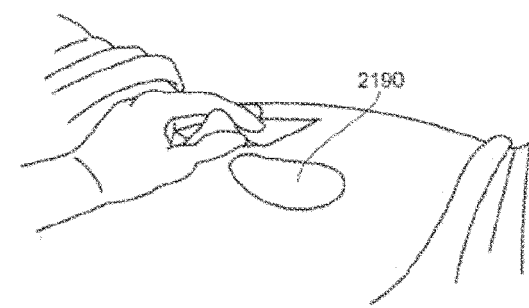
FIG. 21B
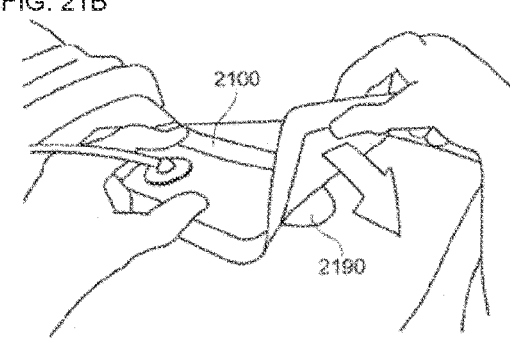
FIG. 21C
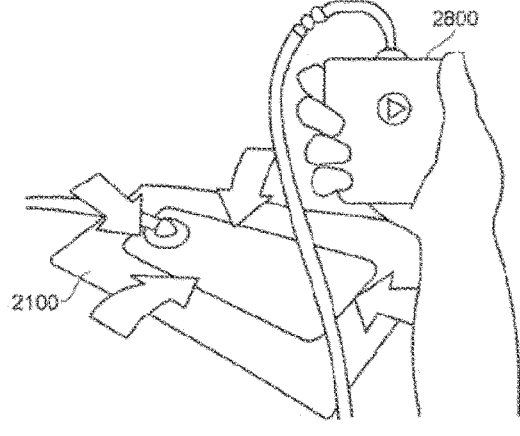

600
FIG. 25A
604
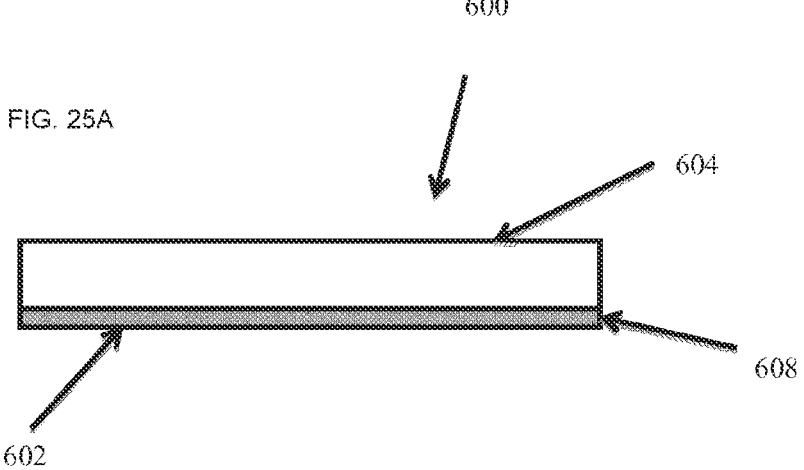
602
608
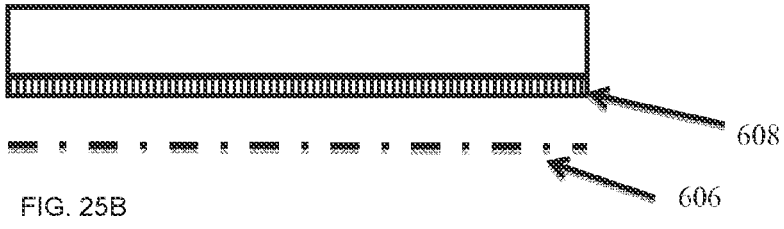
608
606
FIG. 25B

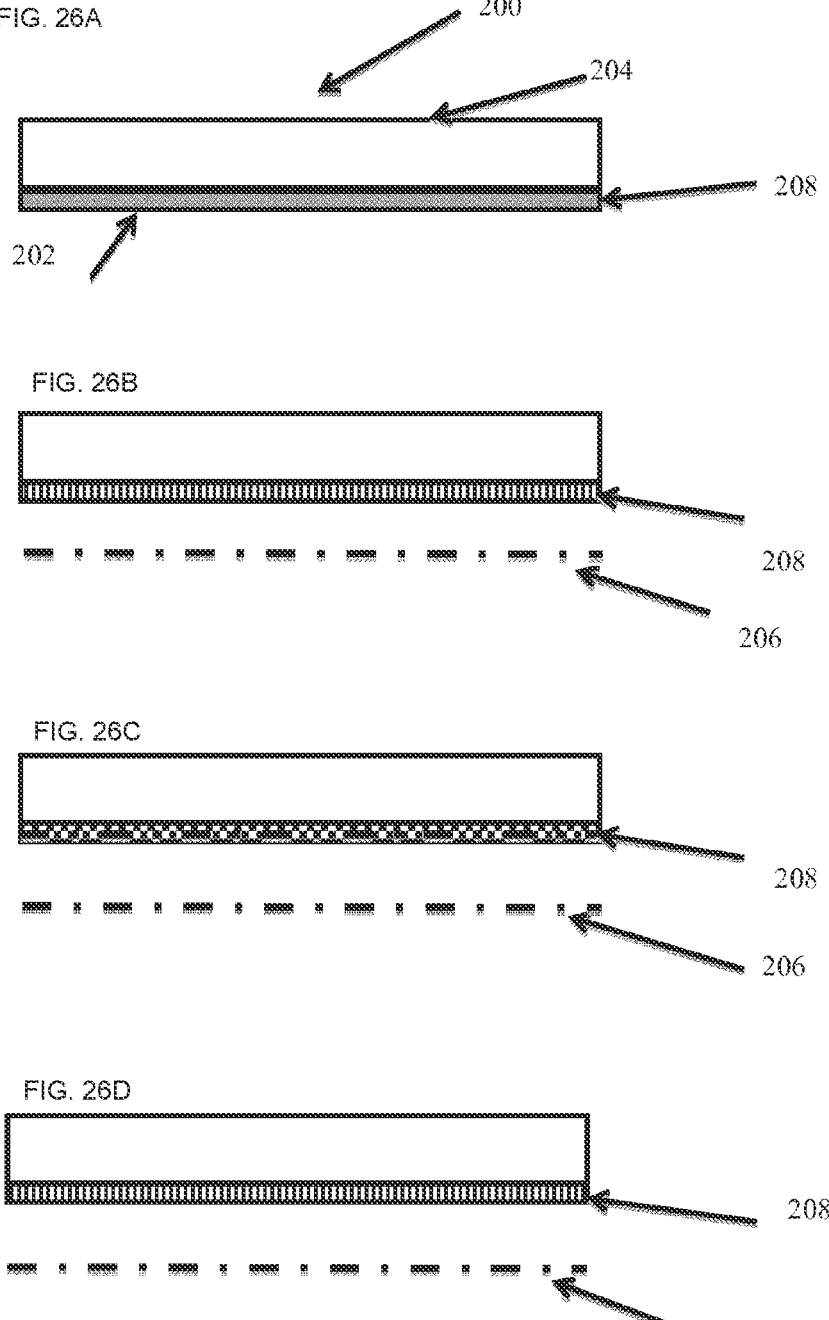

200

214    212    216

210

220

206

202

204

208

218

216    208

210

220

202

218

208

300

FIGURE 36A
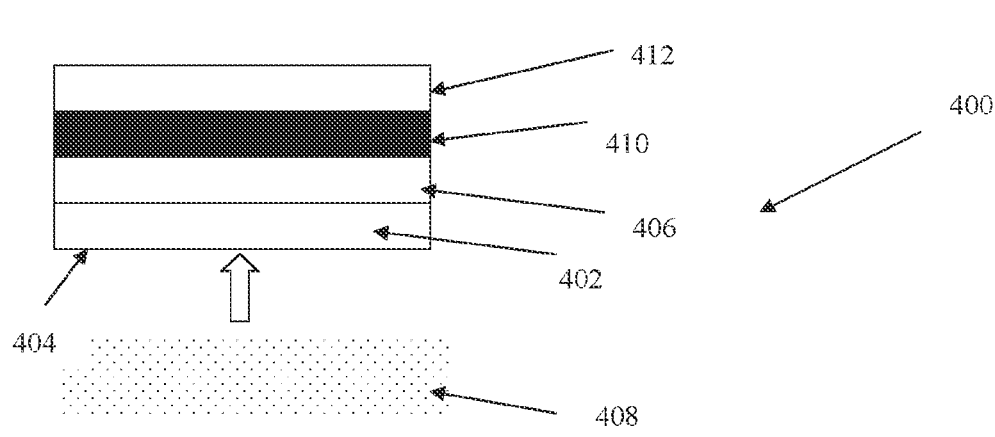
FIGURE 36B    Cross section    Plan view
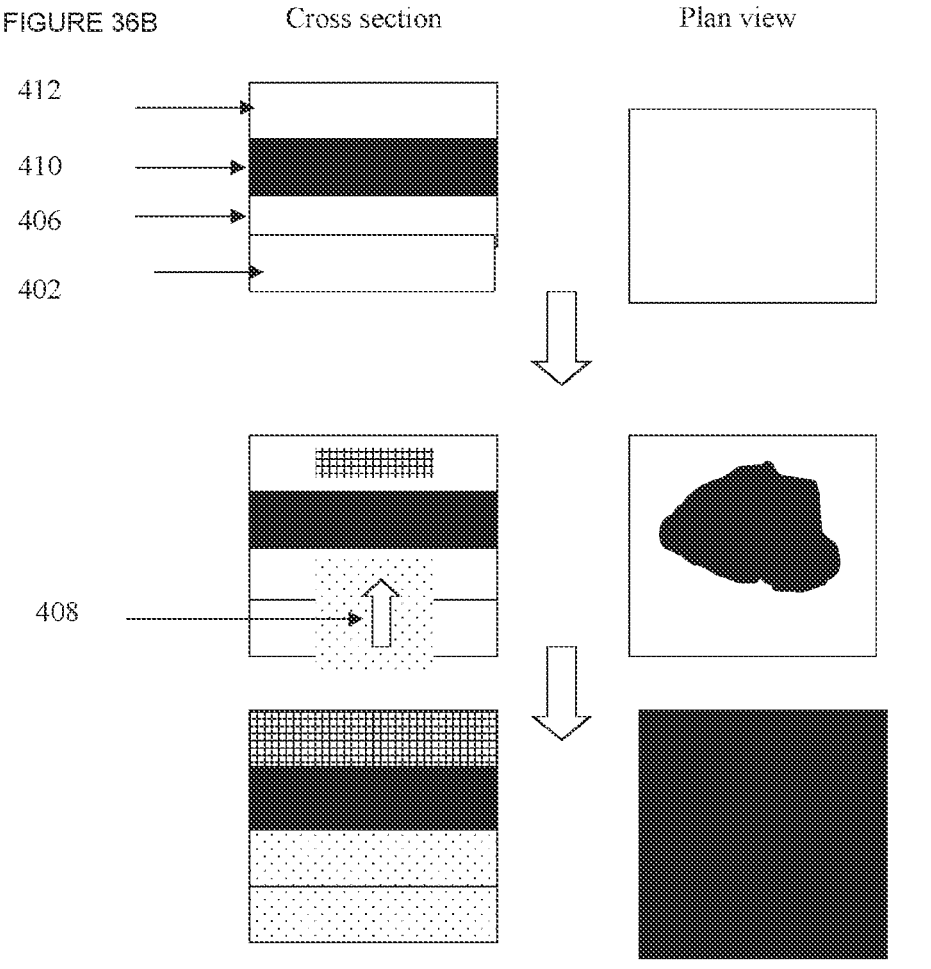

110

112
Define Region of Interest in Wound Dressing Image

114
Extract RGB Values for Each Pixel in Defined Region

116
Average Individual Pixel RGB Values to Determine Dressing RGB Values

118
Define Region of Interest for Each Color Block in a Color Calibration Strip

120
Extract RGB Values for Each Pixel in Region of Interest for Each Color Block 122
Average Individual Pixel RGB Values to Determine Calibration RGB Values 124
Apply Algorithm to Calculate pH Value from Dressing RGB Values and Calibration RGB Values

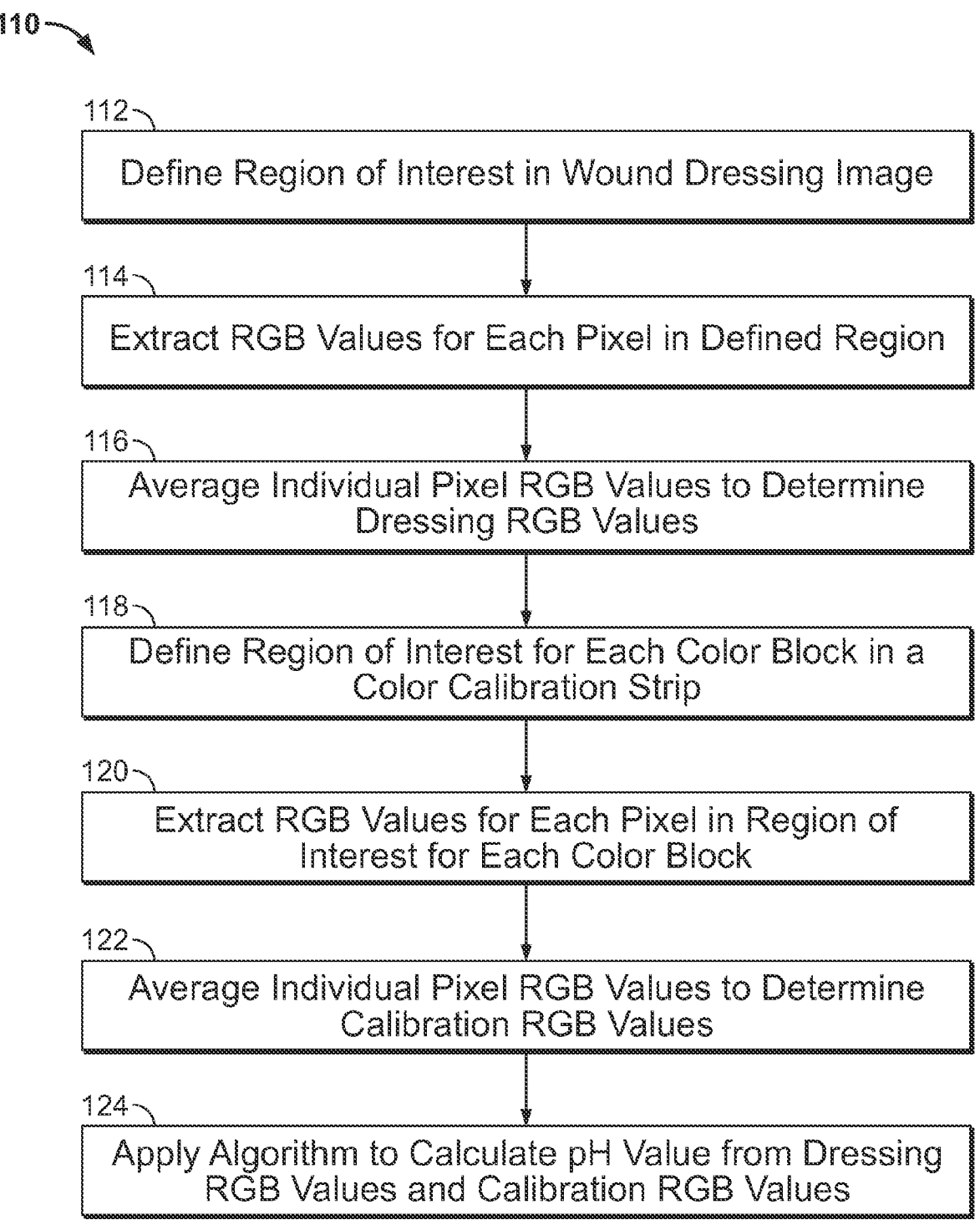

PH AND MOISTURE INDICATOR DEVICES AND FORMULATIONS

Section 1 and FIGS. 1-17 of this application contain the disclosure of application Ser. No. 15/804,748, titled "pH Indicator Device and Formulation," filed Nov. 6, 2017, published as US 2018/0196021, which is a continuation of application Ser. No. 14/650,547, filed Jun. 8, 2015 published as US 2015/0308994 and patented as U.S. Pat. No. 9,829, 471, which is a national phase entry of PCT/EP2014/071520 filed Oct. 8, 2014 which claims priority to GB 1317746.4 filed Oct. 8, 2013, all of which are incorporated by reference in their entirety.

BACKGROUND SECTION 1 ENTITLED PH INDICATOR DEVICE AND FORMULATION

The need to reliably test the pH of a fluid sample is a requirement in a plethora of industries, particularly where the pH is indicative of potential quality, safety or health concerns. pH measurements are important in, for example, medicine, biology, chemistry, agriculture, forestry, food science, environmental science, oceanography, civil engineering, chemical engineering, nutrition, water treatment and water purification.

The pH of water is routinely tested. The pH of drinking water is routinely monitored to ensure that it is safe to drink, whereas the water in swimming pools is routinely tested to ensure that it is safe to swim in. Monitoring alterations in the pH of fish ponds or river water can be indicative of environmental pollution. In agriculture and horticulture, knowledge of the pH of the soil is not only instructive in the selection of suitable crops but also discerns whether there are local environmental issues, such as pollution. In the food and brewing industries, maintaining a proper pH range is essential in many of the physical and chemical reactions that take place during food and drink processing. Monitoring the pH of bodily fluids can be a useful diagnostic. For example, it has been demonstrated that the pH of saliva can predict susceptibility to a range of diseases, including cancer, heart disease and osteoporosis.

pH testing is conventionally performed using pH meters, but these are impractical for a variety of applications as they require regular calibration using standard buffer solutions. Furthermore, the glass electrodes are fragile and must be kept constantly wet, normally in an acidic solution, in order to avoid dehydration of the pH sensing membrane and subsequent dysfunction of the electrode. Disposable pH test strips are available, but due to the permanence of the colour change as a function of pH of the test sample, the strips are unable to demonstrate any changes in pH over time. Additionally, the disposable characteristic adds to the cost implications.

A need exists for a device which enables the real-time, reversible and stable detection of pH in a fluid.

BACKGROUND SECTION 2 ENTITLED PH INDICATOR DRESSING

Section 2 and FIGS. 18-27 of this application contain the disclosure of application Ser. No. 14/650,531, titled "pH Indicator Dressing" filed Jun. 8, 2015, published as US 2016/0262672, which is a national phase entry of PCT/EP2014/071510 filed Oct. 8, 2014 which claims priority to GB 1317742.3 filed Oct. 8, 2013, all of which are incorporated by reference in their entirety.

The field of wound care management has long understood that the pH of a wound can be an indication of wound healing status and can indicate when further action may be necessary to aid wound healing. The pH can affect many factors including oxygen release, angiogenesis, protease activity and bacterial toxicity. Acute and chronic wounds with an elevated alkaline pH have been shown to have lower rates of healing than wounds in which the pH is closer to neutral. For example, if a chronic wound has a pH of between 6 to 7.5 this indicates that wound healing is progressing well. In comparison, if the pH is between 7.5 and 8, this indicates that the wound should be monitored and a pH of above 8 indicates that clinical intervention is required. It is therefore important to be able to monitor wound pH in order to be able to assess wound healing and intervene, if necessary.

Some current wound dressings utilize a pH indicator dye provided on a colour strip integrated within the dressing. The dye changes colour (e.g., from yellow to purple) if the pH value is between 6.5 and 8.5, an indication of an infected wound. The dye is not sufficiently sensitive to provide an indication of the incremental change in pH between 6.5 and 8.5. Additionally, the dye does not provide an indication of the pH at the wound surface but rather the pH of the wound exudate at the point in the dressing where it is measured. As the pH of wound exudate can be affected by numerous external factors, including the composition of the dressing itself, the measurement of the pH of wound exudate at any significant distance away from the wound surface is often inaccurate. Whilst a pH probe allows direct measurement of the pH at the wound surface, its use can result in tissue disruption and localised cell death, such that the probe requires regular calibration. Moreover, the measurement only provides a snap-shot of the pH of a specific area of the wound at a single point in time and provides no indication of the pH changes over time.

BACKGROUND SECTION 3 ENTITLED MOISTURE INDICATING SYSTEM

Section 3 and FIGS. 28-32 of this application contain the disclosure of application Ser. No. 14/893,361, titled "Moisture Indicating System" filed Nov. 23, 2015, published as US 2016/0100987, which is a national phase entry of PCT/ GB2014/051574 filed May 22, 2014 which claims priority to GB 1309369.5 filed May 24, 2013, all of which are incorporated by reference in their entirety.

The field of wound care management has long understood that keeping wounds optimally moist can help the cells in the wound area grow and migrate to the proper location to help the wound heal. Achieving an optimal moist environment relies on good clinical judgement to determine the correct moisture levels, since too little moisture can desiccate the wound and too much can lead to maceration of the wound bed and surrounding tissue. It is therefore important to be able to monitor moisture, to properly and optimally change the bandage, while still allowing the wound to heal undisturbed. Common techniques for performing such monitoring rely on visual indications of excess moisture or strike-through on wound dressings. Commonly used indications include visual changes on backing materials or leakage from the dressing.

Some current wound dressings utilize an indicator layer containing a dye which changes colour on contact with wound exudate. A typical dye is gentian violet, which changes from violet to purple when wet, indicating that the dressing is saturated. That change is typically hard to perceive and therefore users often find it unreliable. Other current wound dressings, for example the DuoDerm® Signal dressing sold by Convatec, rely on fluid leaking from the wound into an area behind an impermeable outer covering of the dressing, causing a blister to become visible. Once the edge of the blister reaches an indicator line marked on the outer surface of the dressing changing is required. As the indicator is merely a blister on the surface of the dressing, it is often difficult to read. Additionally, the blister can enlarge and fill with fluid that exceeds the requirements of a healing environment and fosters an environment for bacterial colonization. There is a need in the art for a moisture indicating wound dressing in which the moisture indicator within the dressing provides more sensitive moisture detection with a more ascertainable signal to the user.

BACKGROUND SECTION 4 ENTITLED
MOISTURE INDICATOR DRESSING

Section 4 and FIGS. 33-37 of this application contain the disclosure of application Ser. No. 14/759,786, titled "Moisture Indicating Dressing" filed Jul. 8, 2015, published as US 2015/0351970, which is a national phase entry of PCT/GB2014/050048 filed Jan. 9, 2014 which claims priority to GB 1300470.0 filed Jan. 11, 2013, all of which are incorporated by reference in their entirety.

There is a need in the art for a moisture indicating wound dressing in which the moisture indicator within the dressing provides a more ascertainable signal to the user. Further, there is a need in the art for a dressing in which the user is able to monitor the moisture levels within different parts of the dressing. Negative pressure wound therapy (NPWT) is a therapeutic technique that utilizes a vacuum dressing to promote wound healing, particularly in chronic wounds. The continued vacuum draws out fluid from the wound and increases blood flow to the area. There is a need to be able to determine within a NPWT system if any part of the fluid outlet tube which is concealed within the dressing has a leak, as this would result in sub-optimal therapy.

BACKGROUND SECTION 5 ENTITLED
SYSTEMS AND METHODS FOR WOUND
MONITORING

Section 5 and FIGS. 38-50 of this application contain the disclosure of application Ser. No. 15/113,775, titled "Systems and Methods for Wound Monitoring" filed Jul. 22, 2016, published as US 2017/000407, which is a national phase entry of PCT/EP2015/050964 filed Jan. 20, 2015 which claims priority to GB 1401112.6 filed Jan. 23, 2014, all of which are incorporated by reference in their entirety.

Wound treatment often involves monitoring a wound during healing for indications of the status and progress of the wound. Monitoring indications of wound health can indicate the efficacy of delivered treatment or signal to a physician a need for a change in treatment. One indicator in particular that is useful for this monitoring is the pH level of the wound tissue. The pH of the tissue can indicate or affect a number of factors relevant to wound healing, such as oxygen release, angiogenesis, protease activity, and bacterial toxicity. For example, wounds having elevated alkaline pH levels have been shown to have lower rates of healing than wounds in which the pH is closer to or below a neutral 7.0 pH level. For example, if a chronic wound has a pH between 6 and 7.5, this often indicates that wound healing is progressing well and treatment is working. If the pH rises to between 7.5 and 8.5, this can be an indication that the wound should be monitored and treatment adjusted to lower the pH level. By monitoring this pH level over the course of the wound healing, a physician may be better able to assess whether healing is progressing well or whether intervention or a change in treatment is needed.

Direct measurement of wound pH levels, for example using a pH pRGBe or applying a color sensitive pH strip, may be unsuitable for pH monitoring during wound healing. The use of a pRGBe or strip may disrupt or irritate the wound and hamper wound healing. To facilitate wound monitoring, a pH-sensitive bandage may be provided that changes color as the pH of the wound changes. These bandages can be a quick and easy indication to a patient or a physician of the pH of the wound to which the bandage is applied, and the changing color of the wound dressing can provide a signal that the pH of that wound is changing. While these bandages provide helpful indications, interpretation of the color indicators is reliant on the subjective assessment of the patient or physician. Often that subjective judgment involves comparing the color of the dressing to a standard color strip or scale and estimating where on the scale the indicated pH falls. As a result, the assessment and judgment is often limited in accuracy and resolution. The color determination may also be hampered by differences in color perception between individuals, differences in lighting conditions when a bandage is assessed, color blindness, or other conditions that affect color perception.

SUMMARY SECTION 1

Section 1 of this application discloses devices and methods related to devices having pH indicators for monitoring the pH of a fluid. Other advantages and improvements will be apparent to one of skill in the art upon review of the application.

In one aspect, a device is provided for determining pH of a fluid sample. The device preferably includes a surface configured to contact the fluid and a pH indicator covalently immobilised thereon, wherein the pH indicator has a first colour prior to contact with the fluid and changes colour along a colour spectrum as a function of the pH of the fluid. In embodiments, the pH indicator changes colour in response to change in pH and this colour change is detectable at, for example, intervals of about a 0.1 unit, about 0.2 unit, about 0.3 unit about 0.4 unit or about 0.5 unit interval of pH. It is envisaged that the detection level will vary based on the type of detection means utilised. For example, an electronic detector such as a colour meter capable of detecting changes in colour of light, has the capability to detect a 0.1 unit change in pH. In comparison, the human eye is only capable of visually detecting a colour change which is associated with about a 0.5 unit change in pH. In embodiments, the pH indicator utilised in the device is able to detect the pH between about pH 0 and about pH 14 and indicates changes in pH by way of a colour change along a colour spectrum, with each colour in the spectrum being associated with a particular pH. In embodiments, the pH indicator is able to detect a pH between about pH 5.0 and about pH 10.0. In embodiments, the pH indicator is able to detect a pH between about pH 5.5 and about pH 9.5. More particularly the pH indicator is able to detect a pH between about pH 6.5 and about pH 9.5. Suitable pH indicators include phenylazo compounds such as those listed in Table 1 which are available from Fraunhofer EMFT, Germany.

US 12,578,318 B2

5                                                                                                    6

TABLE 1

Phenylazo compounds

| Code | Chemical name |
| --- | --- |
| GJM-514 | 2-[4(2-hydroxyethylsulfonyl)-phenyl]diazenyl]-4-methylphenol |
| GJM-546 | 1-hydroxy-4-[4[(hydroxyethylsulphonyl)-phenylazo]-napthalene-2-sulphonate |
| GJM-492 | 2-fluoro-4-[4[(2-hydroxyethanesulphonyl)-phenylazo]-6-methoxy phenol |
| GJM-534 | 4-[4-(2-hydroxyethylsulphonyl)-phenylazo]-2,6-dimethoxyphenol |

In some embodiments, the pH indicator is a triarylmethane dye. In some embodiments, the pH indicator is a fluorescent dye.

In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments the combination comprises at least three phenylazo compounds selected from the group listed in Table 1. In embodiments, the combination comprises at least one phenylazo compound selected from the group listed in Table 1 and at least one compound that is not a phenylazo compound. In embodiments, derivatives or modifications of the phenylazo compounds listed in Table 1 are envisaged.

In embodiments, the device is a cellulosic material, for example a cellulose pad. In embodiments, the device is a non-woven mesh or perforated film.

In some embodiments, the fluid is a liquid. Non-limiting examples includes water. In some embodiments, the fluid is a gas, for example for use in a face mask. In some embodiments, the fluid is a moisture. Non-limiting examples include the moisture associated with a soil sample. In some embodiments, the fluid is a bodily sample. Non-limiting examples include, saliva, urine, blood, sweat/perspiration.

In another aspect, a device is provided for determining pH of a fluid sample. The device preferably includes: (a) a fluid-contacting surface, (b) an opposing non-fluid contacting surface, (c) a pH indication zone comprising a pH indicator covalently immobilised therein which indicates the pH of a fluid, wherein the colour of the pH indicator changes in response to a change in the pH of the fluid, and (d) at least one conduit for directing fluid towards the pH indication zone. The conduit helps direct fluid toward the pH indicator without materially altering the pH en route to the indicator. In certain embodiments, the material of the conduit contains no acid or base functionality, that is to say, it is neutral and can not remove any acid or base entities from the fluid until it reaches the pH indicating system. In certain embodiments, the device has an outer surface and the pH indication zone is located at or near the outer surface. In other embodiments, the device has a peripheral edge extending between the fluid contacting surface and the opposing non-fluid contacting surface and pH indication zone is located at or near to this peripheral edge. In certain embodiments, the conduit directs fluid laterally towards the pH indication zone. In embodiments, the pH indicator changes colour in response to change in pH and this colour change is detectable at, for example, intervals of about a 0.1 unit, about 0.2 unit, about 0.3 unit about 0.4 unit or about 0.5 unit interval of pH. It is envisaged that the detection level will vary based on the type of detection means utilised. For example, an electronic detector such as a colour meter has the capability to detect a 0.1 unit change in pH. In comparison, the human eye is only capable of visually detecting a colour change which is associated with about a 0.5 unit change in pH. In embodiments, the pH indicator utilised in the device is able to detect the pH between pH 0 and 14 and indicates changes in pH by way of a colour change along a colour spectrum, with each colour in the spectrum being associated with a particular pH. In embodiments, the pH indicator is able to detect pH between about pH 5 and about pH10. Particularly, the pH indicator is able to detect pH between about pH 5.5 and about pH 9.5. More particularly, the pH indicator is able to detect pH between about pH 6.5 and about pH 9.5. Suitable pH indicators include phenylazo compounds such as those selected from the group listed in Table 1. In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments, the combination comprises at least three phenylazo compounds selected from the group listed in Table 1. In embodiments, the combination comprises at least one phenylazo compound selected from the group listed in Table 1 and at least one compound that is not a phenylazo compound. In embodiments, derivatives or modifications of the phenylazo compounds listed in Table 1 are envisaged.

In a further aspect, a formulation is provided for indicating pH of a fluid. Advantageously, the pH indicator is covalently immobilised within the formulation and is therefore not washed away by the fluid upon contact. The formulation preferably includes a dye that functions as a pH indicator. The dye may include a phenylazo compound, where the colour of the phenylazo compound changes in response to a change in the pH of the fluid. In embodiments, the pH dye changes colour in response to a 0.5 unit interval change in pH. For example, the pH indicator has a different colour for each 0.5 unit interval change in pH. The pH indicator utilised in the device is able to detect the pH between pH 5 and 10, particularly between pH 5.5 and 9.5 and more particularly between pH 6.5 and 9.5. Suitable pH indicators include phenylazo compounds such as those selected from the group listed in Table 1. In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments, the combination comprises at least three phenylazo compounds selected from the group listed in Table 1. In embodiments, the combination comprises at least one phenylazo compound selected from the group listed in Table 1 and at least one compound that is not a phenylazo compound.

In embodiments, derivatives or modifications of the phenylazo compounds listed in Table 1 are envisaged. In embodiments, the formulation is applied to a device for use in detecting pH at the point of manufacture. In embodiments, the formulation is an adhesive. In embodiments, the adhesive is a low tack adhesive, for example a silicon adhesive. In other embodiments, it is envisaged that the formulation is a gel, for example, a conformable semi-rigid or rigid gel, that does not disintegrate upon contact with the fluid to be tested. The formulation can be used in a device according to the first and/or second aspect.

In another aspect, a method is provided for monitoring the pH of a fluid. The method preferably comprises the steps of: (a) providing a device comprising a surface configured to contact the fluid, said surface having a pH indicator covalently bound thereto, wherein the pH indicator has a first colour prior to contact with the fluid and changes colour as a function of the pH of the fluid, (b) contacting the device with the fluid, (c) assessing the colour of the pH indicator. It is envisaged that the method can be utilised in numerous applications in which the knowledge of the pH of a fluid sample is paramount to determining quality control or safety. Non-limiting examples of potential applications include: food storage; packaging spoilage indicators; wine; brewing; analysis of drinking water, swimming pool water, river water or fish ponds; agriculture and horticulture; clothing, for example perspiration analysis; in-line monitoring of processes, gases, liquids; skin care—medical (dermatology) or cosmetic; coatings of containers and surfaces to detect changes/inconsistencies; monitoring drug release or stability.

In a further aspect, a device comprises a fluid contacting surface having a pH indicating means covalently bound thereto, wherein the pH indicating means has a first colour prior to contact with a fluid and changes colour as a function of the pH of the fluid.

In another aspect a device comprises a pH indicating means, wherein the pH indicating means has a first colour prior to contact with a fluid and changes colour as a function of the pH of the fluid and a conduit means for directing the fluid towards the pH indicating means.

SUMMARY SECTION 2

Section 2 of this application discloses devices and methods related to wound dressings having pH indicators for monitoring the pH at the wound surface. The disclosure also includes dressings in which the user is able to visually monitor incremental changes in the pH of the wound over time, using a pH scale. To monitor the pH, the pH indicator changes visually (e.g., by changing colour) as a function of the pH of the wound exudate. This provides a visual indication of the wound's pH status and enables an assessment to be made a-; to whether any therapeutic intervention is required in order to facilitate healing. Other advantages and improvements will be apparent to one of skill in the art upon review of the application.

In embodiments, the device is a conformable, non-woven mesh or perforated film. The device can be provided in a range of sizes suitable to fit or cover a wound. Alternatively, the device can be cut to fit or cover the wound. Devices which fit or cover the wound enable the pH to be mapped across the wound rather than at selected locations. This is particularly advantageous as the pH of the wound is often not uniform across the wound. In alternative embodiments, the device can be used in isolation and placed in the wound between dressing changes in order to detect the pH of the wound. For example, the device can be incorporated into a dipstick format that can be placed into the wound between dressing changes. Alternatively, the device can be used in conjunction with a secondary wound dressing of the clinician's choice. In that scenario, the pH is assessed upon application to and removal of the device/secondary dressing from the wound. In embodiments, the device is positioned at or near a lower surface of the dressing. In certain embodiments, the device is the wound contacting layer of the secondary dressing.

In another aspect, a wound dressing is provided with a pH indicator. The pH indicator preferably includes: (a) a wound-contacting surface, (b) an opposing non-wound contacting surface, (c) a pH indication zone comprising a pH indicator which indicates the pH of a wound exudate, wherein the colour of the pH indicator changes in response to a change in the pH of the wound exudate, and (d) at least one conduit for directing wound exudate towards the pH indication zone. The conduit helps direct wound exudate toward the pH indicator without materially altering the exudate pH en route to the indicator. In certain embodiments, the material of the conduit contains no acid or base functionality, that is to say, it is neutral and cannot remove any acid or base entities from the exudate until it reaches the pH indicating system. In certain embodiments, the wound dressing has an outer surface and the pH indication zone is located at or near the outer surface. In other embodiments, the dressing has a peripheral edge extending between the wound-contacting surface and the opposing non-wound contacting surface and pH indication zone is located at or near to this peripheral edge. In certain embodiments, the conduit directs wound exudate laterally towards the pH indication zone. In embodiments, the pH indicator changes colour in response to change in pH and this colour change is detectable at, for example, intervals of about a 0.1 unit, about 0.2 unit, about 0.3 unit about 0.4 unit or about 0.5 unit interval of pH. It is envisaged that the detection level will vary based on the type of detection means utilised. For example, an electronic detector such as a colour meter has the capability to detect a 0.1 unit change in pH. In comparison, the human eye is only capable of visually detecting a colour change which is associated with about a 0.5 unit change in pH. In a wound care setting, wound exudate pH can be detected across a broad range. In embodiments, the pH indicator utilised in the device is able to detect the pH between pH 5 and 10 and indicates changes in pH by way of a colour change along a colour spectrum, with each colour in the spectrum being associated with a particular pH. In embodiments, the pH indicator is able to detect wound pH between about pH 5 and about pH 10. Particularly, the pH indicator is able to detect wound pH between about pH 5.5 and about pH 9.5. More particularly, the pH indicator is able to detect wound pH between about pH 6.5 and about pH 9.5. Suitable pH indicators include phenylazo compounds such as those selected from the group listed in Table 1. In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments, the combination comprises at least three phenylazo compounds selected from the group listed in Table 1. In embodiments, the combination comprises at least one phenylazo compound selected from the group listed in Table 1 and at least one compound that is not a phenylazo compound. In embodiments, derivatives or modifications of the phenylazo compounds listed in Table 1 are envisaged.

In a further aspect, a formulation is provided for indicating pH of a wound exudate. The formulation preferably includes a dye that functions as a pH indicator. The dye may include a phenylazo compound, where the colour of the phenylazo compound changes in response to a change in the pH of the wound exudate. In embodiments, the pH dye changes colour in response to a 0.5 unit interval change in pH. For example, the pH indicator has a different colour for each 0.5 unit interval change in pH. The pH indicator utilised in the dressing is able to detect the pH between pH 5 and 10, particularly between pH 5.5 and 9.5 and more particularly between pH 6.5 and 9.5. Suitable pH indicators include phenylazo compounds such as those selected from the group listed in Table 1. In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments, the combination comprises at least three phenylazo compounds selected from the group listed in Table 1. In embodiments, the combination comprises at least one phenylazo compound selected from the group listed in Table 1 and at least one compound that is not a phenylazo compound. In embodiments, derivatives or modifications of the phenylazo compounds listed in Table I are envisaged. In embodiments, the formulation is applied to a device for use in detecting pH at the point of manufacture. In embodiments, the formulation is an adhesive. In embodiments, the adhesive is a low tack adhesive, for example a silicon adhesive. In embodiments, the adhesive is applied to the wound contacting surface of the device. In other embodiments, it is envisaged that the formulation is a gel, for example, a conformable semi-rigid or rigid gel, that is placed into the wound to detect pH and which can be removed from the wound intact. In embodiments, the gel is based on chitosan or carboxymethylcellulose. The formulation can be used in a device and/or a wound dressing according to the first and/or second aspect.

In another aspect, a method is provided for monitoring the pH of a wound. The method preferably comprises the steps of: (a) providing a device comprising a surface configured to contact the wound, said surface having a pH indicator applied thereto, wherein the pH indicator has a first colour prior to contact with the wound exudate and changes colour as a function of the pH of the wound exudate, (b) applying the device to the wound, (c) assessing the colour of the pH indicator. In certain embodiments the method fuliher includes the step of combining the device with a secondary dressing prior to applying the device to the wound. In embodiments of the method, the step of combining the device and the secondary dressing includes adhering the device to the secondary dressing. In certain embodiments, the device forms the wound contacting surface of the secondary dressing. In some embodiments the method additionally includes the step of removing the device (or secondary dressing), inverting the device (or secondary dressing) so that the device becomes visible and then assessing the colour of the pH indicator. In this way a pH map of the wound bed may be generated. Such maps may indicate zones of differing pH across the surface of the wound.

In a further aspect, a wound dressing comprises a wound contacting surface having a pH indicating means wherein the pH indicating means has a first colour prior to contact with the wound exudate and changes colour as a function of the pH of the wound exudate.

In another aspect a wound dressing comprises a pH indicating means, wherein the pH indicating means has a first colour prior to contact with wound exudate and changes colour as a function of the pH of the wound exudate and a conduit means for directing the wound exudate towards the pH indicating means.

SUMMARY SECTION 3

Section 3 of this application discloses devices and methods related to wound dressings having moisture indicators. The underlying mechanism for monitoring the wound exudate loading within a wound dressing utilises a colour change of a pH indicator provided within the dressing. The colour change is driven by the increased acidity or alkalinity of a wound exudate as it migrates through the dressing. This alteration in the pH of the wound exudate is a consequence of the exudate dissolving a soluble composition which is provided within the dressing and which consequently releases hydrogen or hydroxide ions into the wound exudate. The modified wound exudate, loaded with the hydrogen or hydroxide ions, has a pH which is either more acidic or more alkaline than the unmodified wound exudate. As a result, the modified wound exudate causes a more amplified change in the colour of the pH indicator than would be caused by the unmodified wound exudate. A device is disclosed which includes (i) a soluble composition capable of releasing hydrogen or hydroxide ions upon solubilisation and (ii) a colour-based pH indicator, wherein the colour of the pH indicator is correlated to a pH The device can be used in combination with a conventional wound dressing. Alternatively, the device can be manufactured as a component of a wound dressing. The colour change of the pH indicator provides a visual indication of the wound exudate loading within the dressing. A colour change is indicative of the wound exudate reaching the part of the dressing where the device is located.

In one aspect, a device includes a first composition which has a first colour and which changes to a second colour in response to a change in pH and a second composition which dissolves upon contact with a wound exudate to release hydrogen or hydroxide ions, the wound exudate loaded with the released hydrogen or hydroxide ions interacts with the first composition to cause the change to the second colour. In certain embodiments, the first and second compositions are impregnated into different carrier materials within the device. In certain embodiments, the carrier materials are physically separated by a spacer material. In certain embodiments, the first and second compositions are impregnated into the same carrier material within the device. In certain embodiments, the first and second compositions which are impregnated within the same carrier material are physically separated, for example, at least one of the first or second compositions is encapsulated in a soluble barrier which dissolves upon contact with wound exudate to enable interaction between the compositions.

In another aspect, a wound dressing is disclosed which includes a device which indicates wound exudate loading. The device includes: a first composition which has a first colour and which changes to a second colour in response to pH, and a second composition which dissolves upon contact with a wound exudate to release hydrogen or hydroxide ions into the wound exudate and wherein the wound exudate loaded with the hydrogen or hydroxide ions causes the first composition to change to the second colour. In certain embodiments, the wound dressing includes an absorbent layer which has a wound-facing surface and an opposing non-wound-facing surface, and the device is positioned within the dressing such that the device is in contact with the non-wound-facing surface of the absorbent layer. In certain embodiments, the wound dressing has a peripheral edge and the device extends outwardly from the peripheral edge. In certain embodiments, the device forms an annular flange or annular ring, which partially or fully encircles the peripheral edge of the dressing.

In another aspect, a device is disclosed which indicates wound exudate loading within a wound dressing. The device includes a pH-dependent moisture indicating means and a means of generating ions. Contact between the wound exudate and the means of generating results in a wound exudate which is loaded with ions and which interacts with the pH-dependent moisture indicating means to cause a visual change. In certain embodiments, the ions generated are hydrogen or hydroxide ions. In certain embodiments, the visual change is a colour change from a first colour to a second colour.

In a further aspect, a device is disclosed which indicates wound exudate loading within a wound dressing, the device includes a first composition which transforms from a first state to a second state and a second composition which dissolves upon contact with the wound exudate and which forces the transformation of the first composition from the first state to the second state upon contact therewith. In certain embodiments, the first state is a first colour and the second state is a second colour. In certain embodiments, the second composition releases ions into the wound exudate to alter analyte levels within the wound exudate. In certain embodiments, the wound exudate with released ions causes a change to the second state.

In another aspect, methods are disclosed for monitoring loading of a wound dressing by a wound exudate. The methods include steps of (a) locating a first composition within the wound dressing, wherein the first composition has a first colour prior to contact with the wound exudate and which changes to a second colour in response to a pH change; (b) locating a second composition within the wound dressing, wherein the second composition dissolves upon contact with a wound exudate to release hydrogen or hydroxide ions into the wound exudate; (c) applying the wound dressing to the wound; (d) contacting the second composition with the wound exudate as the wound exudate passes through the dressing, thereby dissolving the second composition and releasing hydrogen or hydroxide ions into the wound exudate; and (e) contacting the first composition with the wound exudate loaded with the released hydrogen or hydroxide ions to cause the first composition to change to the second colour and wherein the development of the second colour indicates that the wound dressing is saturated at the location of the second composition prior to its disso-lution. The methods further include the step of removing the dressing when the second colour becomes visible.

In another aspect, methods are disclosed for monitoring loading of a wound dressing by a wound exudate. The methods utilise the dissolution of a soluble component provided at a location with the wound dressing by the wound exudate to cause a component which has a first state prior to contact with the wound exudate loaded with the solubilised component to change to a second state upon said contact, thereby indicating that the wound dressing in saturated at the location of the soluble component.

In further aspects, methods are disclosed for monitoring loading of a wound dressing by a wound exudate, the methods include steps of: (a) providing a wound dressing containing a first composition that can be solubilised into ions and a second composition containing a pH indicator that indicates a pH change; (b) flowing wound exudate into contact with the dressing to solubilise the ions; and (c) contacting the second composition with the solubilised ions until a pH is indicated.

SUMMARY SECTION 4

Section 4 of this application discloses devices and meth-ods related to wound dressings, having moisture indicators. The mechanism of monitoring the moisture levels within the wound dressing is dependent on the moisture indicator becoming exposed or concealed to the user by a physical transformation of a part of the dressing. This provides a visual indication of the dressing's saturation and enables an assessment to be made as to whether the dressing requires changing. Using a moisture indicator within the dressing allows the status of the dressing to be assessed without disturbing the wound and disrupting the healing process.

In one aspect, a wound dressing includes an absorbent layer and a moisture indicator which indicates wound exu-date loading within the dressing, with the visibility of the moisture indicator changing as a result of a physical trans-formation of a first material within the dressing. In some embodiments, the physical transformation of the first mate-rial of the dressing occurs when it is directly contacted by wound exudate. In alternative embodiments, the physical transformation of the first material of the dressing occurs when a second material in the dressing is contacted by wound exudate. For example, the second material may be the absorbent layer. In some embodiments, the physical transformation is a change in the appearance of the first material which causes at least a part of the moisture indicator to become revealed or concealed to the user. Such an alteration in the visibility of the moisture indicator provides an indication of the level of saturation. In certain embodi-ments, the physical transformation is, for example, a trans-formation from a dry material to a wet material, from a solid material to a gel or gel-like material and vice versa, or from a substantially transparent/translucent material to substan-tially opaque material and vice versa. In certain embodi-ments the transformation is reversible. In some embodi-ments, the moisture indicator is a coloured moisture indicator, a coloured substrate and a water-soluble coloured dye. In some embodiments a plurality of moisture indicators are distributed within the dressing, each indicator being configured to indicate wound exudate loading within a part of the dressing. In certain embodiments, each of the plurality of indicators is a coloured moisture indicator having a different colour, with the visibility of each colour indicating the saturation of a different part of the dressing. In some embodiments, the coloured moisture indicators can be used to indicate the vertical and/or horizontal spread of wound exudate throughout the dressing.

In another aspect, a wound dressing is disclosed which includes at least a fluid outlet tube extending through at least a portion of the dressing and a moisture indicator associated with the fluid outlet tube, wherein the visibility of the moisture indicator provides an indication of fluid leakage from the tube. In certain embodiments the moisture indicator is wrapped around a portion of the fluid outlet tube. In some embodiments the moisture indicator is a water-soluble coloured dye bound to the fluid outlet tube, and wherein the dye becomes visible if it is caused to diffuse through the dressing as a result of fluid leakage from the tube.

In another aspect, methods are disclosed for monitoring saturation of a wound dressing by wound exudate, the methods include (a) providing a wound dressing comprising an absorbent element and a moisture indicator, wherein the visibility of the indicator indicates wound exudate loading of the wound dressing; (b) applying the wound dressing to a wound; and (c) monitoring the visibility of the indicator. In some embodiments the moisture indicator is a coloured layer that extends horizontally within the dressing and the dressing includes a component that physically transforms to alter the visibility of the coloured layer. In certain implementations, the method includes the step of removing the dressing when a pre-determined amount of the coloured layer becomes visible. In alternative implementations, the method includes the step of removing the dressing when a pre-determined area of the coloured layer becomes invisible. In some embodiments, the moisture indicator is a water-soluble coloured dye disposed within the dressing. The methods further include the step of removing the dressing when the coloured dye becomes visible as a result of diffusion of the coloured dye.

SUMMARY SECTION 5

Disclose herein in section 5 of the application are systems, devices, and methods for wound monitoring, and in particular for monitoring wound pH levels to assess the efficacy and need for intervention in wound treatment. The approaches described provide a system and method for determining and monitoring changes in a wound pH level and applying the wound pH information to determine any needed changes in treatment. These systems and methods, when used in combination with pH indicative wound dressings, can provide a quick and accurate indication or assessment to a physician or a patient of current wound status and treatment progression.

The embodiments described herein automate the calculation of a pH value from a bandage color. This reduces the subjectivity of the bandage reading and reduces the variance in readings that can result from that subjectivity. After a physician, patient, or other user takes a photo of the bandage, the image is processed to determine the indicated pH using a computer-implemented process. This process analyzes all users' images, thus reducing the variation caused by color blindness or other differences in color perception between individuals. The image processing can also correct for lighting or image quality differences between readings, thus improving accuracy compared to the subjective human determinations. The image processing thus provides accurate and reliable pH readings across a variety of conditions. Because the bandage itself indicates the pH, these helpful readings can be taken without moving the wound dressing. As a result, the risk of infection and hampering wound healing is reduced compared to manual inspections of the wound directly.

In one aspect, a method of monitoring a wound includes the steps of capturing an image of a wound dressing with a user device and then determining the color of a pH indicator on the wound dressing by extracting RGB (Red, Green and Blue) values from the captured image. A pH value is calculated for the wound dressing from the dressing RGB values, and an indication of the calculated pH value is displayed on the user device.

In some implementations, the method includes displaying a guiding frame during image capture on the user device. The guiding frame provides an indication of proper wound dressing alignment to a user. The method also includes detecting the alignment of the wound dressing relative to the displayed guide frame on the user device, and the image may be automatically captured by the user device when the wound dressing is properly aligned with the guiding frame.

In certain implementations, the method also includes rejecting an image having inadequate light or excessive shadow and displaying on the user device a request to a user to capture a new image. The method may also include displaying an option to accept or reject the calculated pH value on the user device when the calculated pH value is displayed.

In certain implementations, the method includes storing the calculated pH value in a record of pH values in memory on the user device. User input identifying a particular patient is received with the user device and the stored record is associated with the particular patient. In some embodiments, the user input includes a selection of the particular patient from a list of stored patients, while in other embodiments the user input includes identification information for a new patient. The method also includes displaying a trend of pH values for the particular patient on the user device, where the displayed trend may include at least one of a graph and a list of pH values.

In certain implementations, extracting dressing RGB values from the captured image includes determining individual pixel RGB values for each one of a plurality of pixels in the wound dressing image and averaging the individual pixel RGB values for the plurality of pixels to determine the dressing RGB values. Such methods include defining a center point of the captured image and defining a dressing circle region around the center point of the image where the dressing circle region includes the plurality of pixels for which the individual pixel RGB values are determined. For example, the dressing circle region may have a radius between about 5 and about 100 pixels, or between about 10 and about 50 pixels, or between about 20 and about 30 pixels.

In certain implementations, the method includes capturing an image of a color calibration strip with the user device. The color calibration strip may be captured in the same image as the wound dressing or may be captured in a separate image. Such methods include extracting calibration RGB values from the image of the color calibration strip for each of a plurality of color blocks that are included in the color calibration strip. Each color block is associated with a standardized pH value, and the pH value for the wound dressing is calculated using the dressing RGB values and the calibration RGB values. Extracting calibration RGB values for each of the plurality color blocks may include determining individual pixel RGB values for each one of a plurality of pixels in a color block and averaging the individual pixel RGB values for the plurality of pixels in the color block to determine the calibration RGB values for that color block. The methods may also include defining a center point of each of the plurality of color blocks which may be defined from alignment indicators positioned on either side of the color calibration strip. A calibration circle region is then defined around the center point of each color block and the calibration circle regions include the plurality of pixels for which the individual pixel RGB values are determined in each color block. For example, each of the calibration circle regions may have a radius between about 3 and about 10 pixels, or may have a radius of about 5 pixels.

In certain implementations calculating a pH value for the wound dressing includes calculating a distance between the dressing RGB values and each of the calibration RGH values in a three dimensional space. For example, the two smallest calculated distances are determined and the pH value for the wound dressing is calculated based on the RGB calibration values and standardized pH values associated with the two smaller distances. The method may also include normalizing the dressing RGB values to align defined by the two RGB calibration values associated with the two shortest distances and calculating the pH value for the wound dressing from the normalized position of the dressing RGB values on the line.

In one aspect, a method of monitoring a wound includes receiving an image of a wound dressing at a computing device, such as a server, and determining the color of the pH indicator on the wound dressing by extracting dressing RGB values from the received image. The method includes calculating a pH value for the wound dressing from the dressing RGB values and transmitting an indication of a calculated pH value from the server.

In certain implementations, the method also includes rejecting an image having an inadequate light or excessive shadow at the server and transmitting a request from the server to a user to capture a new image. The method may include displaying the calculated pH value with an option to accept or reject the calculated value on the user device.

In certain implementations, the method includes storing the calculated pH value in a record of pH values in memory on the server. User input identifying a particular patient is received and the stored record is associated with the particular patient. The user input may include a selection of the particular patient from a list of stored patients or may include identification information for a new patient. The method may include transmitting a trend of pH values for the particular patient from the server for display on a user device in communication with the server. The trend may include at least one of a graph and a list of pH values.

In certain implementations, extracting dressing RGB values from the received image includes determining individual pixel RGB values for each one of a plurality of pixels in the image and averaging the individual pixel RGB values for the plurality of pixels to determine the dressing RGB values. In such a method a center point of the received image is defined and a dressing circle region is defined around the center point of the received image where the dressing circle region includes the plurality of pixels for which the individual pixel RGB values are determined. For example, the dressing circle region may have a radius between about 5 and about 100 pixels, or between about 10 and about 50 pixels, or between about 20 and about 30 pixels.

In certain implementations the method includes receiving an image of a color calibration strip at a computing device, such as a server. The color calibration strip may be received in the same image as the wound dressing or may be received in a separate image. The method includes extracting calibration RGB values from the image of the color calibration strip for each of a plurality of color blocks in the color calibration strip. Each color block is associated with a standardized pH value and the pH value for the wound dressing is calculated using the dressing RGB values and the calibration RGB values. The extracting calibration RGB values for each of the plurality of color blocks includes determining individual pixel RGB values for each one of a plurality of pixels in a color block and averaging the individual pixel RGB values for the plurality of pixels in the color block to determine the calibration RGB values for that color block. A center point of each of the plurality of color blocks is defined and the center points are defined from alignment indicators positioned on either side of the color calibration strip. A calibration circle region may be defined around the center point of each color block and the calibration circle regions may include the plurality of pixels for which the individual pixel RGB values are determined in each color block. For example, the calibration circle regions may have a radius between about 3 and about 10 pixels, or may have a radius of about 5 pixels.

In certain implementations, the method includes calculating a distance between the dressing RGB values and each of the calibration RGB values in a three dimensional space. For example, the two smallest calculated distances are determined and the pH value for the wound dressing is calculated based on the RGB calibration values and standardized pH values associated with the two shortest distances. The method may also include normalizing the dressing RGR values to a line defined by the two RG-B calibration values associated with the two shortest distances and calculating the pH value for the wound dressing from the normalized position of the dressing RGB values on the line.

In one aspect, a method of monitoring a wound includes capturing an image of a wound dressing having a pH indicator with a user device, transmitting the captured image from the user device, receiving a pH value at the user device for the wound dressing in the captured image and displaying an indication of the received pH value on the user device.

In certain implementations, the method includes displaying a guiding frame on the user device during image capture, where the guiding frame provides an indication of proper wound dressing alignment to a user. The method may include detecting, with the user device, the alignment of the wound dressing relative to the displayed guide frame, and the image may be automatically captured by the user device when the wound dressing is properly aligned with the guiding frame. In certain implementations, the method includes rejecting, with the user device, an image having inadequate light or excessive shadow and displaying, on the user device, a request to a user to capture a new image. In certain implementations, the method includes displaying, on the user device, an option to accept or reject the received pH value when the received pH value is displayed.

In certain implementations, the method includes storing, in memory on the user device, the received pH value in a record of pH values. User input is received with the user device, and the user input identifies a particular patient. The stored record is associated with the particular patient. The user input may include a selection of the particular patient from a list of stored patients, or may include identification information for a new patient. The method includes displaying, on the user device, a trend of pH values for the particular patient, and the displayed trend may include at least one of a graph and a list of pH values.

In certain implementations, the method includes determining, at a computing device, such as a server, in communication with the user device, individual pixel RGB values for each one of a plurality of pixels in the captured image; averaging, at the server, the individual pixel RGB values for the plurality of pixels to determine dressing RGB values; and calculating, at the server, the pH value for the wound dressing from the dressing RGB values. A center point of the captured image is defined, and a dressing circle region is defined around the center point of the captured image. The dressing circle region comprises the plurality of pixels for which the individual pixel RGB values are determined. For example, the dressing circle region may have a radius between about 5 and about 100 pixels, or between about 10 and about 50 pixels, or between about 20 and about 30 pixels.

In certain implementations, the method includes capturing, with the user device, an image of a color calibration strip. The color calibration strip may be captured in the same image as the wound dressing, or may be captured in a separate image. The method includes extracting, at the server in communication with the user device, calibration RGB values from the image of the color calibration strip for each of a plurality of color blocks in the color calibration strip. Each color block is associated with a standardized pH value, and the pH value for the wound dressing is calculated at the server using the calibration RGB values. Extracting calibration RGB values for each of the plurality of color blocks includes determining, at the server, individual pixel RGB values for each one of a plurality of pixels in a color block and averaging, at the server, the individual pixel RGB values for the plurality of pixels in the color block to determine the calibration RGB values for the color block. In certain implementations, a center point is defined for each of the plurality of color blocks, and the center points are defined from alignment indicators positioned on either side of the color calibration strip. A calibration circle region is defined around the center point of each color block, wherein each of the calibration circle regions comprises the plurality of pixels for which the individual pixel RGB values are determined in each color block. For example, each of the calibration circle regions may have a radius between about 3 and about 10 pixels, or may have a radius of about 5 pixels.

In certain implementations, the method includes calculating, at the server, a distance between the dressing RGB values and each of the calibration RGB values in a three-dimensional space. For example, the method includes determining the two smallest calculated distances and calculating the pH value for the wound dressing based on the RGB calibration values and standardized pH values associated with the two smallest distances. The method also may include normalizing the dressing RGB values to a line defined by the two RGB calibration values associated with the two shortest distances and calculating the pH value for the wound dressing from the normalized position of the dressing RGB values on the line.

In one aspect, a non-transitory computer-readable medium for monitoring a wound is encoded with machine-readable instructions for performing the methods described in any of the paragraphs of Section 5 above.

In one aspect, a device for monitoring a wound includes memory, a display, and processing circuitry in communication with the memory and the display, the processing circuitry being configured to perform any of the methods described in any of the paragraphs of Section 5 above.

In one aspect, a computing device, such as a server, for monitoring a wound includes memory, communications circuitry coupled to a network for transmitting and receiving communications over the network, and processing circuitry associated with the communications circuitry and the memory, the processing circuitry being configured to perform any of the methods described in any of the paragraphs of Section 5 above.

In one aspect, a device for monitoring a wound includes memory, communications circuitry coupled to a network for transmitting and receiving communications over the network, and processing circuitry associated with the communications circuitry and the memory, the processing circuitry being configured to perform any of the methods described in any of the paragraphs of section 5 above.

In one aspect, a system for monitoring a wound includes a computing device, such as server described in Section 5 above, and the device described in Section 5 above.

In one aspect, a system for monitoring a wound includes means for capturing an image of a wound dressing and means for determining the color of a pH indicator on the wound dressing, wherein the means for determining the color comprises means for extracting RGB values from the captured image. The system also includes means for calculating a pH value for the wound dressing from the dressing RGB values and means for displaying an indication of the calculated pH value.

In certain implementations, the system includes means for displaying a guiding frame during image capture, wherein the guiding frame provides an indication of proper wound dressing alignment to a user. The system includes means for detecting the alignment of the wound dressing relative to the displayed guide frame, and the image is automatically captured by the means for capturing when the wound dressing is properly aligned with the guiding frame. The system may also include means for rejecting an image having inadequate light or excessive shadow and means for displaying a request to a user to capture a new image. The system may also include means for displaying an option to accept or reject the calculated pH value when the calculated pH value is displayed.

In certain implementations, the system includes means for storing the calculated pH value in a record of pH values. The system includes means for receiving user input identifying a particular patient, wherein the stored record is associated with the particular patient. The user input may be a selection of the particular patient from a list of stored patients, or may be identification information for a new patient. The system includes means for displaying a trend of pH values for the particular patient, and the displayed trend comprises at least one of a graph and a list of pH values.

In certain implementations, the means for extracting dressing RGB values from the captured image comprises means for determining individual pixel RGB values for each one of a plurality of pixels in the image and means for averaging the individual pixel RGH values for the plurality of pixels to determine the dressing RGB values. The system includes means for defining a center point of the captured image, and may include means for defining a dressing circle region around the center point of the captured image, wherein the dressing circle region comprises the plurality of pixels for which the individual pixel RGB values are determined. For example, the dressing circle region may have a radius between about 5 and about 100 pixels, or between about 10 and about 50 pixels, or between about 20 and about 30 pixels.

In certain implementations, the system includes means for capturing an image of a color calibration strip. The color calibration strip may be captured in the same image as the wound dressing, or may be captured in a separate image. The system includes means for extracting calibration RGB values from the image of the color calibration strip for each of a plurality of color blocks in the color calibration strip. Each color block is associated with a standardized pH value, and the pH value for the wound dressing is calculated using the dressing RGB values and the calibration RGB values. The means for extracting calibration RGB values for each of the plurality of color blocks comprises means for determining individual pixel RGB values for each one of a plurality of pixels in a color block and means for averaging the individual pixel RGB values for the plurality of pixels in the color block to determine the calibration RGB values for the color block.

In certain implementations, the system includes means for defining a center point of each of the plurality of color blocks, and the center points are defined from alignment indicators positioned on either side of the color calibration strip. The system includes means for defining a calibration circle region around the center point of each color block, wherein each of the calibration circle regions comprises the plurality of pixels for which the individual pixel RGB values are determined in each color block. For example, each of the calibration circle regions may have a radius between about 3 and about 10 pixels, or may have a radius of about 5 pixels.

In certain implementations, the system includes means for calculating a distance between the dressing RGB values and each of the calibration RGB values in a three-dimensional space. For example, the system includes means for determining the two smallest calculated distances and means for calculating the pH value for the wound dressing based on the RGB calibration values and standardized pH values associated with the two smallest distances. The system may also include means for normalizing the dressing RGR values to a line defined by the two RGB calibration values associated with the two shortest distances and means for calculating the pH value for the wound dressing from the normalized position of the dressing RGB values on the line.

In one aspect, a system for monitoring a wound includes means for receiving an image of a wound dressing and means for determining the color of a pH indicator on the wound dressing, wherein the means for determining the color comprises means for extracting dressing RGB values from the received image. The system also includes means for calculating a pH value for the wound dressing from the dressing RGB values and means for transmitting an indication of the calculated pH value.

In certain implementations, the system includes means for rejecting an image having inadequate light or excessive shadow and means for transmitting a request to a user to capture a new image. The system has means for displaying the calculated pH value with an option to accept or reject the calculated pH value.

In certain implementations, the system includes means for storing the calculated pH value in a record of pH values. Means for receiving user input identifying a particular patient is provided, wherein the stored record is associated with the particular patient. The user input may include a selection of the particular patient from a list of stored patients, or may include identification information for a new patient. The system includes means for transmitting a trend of pH values for the particular patient for display on a user device in communication with the means for transmitting, and the trend comprises at least one of a graph and a list of pH values.

In certain implementations, the means for extracting dressing RGB values from the received image comprises means for determining individual pixel RGB values for each one of a plurality of pixels in the image and means for averaging the individual pixel RGH values for the plurality of pixels to determine the dressing RGB values. The system includes means for defining a center point of the received image and means for defining a dressing circle region around the center point of the received image, wherein the dressing circle region comprises the plurality of pixels for which the individual pixel RGB values are determined. For example, the dressing circle region may have a radius between about 5 and about 100 pixels, or between about 10 and about 50 pixels, or between about 20 and about 30 pixels.

In certain implementations, the system includes means for receiving an image of a color calibration strip. The color calibration strip may be in the same received image as the wound dressing, or may be in a separate image. The system includes means for extracting calibration RGB values from the image of the color calibration strip for each of a plurality of color blocks in the color calibration strip. Each color block is associated with a standardized pH value, and the pH value for the wound dressing is calculated using the dressing RGB values and the calibration RGB values. The means for extracting calibration RGB values for each of the plurality of color blocks comprises means for determining individual pixel RGB values for each one of a plurality of pixels in a color block and means for averaging the individual pixel RGB values for the plurality of pixels in the color block to determine the calibration RGB values for the color block.

In certain implementations, the system includes means for defining a center point of each of the plurality of color blocks. The center points are defined from alignment indicators positioned on either side of the color calibration strip. The system includes means for defining a calibration circle region around the center point of each color block, wherein each of the calibration circle regions comprises the plurality of pixels for which the individual pixel RGB values are determined in each color block. For example, each of the calibration circle regions may have a radius between about 3 and about 10 pixels, or may have a radius of about 5 pixels.

In certain implementations, the system includes means for calculating a distance between the dressing RGB values and each of the calibration RGB values in a three-dimensional space. For example, the system includes means for determining the two smallest calculated distances and means for calculating the pH value for the wound dressing based on the RGB calibration values and standardized pH values associated with the two smallest distances. The system may also include means for normalizing the dressing RGB values to a line defined by the two RGB calibration values associated with the two shortest distances and means for calculating the pH value for the wound dressing from the normalized position of the dressing RGB values on the line.

In one aspect, a system for monitoring a wound includes means for capturing an image of a wound dressing having a pH indicator, means for transmitting the captured image, means for receiving a pH value for the wound dressing in the captured image, and means for displaying an indication of the received pH value.

In certain implementations, the system includes means for displaying a guiding frame during image capture, wherein the guiding frame provides an indication of proper wound dressing alignment to a user. The system may also include means for detecting the alignment of the wound dressing relative to the displayed guide frame, wherein the image is automatically captured by the means for capturing when the wound dressing is properly aligned with the guiding frame. The system may include means for rejecting an image having inadequate light or excessive shadow and means for displaying a request to a user to capture a new image. The system may also include means for displaying an option to accept or reject the received pH value when the received pH value is displayed.

In certain implementations, the system includes means for storing the received pH value in a record of pH values. User input identifying a particular patient is received, and the stored record is associated with the particular patient. The user input may include a selection of the particular patient from a list of stored patients or may include identification information for a new patient. The system includes means for displaying a trend of pH values for the particular patient, and trend comprises at least one of a graph and a list of pH values.

In certain implementations, the system includes means for determining individual pixel RGB values for each one of a plurality of pixels in the captured image, means for averaging the individual pixel RGB values for the plurality of pixels to determine dressing RGB values, and means for calculating the pH value for the wound dressing from the dressing RGB values. The system includes means for defining a center point of the captured image and means for defining a dressing circle region around the center point of the captured image, wherein the dressing circle region comprises the plurality of pixels for which the individual pixel RGB values are determined. For example, the dressing circle region may have a radius between about 5 and about 100 pixels, or between about 10 and about 50 pixels, or between about 20 and about 30 pixels.

In certain implementations, the system includes means for capturing an image of a color calibration strip. The color calibration strip may be captured in the same image as the wound dressing, or may be captured in a separate image. The system includes means for extracting calibration RGB values from the image of the color calibration strip for each of a plurality of color blocks in the color calibration strip. Each color block is associated with a standardized pH value, and the pH value for the wound dressing is calculated using the calibration RGB values. The means for extracting calibration RGB values for each of the plurality of color blocks comprises means for determining individual pixel RGB values for each one of a plurality of pixels in a color block and means for averaging the individual pixel RGB values for the plurality of pixels in the color block to determine the calibration RGB values for the color block.

In certain implementations, the system includes means for defining a center point of each of the plurality of color blocks, and the center points are defined from alignment indicators positioned on either side of the color calibration strip. The system includes means for defining a calibration circle region around the center point of each color block, wherein each of the calibration circle regions comprises the plurality of pixels for which the individual pixel RGB values are determined in each color block. For example, each of the calibration circle regions may have a radius between about 3 and about 10 pixels, or may have a radius of about 5 pixels.

In certain implementations, the system includes means for calculating a distance between the dressing RGB values and each of the calibration RGB values in a three-dimensional space. For example, the system includes means for determining the two smallest calculated distances and means for calculating the pH value for the wound dressing based on the RGB calibration values and standardized pH values associated with the two smallest distances. The system may also include means for normalizing the dressing RGB values to a line defined by the two RGB calibration values associated with the two shortest distances and means for calculating the pH value for the wound dressing from the normalized position of the dressing RGB values on the line.

In one aspect, a system for monitoring a wound includes a system described above.

Variations and modifications of these embodiments will occur to those of skill in the art after reviewing this disclosure. The foregoing features and aspects may be implemented, in any combination and sub-combinations (including multiple dependent combinations and sub-combinations), with one or more other features described herein. The various features described or illustrated above, including any components thereof, may be combined or integrated in other systems. Moreover, certain features may be omitted or not implemented.

Further areas of applicability of the disclosed devices and methods will become apparent from the detailed description provided hereinafter. It should be understood that the detailed description and specific examples, while indicating particular embodiments, are intended for purposes of illustration only and are not intended to limit the scope of the. Disclosure or any of the claims that may be pursued.

DESCRIPTION OF THE DRAWINGS SECTION

1

The foregoing and other objects and advantages will be appreciated more fully upon consideration of the following detailed description, taken in conjunction with the accompanying drawings, in which like reference numbers refer to like parts throughout. These depicted •embodiments are to be understood as illustrative and not limiting in any way:

FIG. 3 is a photograph of a Post-Op sample dyed with GJM-514, illustrating changes in colour of the dye in response to solution changing pH along a pH unit interval scale.

Figure 3:
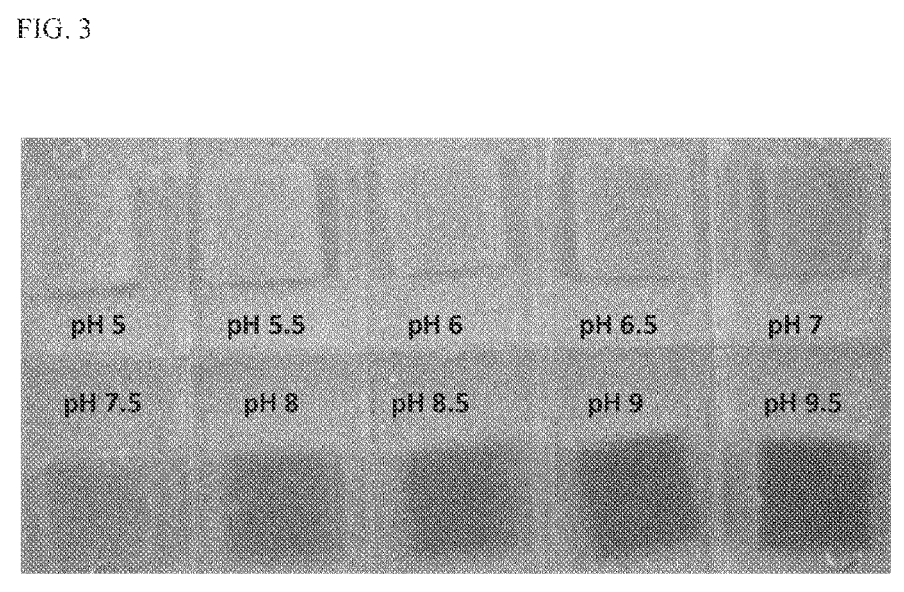

FIGS. 4A-F are graphic representations of colour pen measurements for the Post-Op sample illustrated in FIG. 3.

Figure 5:
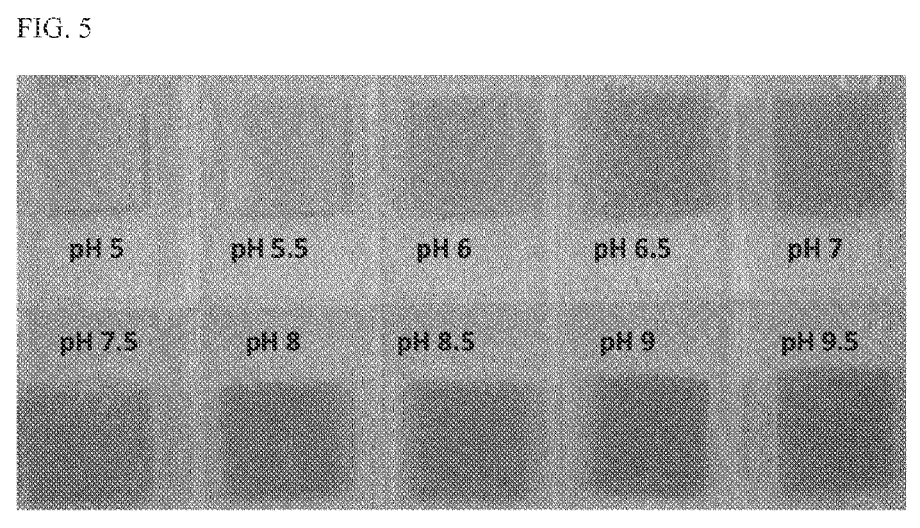

FIG. 5 is a photograph of a Post-Op sample dyed with a first-combination of dyes, illustrating changes in colour of the dye combination in response to a solution changing pH along a pH unit interval scale.

FIGS. 6A-D are graphic representations of colour pen measurements for the Post-Op sample illustrated in FIG. 5.

Figure 7:
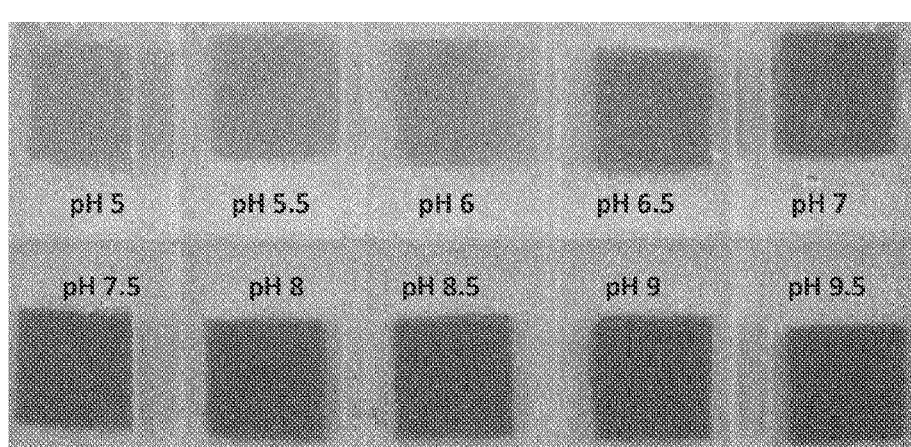

FIG. 7 is a photograph of a Post-Op sample dyed with a second combination of dyes, illustrating changes in colour of the dye combination in response to a buffered solution changing pH along a pH unit interval scale.

FIGS. 8A-E are graphic representations of the colour pen measurements for the Post-Op sample illustrated in FIG. 7.

Figure 9:
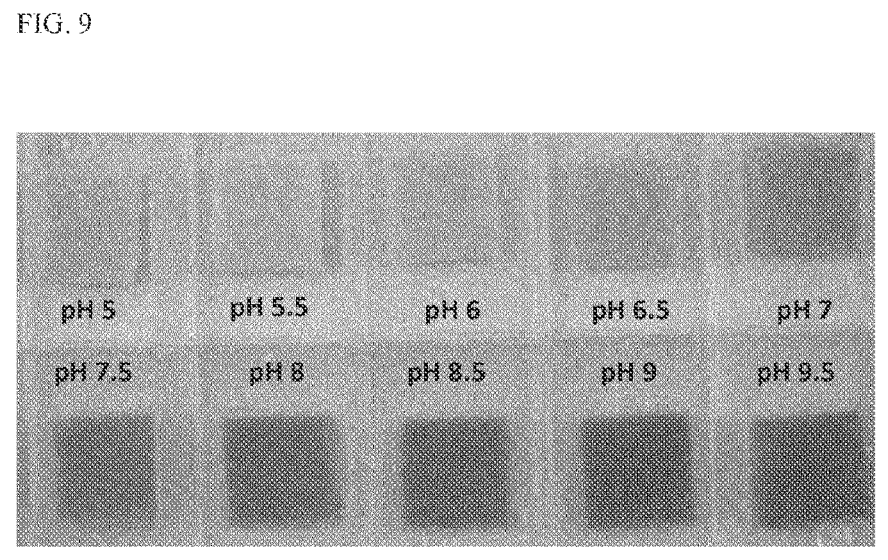

FIG. 9 is a photograph of a Post-Op sample dyed with a third combination of dyes, illustrating changes in colour of the dye combination in response to a buffered solution changing pH along a pH unit interval scale.

FIGS. 10A-F are graphic representations of the colour pen measurements for the Post-Op sample illustrated in FIG. 9.

FIG. 11 is a photograph of a Post-Op sample dyed with a fourth combination of dyes, illustrating changes in colour of the dye combination in response to a buffered solution changing pH along a pH unit interval scale.

FIGS. 12A-E are graphic representations of the colour pen measurements for the Post-Op sample illustrated in FIG. 11.

FIGS. 13A-F are photographs of pH sensitive gauze in ex-vivo wound model with alternating pH 5 and pH 8 horse serum being pumped in.

Figures 13A, 13B, 13C, 13D, 13E, 13F:
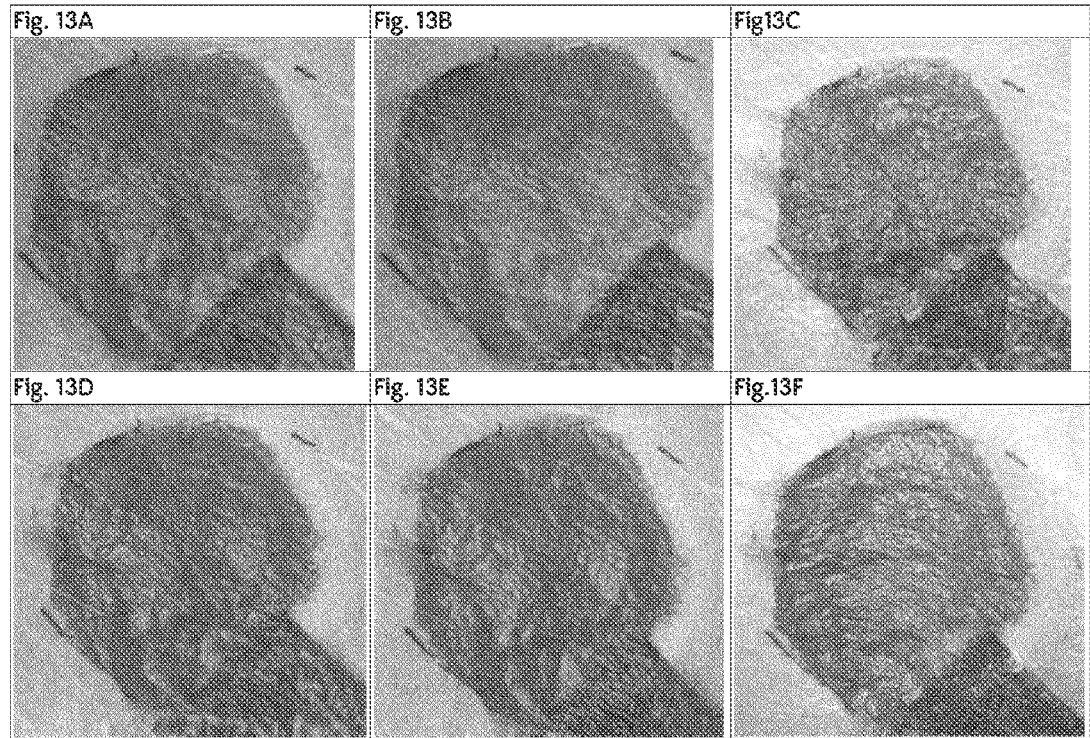

FIG. 13A is a photograph of pH 5 after 2.5 hours approx.

FIG. 13B is a photograph of pH 5 after 5.5 hours approx.

FIG. 13C is a photograph of pH 8 after 8 hours approx.

FIG. 13D is a photograph of pH 5 after 3.5 hours approx.

FIG. 13E is a photograph of pH 5 after 5.5 hours approx. with the flow rate of horse serum increased at 3.5 hours.

FIG. 13F is a photograph of pH 5 after 7.5 hours with the flow rate of horse serum increased at 3.5 hours and at 5.5 hours.

FIGS. 14A to F are photographs of pH sensitive foam (V.A.C. White Foam trade mark of KCT) in an ex-vivo wound model with alternating pH5 and pH 8 horse serum being pumped in.

Figures 14A, 14B, 14C, 14D, 14E, 14F:
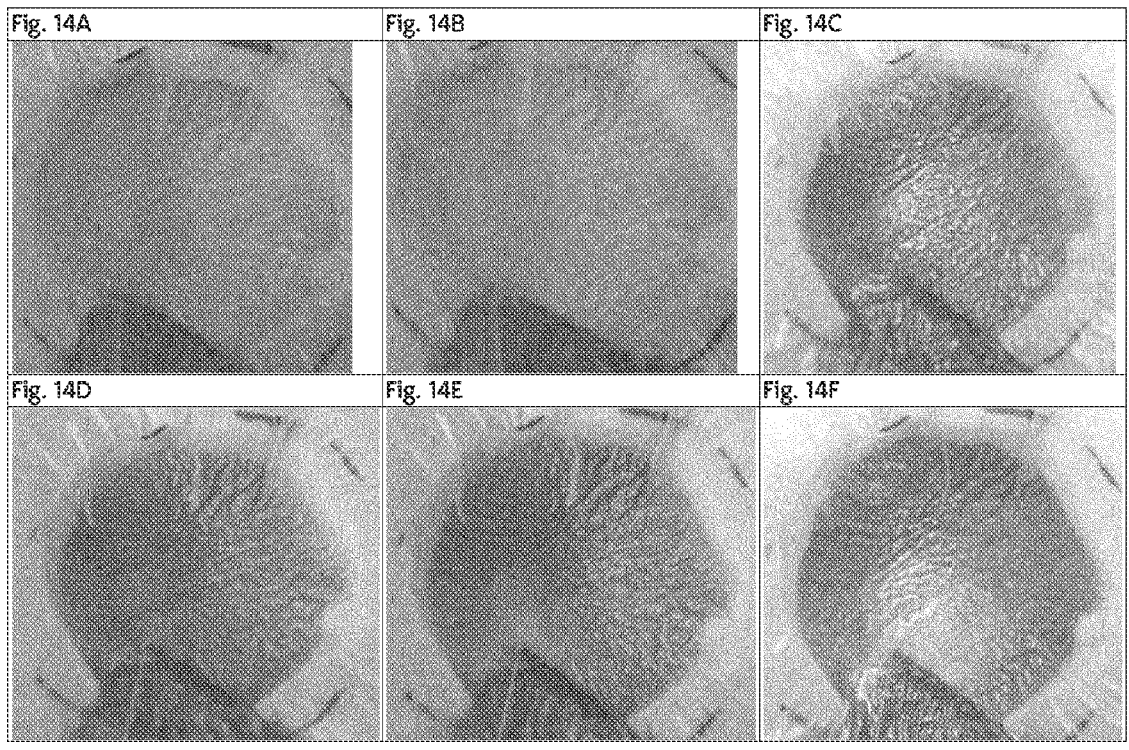

FIG. 14A is a photograph at pH 5 after 2.5 hours approx.

FIG. 14B is a photograph at pH 5 after 5.5 hours approx.

FIG. 14C is a photograph at pH 8 after 15 hours approx.

FIG. 14D is a photograph at pH 5 after 3.5 hours approx.

FIG. 14E is a photograph at pH 5 after 5.5 hours approx., with the flow rate of horse scrum increased at 3.5 hours.

FIG. 14F is a photograph at pH 5 after 7.5 hours approx., with the flow rate of horse serum increased at 3.5 hours and at 5.5 hours.

FIGS. 15A to F are photographs of pH sensitive gauze in an ex-vivo wound model with alternating basic and acidic water being pumped in.

Figures 15A, 15B, 15C, 15D, 15E, 15F:
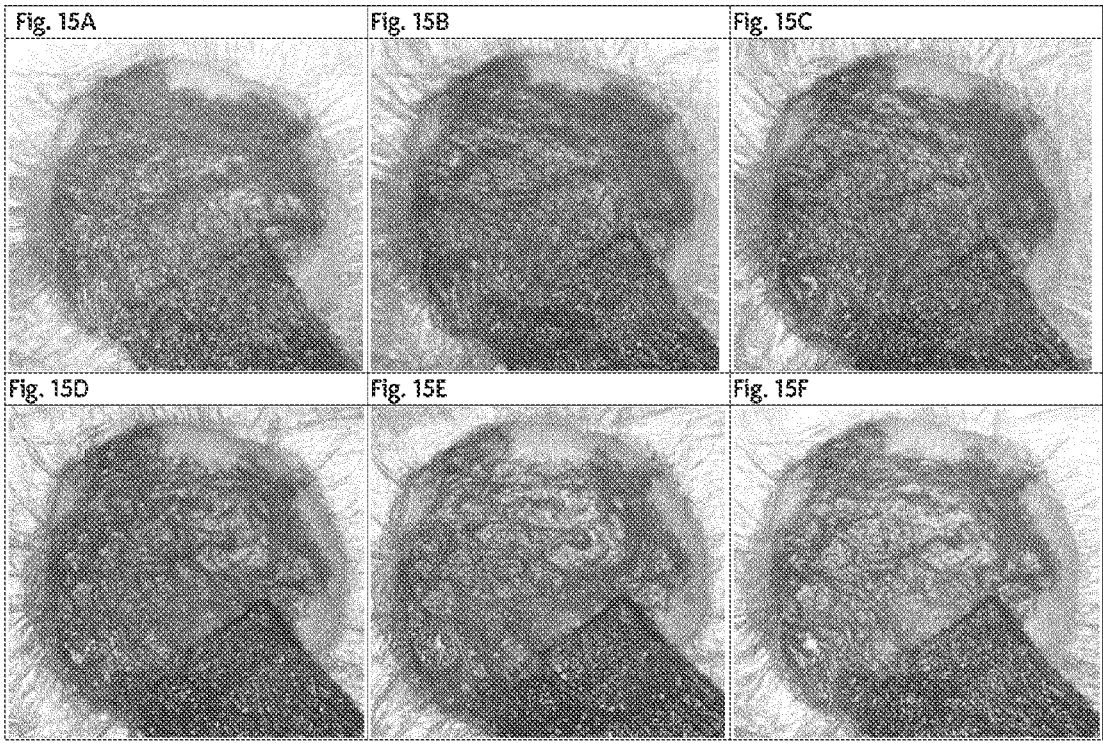

FIG. 15A is a photograph at 8 am Day 1 showing basic pH.

FIG. 15B is a photograph at 12:57 pm Day 1 (5 hours) showing basic pH.

FIG. 15C is a photograph at 08:03 am Day 2 (24 hours) showing basic pH.

FIG. 15D is a photograph at 12:41 pm Day 2 (5 hours) showing acidic pH.

FIG. 15E is a photograph at 15:06 Day 2 (7 hours) showing acidic pH.

FIG. 15F is a photograph at 16:47 Day 2 (9 hours) showing acidic pH.

FIGS. 16A to F are photographs of pH sensitive foam in an ex-vivo wound model with alternating basic and acidic water being pumped in.

FIG. 16A is a photograph at 8 am Day 1 showing basic pH.

FIG. 16B is a photograph at 12:57 pm Day 1 (5 hours) showing basic pH.

FIG. 16C is a photograph at 08:03 am Day 2 (24 hours) showing basic pH.

FIG. 16D is a photograph at 09:06 Day 2 (1 hour) showing acidic pH.

FIG. 16E is a photograph at 15:06 Day 2 (7 hours) showing acidic pH.

FIG. 16F is a photograph at 16:47 Day 2 (9 hours) showing acidic pH.

FIGS. 17A to H are photographs of pH sensitive foam in a clear Perspex wound model with alternating basic and acidic water.

FIG. 17A is a photograph at 8 am Day 1 showing basic pH.

FIG. 17B is a photograph at 12:56 Day 1 (5 hours) showing basic pH.

FIG. 17C is a photograph at 16:20 Day 1 (8.5 hours) showing basic pH.

FIG. 17D is a photograph at 8:02 am Day 2 (24 hours) showing basic pH.

Figures 17E, 17F, 17G, 17H:
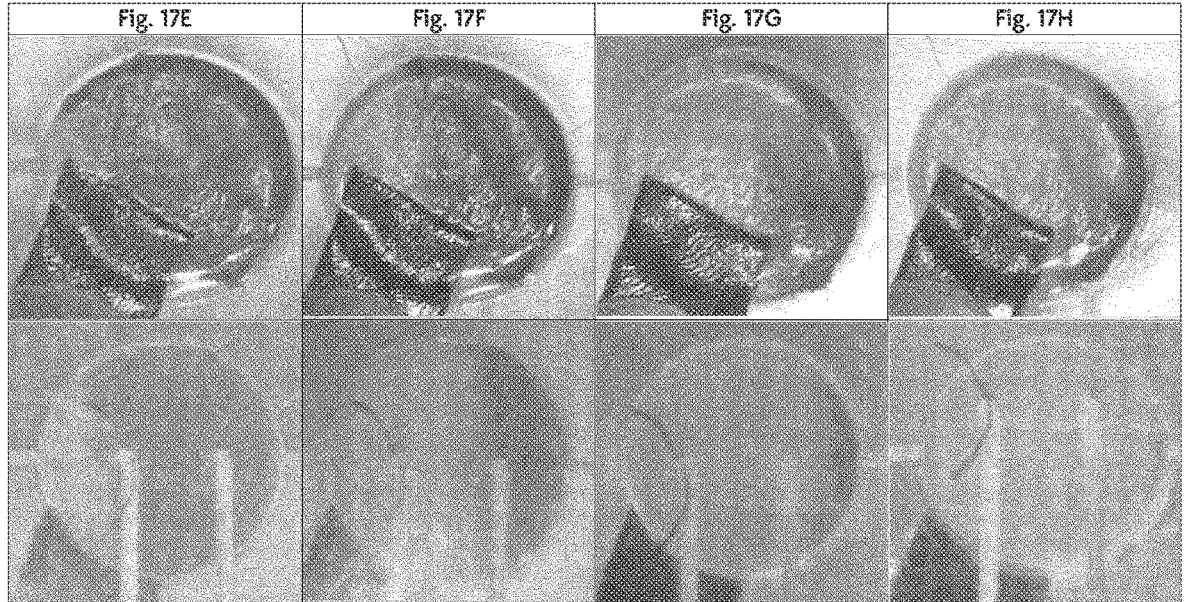

FIG. 17E is a photograph at 09:05 am Day 2 (1 hour) showing acidic pH.

FIG. 17F is a photograph at 10:50 am Day 2 (3 hours) showing acidic pH.

FIG. 17G is a photograph at 13:26 Day 2 (5.5 hours) showing acidic pH.

FIG. 17H is a photograph at 15:05 Day 2 (7 hours) showing acidic pH.

Figure 18:
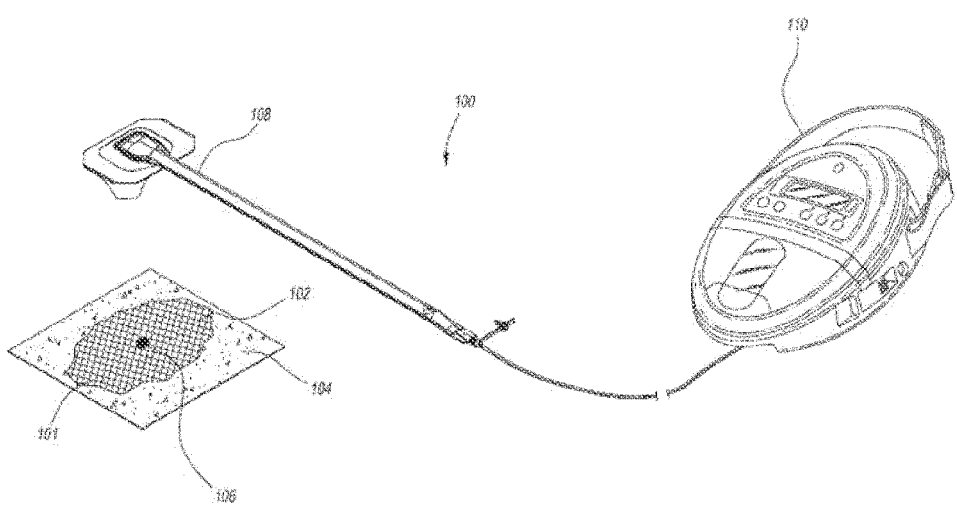

FIG. 18 illustrates an embodiment of a negative pressure system.

Figure 19:
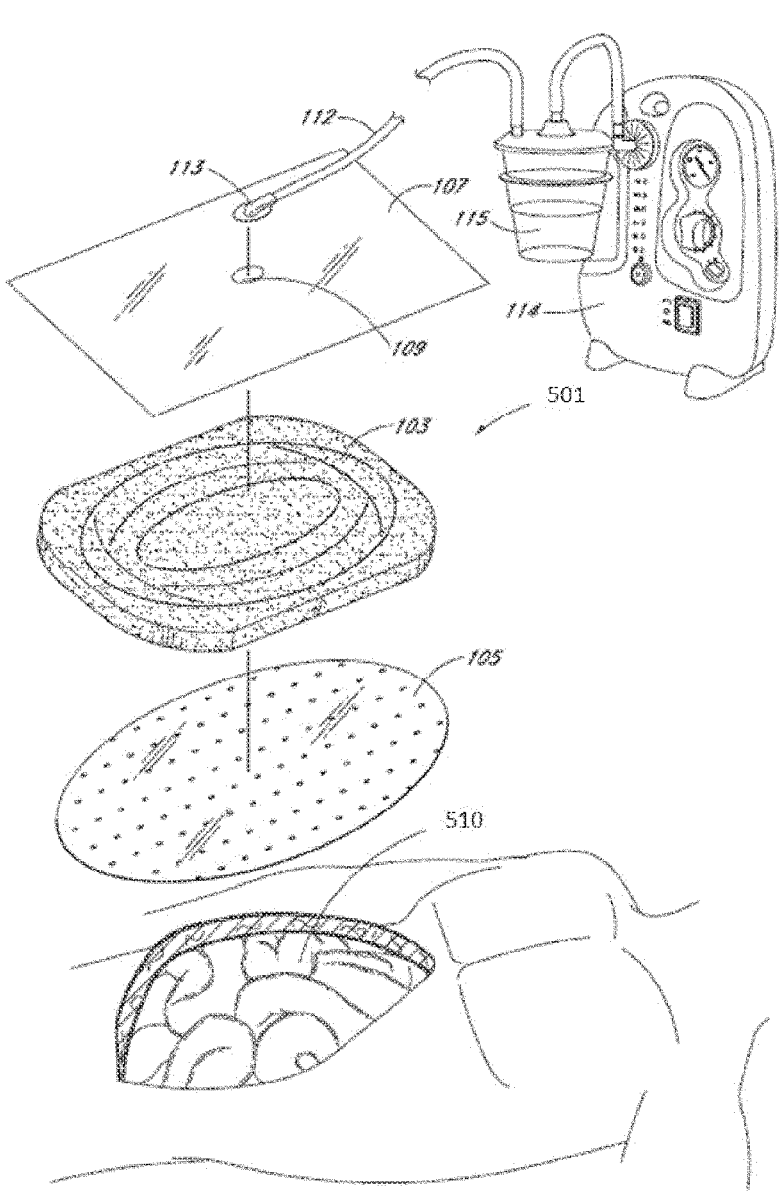

FIG. 19 is a schematic illustration of a system for the treatment of abdominal wounds.

Figure 20:
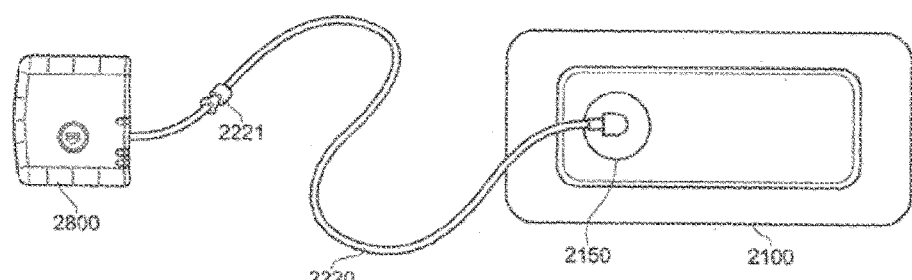

FIG. 20 illustrates an embodiment of a wound treatment system.

FIGS. 21A-D illustrate the use and application of an embodiment of a wound treatment system onto a patient which may be used with any dressing embodiment disclosed wherein.

Figure 22:
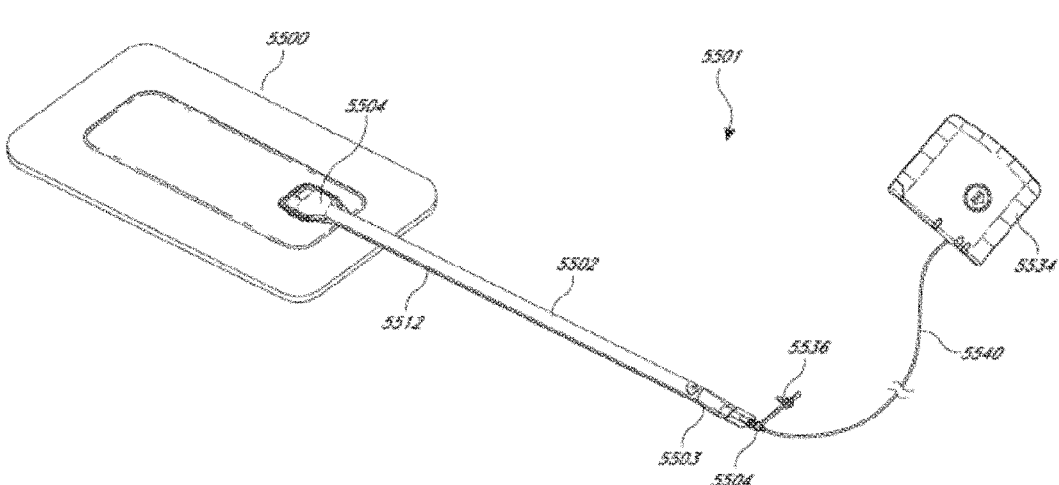

FIG. 22 illustrates an embodiment of a negative pressure wound treatment system employing a wound dressing capable of absorbing and storing wound exudate and a flexible suction adapter.

Figure 23:
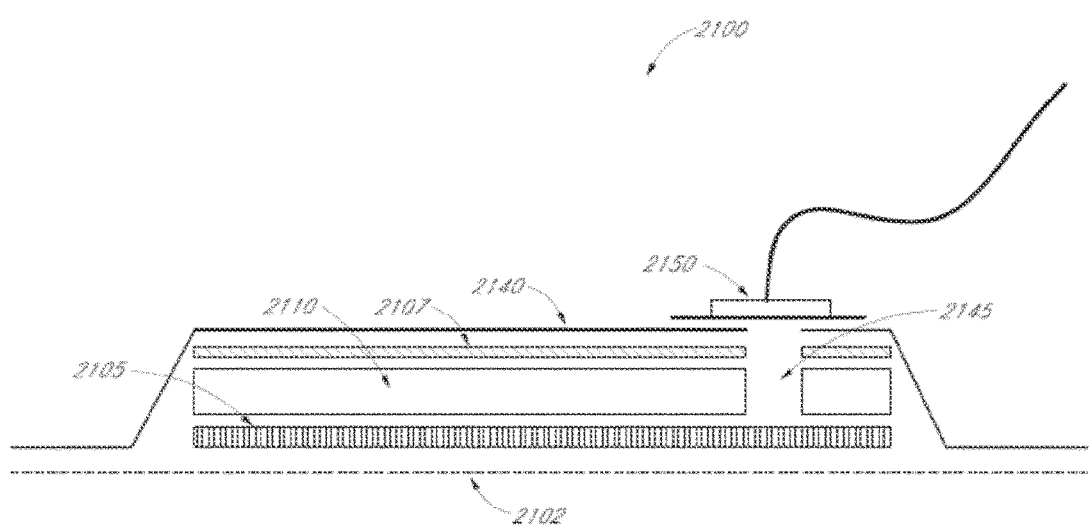

FIG. 23 illustrates another embodiment of a wound dressing in cross-section.

Figure 24:
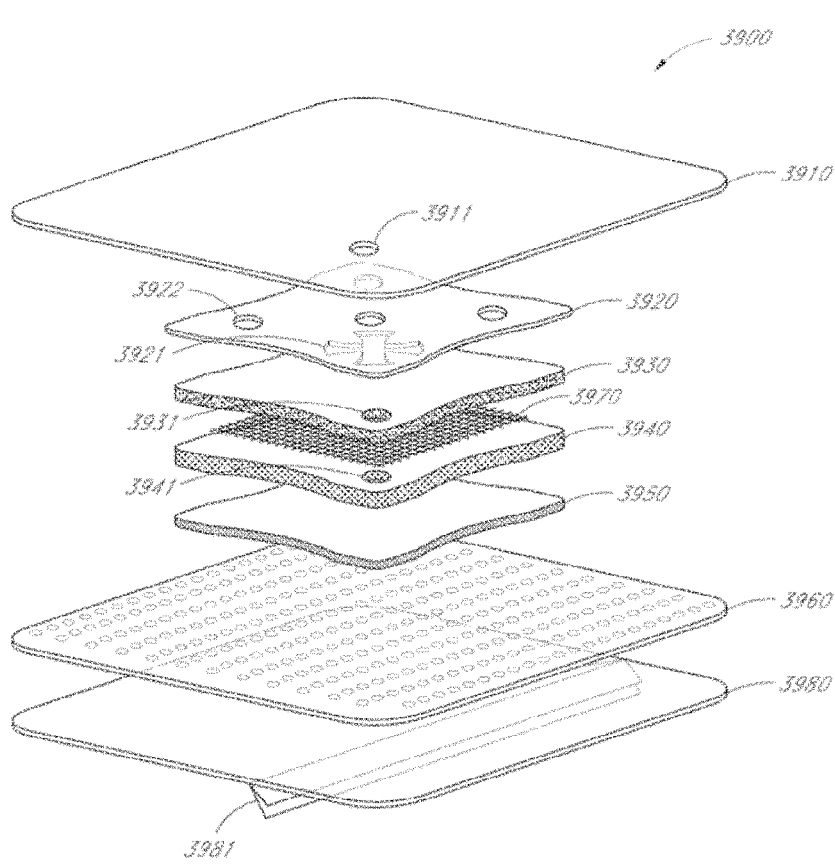

FIG. 24 illustrates an exploded view of another embodiment of a wound dressing.

FIGS. 25A and 25B are side cross-sectional views of an illustrative device having a pH indicator, the colour of which changes as a result of alterations in the pH of the wound exudate.

FIGS. 26A-D illustrate side cross-sectional views of an illustrative wound dressing having a device shown in FIGS. 25A and 25B applied to is wound-facing surface.

Figure 27A:
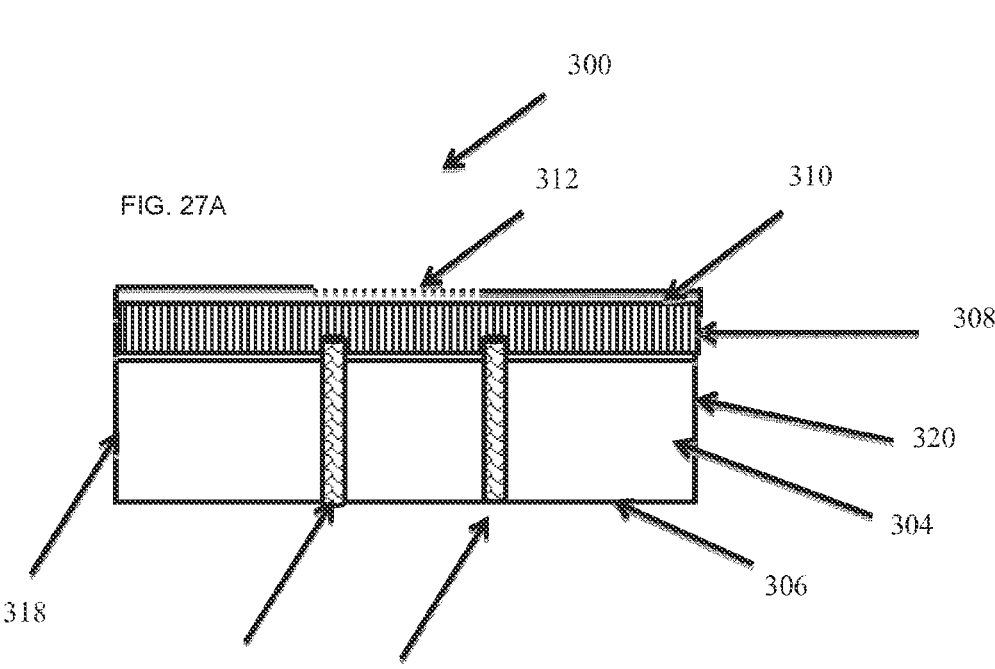
Figure 27B:
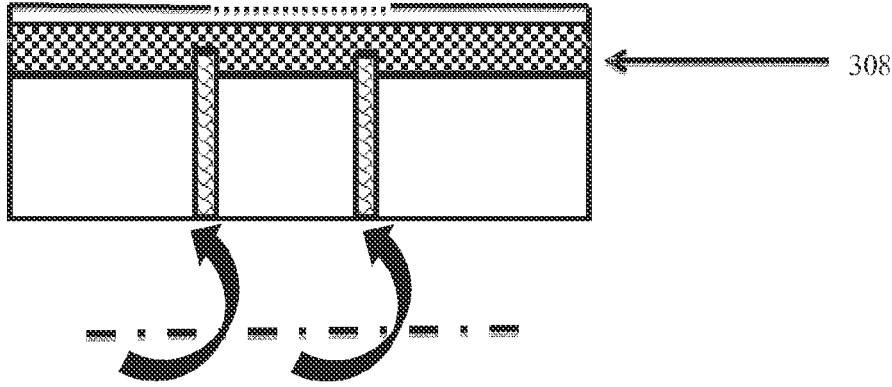

FIGS. 27A and 27B are side cross-sectional views of an illustrative wound dressing in which wound exudate is guided via a conduit to a pH indication zone which includes a pH indicator, the colour of the indicator changes as a result of alterations in the pH of the wound exudate.

Figure 28A:
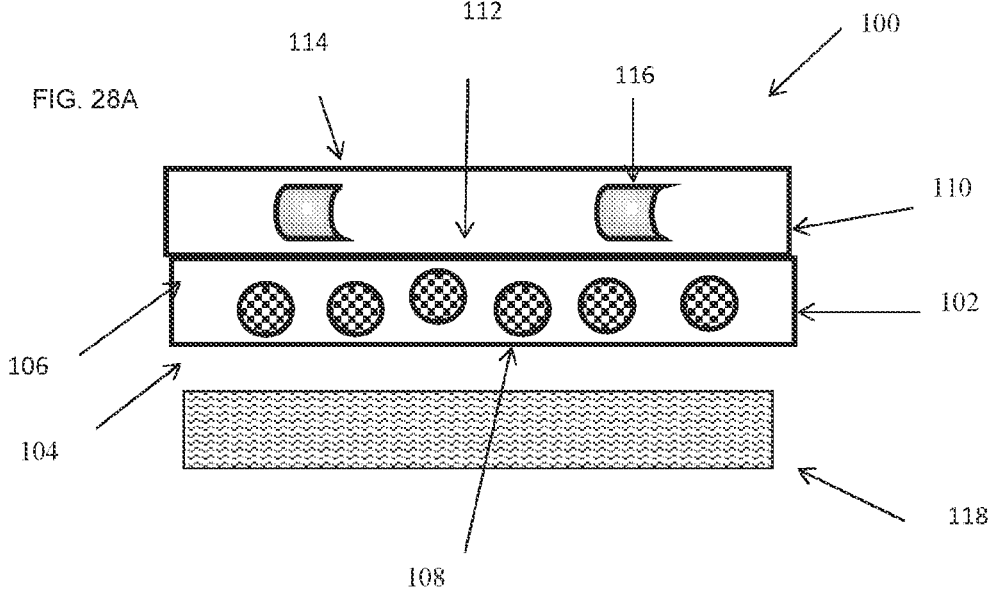
Figure 28B:
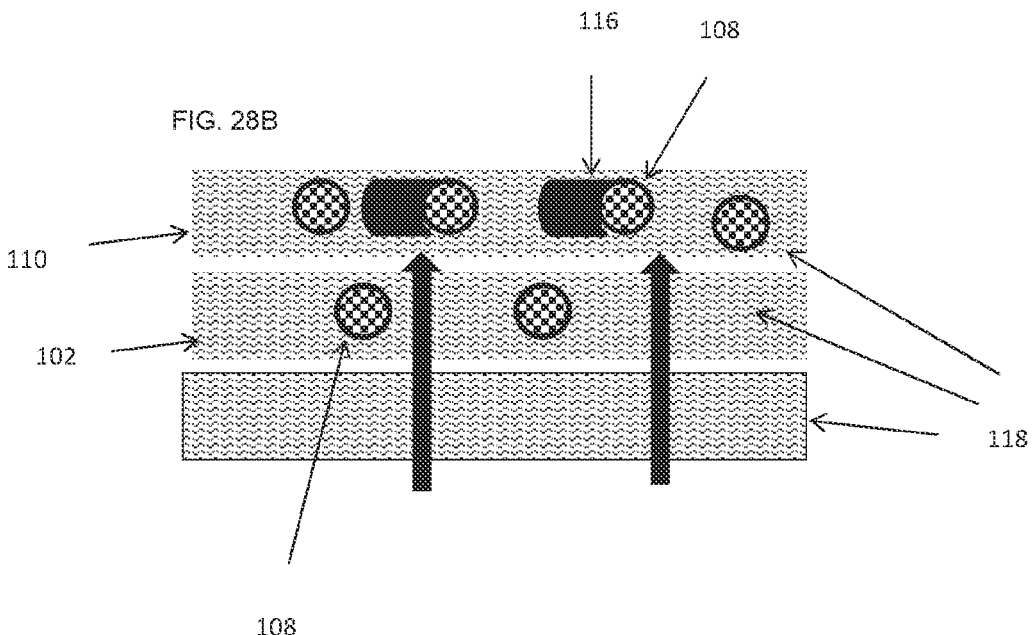

FIGS. 28A and 28B are side cross-sectional views of an illustrative device in which the colour of a pH indicator changes from a first colour to a second colour.

Figure 29A:
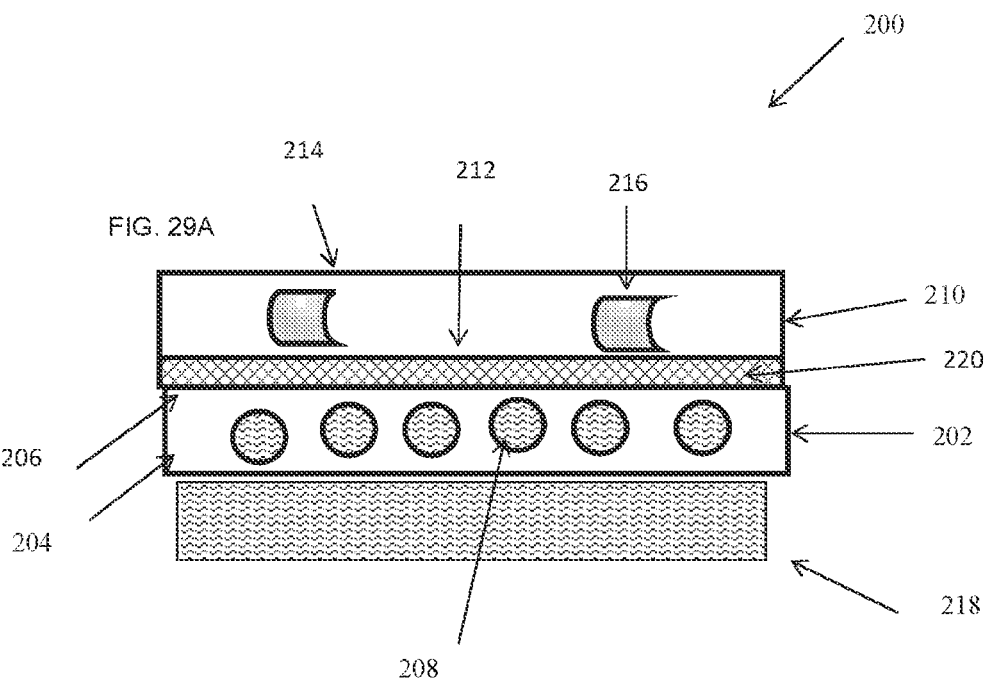
Figure 29B:
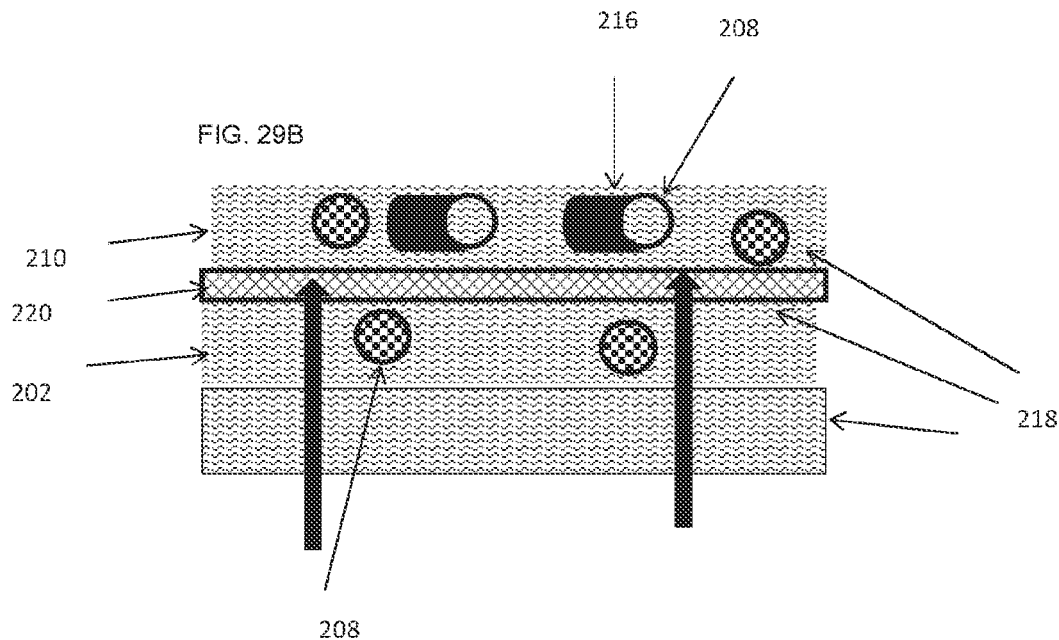

FIGS. 29A and 29B are side cross-sectional views of the device illustrated in FIGS. 28A and 28B having a spacer layer to physically separate a soluble composition and a pH indicator.

Figure 30A:
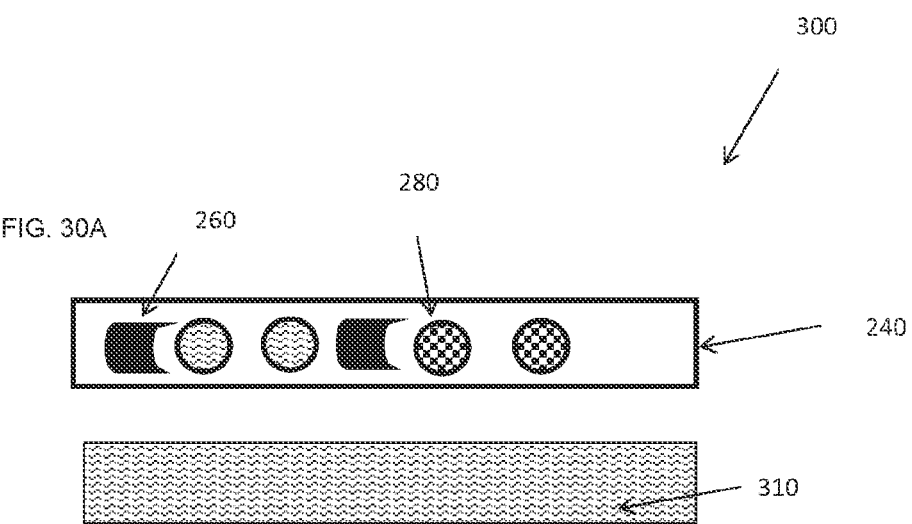
Figure 30B:
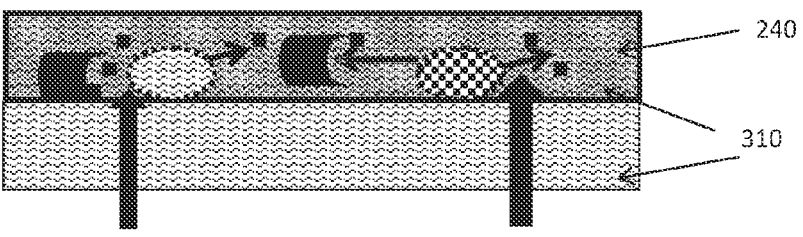

FIGS. 30A and 30B are side cross-sectional views of an illustrative device, in which a soluble composition is encapsulated with a soluble barrier.

Figures 31A, 31B:
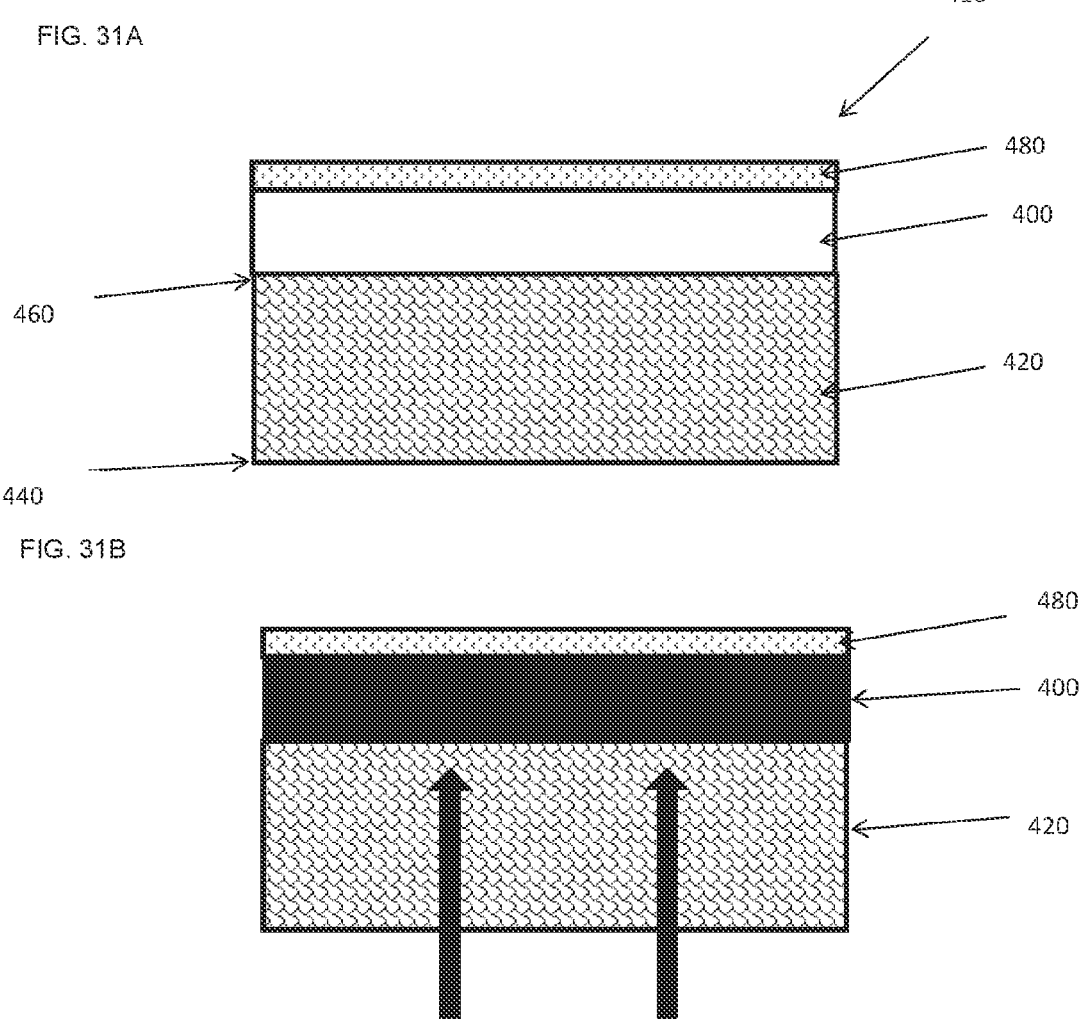

FIGS. 31A and 31B are side cross-sectional views of an illustrative combination of a wound dressing and a device as disclosed herein.

Figure 32A:
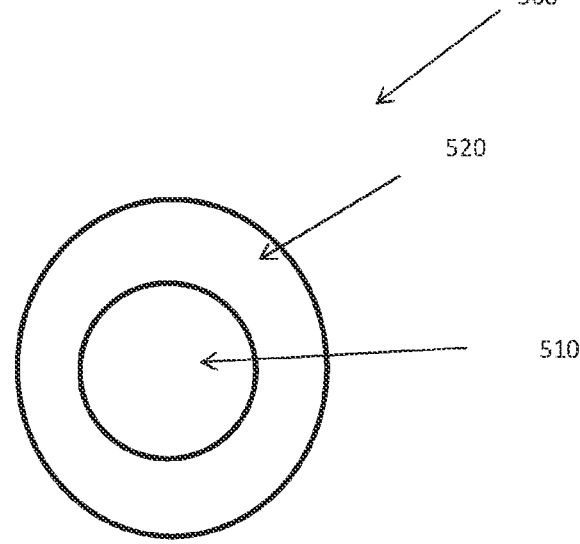
Figure 32B:
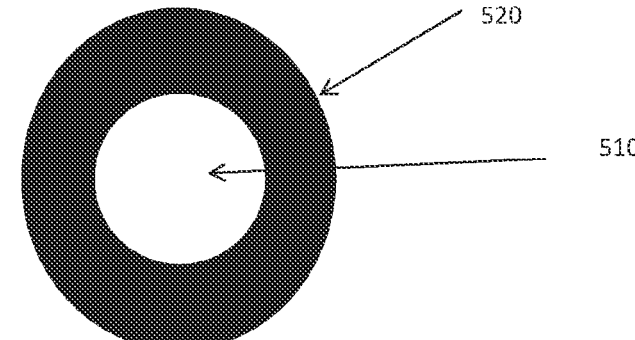

FIGS. 32A and 32B are plan views of an illustrative combination of a wound dressing and a device as disclosed herein.

Figures 33A, 33B:
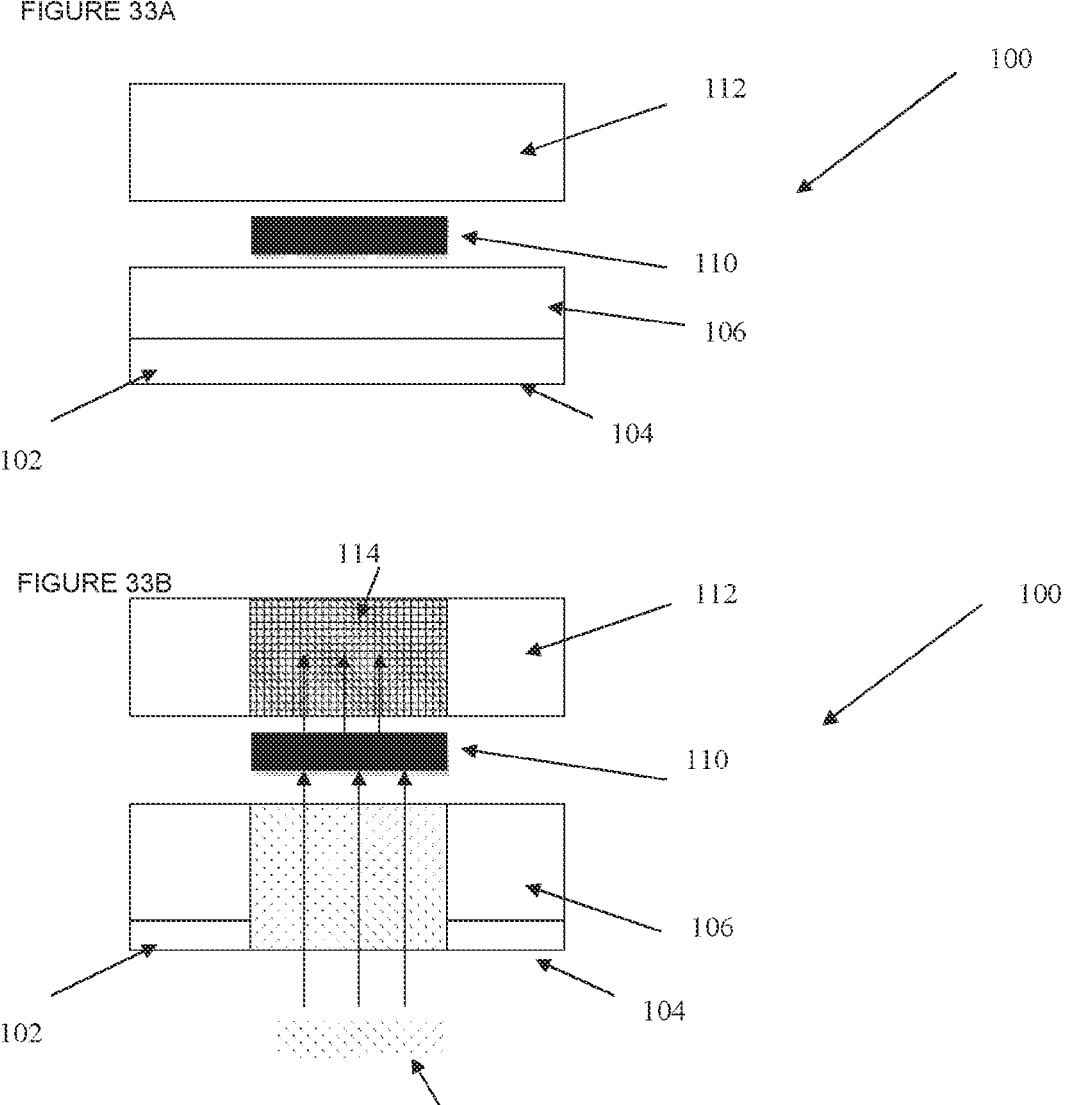

FIGS. 33A and 33B are side cross-sectional views of an illustrative wound dressing having a moisture indicator, the visibility of which alters as a result of a physical transformation of a first material of the dressing.

Figure 34A:
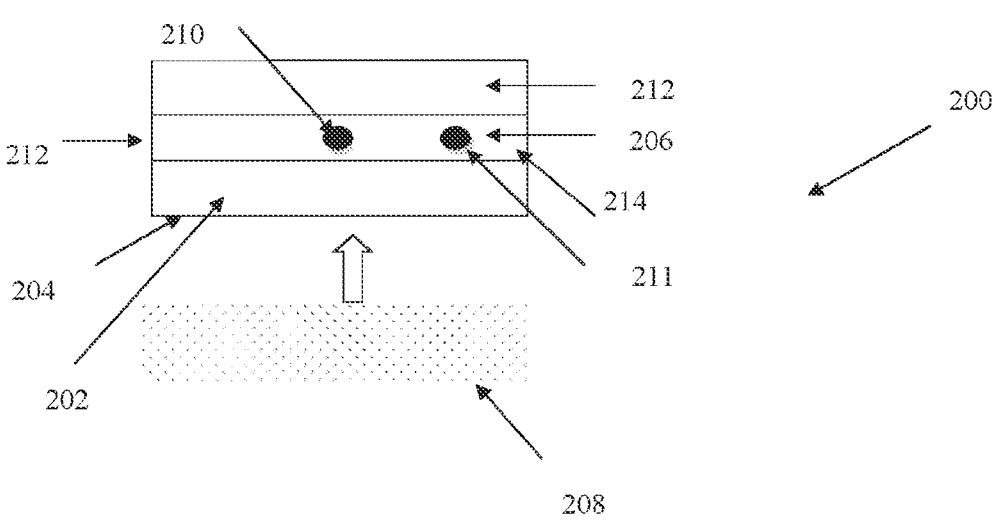
Figure 34B:
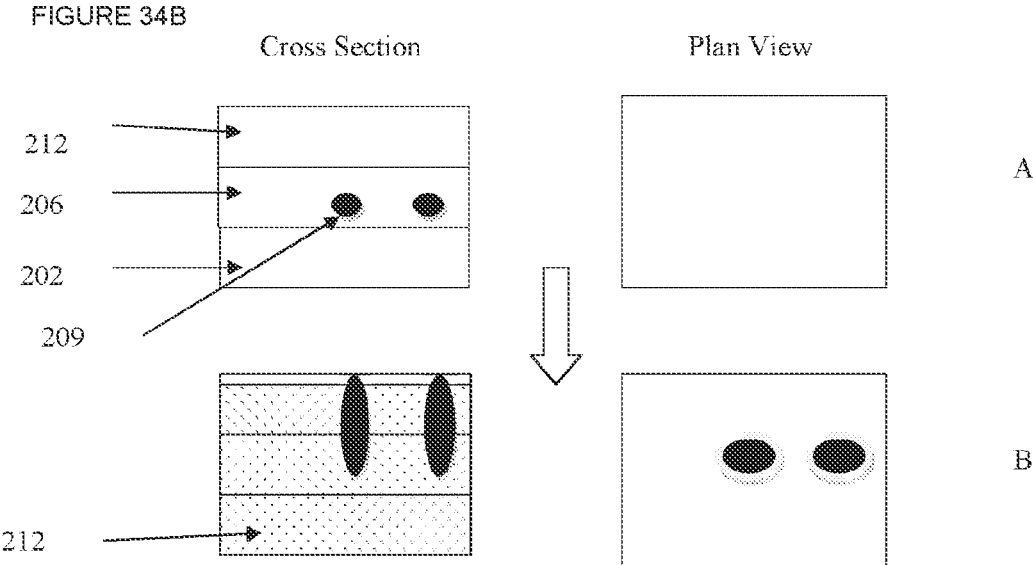

FIGS. 34A and 34B are side cross-sectional and plan views of an illustrative wound dressing in which a water-soluble coloured moisture indicator becomes visible as the dressing becomes saturated.

Figure 35A:
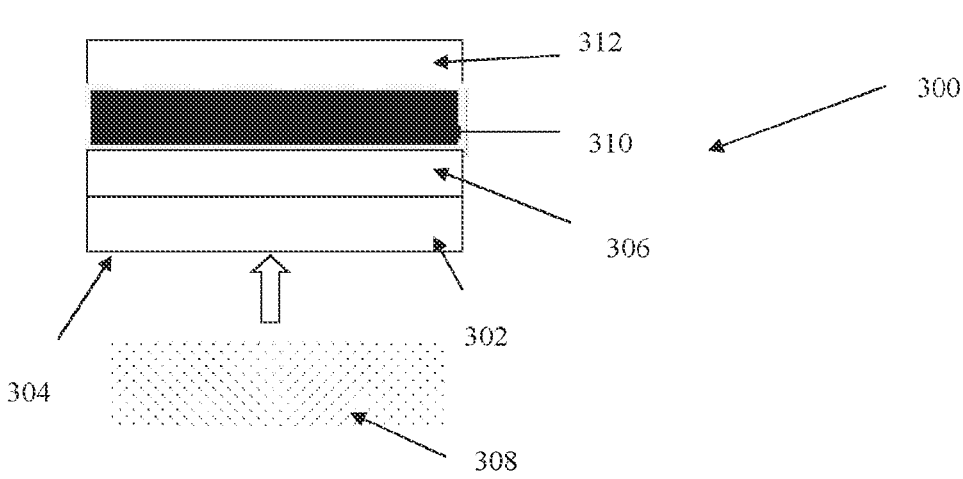
Figure 35B:
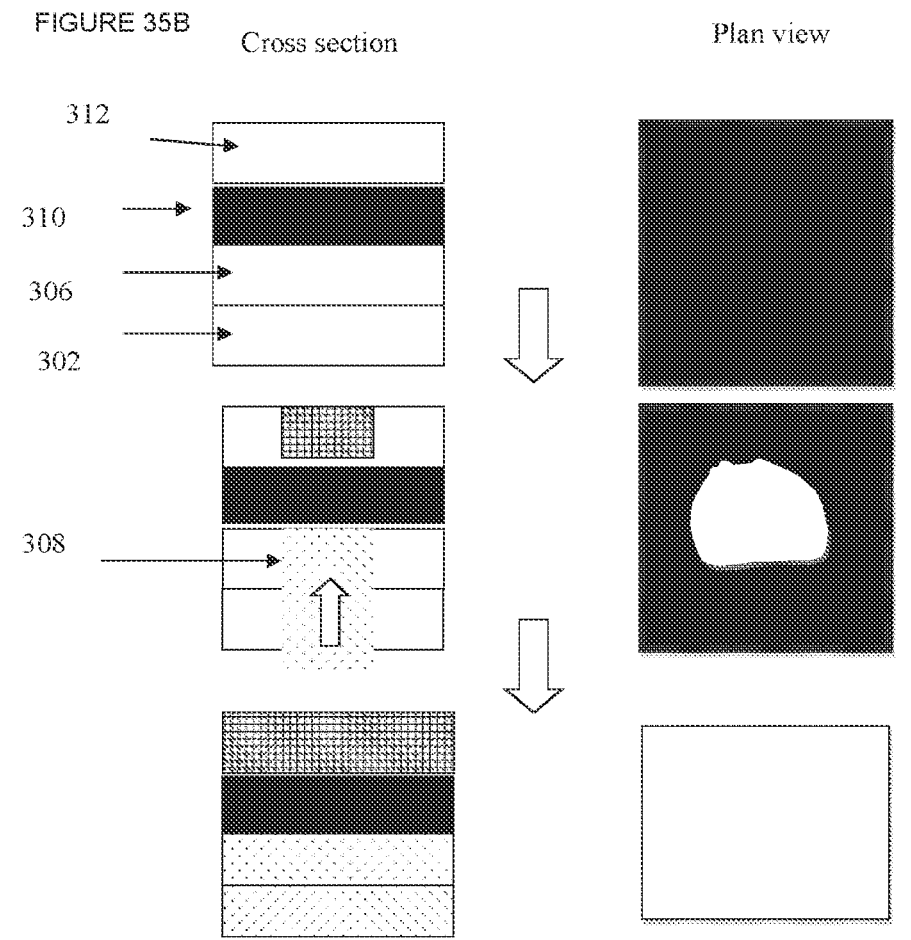

FIGS. 35A and 35B are side cross-sectional and plan views of an illustrative wound dressing in which a coloured moisture indicator becomes invisible as a result of the physical transformation of a first material from transparent to opaque.

FIGS. 36A and 36B are side cross-sectional and plan views of an illustrative wound dressing in which a coloured moisture indicator becomes visible as a result of the physical transformation of a first material from opaque to transparent.

Figure 37A:
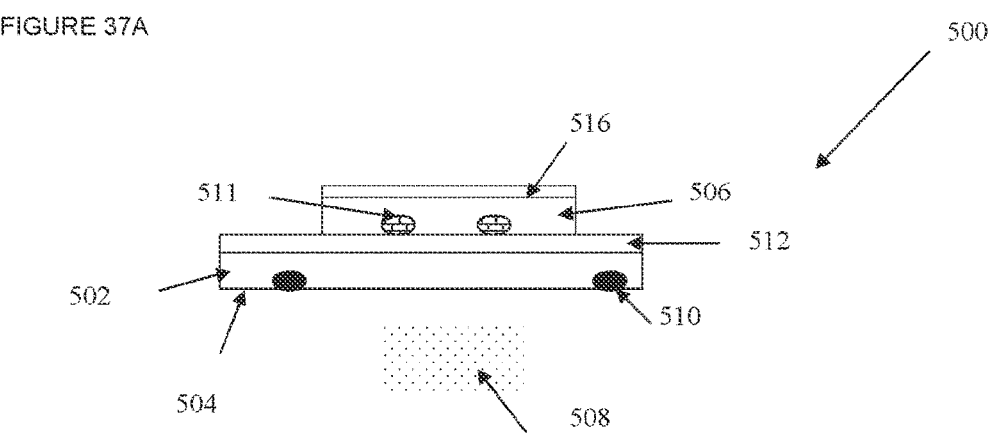
Figure 37B:
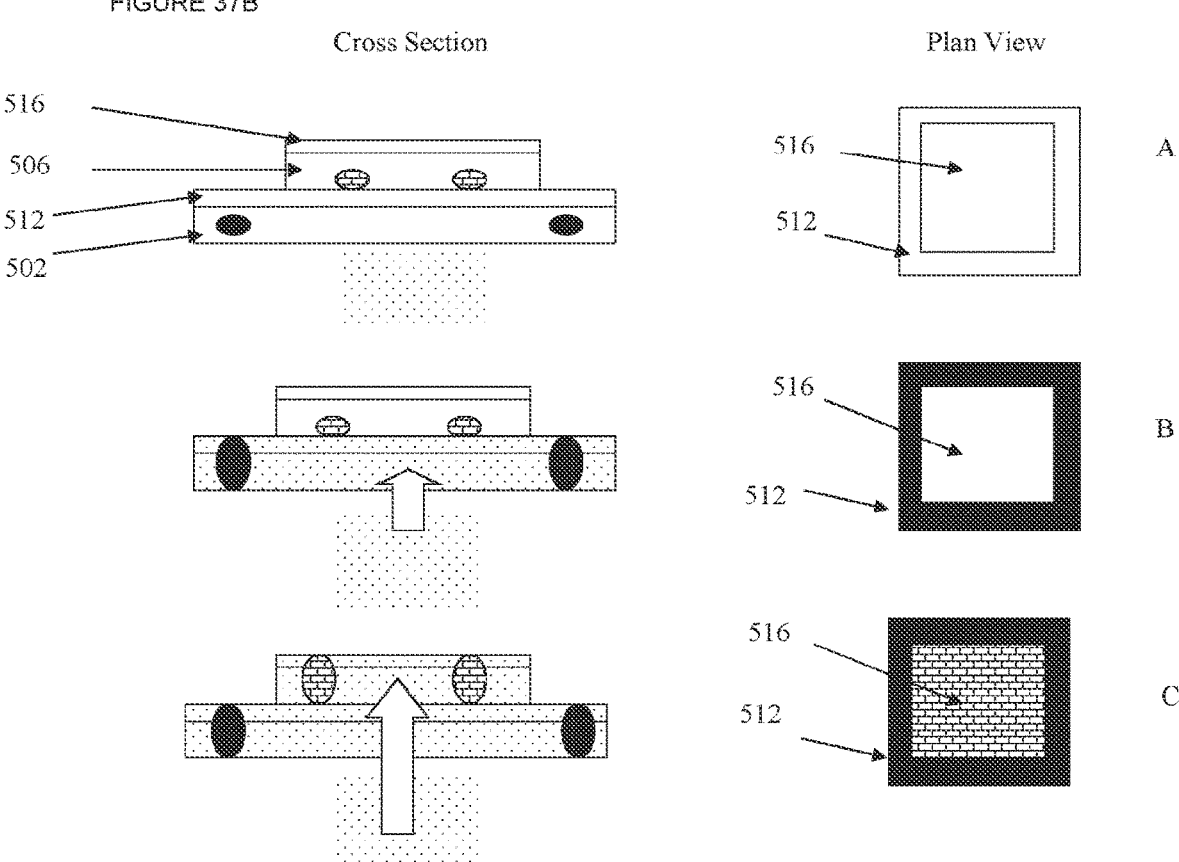

FIGS. 37A and 37B are side cross-sectional and plan views of a plan view of an illustrative wound dressing in which a coloured moisture indicator is associated with multiple layers of the dressing and becomes visible as a result of the physical transformation of a first material associated with each layer.

Figure 38:
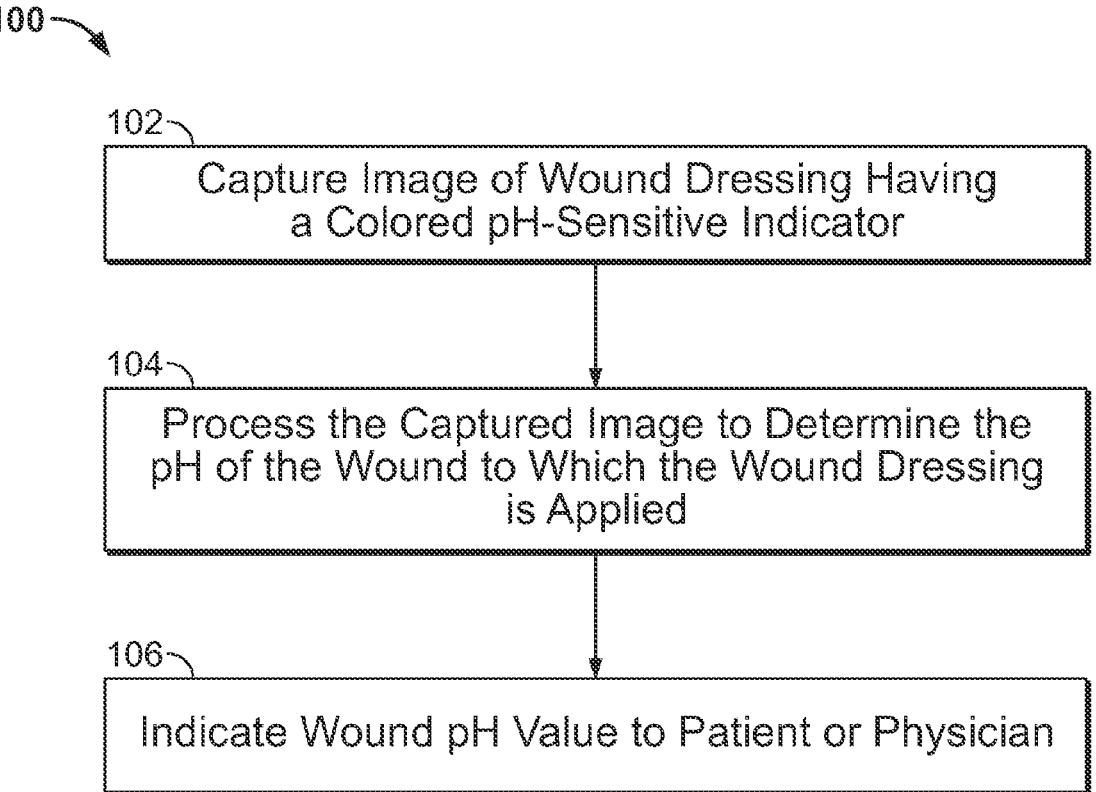

FIG. 38 shows a flow chart for a method of monitoring wound pH levels according to some implementations.

FIG. 39 shows a flow chart for a method of processing a wound dressing image and calculating a pH level based on the color of the image according to some implementations.

Figure 40:
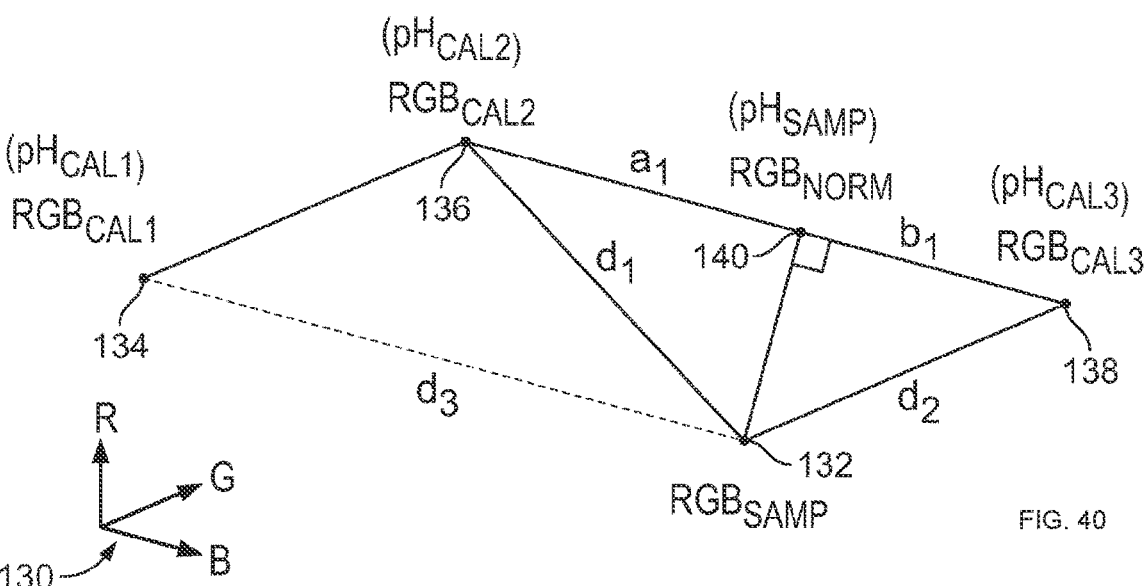

FIG. 40 shows a visual representation of a pH calculation process according to some implementations.

Figure 41:
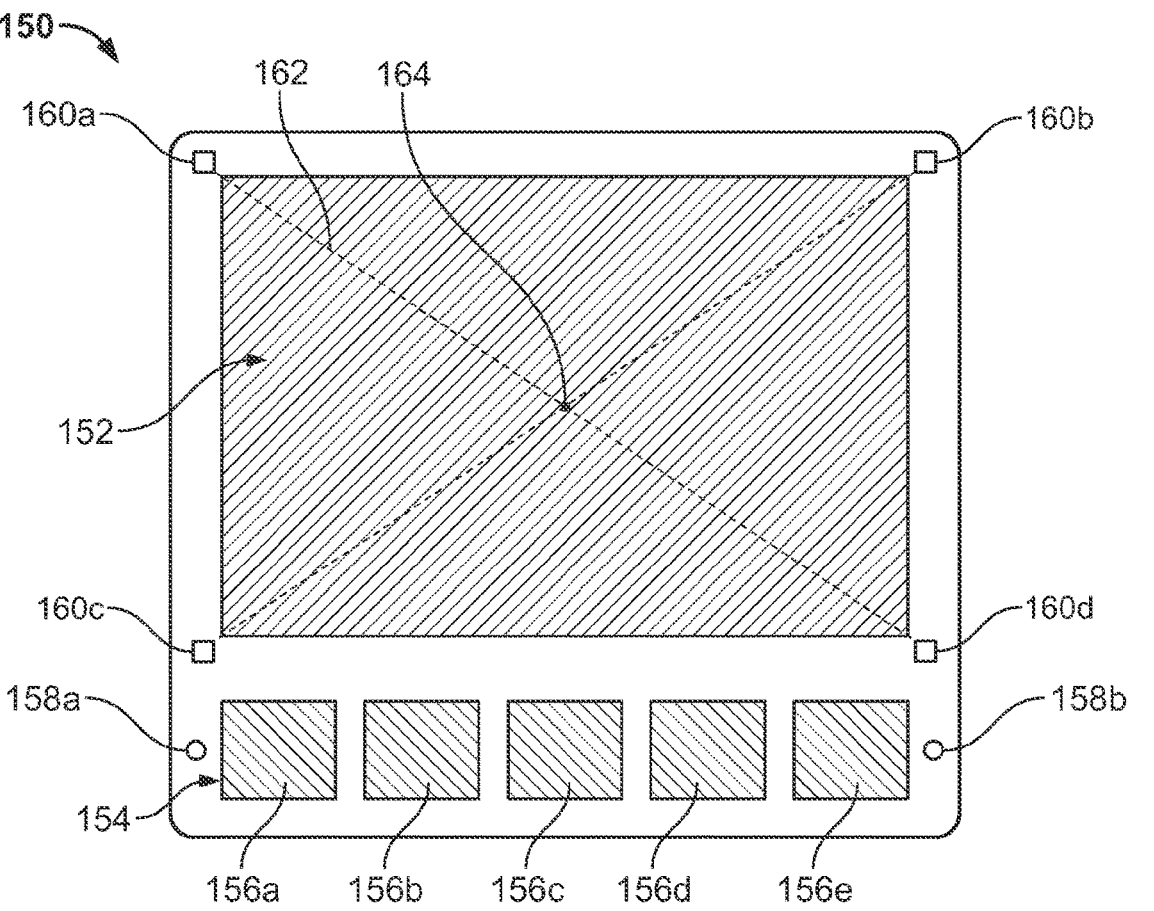

FIG. 41 shows an illustrative pH-sensitive wound dressing according to some implementations.

Figure 42:
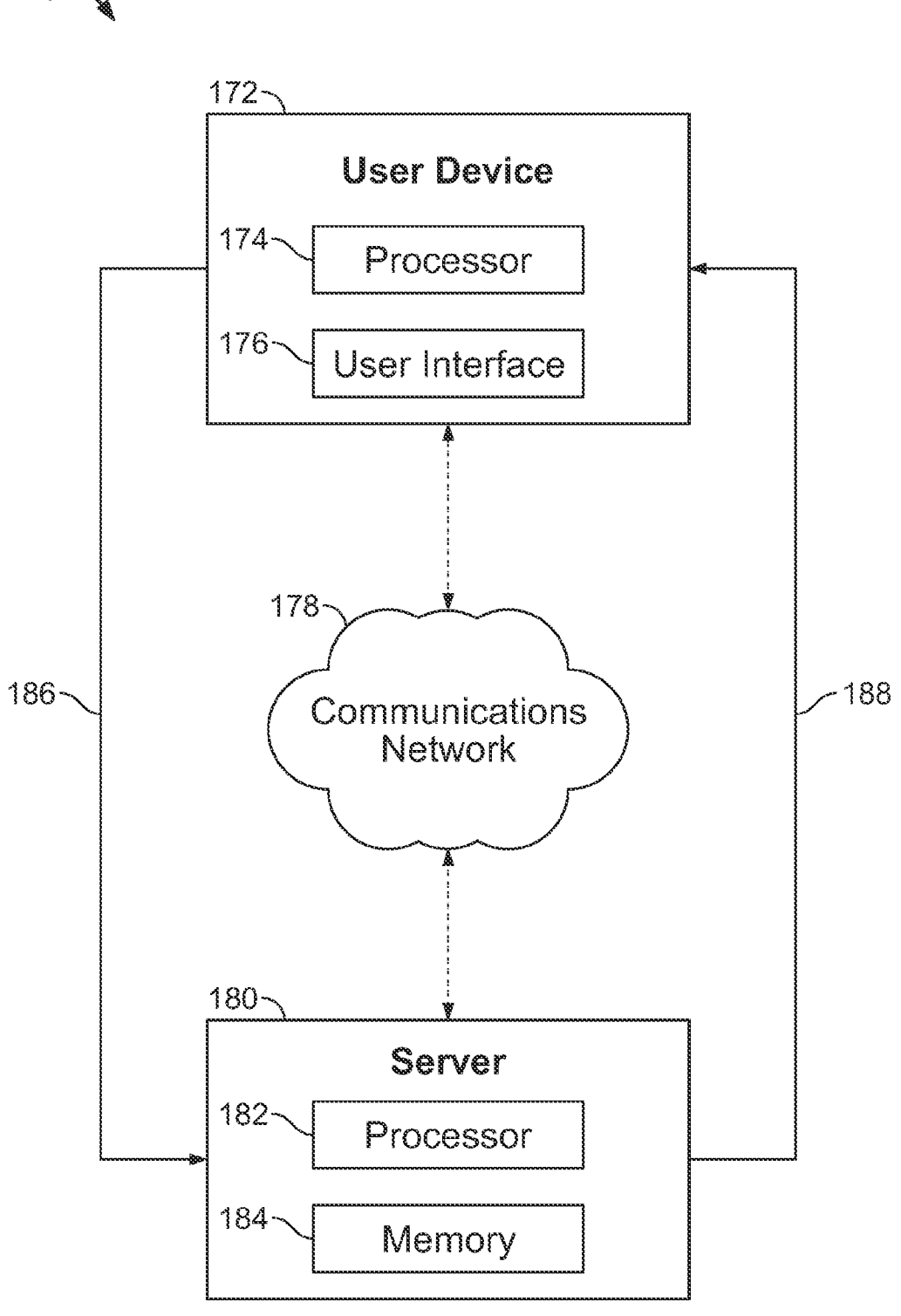

FIG. 42 shows an illustrative system including a user device, a server, and a communications network according to some implementations.

Figure 43:
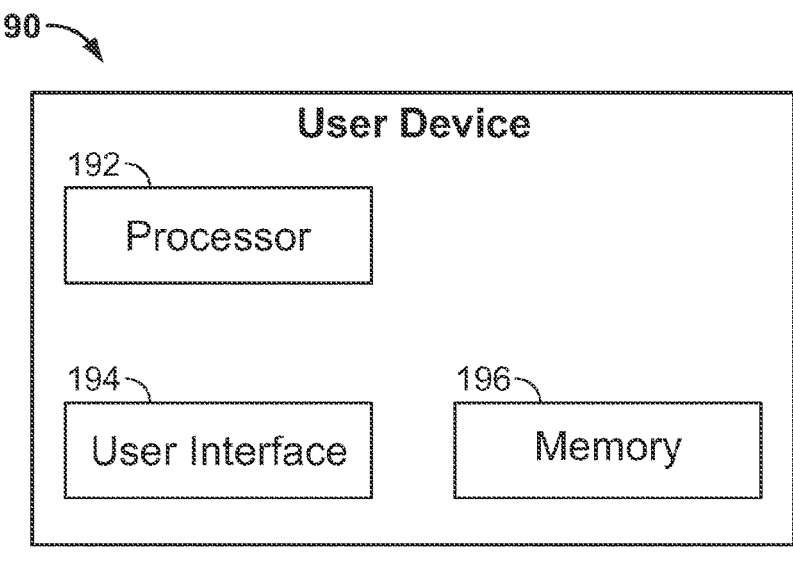

FIG. 43 shows an illustrative user device according to some implementations.

Figure 44:
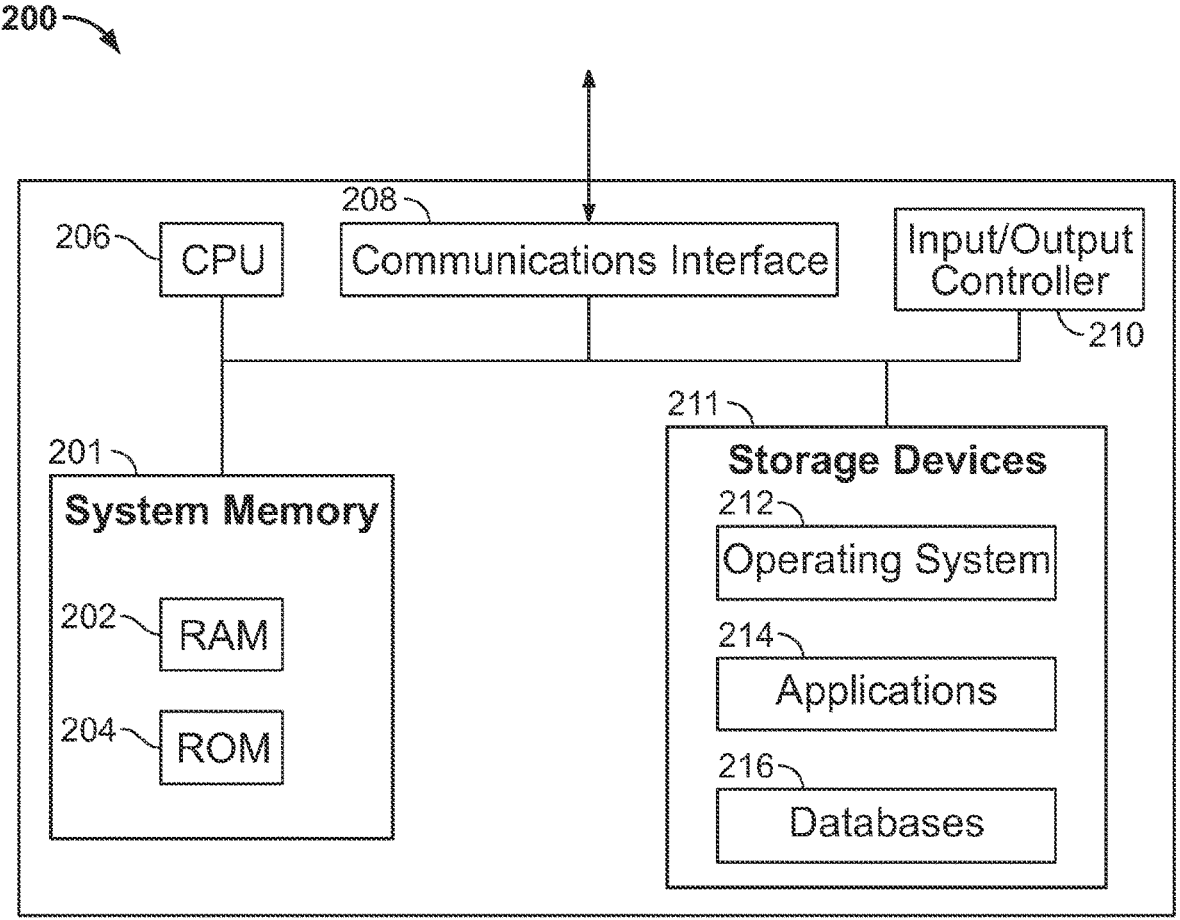

FIG. 44 shows an illustrative computing device according to some implementations.

FIGS. 45-50 show illustrative user device screenshots according to some implementations.

DETAILED DESCRIPTION SECTION 1

To provide an understanding of the devices and methods describe herein, certain illustrative embodiments and examples will now be described.

Reference numbers cited in Section 1 correspond to the reference numbers used in FIGS. 1-17.

Figures 1A, 1B:
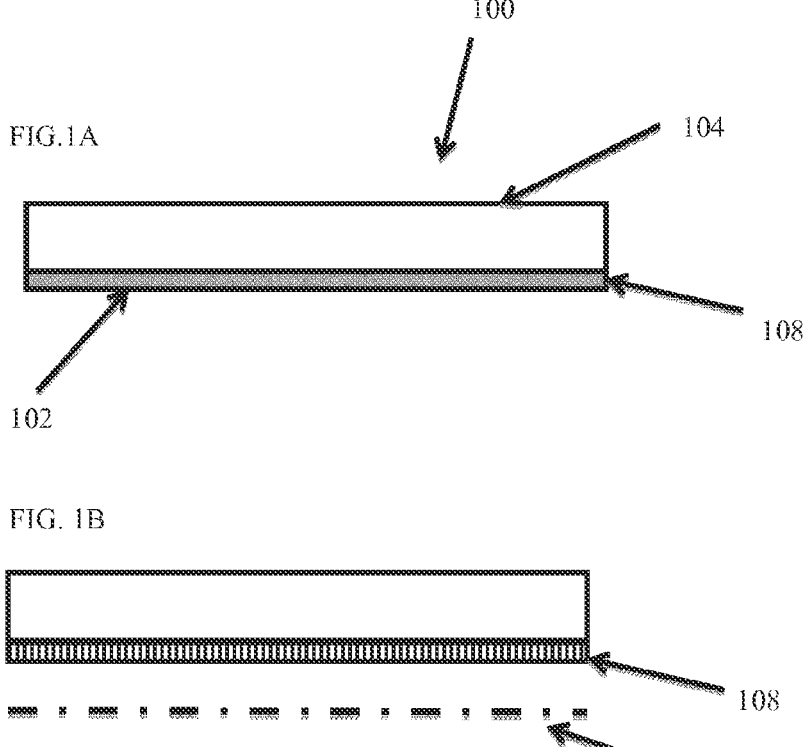
FIGS. 1A and 1B are side cross-sectional views of an illustrative device having a pH indicator, the colour of which changes as a result of alterations in the pH of a fluid.

FIG. 1A depicts a device 100 having a fluid-contacting surface 102 and an opposing non-fluid-contacting surface 104. FIG. 1B depicts the device 100 being brought into contact with a fluid 106. The device 100 can be made of any material that is suitable for contact with the fluid without disintegrating.

The device further includes a pH indicator 108 which is applied to one or both of surfaces 102 and/or 104. The pH indicator is covalently immobilised on or adjacent to the surface 102 and/or 104 so that it is not washed away by the fluid.

In embodiments, the pH indicator is chemically bound to the surface 102 and/or 104. For example, the pH indicator is covalently bound directly to the surface 102 and/or 104. In alternative embodiments, the surface 102 and/or 104 is provided within an adhesive and the pH indicator is covalently bound to reactive moieties within the adhesive. For example, a conventional acrylic adhesive, such as K5 (Smith & Nephew, Inc) used in the construction of wound dressings contains residues of 2-hydroxy-ethylmethacrylate, which provide a reactive functional hydroxyl (OH) group, pendant to the polymer backbone, to which the pH indicator can be covalently bound. Other suitable adhesives include acrylic-based adhesives with pendant OH or COOR groups.

In embodiments on which the pH indicator is only applied to one surface of a non-porous device, then an indication, for indicating which side the pH indicator is applied to may be provided. This indication allows the user to appropriately orient the device during placement on or in the fluid to ensure that the surface which has the pH indicator is correctly orientated and comes into contact with the fluid.

The pH indicator may be applied across substantially the entire surface 102 and/or 104, to allow any variations in the pH at the meniscus of the fluid sample to be identified. Alternatively, the pH indicator may be applied to discrete areas of surfaces 102 and/or 104. The pH indicator exhibits a first colour prior to contact with a fluid and changes colour as a function of the pH of the fluid. The first colour of the pH indicator may be colourless.

The pH indicator is capable of reversibly changing colour in response to pH. In embodiments, the pH indicator is a phenylazo compound. In certain embodiments, the phenylazo compound is selected from the group listed in Table 1. In some embodiments, the phenylazo compound is not 2-[4(2-hydroxyethylsulfonyl)-phenyl]diazenyl]-4-methylphenol. In some embodiments, the phenylazo compound is not hydroxy-4-[4[(hydroxyethylsulphonyl)-phenylazo]-napthalene-2-sulphonate. In some embodiments, the phenylazo compound is not 2-fluoro-4-[4[(2-hydroxyethanesulphonyl)-phenylazo]-6-methoxy phenol. In some embodiments, the phenylazo compound is not 4-[4-(2-hydroxyethylsulphonyl)-phenylazo]-2,6-dimethoxyphenol. In certain embodiments, the phenylazo compound is 2-[4(2-hydroxyethylsulfonyl)-phenyl]diazenyl]-4-methylphenol. In some embodiments, the pH indicator includes a plurality of phenylazo compounds. In some embodiments, the pH indicator includes a combination of phenylazo compounds, for example a combination of phenylazo compounds selected from the group listed in Table 1. In some embodiments, the pH indicator includes a combination of two phenylazo compounds. In some embodiments, the pH indicator includes a combination of three phenylazo compounds. In some embodiments, 2-[4(2-hydroxyethylsulfonyl)-phenyl]diazenyl]-4-methylphenol is combined with at least one other phenylazo compound selected from the group listed in Table 1. The ratio of phenylazo compound may be 1:1, but other ratios are envisaged, for example, but in no way limiting, 0.5:1.5 or 1.5:0.5 or 1:2 or 2:1 or 1:0.1. In alternative embodiments, the pH indicator includes at least one phenylazo compound, for example a phenylazo compound selected from the group listed in Table 1 and at least one other compound that is not a phenylazo compound. In certain embodiments, the pH indicator is not a phenylazo compound.

Figure 2A:
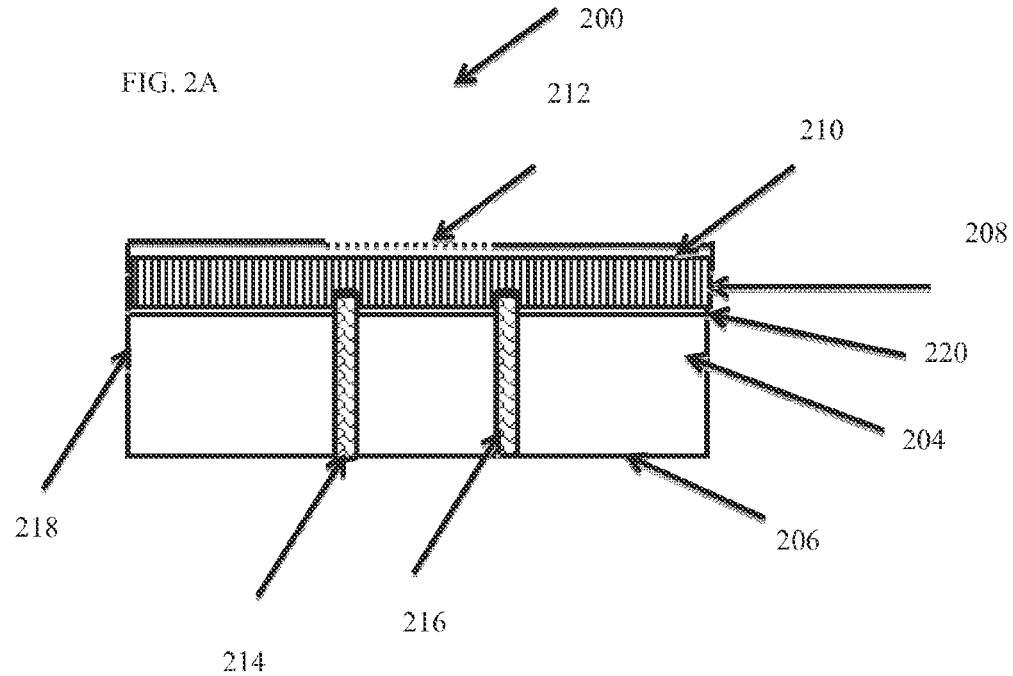
FIGS. 2A and 2B are side cross-sectional views of an illustrative device in which a fluid is guided via a conduit to a pH indication zone which includes a pH indicator, the colour of the indicator changes as an indication of the pH of the fluid.
Figure 2B:
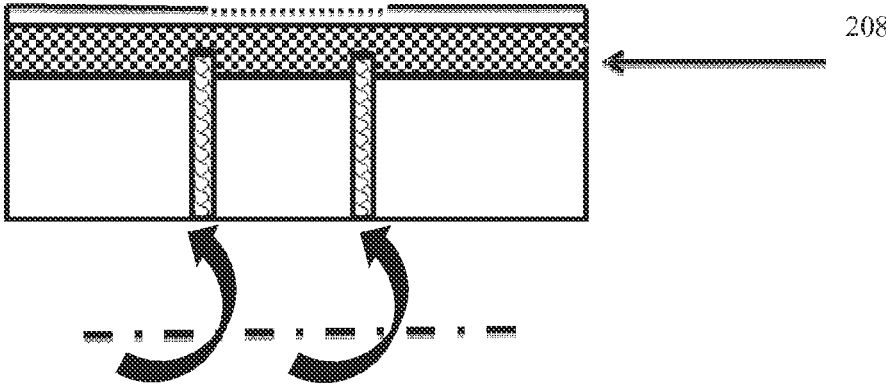

FIGS. 2 A&B illustrate a device in which temporal changes in pH can be monitored whilst the device is in situ. FIG. 2A shows a side cross-sectional view of a device 200 comprising an absorbent element 204, the lower surface of which is a fluid-contacting surface 206. The device also comprises a pH indication zone 208 which is located at or adjacent to the opposing non fluid-contacting surface 210. This pH indication zone includes a, pH indicator (e.g., as disclosed herein) which is capable of reversibly changing colour in response to changes in pH. In this illustrated embodiment, the pH indication zone 208 is disposed above the absorbent layer 204, so the pH indicator can be monitored over time without having to remove the device from any substrate that it is adhered to.

A transparent layer 212 overlays at least part of the pH indication zone, which protects the integrity of the pH indicator but still allows the user to monitor the colour of the pH indicator over time. The device includes at least one conduit that is configured to direct fluid to the pH indication zone 206, ensuring that the pH of the fluid is not materially altered as it passes through the components of the device. One or a plurality of conduits could be used. As shown in FIGS. 2 A&B, two conduits are used, although one or more other conduits could also be included. The two conduits 214 and 216 are oriented vertically and extend across the device.

The conduits are preferably sealed, so as to not exchange fluid with the absorbent layer, but are in communication with the pH indication zone 208 and direct the fluid to the pH indication zone 208 located in the upper part of the device. The conduits may be in the form of narrow capillaries which transmit the fluid towards the pH indication zone 208. The conduits may incorporate or may be formed from wicking materials, for example, woven, non-woven, knitted, tows or fibres made of suitable materials to facilitate wicking of the fluid towards the pH indication zone 208. In alternative embodiments, a pH indication zone is provided at or near a lateral edge 218 or 220 of the device and at least one conduit is provided within the device to direct the fluid laterally to the pH indication zone. In some embodiments, the pH indication zone is provided in a layer of the device which forms an outer surface of the device and a transparent cover layer is not used. In some embodiments, the conduits may take the form of a long strip or be of an elongated lozenge shape when viewed from the fluid-contacting surface. Alternatively, the conduit may be formed of crosses or quadri-lateral shapes.

Methods of immobilising a phenylazo dye on the devices illustrated in FIGS. 1 and 2 are also contemplated. An example includes the following steps:

In a first step, 25 mg of a phenylazo pH indicating dye, for example a phenylazo pH indicating dye selected from the group listed in Table 1, is reacted with 140 μl concentrated sulphuric acid for 30 mins to form a dye solution.

In a second step, 200 ml of distilled water is added to the dye solution formed in the first step.

In a third step, 406 μl of a 32% w/v solution of sodium hydroxide is added to the solution formed in the second step.

In a fourth step, 25.45 ml of a 2.36M solution of sodium carbonate is added to the solution formed in the third step.

In a fifth step, 1.35 ml of a 32% w/v solution of sodium hydroxide is added to the solution formed in the fourth step and the volume made up to 250 ml with distilled water.

In a sixth step, a material on which the pH indicating dye is to be bound is placed in the solution and left to react for approximately 1-2 hours. Examples of suitable materials include, but are not limited to: TENCEL fibres of the Durafiber product, polyurethane foam of the Allevyn product, cellulose pad of the Opsite Post-op product, or KS adhesive-coated polyurethane film, all available from Smith & Nephew, Inc. The material is then washed with distilled water until no dye is released. The material is then dried.

DETAILED DESCRIPTION SECTION 2

To provide an understanding of the devices and methods describe herein, certain illustrative embodiments and examples will now be described.

Reference numbers cited in Section 2 correspond to the reference numbers used in FIGS. 18-27.

Embodiments disclosed herein relate to apparatuses and methods to treat and/or evaluate a wound, including pump components, wound dressing components, and apparatuses that incorporate one or more pH indicators and may be used to apply negative pressure wound therapy. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, stemiotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Some of the wound dressings described herein may be used as part of a negative pressure or reduced pressure system. As is used herein, reduced or negative pressure levels, such as –X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of –X mmHg reflects absolute pressure that is X mmHg below 760 mmHg or, in other words, an absolute pressure of (760–X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than-60 mmHg).

The negative pressure range for some embodiments of the present disclosure can be approximately –80 mmHg, or between about –20 mmHg and –200 mmHg. Note that these pressures are relative to normal ambient atmospheric pressure. Thus, –200 mmHg would be about 560 mmHg in practical terms. In some embodiments, the pressure range can be between about –40 mmHg and –150 mmHg. Alternatively a pressure range of up to –75 mmHg, up to –80 mmHg or over –80 mmHg can be used. Also in other embodiments a pressure range of below –75 mmHg can be used. Alternatively, a pressure range of over approximately –100 mmHg, or even –150 mmHg, can be supplied by the negative pressure apparatus. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described herein may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092, 042, titled "Wound Dressing And Method Of Use," filed Apr. 21, 2011, published as US 2011/0282309.

FIG. 18 illustrates an embodiment of a negative pressure treatment system 100 that comprises a wound packer 102 inserted into a wound 101. The wound packer 102 may comprise porous materials such as foam, and in some embodiments may comprise one or more embodiments of wound closure devices described in further detail herein. In some embodiments, the perimeter or top of any wound closure device inserted into the wound 101 may also be covered with foam or other porous materials. A drape 104 may be placed over the wound 101, and is preferably adhered or sealed to the skin on the periphery of the wound 101 so as to create a fluid-tight seal. An aperture 106 may be made through the drape 104—which can be manually made or preformed into the drape 104—so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922, 118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins. In certain embodiments, a pH indicator dye, as will be described in more detail later in the specification, may be incorporated into the wound filler to visually indicate the pH of the wound.

Turning to FIG. 19, treatment of a wound with negative pressure in certain embodiments uses a negative pressure treatment system 501 as illustrated schematically here. In this embodiment, a wound site 510, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening-particularly in the abdominal cavity-remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 510 can be beneficial to a patient.

Accordingly, certain embodiments provide for a wound contact layer 105 to be placed over the wound site 510. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 510 or the transmittal of negative pressure to the wound site 510. Additional embodiments of the wound contact layer 105 are described in further detail below. In certain embodiments, a pH indicator dye, as will be described in more detail later in the specification, may be incorporated into the wound contact layer to visually indicate the pH of the wound.

Certain embodiments of the negative pressure treatment system 101 may also use a porous pad 103, which can be disposed over the wound contact layer 105. This pad 103 can be constructed from a porous material, for example foam, that is soft, resiliently flexible, and generally conformable to the wound site 510. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other aspects of the pad 103 are discussed in further detail below. In some embodiments, a pH indicator dye, as will be described in more detail later in the specification, may be incorporated into the porous pad to visually indicate the pH of the wound.

Preferably, a drape 107 is used to seal the wound site 510. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfoli and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections. In certain embodiments, a pH indicator dye, as will be described in more detail later in the specification, may be incorporated into the drape to visually indicate the pH of the wound.

The negative pressure system 501 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also pemlit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

FIG. 20 illustrates an embodiment of a negative pressure wound treatment comprising a wound dressing 2100 in combination with a pump 2800. As stated above, the wound dressing 2100 can be any wound dressing embodiment disclosed herein this section or elsewhere in the specification or have any combination of features of any number of wound dressing embodiments disclosed herein. Here, the dressing 2100 may be placed over a wound as described previously, and a conduit 2220 may then be connected to the port 2150, although in some embodiments the dressing 2100 may be provided with at least a portion of the conduit 2220 pre-attached to the port 2150. Preferably, the dressing 2100 is provided as a single article with all wound dressing elements (including the port 2150) pre-attached and integrated into a single unit. The wound dressing 2100 may then be connected, via the conduit 2220, to a source of negative pressure such as the pump 2800. The pump 2800 can be miniaturized and portable, although larger conventional pumps may also be used with the dressing 2100. In some embodiments, the pump 2800 may be attached or mounted onto or adjacent the dressing 2100. A connector 2221 may also be provided so as to permit the conduit 2220 leading to the wound dressing 2100 to be disconnected from the pump, which may be useful for example during dressing changes. In certain embodiments, a pH indicator dye, as will be described in more detail later in the specification, may be incorporated into the wound dressing 2100 to visually indicate the pH of the wound.

Figure 21D:
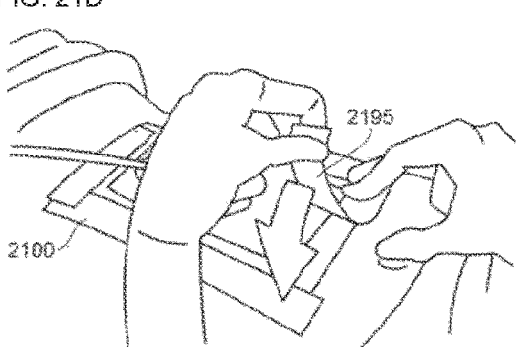

FIGS. 21A-D illustrate the use of an embodiment of a negative pressure wound treatment system being used to treat a wound site on a patient. FIG. 21A shows a wound site 2190 being cleaned and prepared for treatment. Here, the healthy skin surrounding the wound site 2190 is preferably cleaned and excess hair removed or shaved. The wound site 2190 may also be irrigated with sterile saline solution if necessary. Optionally, a skin protectant may be applied to the skin surrounding the wound site 2190. If necessary, a wound packing material, such as foam or gauze, may be placed in the wound site 2190. This may be preferable if the wound site 2190 is a deeper wound.

After the skin surrounding the wound site 2190 is dry, and with reference now to FIG. 21B, the wound dressing 2100 may be positioned and placed over the wound site 2190. Preferably, the wound dressing 2100 is placed with the wound contact layer 2102 over and/or in contact with the wound site 2190. In some embodiments, an adhesive layer is provided on the lower surface 2101 of the wound contact layer 2102, which may in some cases be protected by an optional release layer to be removed prior to placement of the wound dressing 2100 over the wound site 2190. Preferably, the dressing 2100 is positioned such that the port 2150 is in a raised position with respect to the remainder of the dressing 2100 so as to avoid fluid pooling around the port. In some embodiments, the dressing 2100 is positioned so that the port 2150 is not directly overlying the wound, and is level with or at a higher point than the wound. To help ensure adequate sealing for negative pressure wound therapy, the edges of the dressing 2100 are preferably smoothed over to avoid creases or folds. In embodiments, a pH indicator dye, as will be described in more detail later in the specification, may be incorporated into the adhesive layer and/or the wound contact layer to visually indicate the pH of the wound.

With reference now to FIG. 21C, the dressing 2100 is connected to the pump 2800. The pump 2800 is configured to apply negative pressure to the wound site via the dressing 2100, and typically through a conduit. In some embodiments, and as described above in FIG. 20, a connector may be used to join the conduit from the dressing 2100 to the pump 2800. Upon the application of negative pressure with the pump 2800, the dressing 2100 may in some embodiments partially collapse and present a wrinkled appearance as a result of the evacuation of some or all of the air underneath the dressing 2100. In some embodiments, the pump 2800 may be configured to detect if any leaks are present in the dressing 2100, such as at the interface between the dressing 2100 and the skin surrounding the wound site 2190. Should a leak be found, such leak is preferably remedied prior to continuing treatment.

Turning to FIG. 21D, additional fixation strips 2195 may also be attached around the edges of the dressing 2100. Such fixation strips 2195 may be advantageous in some situations so as to provide additional sealing against the skin of the patient surrounding the wound site 2190. For example, the fixation strips 2195 may provide additional sealing for when a patient is more mobile. In some cases, the fixation strips 2195 may be used prior to activation of the pump 2800, particularly if the dressing 2100 is placed over a difficult to reach or contoured area. Treatment of the wound site 2190 preferably continues until the wound has reached a desired level of healing. In some embodiments, it may be desirable to replace the dressing 2100 after a certain time period has elapsed, or if the dressing is full of wound fluids. During such changes, the pump 2800 may be kept, with just the dressing 2100 being changed. In certain embodiments, a pH indicator dye, as will be described in more detail later in the specification, may be incorporated into the fixation strips to visually indicate the pH of the wound.

FIG. 22 illustrates an embodiment of a negative pressure wound treatment system 5501 employing a wound dressing 5500 in conjunction with a flexible suction adapter 5512. The wound dressing 5500 may be similar to the dressings illustrated in FIGS. 20-21D. Here, the flexible suction adapter 5512 may comprise a bridge 5502 having a proximal end 5503 and a distal end 5505 and an applicator 5504 at the distal end 5505 of the bridge 5502. A connector 5504 is preferably disposed at the proximal end 5503 of the bridge 5502. A cap 5536 may be provided with the system 5501 (and can in some cases, as illustrated, be attached to the connector 5504). The cap 5536 can be useful in preventing fluids from leaking out of the proximal end 5503. The system 5501 may include a source of negative pressure such as a pump or negative pressure unit 5534 capable of supplying negative pressure. The pump optionally comprises a canister or other container for the storage of wound exudates and other fluids that may be removed from the wound. In some embodiments, the pump 5534 can be a PICO™ pump, as sold by Smith & Nephew, which does not include a canister, and wound exudate removed from the wound by negative pressure is retained within the wound dressing. The pump 5534 may be connected to the connector 5504 via a tube 5540. In use, the dressing 5500 is placed over a suitably-prepared wound, which may in some cases be filled with a wound packing material such as foam or gauze. Subsequently, with the pump 5534 connected via the tube 5540 to the connector 5504, the pump is activated, thereby supplying negative pressure to the wound. Application of negative pressure may be applied until a desired level of healing of the wound 5530 is achieved.

With reference now to FIG. 23, which shares many of the elements illustrated in the previous FIGS. 18-22, the embodiment of the wound dressing illustrated here comprises the backing layer 2140, an optional masking layer 2107, and absorbent layer 2110. All of these layers may optionally have a cut or opening made therethrough which communicate directly to an optional transmission layer 2105 so as to form an orifice 2145. Wound contact layer 2102 may be adhered to a lower surface of the backing layer 2140 to enclose the absorbent layer 2110. The suction port 2150 is preferably situated above an opening in the backing layer 2140 and communicates with the optional orifice 2145. A filter (not shown) may be provided on or below the suction port 2150 to prevent liquid from passing through the opening in the backing layer 2140. In certain embodiments, a pH indicator dye, as will be described in more detail later in the specification, may be incorporated into the filter to visually indicate the pH of the wound.

In particular for embodiments with a single port 2150, it may be preferable for the port 2150 to be located in an off-center position. Such a location may permit the dressing 2100 to be positioned onto a patient such that the port 2150 is raised in relation to the remainder of the dressing 2100. So positioned, the port 2150 and the filter may be less likely to come into contact with wound fluids that could prematurely occlude the filter so as to impair the transmission of negative pressure to the wound site.

FIG. 24 illustrates another embodiment of a wound dressing 3900. The wound dressing may comprise a release layer

3980, wound contact layer 3960, a transmission layer 3950, an acquisition distribution layer 3940, an adhesive layer 3970, an absorbent layer 3930, an obscuring layer 3920, and a backing layer 3910. One or more of the aforementioned layers may be optional. Although FIG. 24 illustrates a dressing having one particular shape, the construction of the layers can be applied to any of the embodiments identified herein this section or elsewhere in the specification. In certain embodiments, a pH indicator dye, as will be described in more detail later in the specification, may be incorporated into the release layer 3980, wound contact layer 3960, transmission layer 3950, acquisition distribution layer 3940, adhesive layer 3970, absorbent layer 3930, obscuring layer 3920, and/or the backing layer 3910 to visually indicate the pH of the wound. The dressing may incorporate one or more viewing windows (not shown) to allow a clinician and/or user to easily view any component within the dressing that may be impregnated with a pH indicator dye. Such viewing windows may be incorporated into any of the layers overlying a layer incorporating a pH indicator dye. By utilizing the one or more viewing windows, a clinician is then able to monitor the pH of the wound through visually observing changes in the color of the dressing component impregnated with a pH indicator dye.

The dressing 3900 may be connected to a port (not shown) provided over the opening 3911 in the backing layer 3910, such as described with respect to the above embodiments. At least the backing layer 3910, obscuring layer 3920, absorbent layer 3930, and acquisition distribution layer 3940 may optionally have openings underlying the port. In some embodiments, the opening 3921 in the obscuring layer may be cross-shaped. As illustrated, the cross-shaped opening 3921 may comprise four arms of roughly equal length extending outward from a central point of intersection of the arms, wherein the sides of each arm are angled or arced such that the far end of each arm is wider than the end closest to the intersection. The far ends of the four arms may comprise arcs, for example four arcs from a single circle, giving the cross a rounded shape. The opening 3911 in the backing layer 3910, opening 3931 in the absorbent layer 3930, and opening 3941 in the acquisition distribution layer 3940 may be aligned with the central intersection point of the cross-shaped opening 3921. The openings 3911, 3931, and 3941 may be the same size or of varying sizes.

The backing layer 3910 (as well as the backing layer of previously described embodiments) may comprise, in some embodiments, EU33 film and may optionally have a pressure-sensitive adhesive provided on a lower surface thereof. For example, the adhesive may be a water dispersible acrylic adhesive, for example KS. The adhesive may be able to be pattern spread, and may be hydrophilic.

The obscuring layer 3920 may be provided to increase patient comfort by masking the presence of wound exudate absorbed by the inner layers of the dressing. The obscuring layer 3920 may have an outer perimeter that is spaced 1 mm, or approximately 1 mm, or 0.5 mm to 3 mm, or approximately 0.5 to approximately 3 mm, beyond the adjacent perimeter edge of the dressing layer or layers provided beneath it, for example the absorbent layer 3930, AOL 3940, and/or transmission layer 3950. The obscuring layer 3920 may be provided with a plurality of viewing windows 3922 which may be used to assess the spread of exudate across the dressing 3900. The cross-shaped opening 3921 may be used as a viewing window to ascertain the level of saturation of the layer or layers underlying an attached port. The width of the cross-shaped opening 3921 may be greater than the width of an attached port to enable such assessment. Some embodiments of the obscuring layer 3920 (including other embodiments of the obscuring layer previously described) may comprise polypropylene spunbond material of suitable colors such as described above, including medical blue. Further, some embodiments of the obscuring layer 3420 may comprise a hydrophobic additive or coating.

The absorbent layer 3930 may be configured to absorb and retain exudate from a patient's wound. The absorbent layer 3930 will preferably be constructed from a material which has good absorbent qualities under negative pressure. In some embodiments (including any of the earlier described embodiments), the absorbent layer may comprise cellulose fibers or air-laid materials. Some embodiments may comprise a cellulose fibers with 40-80% superabsorbent particles (SAP), for example 40%-60% (or about 40% to about 60%) SAP or 60%-80% (or about 60% to about 80%) SAP. Heat fusible fibers can optionally be used to assist in holding the structure of the absorbent pad together. Some embodiments may combine cellulose fibers and air-laid materials, for example as a hybrid bonded airlaid composite in the range of 400-500 gsm (or about 400 to about 500 gsm), for example 460 (or about 460) gsm. The absorbent layer 3930 may include polyacrylate superabsorber powder to increase the absorbent capabilities of the material. Some embodiments of the absorbent layer 3930 comprise a tissue dispersant layer. This may, in some embodiments, be provided along the lower surface of the layer, resulting in an asymmetric construction of the absorbent layer. The tissue dispersant layer may comprise a heat fusible binder to aid in holding the layer structure together. The tissue dispersant layer may provide the advantage of enabling fluid transport. In some embodiments, the tissue dispersant layer may comprise a hot melt adhesive such as ethylene vinyl acetate (EVA), for example applied as a solution to cellulose fibers of the absorbent layer.

The adhesive layer 3970 may bond an upper surface of the acquisition distribution layer 3940 to a lower surface of the absorbent layer 3930. As illustrated, in some embodiments the adhesive layer 3970 may comprise an adhesive web or net. In other embodiments, the adhesive layer 3970 may comprise adhesive tape. Yet other embodiments may employ a hot melt adhesive, such as EVA. For example, EVA powder may be sprinkled over the ADL 3940, which may then be heat bonded to the adhesive layer 3970. In some embodiments the acquisition distribution layer 3940 and the absorbent layer 3930 may be stitched or sewn together, and the adhesive layer 3970 may comprise suitable fibers, strands, or threads. Preferred embodiments of the adhesive layer 3970 are hydrophilic so as not to affect the transport of water and/or water-based solutions between the acquisition distribution layer 3940 and absorbent layer 3930. In some embodiments, the adhesive layer may comprise a fine sprinkle of adhesive powder such that the acquisition distribution layer 3940 and absorbent layer 3930 are not bonded together across the entire upper and lower surfaces, respectively, but may be merely tacked together in a number of locations. However, some embodiments of the dressing may be constructed without the use of an adhesive between the acquisition distribution layer 3940 and absorbent layer 3930.

The acquisition distribution layer (ADL) 3940 may be constructed so as to advantageously horizontally wick fluid, such as wound exudate, as it is absorbed upward through the layers of the dressing 3900. Such lateral wicking of fluid may allow maximum distribution of the fluid through the absorbent layer 3930, enabling the absorbent layer 3930 to reach its full holding capacity. Some embodiments of the ADL 3440 (including any embodiments of the ADL previously described) may comprise cellulose in the range of 40-160 gsm (or about 40 to about 160 gsm), for example 80 (or about 80) gsm. The ADL may be constructed from a material which resists compression under the levels of negative pressure commonly applied during negative pressure therapy.

Some embodiments of the dressing 3900 may optionally comprise a spacer or transmission layer 3950. The transmission layer 3950 may comprise a porous material or 3D fabric configured to allow for the passage of fluids therethrough away from the wound site and into the upper layers of the dressing 3400. In particular, the transmission layer 3450 should remain open under the typical pressures that will be applied during negative pressure wound therapy as described above, so that the whole wound site sees an equalized negative pressure. In some embodiments, the acquisition distribution layer 3940 may be sufficient to maintain even transmission of negative pressure throughout the dressing 3900 and the transmission layer 3950 may be excluded. An outer perimeter of the transmission layer may be spaced 5 mm, or approximately 5 mm, or 2 mm to 8 mm, or approximately 2 mm to approximately 8 mm, inward of the adjacent perimeter edge of the dressing layer positioned above the transmission layer, for example the ADL 3940 or absorbent layer 3930.

The dressing 3900 may optionally comprise a wound contact layer 3960 for sealing the dressing 3900 to the healthy skin of a patient surrounding a wound area. The wound contact layer 3960 may comprise flexible polyurethane film, and may be provided with a silicone adhesive on a lower surface thereof. The wound contact layer 3960 may be perforated to allow for the transmission of fluids such as wound exudate therethrough, so that the fluids may be passed through or retained by the inner layers of the dressing 3900. Prior to use, the wound contact layer 3960 may be protected by a protective release layer 3980, which may be provided with at least one set of flaps 3981 for removing or peeling off the release layer 3980.

Further details regarding wound dressings that may be utilized with a negative pressure system, and further details regarding negative pressure systems and their methods of use are described in: PCT App. No. PCT/IB2013/002060, titled "Wound Dressing and Method of Treatment," filed Jul. 31, 2013, U.S. Pat. No. 8,791,315, titled Systems and Methods for Using Negative Pressure Wound Therapy to Manage Open Abdominal Wounds," filed Sep. 20, 2010, and U.S. patent application Ser. No. 13/092,042, titled "Wound Dressing and Method of Use," filed Apr. 21, 2011, all of which are hereby incorporated by reference in their entirety.

FIG. 25A depicts a device 600 having a wound-contacting surface 602 and an opposing non-wound-contacting surface 604. FIG. 25B depicts the device 600 in situ on a wound 606. The device 600 can be made of any material that is suitable for contact with the wound. Wound contact layers are known in the art and include the PROFORE wound contact non-adherent dressing (Smith and Nephew, Inc), the MEPITEL Soft Silicone Wound Contact Layer (MOInlycke Health Care US, LLC), CUTICERIN, a low-adherent acetate gauze (Smith and Nephew, Inc) and the DRYNET Wound Veil (Smith and Nephew, Inc). Conventionally wound contact layers are characterised by being conformable, transparent, non-adherent sheets that are placed on or in an open wound bed to protect the tissue from direct contact with other agents or dressings applied to the wound. Wound contact layers are also typically porous to allow wound exudate to pass through for absorption by an overlying, secondary dressing.

Device 600 may be porous and can be a made of a non-woven, a perforated film or a mesh. Alternatively, in applications in which the device 600 is to be transiently placed into the wound to measure pH between dressing changes, the device 600 may be non-porous.

The device further includes a pH indicator 608 which is applied to one or both of surfaces 602 and/or 604. The pH indicator is immobilised on or adjacent to the surface 602 and/or 604 so that it is not washed away by the wound exudate. As described elsewhere in the Specification, the pH indicator may be utilized in combination with the dressings disclosed in FIGS. 18-24. In embodiments, the pH indicator may be incorporated into any of the various components disclosed in the dressings of FIGS. 18-24.

In embodiments, the pH indicator is chemically bound to the surface 602 and/or 604. For example, the pH indicator is covalently bound to the surface 602 and/or 604. In alternative embodiments, the surface 602 and/or 604 is provided within an adhesive and the pH indicator is covalently bound to reactive moieties within the adhesive. For example, a conventional acrylic adhesive, such as KS (Smith & Nephew, Inc) used in the construction of wound dressings contains residues of 2-hydroxy-ethylmethacrylate, which provide a reactive functional hydroxyl (OH) group, pendant to the polymer backbone, to which the pH indicator can be covalently bound. Other suitable adhesives include acrylic-based adhesives with pendant OH or COOH groups.

In alternative embodiments, the pH indicator is physically entrapped at or adjacent to the surface. For example, the pH indicator is entrapped within a soluble microsphere, for example a microsphere made of a hydrophilic soluble polymer. Alternatively, the pH indicator is retained between layers of a soluble material, such as a polyvinyl alcohol film which is positioned adjacent to the surface.

In embodiments on which the pH indicator is only applied to one surface of a non-porous device, then an indication, for indicating which side the pH indicator is applied to may be provided. This indication allows the user to appropriately orient the device during placement on or in a wound to ensure that the surface which has the pH indicator provides the wound-contacting surface.

The pH indicator may be applied across substantially the entire surface 602 and/or 604, to allow the pH across the entire wound bed to be mapped. Alternatively, the pH indicator may be applied to discrete areas of surfaces 602 and/or 604. The pH indicator exhibits a first colour prior to contact with a wound exudate and changes colour as a function of the pH of the wound. The first colour of the pH indicator may be colourless.

The pH indicator is capable of reversibly changing colour in response to pH. In embodiments, the pH indicator is a phenylazo compound. In certain embodiments, the phenylazo compound is selected from the group listed in Table 1. In some embodiments, the phenylazo compound is not 2-[4(2-hydroxyethylsulfonyl)-phenyl]diazenyl]-4-methylphenol. In some embodiments, the phenylazo compound is not hydroxy-4-[4[(hydroxyethylsulphonyl)-phenylazo]-napthalene-2-sulphonate. In some embodiments, the phenylazo compound is not 2-fluoro-4-[4[(2-hydroxyethanesulphonyl)-phenylazo]-6-methoxy phenol. In some embodiments, the phenylazo compound is not 4-[4-(2-hydroxyethylsulphonyl)-phenylazo]-2,6-dimethoxyphenol. In certain embodiments, the phenylazo compound is 2-[4(2-hydroxyethyl sulfonyl)-phenyl]diazenyl]-4-methylphenol. In some embodiments, the pH indicator includes a plurality of phenylazo compounds. In some embodiments, the pH indicator includes a combination of phenylazo compounds, for example a combination of phenylazo compounds selected from the group listed in Table 1. In some embodiments, the pH indicator includes a combination of two phenylazo compounds. In some embodiments, the pH indicator includes a combination of three phenylazo compounds. In some embodiments, 2-[4(2-hydroxyethylsulfonyl)-phenyl]diazenyl]-4-methylphenol is combined with at least one other phenylazo compound selected from the group listed in Table 1. The ratio of phenylazo compound may be 1:1, but other ratios are envisaged, for example, but in no way limiting, 0.5:1.5 or 1.5:0.5 or 1:2 or 2:1 or 1:0.1. In alternative embodiments, the pH indicator includes at least one phenylazo compound, for example a phenylazo compound selected from the group listed in Table 1 and at least one other compound that is not a phenylazo compound. In certain embodiments, the pH indicator is not a phenylazo compound.

As shown in FIG. 26, the device 200 comprises a pH indicating dye for indicating the pH of the wound exudate at the wound surface. FIG. 26A shows a side cross-sectional view of a device 200 which comprises a wound-contacting surface 202 and an opposing non-wound-contacting surface 204. A pH indicator 208 is provided on surface 202. The first colour of the pH indicator, prior to contact with wound exudate, may be colourless. In some embodiments, the device is an integral part of the wound dressing and functions as the wound-contacting layer. In alternative embodiments, the device is used in conjunction with a clinician's choice of a secondary dressing. For example, the non-wound-contacting surface 204 can be adhered to the wound-facing surface of a secondary dressing. Alternatively, the device 200 can be placed in or on the wound and the secondary dressing secured to device 200 using, for example, adhesive tape or adhesive film.

FIG. 26B-D illustrate changes in wound pH over time and the reversible response of the pH indicator 206. In FIG. 26B, the wound dressing has been placed on the wound 206 and the pH indicator 208 has changed colour in response to a change in pH of the wound 206 exudate. For example, if the wound exudate has pH X, the pH indicator 208 will change colour to the colour that is correlated with pH X. Because the wound dressing is in situ this colour change will not be visible unless the dressing is removed or the other constituent parts of dressing are transparent. In FIG. 26C, the pH of the wound exudate has altered to pH Y, and the pH indicator 208 changes colour in response to this pH change, with the colour of the pH indicator changing colour to the colour that is correlated with pH Y. Again, because the wound dressing is in situ this colour change will not be visible unless the dressing is removed. In FIG. 26D, the pH of the wound has reverted to pH X and the pH indicator 208, due to its reversibility, has reverted to colour X. At this point, the dressing is removed and the clinician can correlate the colour X with a pH scale and determine that the pH is pH X. This dressing thus provides a "snap shot" of the pH at the time of dressing removal. The clinician will be unaware that the pH changed to pH Y during the time that the dressing was in place.

FIG. 27 illustrates a wound dressing in which temporal changes in pH can be monitored whilst the dressing is in situ on the wound. FIG. 27A shows a side cross-sectional view of a wound dressing 300 comprising an absorbent element 304, the lower surface of which is a wound contacting surface 306. The dressing also comprises a pH indication zone 308 which is located at or adjacent to the opposing non wound-contacting surface 310. This pH indication zone includes a pH indicator (e.g., as disclosed herein) which is capable of reversibly changing colour in response to changes in pH. In this illustrated embodiment, the pH indication zone 308 is disposed above the absorbent layer 304, so the pH indicator can be monitored over time without having to remove the dressing from the patient.

A transparent layer 312 overlays at least part of the pH indication zone, which protects the integrity of the pH indicator but still allows the clinician to monitor the colour of the pH indicator over time. The dressing includes at least one conduit that is configured to direct wound exudate from the wound to the pH indication zone 308, ensuring that the pH of the wound exudate is not materially altered as it passes through the components of the wound dressing. One or a plurality of conduits could be used. As shown in FIG. 27, two conduits are used, although one or more other conduits could also be included. The two conduits 314 and 316 are oriented vertically and extend across the absorbent layer. The conduits are preferably sealed, so as not to exchange fluid with the absorbent layer, but are in communication with the pH indication zone 308 and direct the wound exudate to the pH indication zone 308 located in the upper part of the dressing. The conduits may be in the form of narrow capillaries which transmit the fluid towards the pH indication zone 308. The conduits may incorporate or may be formed from wicking materials, for example, woven, non-woven, knitted, tows or fibres made of suitable materials to facilitate wicking of the wound exudate towards the pH indication zone 308. In alternative embodiments, a pH indication zone is provided at or near a lateral edge 318 or 320 of the dressing and at least one conduit is provided within the dressing to direct the wound exudate laterally to the pH indication zone. In some embodiments, the pH indication zone is provided in a layer of the dressing which forms an outer surface of the dressing and a transparent cover layer is not used. In some embodiments, the conduits may take the form of a long strip or be of an elongated lozenge shape when viewed from the wound contact surface. Alternatively, the conduit may be formed of crosses or quadrilateral shapes. In this way it is possible to transmit wound exudate across the area of the wound to the pH indication zone.

Whilst FIG. 27 depicts a discrete pH indication zone that is provided above the absorbent element, it is envisaged that the pH indication zone can be provided in alternative locations within the dressings. It is also envisaged that the pH indication zone can exhibit additional functionality. For example, the dressing can comprise any combination of the following components; a top film, a super-absorbent layer, an absorbent layer, a spacer layer and a wound contact layer, with each component being present in the singular or plural, and the pH indication zone is or is provided within at least one of these layers. In alternative embodiments, an adhesive layer associated with at least one of these layers consists of or comprises the pH indication zone. Example wound dressing assemblies include, but are not limited to;

(a) Top film; pH indication zone; wound contacting layer;
  (b) Top film; pH indication zone; spacer layer; wound contacting layer;
  (c) Top film; spacer layer (=pH indication zone); wound contacting layer;
  (d) Top film; pH indication zone; spacer layer; absorbent layer; wound contacting layer;
  (e) Top film; pH indication zone; spacer layer; super-absorbent layer; absorbent layer, wound contacting layer;
  (f) Top film; pH indication zone; spacer layer; super-absorbent layer; wound contacting layer;
  (g) Top film, pH indication zone; absorbent layer; wound contacting layer;
  (h) Top film, pH indication zone; super-absorbent layer; wound contacting layer.

Methods of immobilising a phenylazo dye on the devices and/or wound dressings illustrated in FIGS. 18-27 are also contemplated.

An example includes the following steps:

In a first step, 25 mg of a phenylazo pH indicating dye, for example a phenylazo pH indicating dye selected from the group listed in Table 1, is reacted with 140 µl concentrated sulphuric acid for 30 mins to form a dye solution.

In a second step, 200 ml of distilled water is added to the dye solution formed in the first step.

In a third step, 406 µl of a 32% w/v solution of sodium hydroxide is added to the solution formed in the second step.

In a fourth step, 25.45 ml of a 2.36M solution of sodium carbonate is added to the solution formed in the third step.

In a fifth step, 1.35 ml of a 32% w/v solution of sodium hydroxide is added to the solution formed in the fourth step and the volume made up to 250 ml with distilled water.

In a sixth step, a material on which the pH indicating dye is to be bound is placed in the solution and left to react for approximately 1-2 hours. Examples of suitable materials include, but are not limited to: TENCEL fibres of the Durafiber product, polyurethane foam of the Allevyn product, cellulose pad of the Post-op product, or K5 adhesive-coated polyurethane film, all available from Smith & Nephew, Inc. The material is then washed with distilled water until no more dye is released. The material is then dried.

EXAMPLES SECTION 1 AND 2

A sample of the pad from an Opsite Post-Op dressing (Smith & Nephew, Inc) was prepared in different samples, and each sample was covalently bound with one or a combination of phenylazo dyes, selected from GJM-514, GJM-492, GJM-546, and GJM-534. The structures of these dyes are shown in Table 1. It was discovered that these dyes had colour-changing characteristics that varied according to changes in pH. The Post-Op samples were covalently bound with GJM-514 alone or with GJM-514 combined with one of GJM-492, GJM-546 and GJM-534 using the method as described above in relation to FIGS. 1-3. The Post-Op material was exposed to buffered solutions having a pH of 5, 5.5, 6, 6.5, 7, 7.5, 8, 8.5, 9 and 9.5. Photographs were taken of each sample to demonstrate the visible changes in colour. A colour pen (for example, Dr Lange Colour Pen), a pen-type colorimeter was used to detect marginal colour changes which are undetectable by the human eye. Colour pen measurements include, but are not limited, to three different readings: the L*, a* and b* values.

L* represents the lightness/luminosity of the colour
    L*=0 is black
    L*=100 is diffuse white
  a* is the colour's position between red/magenta and green
    A positive a* value indicates magenta
    A negative a* value indicates green
  b* is the colours position between yellow and blue
    a positive b* value indicates yellow
    a negative b* value indicates blue

Example 1: Post-Op Pad Dyed with GJM-514

A sample of the pad from an Opsite Post-Op dressing (Smith & Nephew) was covalently bound with the dye GJM-514 was exposed to buffered solutions at pH 5-pH 9.5. The panel of photographs in FIG. 3 demonstrates the colour change of GJM-514 over this pH range, going from yellow in colour (at pH5) to pink (at pH 9.5).

Table 2 illustrates the colour pen measurements (L*, a* and b*) of the colour of the GJM-514 dye over a pH range of pH 5-pH 9.5. An optimal dye for use as a pH indicator is one which demonstrates a linear change in a measurement of a specific parameter of colour (for example L*, a* or b*) over a broad pH range. Outside of the linear region, the dye is either unable to change colour in response to a change in pH or the change in colour is so minimal that it is undetectable.

TABLE 2

| pH | L* | a* | b* |
|---|---|---|---|
| 5 | 63.3 | −1.9 | 41.5 |
| 5.5 | 69.2 | 0.3 | 36.2 |
| 6 | 65.7 | 1.4 | 35.1 |
| 6.5 | 59.3 | 1.2 | 35.5 |
| 7 | 56.9 | 2 | 33.6 |
| 7.5 | 55.4 | 4.8 | 30.6 |
| 8 | 46.8 | 10.4 | 21.4 |
| 8.5 | 43.3 | 15.6 | 15.4 |
| 9 | 40.2 | 21.3 | 8.7 |
| 9.5 | 37.5 | 24.8 | 4.9 |

Figure 4A:
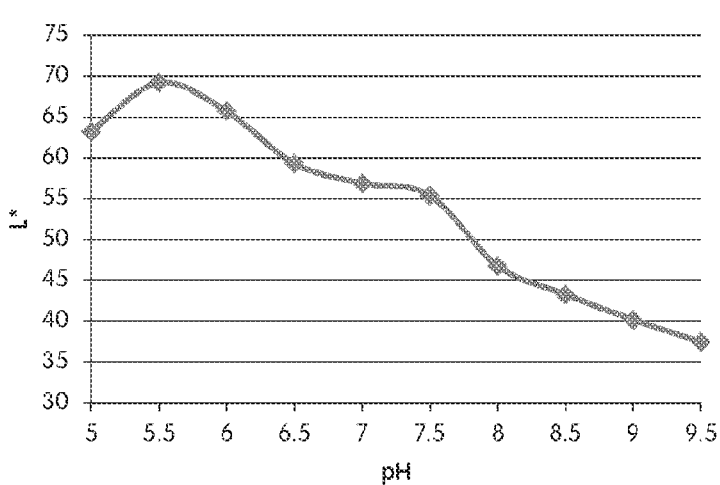
Figure 4B:
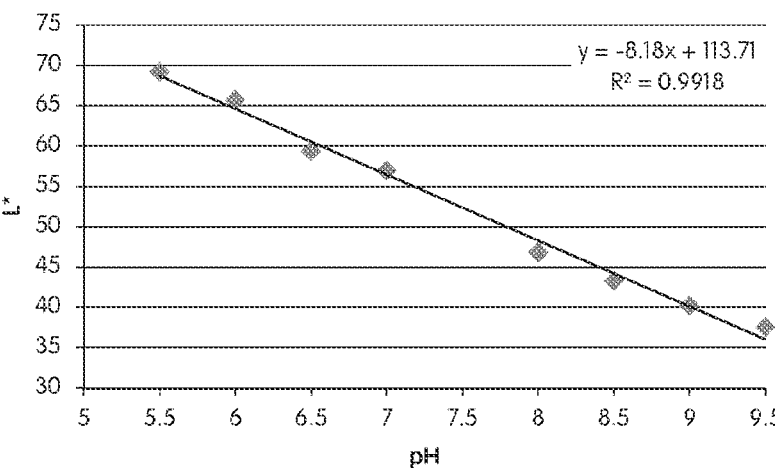

FIGS. 4A and 4B illustrate the L* measurements taken of the GJM-514 dye with the colour pen presented graphically. The L* results of FIG. 4A show that the L* value decreases from pH 5.5 to pH 9.5 as the luminosity of the dye decreases relative to the increasing pH. These results have also been plotted in FIG. 4B and demonstrate a linear region between pH 7.5 and 9.5. The trend line has a gradient of −8.18 and an R2 value of 0.9918.

Figure 4C:
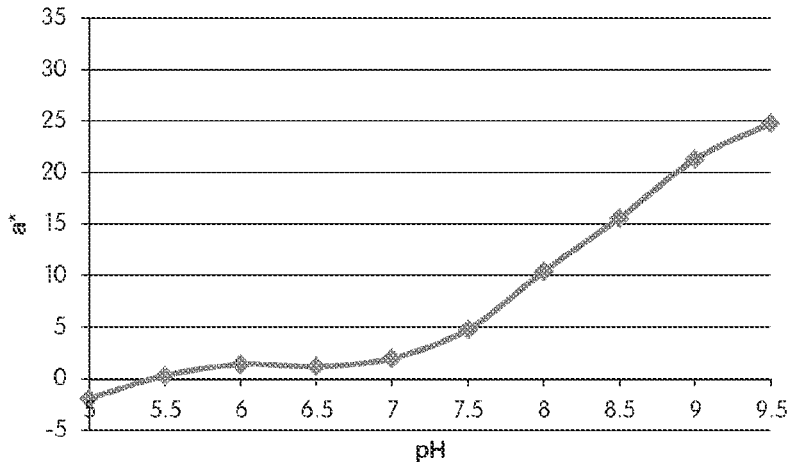
Figure 4D:
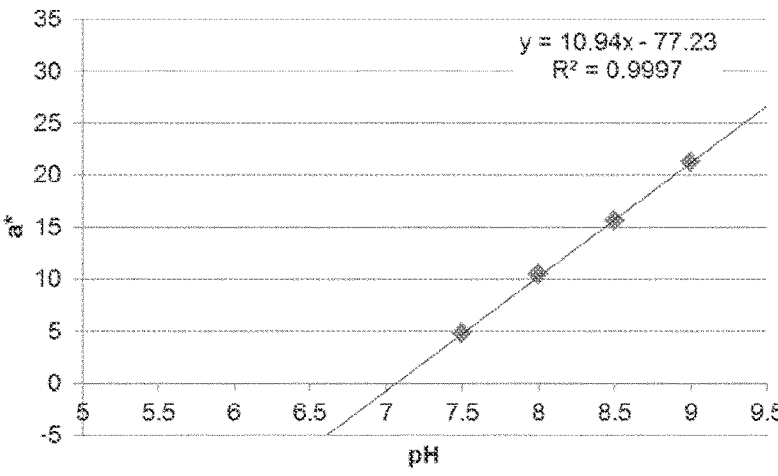

FIGS. 4C and 4D illustrate the a* measurements taken of the GJM-514 dye with the colour pen presented graphically. FIG. 4C illustrates the a* measurements taken at various pH values between pH 5-pH 9.5. FIG. 4D illustrates the a* measurements at various pH values•over the linear portion of the trend line, between pH 7.5 and 9. The trend line has a gradient of 10.94 and an $R^2$ value of 0.9997.

Figure 4E:
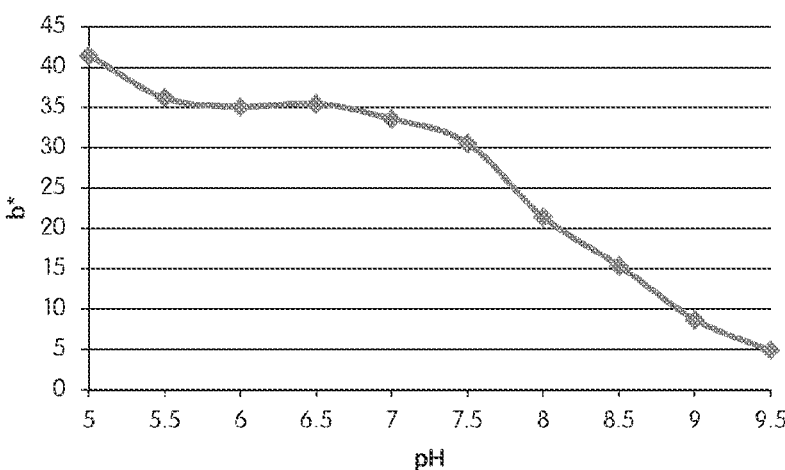
Figure 4F:
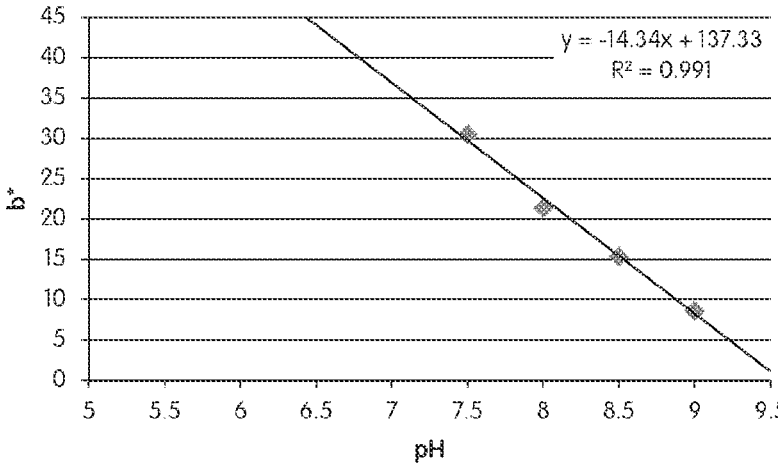

FIGS. 4E and 4F illustrate a graphical representation of the b* measurements taken of the GJM-514 dye. FIG. 4E shows the b* measurements taken at various pH values between pH 5-pH 9.5. FIG. 4E illustrates the b* measurements at various pH values over the linear portion of a trend line. From FIG. 4E it can be seen that the values are fairly consistent and steady between pH 5.5 and pH 7, and after pH 7 they start to decrease. FIG. 4F shows that the results give a linear downward trend between pH 7.5 and pH 9, with a gradient of −14.34 and an $R^2$ value of 0.991.

Taking into account the colour pen results and photographs of the samples, the most accurate working range for GJM514 is between pH 7.5 and pH 9. The linear trend line of the b* measurements has a steeper gradient (−14.34) than the a* measurements (10.94) and therefore b* would be used preferentially to give a more accurate indication of the pH of the dressing when using an optical reader rather than the human eye.

Example 2: Post-Op Pad Dyed with GJM-514:GJM-492 (1:1)

A sample of the pad from an Opsite Post-Op dressing (Smith & Nephew) was covalently bound with the dye GJM-514:GJM-492 at a 1:1 ratio was exposed to buffered solutions at pH 5-pH 9.5. The panel of photographs in FIG. 5 demonstrates the colour change over this pH range, going from yellow in colour (at pH 5) to orange in colour (at pH 9.5).

Table 3 illustrates the colour pen measurements (L*, a* and b*) of the colour of the GJM-514:GJM-492 dye combination over a pH range of pH 5-pH 9.5.

TABLE 3

| pH | L* | a* | b* |
|---|---|---|---|
| 5 | 53.8 | 11.5 | 43.3 |
| 5.5 | 50.7 | 17.4 | 37.9 |
| 6 | 45.3 | 23.9 | 37.5 |
| 6.5 | 40.4 | 29.9 | 35.4 |
| 7 | 39.7 | 30.9 | 33.8 |
| 7.5 | 39.9 | 30.4 | 29.9 |
| 8 | 34.5 | 31.5 | 29.2 |
| 8.5 | 37.4 | 28 | 29.3 |
| 9 | 33.8 | 30.7 | 25 |
| 9.5 | 33.1 | 31.3 | 23.2 |

Figure 6A:
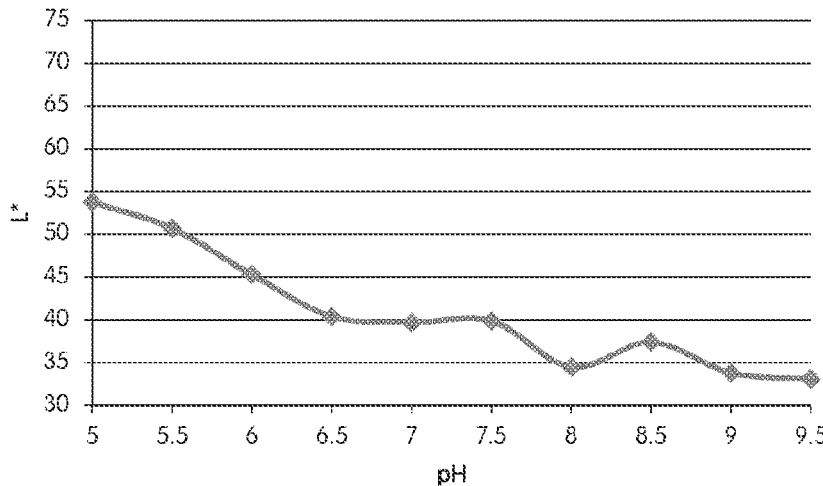

FIG. 6A illustrates the L* measurements taken with the colour pen presented graphically. The L* results presented in FIG. 6A show that the value for L* decreases over the range of pH 5.5 to pH 9.5 but does not follow a linear downward trend. The L* value is therefore not considered to be a reliable indicator of the colour change of this dye combination over the pH range tested.

Figure 6B:
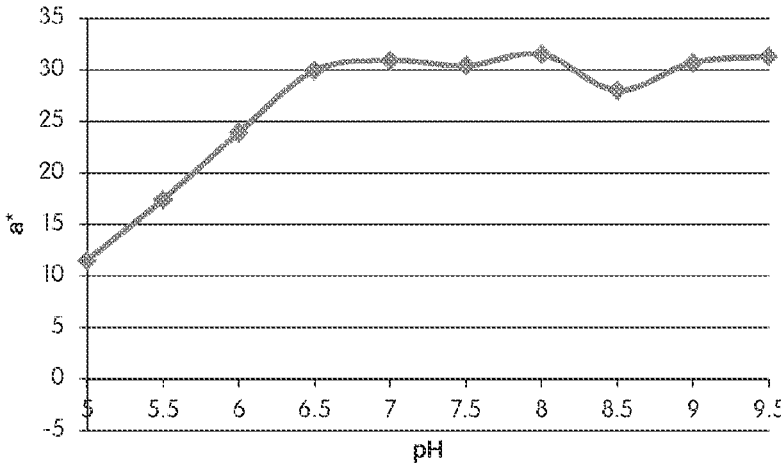
Figure 6C:
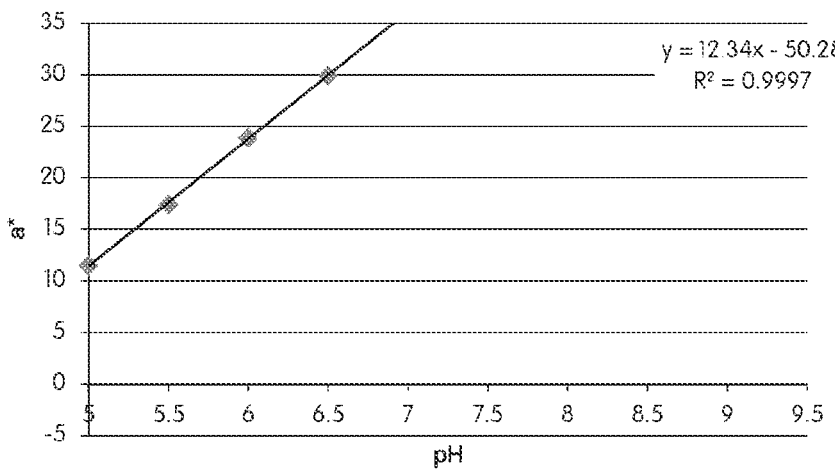

FIGS. 6B and 6C illustrate the a* measurements taken with the colour pen presented graphically. FIG. 6B illustrates the a* measurements taken at various pH values between pH 5-pH 9.5. FIG. 6C illustrates the a* measurements at various pH values over the linear portion of a-trend line. An upwardly linear trend (gradient=12.34, $R^2$=0.9997) is identifiable between pH 5 and 6.5, demonstrating that there is a detectable change in colour along the red/magenta to green scale over this pH range.

Figure 6D:
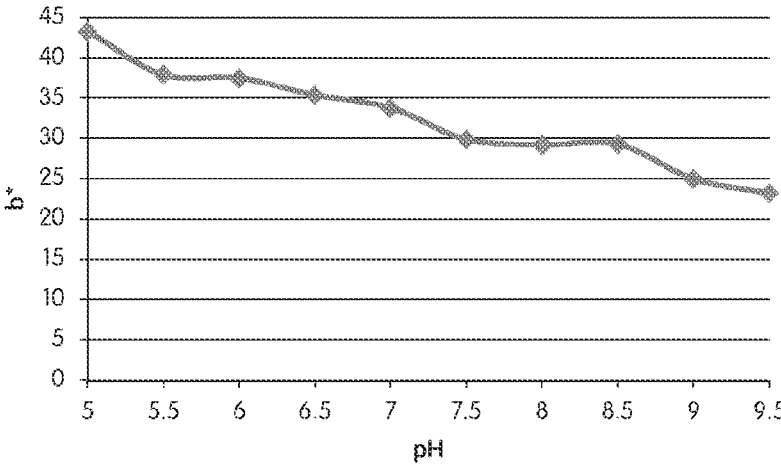

FIG. 6D illustrates a graphical representation of the b* measurements taken with the colour pen. It can be seen that there is not a significant change in b* value, but there is a downwards trend.

Taking into account the colour pen results and photographs of the samples, the working range for this dye combination appears to be between pH 5 and pH 6.5. With a* giving a useable trend line for this region that could be used to estimate the pH from the material colour.

Example 3: Post-Op Pad Dyed with GJM-514:GJM-546 (1:1)

A sample of the pad from an Opsite Post-Op dressing (Smith & Nephew) was covalently bound with the dye GJM 514:546 at a 1:1 ratio was exposed to buffered solutions at pH 5-pH 9.5. The panel of photographs in FIG. 7 demonstrates the colour change over this pH range, going from orange in colour (at pH 5) to pink (at pH 9.5).

Table 4 illustrates the colour pen measurements (L*, a* and b*) of the colour of the GJM-514:GJM-546 dye combination over a pH range of pH 5-pH 9.5.

TABLE 4

| pH | L* | a* | b* |
|---|---|---|---|
| 5 | 45.7 | 22.7 | 44.1 |
| 5.5 | 43.4 | 22.8 | 40.1 |
| 6 | 43.9 | 24.8 | 34.6 |

TABLE 4-continued

| pH | L* | a* | b* |
|---|---|---|---|
| 6.5 | 36.5 | 27 | 25 |
| 7 | 33.4 | 25.7 | 16 |
| 7.5 | 28.3 | 27.8 | 7.1 |
| 8 | 26.9 | 26.6 | 1.3 |
| 8.5 | 25.6 | 29.3 | −0.7 |
| 9 | 24.5 | 28.8 | −2.3 |
| 9.5 | 23.9 | 29.5 | −3.8 |

Figure 8A:
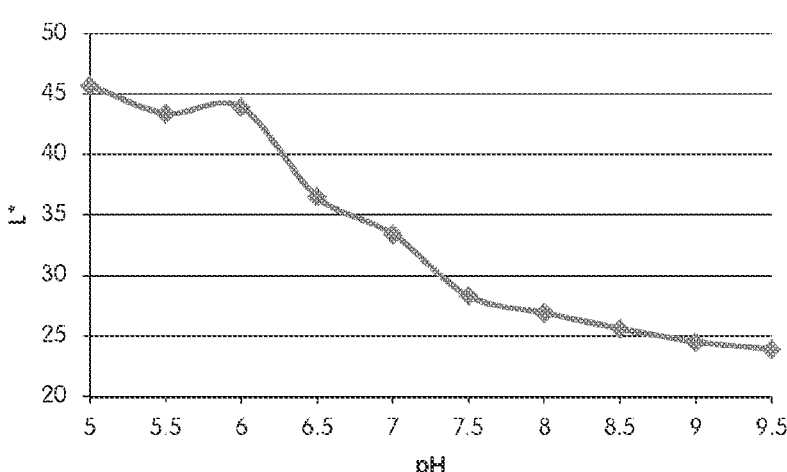
Figure 8B:
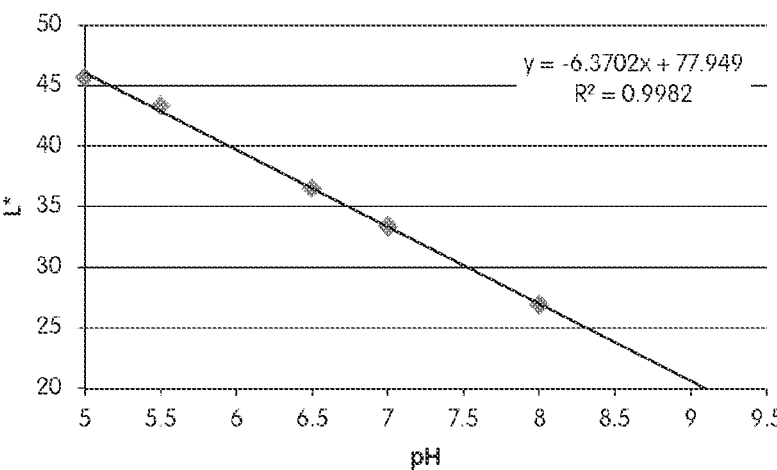

FIGS. 8A and 8B illustrate a graphical representation of the L* measurements taken with the colour pen. FIG. 8A shows all data points whilst FIG. 8B is a re-plot of the data points in the linear region between pH S to pH 8. The trend line has a gradient of −6.3702 with an $R^2$ value of 0.9982.

Figure 8C:
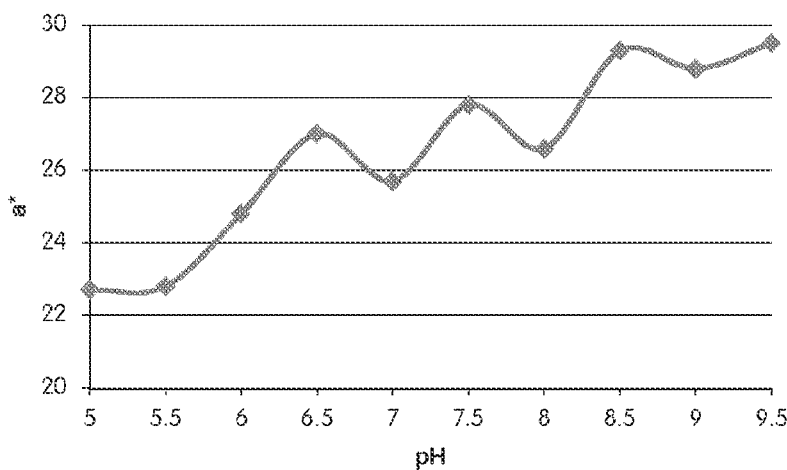

FIG. 8C illustrate the a* measurements taken with the colour pen presented graphically over the pH 5-pH 9.5 range. The results are too variable for the a* measurement to be considered of use in reliably measuring a colour change in the GJM 514:546 dye combination in response to changes in pH.

Figure 8D:
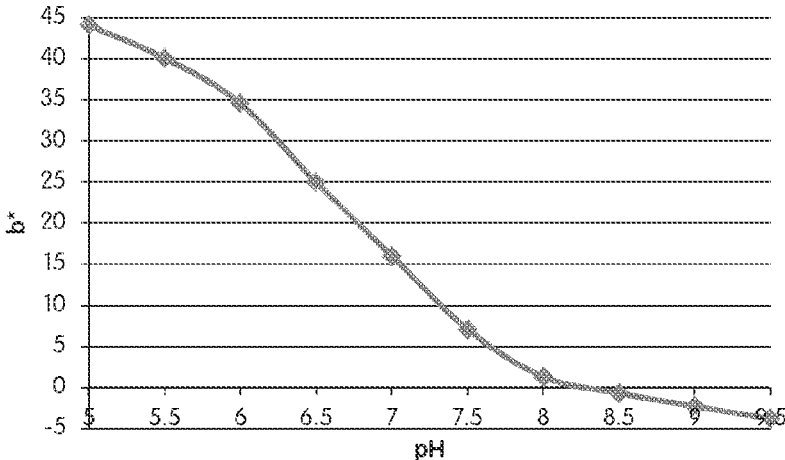
Figure 8E:
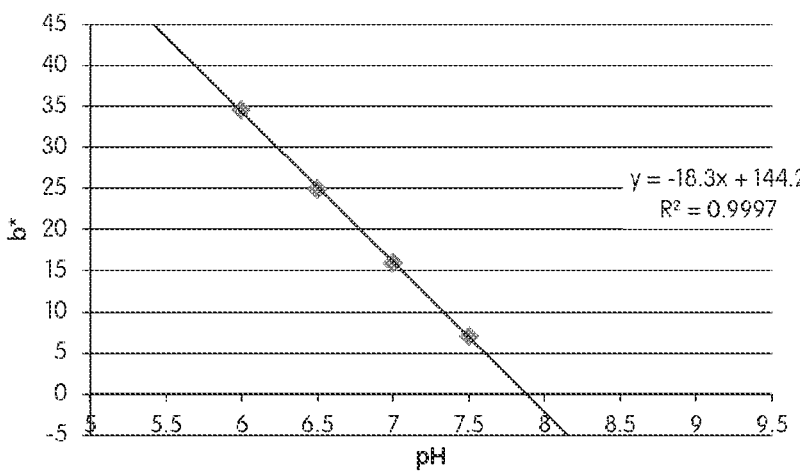

FIGS. 8D and 8E illustrate a graphical representation of the b* measurements taken with the colour pen. FIG. 8E shows the b* measurements taken at various pH values between pH 5-pH 9.5 and it can be seen that the results follow a downward trend from—pH 5 to pH 8, but it appears to plateau after pH 8. FIG. 8E illustrates the b* measurements at various pH values over the linear portion of a trend line which has a gradient of −18.3 and an $R^2$ of 0.9997. As the b* results gave a steeper gradient it is believed that monitoring the b* value would give a more accurate reading of the pH from the dressing colour. The working range for this dye combination appears to be pH 6 to pH 7.5.

Example 4: Post-Op Pad Dyed with GJM 514:534 (1:1)

A sample of the pad from an Opsite. Post-Op dressing (Smith & Nephew) was covalently bound with the dye GJM-514:534 at a 1:1 ratio was exposed to buffered solutions at pH 5-pH 9.5. The panel of photographs in FIG. 9 demonstrates the colour change over this pH range, going from yellow in colour (at pH 5) to red in colour (at pH 9.5).

Table 5 illustrates the colour pen measurements (L*, a* and•b*) of the colour of the GJM-514:GJM-534 dye combination over a pH range of pH 5-pH 9.5

TABLE 5

| pH | L* | a* | b* |
|---|---|---|---|
| 5 | 53.4 | 6.1 | 50.3 |
| 5.5 | 52.3 | 7.5 | 45.4 |
| 6 | 53.8 | 7.6 | 46.1 |
| 6.5 | 49.7 | 9.8 | 35.4 |
| 7 | 43.1 | 16.2 | 29.9 |
| 7.5 | 37.4 | 16.2 | 18.9 |
| 8 | 33.4 | 20.4 | 11.9 |
| 8.5 | 31.9 | 22.8 | 5.3 |
| 9 | 27.7 | 27.6 | 3.6 |
| 9.5 | 28.9 | 29.1 | −0.5 |

Figure 10A:
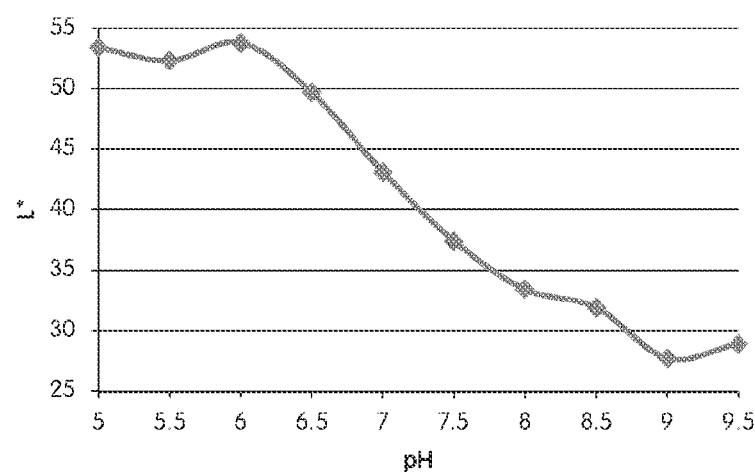
Figure 10B:
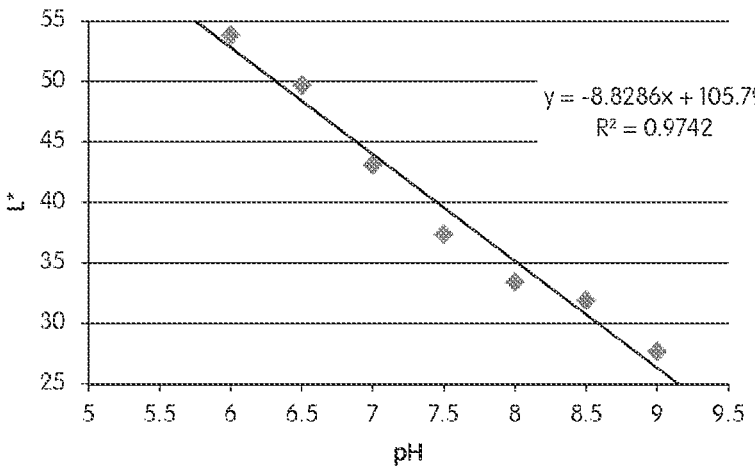

FIGS. 10A and 10B illustrate a graphical representation of the L* measurements taken with the colour pen. FIG. 10A shows all data points whilst FIG. 10B shows only those data points in the linear region. A general downward trend from pH 6 to pH 9 is observed. The trend line has a gradient of −8.8286 and an $R^2$ value of 0.9742.

Figure 10C:
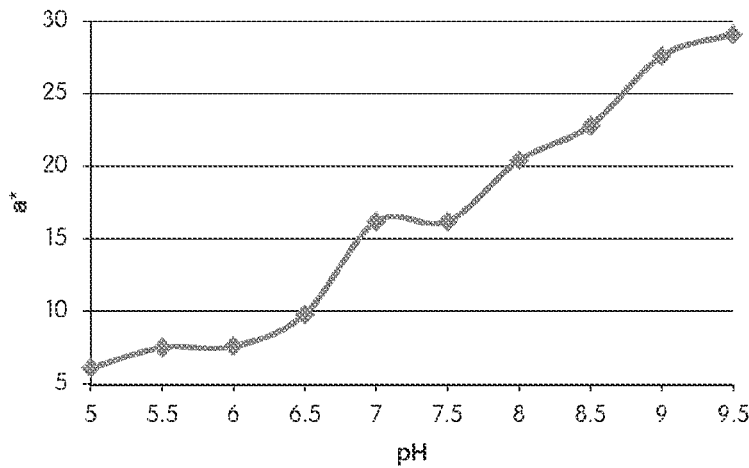
Figure 10D:
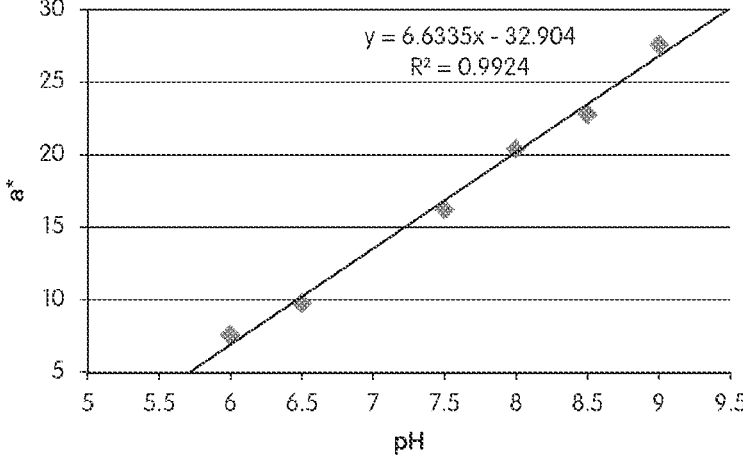

FIGS. 10C and 10D illustrate the a* measurements taken with the colour pen presented graphically. FIG. 10C illustrates the a* measurements taken at various pH values between pH 5-pH 9.5. FIG. 10D illustrates the a* measurements at various pH values over the linear portion of a trend line. The results demonstrate an upwards trend between pH 6 to pH 9, with the trend line having a gradient of 6.6335 and an $R^2$ value of 0:9924.

Figure 10E:
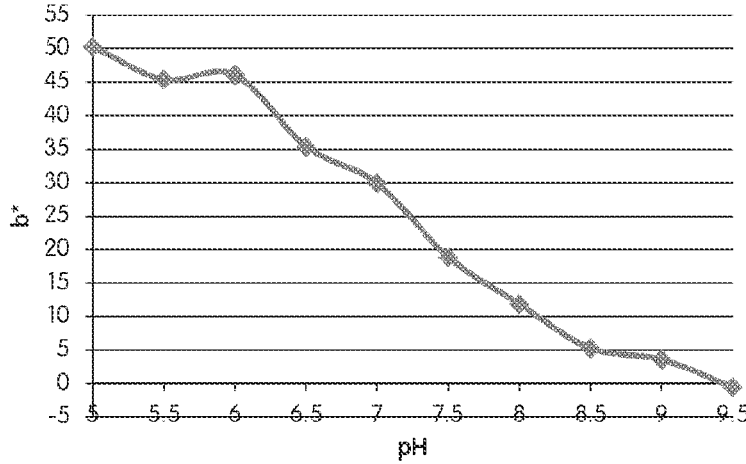
Figure 10F:
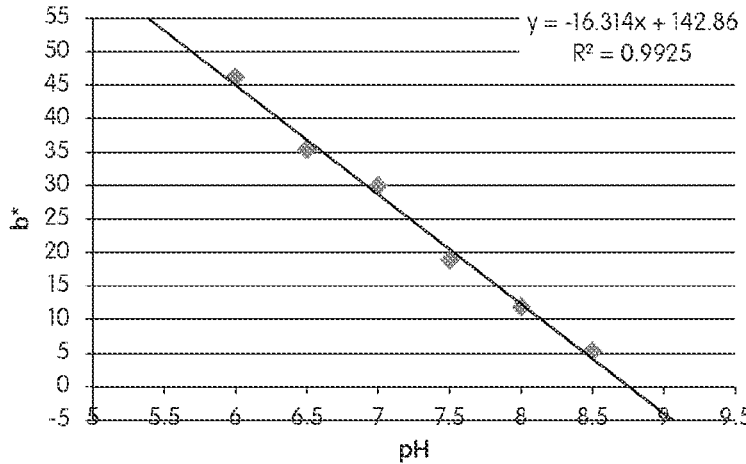

FIGS. 10E and 10F illustrate a graphical representation of the b* measurements taken with the colour pen. FIG. 10E shows the b* measurements taken at various pH values between pH 5-pH 9.5 and it can be seen that the results follow a downward trend until pH 9. The trend line illustrated in FIG. 10F has a gradient −16.314 and an $R^2$ value of 0.9925 between pH 6 and pH9. From the colour pen measurements the working range of this dye combination is between pH 6 and pH 9, and the b* value could be used to accurately measure the pH from the material colour.

Example 5: Post-Op Pad Dyed with GJM 514:534 (1:0.509)

A sample of the pad from an Opsite Post-Op dressing (Smith' & Nephew) was covalently bound with the dye GJM 514:534 at a 1:0.509 ratio was exposed to buffered solutions at pH 5-pH 9.5. The panel of photographs in FIG. 11 demonstrates the colour change over this pH range, going from yellow in colour (at pH 5) to red in colour (at pH 9.5).

Table 6 illustrates the colour pen measurements (L*, a* and b*) of the colour of the GJM-514:GJM-534 dye combination over a pH range of pH 5-pH 9.5.

TABLE 6

| pH | L* | a* | b* |
|---|---|---|---|
| 5 | 55.4 | 4.9 | 43.1 |
| 5.5 | 57.6 | 2.9 | 42.6 |
| 6 | 56.8 | 3.4 | 42.7 |
| 6.5 | 51.2 | 5 | 40 |
| 7 | 49 | 8.8 | 34.7 |
| 7.5 | 39.8 | 11.4 | 23.5 |
| 8 | 39 | 17.6 | 15 |
| 8.5 | 36.5 | 22.4 | 10.1 |
| 9 | 34.2 | 24.3 | 5.8 |
| 9.5 | 32.3 | 25.3 | 0.3 |

Figure 12A:
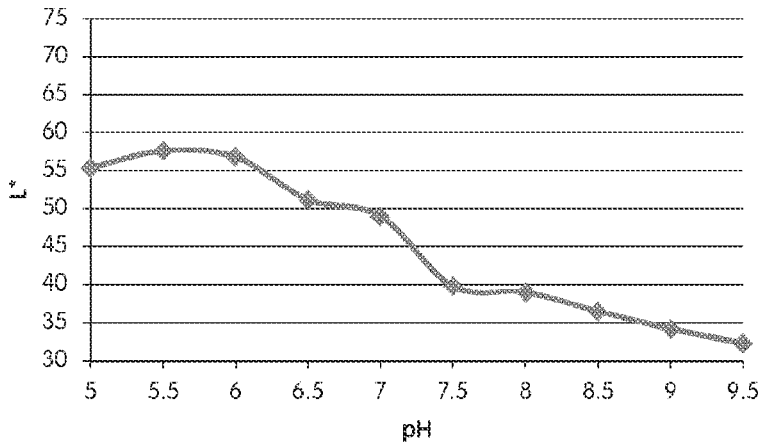

FIG. 12A illustrates a graphical representation of the L* measurements taken with the colour pen. A general downward trend from pH 6 to pH 9.5 is observed.

Figure 12B:
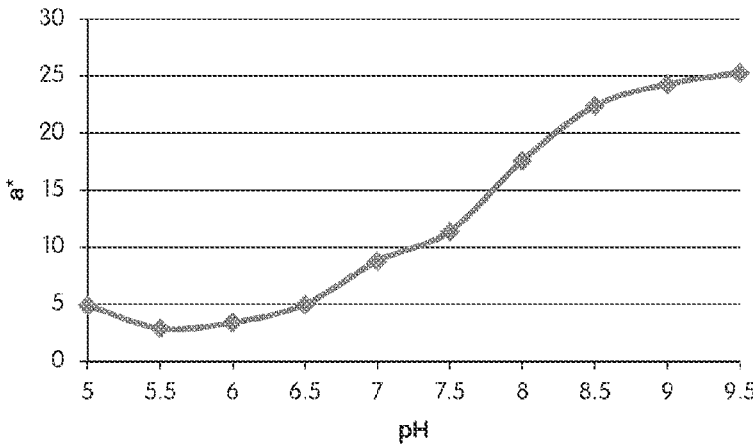
Figure 12C:
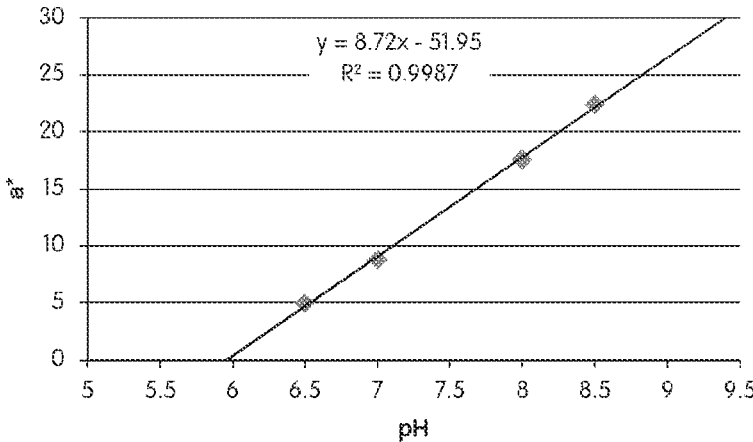

FIGS. 12B and 12C illustrate the a* measurements taken with the colour pen presented graphically. FIG. 12B illustrates the a* measurements taken at various pH values between pH 5-pH 9.5. FIG. 12C illustrates the a* measurements at various pH values over the linear portion of a trend line. The results demonstrate a linear upwards trend between pH 6.5 to pH 8.5, with the trend line having a gradient of 8.72 and an $R^2$ value of 0.9987.

Figure 12D:
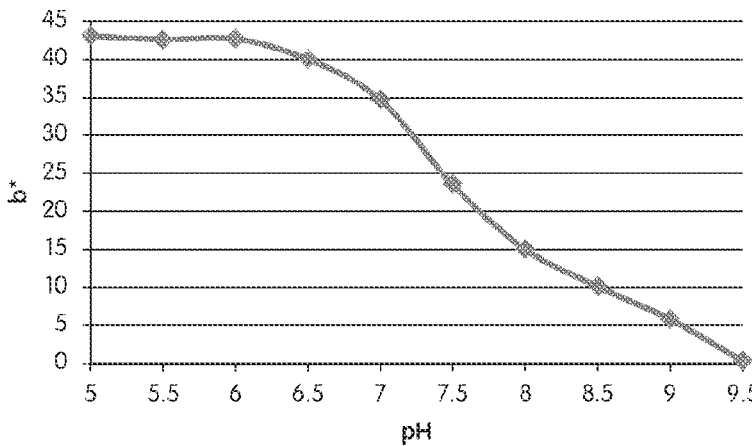
Figure 12E:
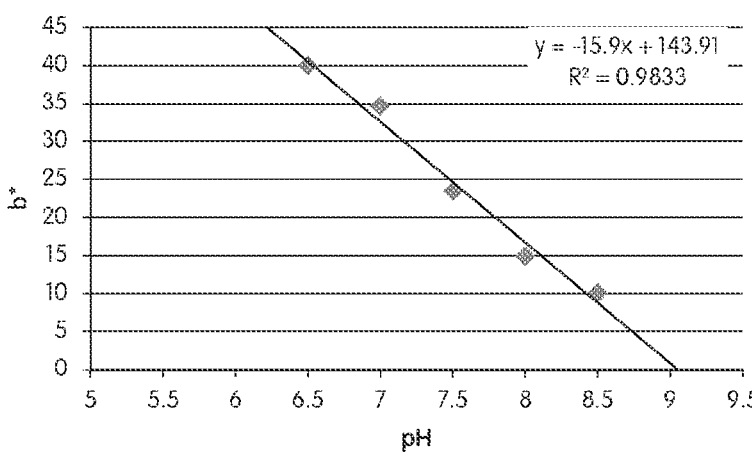

FIGS. 12D and 12E illustrate a graphical representation of the b* measurements taken with the colour pen. FIG. 12D shows the b* measurements taken at various pH values between pH 5-pH 9.5 and it can be seen that the results follow a downward trend between pH 6 and pH 8.5. The trend line illustrated in FIG. 12E has a gradient 15.9 and an $R^2$ value of 0.9833. Taking into account the colour pen results and the photographs of the samples, the working range of this dye combination is between pH 6 and pH 8.5, and the b* value could be used to accurately measure the pH from the material colour.

Examples 6 and 7

Further to the above general method for preparing covalently bonded dye, different materials were also used unto which to bind the dye.

A sample of a gauze (Kerlix Trademark of Covidiene) and polyvinyl alcohol foam (V.A.C. White Foam, trade mark of KCl) were covalently bound with the dye GJM-546 and 492 in a ratio 1:3.92 as described throughout this disclosure.

These latter materials can be used as pH sensing fillers for Negative Pressure Wound Therapy (NPWT). They were evaluated by use of the following models and experiments.
Materials

| Material |
| --- |
| Pork Meat (loin or shoulder 2 kg approx. |
| Intact skin and a surface area 20 × 20 cm approx.) |
| pH sensitive VAC foam |
| pH sensitive gauze |
| Renasys drapes |
| Horse serum |
| Citric Acid |
| Sodium Bicarbonate |

| Equipment |
| --- |
| Renasys EZ plus pump |
| Peristaltic pump |
| Renasys EZ canister |
| Epidural needle |
| Clingfilm |
| Tubing |
| Glass Dish |
| Scalpel |
| pH meter |

Method

Use these solutions to adjust horse serum to pH 5 and pH 8, for use in the meat mode.

1. Place a sheet of cling film in the bottom of a glass dish/tray and place a piece of pork with intact skin upwards on the cling film.
2. Wrap the meat in the cling film and add more if necessary so that the meat is completely sealed.
3. Using a scalpel create 2 wounds each approximately 50 mm in diameter and 25 mm deep in the tissue (and at least 2 cm apart), by removing the skin/fat/muscle, with a relatively flat bottom and minimal tissue flaps.
4. Insert an epidural catheter needle through the side of the wound so that the tip appears at the outside edge of the meat. Use the needle to feed the peristaltic pump tubing through so that it lies at the base of the wound. (Repeat for the other wound).
5. Using small pieces of Flexi-fix and/or adhesive putty ("white-tac") secure and seal the openings where the fluid tubes exit the cling film.
6. The following combinations are to be tested:
   a. Dyed VAC foam
   b. Dyed gauze
7. Add foam to bridge onto intact healthy skin and link both bridges together to work from a single port. Seal over the wounds, fillers and bridging foam with drapes.
8. Make a small hole in the drape where it lies over a foam bridge and attach a port using Flexi-fix strips.
9. Connect the port to a RENASYS NPWT pump (set at −120 mmHg) and switch on.

10. Turn on the peristaltic pump (set to deliver 40 µl/min) to deliver fluid to the wound bed of horse serum at pH 8.
11. Monitor the dressings until fluid starts to appear in the canister (make a note of the length of time)
12. Change the fluid to horse serum at a pH of 5, and leave to flow for the amount of time determined in step 11). Then take a photograph of the dressings.
13. Change the fluid to horse serum at a pH of 8, and leave to flow for the amount of time determined in step 11). Then take a photograph of the dressings.
14. Change the fluid back to horse serum at a pH of 5, and leave to flow for the amount of time determined in step 11). Then take a photograph of the dressings.
15. At the end of the experiment disconnect the tubing and seal the meat in cling film for disposal. Clean all surfaces that had contact with the meat with soap/water.

Determination of the ability of dyed VAC foam and gauze to detect changes in pH of wound fluid.

The pH sensitive gauze and VAC foam were washed after the first meat model experiment and then used in an additional wound model, with pH adjusted water. In addition the extra piece of pH sensitive dyed gauze was placed in a clear Perspex wound model and fluid pumped through.

All wound models were monitored by taking photographs, those carried out in meat could only be monitored from the top surface, but the clear Perspex model could be monitored from all sides.
Results and Discussion The foam was orange in colour when it was loaded into the wound, but the gauze was more of a red colour. It is believed the gauze is red in colour due to the presence of PHMB on the gauze which would make it basic.
Meat Model 1

The experiment was started by pumping pH 5 horse serum into the wound filler for approximately 2.5 hours before fluid started to appear in the canister and the material started to change colour. After approximately 5.5 hours the pH 5 horse serum solution was changed to pH 8 horse serum and this was run overnight. In the morning the solution was then changed back to pH 5 horse serum and was pumped in for several hours (due to time restrictions the flow rate was increased to 80 µl/min after 3.5 hours).

The images of the pH sensitive dyed gauze changing over time can be seen in FIGS. 13A to 13F; showing that the gauze had started to go orange after 5.5 hours of exposure to pH 5 horse serum and after a night of exposure to pH 8 serum the gauze had returned to a red colour. Then after several hours of exposure to pH 5 the gauze was starting to turn orange again at which time the experiment was ended. Upon removal of the gauze it could be seen that the bottom of the gauze was mostly orange and it could be seen that the colour and therefore the pH were changing through the gauze in a direction from the wound bed towards the drape, which can be explained by the fact that the wound tends to fill up like the filling of a bath and therefore the pH takes time to change from one pH to the other as the pumped fluid is slowly transported through the wound filler.

Images of the pH sensitive dyed VAC foam changing over time can be seen in FIGS. 14A to 14F. They show that the foam had gone yellow when exposed to pH 5 horse serum (5.5 hours image), and that when exposed to pH 8 overnight the foam went red. As with the gauze the foam had started to turn yellow/orange after re-exposure to pH 5 serum for several hours before the experiment was ended, the yellow/orange colour can most clearly be seen near the bridging foam.

Meat Model 2

For the second meat model the basic aqueous solution was used first and was left pumping into the model overnight. The next morning the solution was then changed to an acidic aqueous solution and left pumping for several hours.

The images for the pH sensitive gauze can be seen in FIGS. 15A to 15F and show that the gauze went red in colour in basic solution and within 5 hours of the fluid being switched to acidic aqueous solution the gauze had started to turn orange. It is believed that this colour change will originate at the base of the wound and work its way up to the surface as the pH in the wound changes, which as mentioned earlier would be similar to the way in which a bath fills up. It is clear the colour change on the surface starts near the area directly below the port, this can be explained as this is the destination (exit point) of the fluid and so the pH would stabilises around this area on the surface first.

The same trend is seen with the dyed VAC foam, as shown in FIGS. 16A to 16F. The foam turns red when in the presence of basic fluid and when the fluid is changed to acidic the foam starts to turn yellow in colour Like the gauze the colour change seen on the surface is first noticeable around the port where the fluid is removed from the wound.

Clear Perspex Wound Model

The experiment was also carried out using the pH sensitive dyed gauze in a clear Perspex wound model to be able to visualise the colour change throughout the wound. The fluid was not pumped in from the bottom on this occasion but from the left hand side of the wound as seen on the images in FIGS. 17A to 17H. The fluid inlet is on the same side as the port and halfway up the wound wall. It is believed that the area of this wound is smaller than those created in the meat, hence the colour change occurring faster as the pump speed is the same in both experiments. It can be seen that as the basic fluid is pumped into the wound the gauze turns red (at T=0 hours there was already some basic fluid in the wound hence part of the gauze already being red in colour). It can be seen from all the images in FIGS. 17A to 17H, both the top surface of the wound (top image) and the bottom (bottom image of each pair), that the colour change moves across the wound from left to right and that the bottom of the wound is slightly ahead of the upper surface of the wound. This colour change pattern is as expected, as fluid fills up from the bottom and so the pH changes at the bottom before the top. The Perspex model is not as realistic as the meat model as the fluid and content from the meat would mean that the pH could take longer to change due to possible buffering effects.

Conclusions and Recommendations Section 1

Both the pH sensitive dyed VAC foam and gauze, changed colour as they were exposed to different pH solutions. The colours for indicating the different pH's were clearly visible, and the colour could be reversed by addition of the other pH solution to the wound.

DETAILED DESCRIPTION SECTION 3

To provide an understanding of the devices and methods describe herein, certain illustrative embodiments will now be described. For the purpose of clarity and illustration, the devices herein are described as having a pH-dependent moisture indicator which changes colour in response to a pH change.

Reference numbers cited in Section 3 correspond to the reference numbers used in FIGS. 28-32.

FIG. 28 A depicts a device 100 which is designed to be incorporated into a wound dressing in order to indicate the wound exudate loading of the dressing, as will be explained in greater detail below. Device 100 has a first carrier material 102, which can be any material that is permeable to liquid, such as wound exudate. For example, the first carrier material I 02 can be a cellulosic material. A suitable cellulosic material is conventional filter paper. The first carrier material 102 has a wound facing surface 104 and an opposing non-wound facing surface 106. The first carrier material 102 is impregnated with a soluble composition 108 which is a source of hydrogen or hydroxide ions, upon solubilisation by wound exudate. In certain embodiments, the source of hydrogen ions is an acid, such as citric acid. In alternative embodiments, the source of hydroxide ions is an alkali, such as sodium carbonate.

The device also includes a second carrier material 110 which has a wound facing surface 112 and an opposing non-wound facing surface 114. The wound facing surface 112 is located on or adjacent to the non-wound facing surface 106 of the first carrier material 102. In certain implementations, the two surfaces 112 and 106 form a composite. The second carrier material 110 is preferably white, although it is envisaged that other colours could be utilised. The second carrier material 110 is impregnated with a pH indicator 116 which has a first colour and which can change to a second colour upon interaction with hydrogen or hydroxide ions. The second colour is indicative of the pH of the ion-loaded wound exudate. Suitable pH indicators that indicate pH based upon colour are readily apparent to persons skilled in the art, and include for example, a universal indicator solution.

As shown in FIG. 28B, when wound exudate 118 migrates into the first carrier material 112, the soluble composition 108 is at least partially solubilised to release hydrogen or hydroxide ions into the wound exudate. The ions are carried within the wound exudate into the second carrier material 110 as the wound exudate migrates through the dressing. Within the first carrier material 103 the ions interact with the pH indicator. This interaction causes the pH indicator to change from the first colour to the second colour. Because the ion-loaded wound exudate has a pH which is more acidic or more alkaline than the endogenous, unmodified, wound exudate there is a greater shift in the colour of the pH indicator than would occur with endogenous wound exudate. This colour change is thus amplified and easier to perceive by the user. A consideration to be made when choosing the species and concentration of the soluble solution to use in the device is that the release of hydrogen or hydroxide ions into the wound exudate should preferably result in the pH of the wound exudate becoming either very acidic (for example, pH 0, pH 1, pH 2, pH 3) or very alkaline (for example, pH 11, pH 12, pH 13 or pH 14) as changes to these pH's produce colours which are less ambiguous to the patient and/or clinician than colours in the intervening pH range. Also preferred is to minimise the neutralisation of the hydrogen and hydroxide ions by the endogenous wound exudate. It is therefore envisaged that a range of devices can be available, each having different combinations of soluble compositions (e.g., species and concentrations) and pH indicators. This enables the clinician to tailor the use of the device to the clinical situation, for example the wound type. The clinician can test the pH of the endogenous wound fluid and choose the appropriate device accordingly, that is the device which will provide the most perceivable shift in colour upon contact with the ion-loaded wound exudate.

In certain embodiments, the source of hydrogen ions is citric acid and the pH indicator is a universal indicator solution. The universal indicator is loaded onto a cellulosic second carrier material 110 at neutral pH and has a first colour of yellow/orange. The hydrogen ions released by the solubilisation of the citric acid interact with the universal indicator, forcing a change to the second colour. The second colour is red.

In certain embodiments, the source of hydroxide ions is sodium carbonate and the pH indicator is universal indicator. The universal indicator is loaded onto a cellulosic second carrier material 110 at neutral pH and has a first colour of yellow/orange. The hydroxide ions released by the sodium carbonate interact with the universal indicator, forcing a change to the second colour. The second colour is violet/purple.

FIGS. 29A and 29B depict device 200 which is similar to the device illustrated in FIGS. 28A and 28B and which additionally includes a spacer layer 220 positioned between the first carrier material 202 and the second carrier material 210. The device is designed to be incorporated into a wound dressing in order to indicate the wound exudate loading of the dressing. Wound dressings are sterilised before use, and one conventional means of sterilization uses ethylene oxide. A typical treatment protocol contains a high humidity cycle and this risks some degree of premature solubilisation of the soluble composition 208 due to contact with the moisture. The premature solubilisation and consequent interaction of the ions with the pH indicator would be detrimental to the functionality of the product, leading to false results. For example, it could appear that the dressing is saturated, when in fact it is not, leading to unnecessary dressing changes. Minimising premature interaction between the soluble composition and the pH indicator is therefore desirable. This is achieved by physically separating these components within the device so that even if some degree of solubilisation of the soluble composition results from the sterilisation protocol, the ions released are unable to sufficiently interact with the pH indicator to cause a colour change. The spacer layer 220 is therefore incorporated into the device to physically separate the pH indicator 216 and the source of hydrogen or hydroxide ions 208.

The spacer layer 220 can be made of any material that allows a wound exudate which is loaded with ions to migrate through towards the second carrier material. The type of material and its morphology can be chosen in order to tune the moisture level that is required to trigger the indicator system. In some embodiments the spacer layer 220 is a cellulose-based paper, for example, a conventional filter paper. In certain embodiments, the spacer layer 220 is a 3-D fabric, for example, the spacer layer can be a knitted or woven spacer fabric, such as Baltex 7970 weft knitted polyester. In certain embodiments, the spacer layer is a non-woven fabric.

In certain embodiments, the spacer layer is a composite which utilises the differential between filament counts to promote and direct the transport of wound exudate upwards through the device. For example, the spacer layer can consist of a layer of knitted polyester viscose, cellulose or other monofilament fiber which is sandwiched between an upper layer of 84/144 textured polyester and a lower layer of 100 denier flat polyester.

In order to promote wound exudate transport through the spacer layer, the material of the spacer layer is advantageously hydrophilic. In certain embodiments, the material is inherently hydrophilic. Alternatively, a hydrophilic coating can be applied to the material in order to increase the hydrophilic nature of the material. Alternatively, treatments to increase the hydrophilic nature of the material, for example by removing any manufacturing products such as mineral oils, fats and/or waxes may be utilised. Suitable cleaning treatments may include washing with dry cleaning agents, such as perchloroethylene and/or aqueous cleaning agents such as ionic and non-ionic detergents in aqueous solution. Optionally, an additional manufacturing step can subsequently be carried out in which the 3D spacer fabric is washed in a hydrophilic agent (such as, but not limited to, Feran Ice 30 g/l available from the Rudolph Group).

FIG. 30A depicts an alternative embodiment, device 300 which has a single layer of carrier material 240 that is impregnated with both a soluble composition 260 and a pH indicator 280. In order to prevent premature interaction of the components prior to use on a wound, for example during ethylene oxide sterilisation protocols, these components can be physically separated. This physical separation is temporary. A suitable mechanism of separation includes encapsulating at least one of the components in a resorbable coating, spacing the components in the fabric, or otherwise spacing them within the layer. In FIG. 30A, the soluble composition 260 is shown as being encapsulated in a resorbable coating. In alternative embodiments, the pH indicator 280 is encapsulated in a resorbable coating. In further alternative embodiments, both the soluble composition 260 and the pH indicator 280 are encapsulated in a resorbable coating. Suitable resorbable coatings are readily apparent to persons skilled in the art. As illustrated in FIG. 30B, when wound exudate 310 migrates into the device, the resorbable coating dissolves, causing the wound exudate to dissolve the soluble composition 260, thereby releasing the hydrogen or hydroxide ions into the wound exudate. The wound exudate loaded with hydrogen or hydroxide ions interacts with the pH indicator to cause a change in the colour of the pH indicator from a first colour to a second colour. This colour change is indicative that wound exudate has contacted the soluble composition within the device 300.

FIG. 31A illustrates a device/wound dressing composite 410 having a device 400 for indicating the wound exudate loading of the wound dressing combined with a conventional wound dressing. The device 400 can be one of the embodiments of the device 100, 200 or 300 as described above and as illustrated in FIG. 28A, 29A or 30A, or a variant thereof. The wound dressing comprises an absorbent layer 420 which has a wound facing surface 440 and an opposing non-wound facing surface 460. The device 400 is placed near or adjacent to the opposing non-wound facing surface 460 of the absorbent layer 420. The device has a first colour. A barrier layer 480 is used to cover the device to provide additional protection to the wound dressing. Preferably, this barrier layer is made of a material which permits the colour of the pH indicator to be visible therethrough. For example, the barrier layer is made of a substantially transparent material. As illustrated in FIG. 31B, when wound exudate (as indicated by the arrows) migrates through the absorbent layer 420 and reaches the device 400 it causes the dissolution of a soluble composition and the consequent release of hydrogen or hydroxide tons into the wound exudate. The interaction of the wound exudate, loaded with the hydrogen or hydroxide ions, with a coloured pH indicator results in a change in the colour of the pH indicator from a first colour to a second colour. This change to a second colour indicates to the patient or clinician that the wound dressing is saturated at the region of the dressing where the device is located, which, in this embodiment, is at the opposing non-wound facing surface 460 of the absorbent layer.

An example method for fabricating a specific embodiment of the structure illustrated in FIGS. 29A and 29B is outlined below:

In a first step, a first layer is prepared by applying a solution of universal indicator, diluted by 50% with ethanol, to a piece of Whatman No. 1 filter paper (2 cm×2 cm) (SigmaAldrich) until the paper is saturated. The paper is oven-dried overnight at about 40° C.

In a second step, a second layer is prepared by applying a solution of a 2% solution of aqueous sodium carbonate to a second piece of Whatman No. 1 filter paper (2 cm×2 cm) (Sigma-Aldrich) until the paper is saturated. The paper is oven-dried overnight at about 40° c.

In a third step, a three-layered composite is prepared. The upper layer is the first layer, as formed in step 1. The lower layer is the second layer, as formed in step 2. A third, nontreated piece of filter paper is sandwiched between the upper and lower layers to provide a spacer layer. This spacer layer ensures that the sodium carbonate and universal indicator are physically separated, and thereby prevents any soluble sodium carbonate (formed during ethylene oxide sterilisation process) from prematurely interacting with the universal indicator. The three layers are held together by a porous adhesive, the pores permitting migration of wound exudate.

In certain embodiments, the filter paper which functions as a spacer layer is replaced with a 3-D spacer layer, for example, the spacer layer utilised within the PICO product (Smith & Nephew).

An example method for fabricating a specific embodiment of the structure illustrated in FIGS. 31A and 31B is outlined below:

In a first step, a three-layered composite device as described above in relation to FIGS. 29A and 29B is prepared. The lower layer, which is impregnated with the sodium carbonate, is adhered to the upper surface of an absorbent layer. An adhesive barrier film is applied to the upper surface of the upper layer, the upper layer being impregnated with universal indicator.

The devices described herein can be manufactured as a separate element to a wound dressing and combined with a conventional wound dressing by the clinician. Alternatively, the devices can be incorporated into a wound dressing at the point of manufacture. In either case, the devices can be located at different regions of the wound dressing to suit the needs of a particular clinical requirement. As illustrated in FIG. 32A, the device 520 forms an annular ring which extends from and around a peripheral edge of a wound dressing 510. Upon contact with wound exudate, which migrates to the peripheral edge of the device, the device changes from a first colour to a second colour. Dependent upon the positioning of this device, the patient or clinician is informed, by means of a colour change, that the layer of the dressing from which the device extends is loaded with wound exudate.

There is described herein a device for indicating wound exudate loading within a wound dressing. This device comprises a first composition which transforms from a first state to a second state and a second composition which dissolves upon contact with the wound exudate and which forces the transformation of the first composition from the first state to the second state upon contact therewith. The appearance of the second state is indicative of the level of wound exudate loading and the patient and/or clinician can make an informed decision as to whether to change the dressing. In the embodiments of the device described above, the first composition is a pH indicator which displays a colour that correlates with a pH. The first state is a first colour and the second state is a second colour. In the embodiment of the device described above, the second composition is a soluble composition which releases hydrogen or hydroxide ions when it dissolves upon contact with wound exudate. It is contemplated that within the scope of this application alternative compositions can be utilised which interact by different mechanisms to those described above. The underlying principle is that the second composition is altered by contact with wound exudate and that this altered second composition causes a transformation of the first composition from a first state to a second state. This second state is perceivable to the patient and/or clinician and is indicative of the moisture loading of the wound dressing.

In certain embodiments, the first composition is potassium thiocyanate and the second composition is a soluble iron (III) compound, for example, iron (III) sulphate. The first state is a first colour and the second state is a second colour. The first state of the potassium thiocyanate is colourless. Upon contact with wound exudate, ions released from the soluble iron (III) compound interact with the potassium thiocyanate, forcing a transformation to the second state, that is the second colour. The second colour is red. This second state is perceivable to the patient and/or clinician and is indicative of the moisture loading of the wound dressing.

DETAILED DESCRIPTION SECTION 4

To provide an understanding of the devices and methods describe herein, certain illustrative embodiments will now be described. For the purpose of clarity and illustration, the wound dressings herein are described as having a coloured moisture indicator. However, other moisture indicators that are non-colour based can be used. Such other additions and modifications will not depart from the scope hereof.

Reference numbers cited in Section 4 correspond to the reference numbers used in FIGS. 33-37.

FIGS. 33A and 33B depict a wound dressing 100 having a wound contacting layer 102 with a wound-facing or wound-contacting surface 104. FIG. 33B depicts the wound dressing in situ on a wound.

The dressing further includes an absorbent element 106, which can be any material that provides the desired level of absorption of the wound exudate 108. For example, the absorbent element 106 can be a porous foam, particularly a polyurethane foam. Alternatively, the absorbent element 106 can be hydrocolloid-based, hydrogel-based, or alginate-based, or any other suitable absorbent material, or any combination thereof.

The dressing comprises a moisture indicator 110. In embodiments the moisture indicator is a coloured moisture indicator. The indicator does not necessarily change colour upon contact with wound exudate, but its visibility to the user is altered so that it becomes either visible or invisible. This contrasts with certain moisture indicators found in the existing wound dressing which rely on a colour-change of the indicator itself which is often imperceptible. The coloured moisture indicators of the present application can be advantageous to the user as they provide a discernable visual indication of the moisture levels within the dressing. The colour of the indicator is preferably selected so that it is unambiguously discernable against the other parts of the dressing.

The coloured moisture indicator can be a porous coloured substrate, for example a piece of coloured paper through which the wound exudate can diffuse. Alternatively, the coloured moisture indicator can be a water-soluble coloured dye which, upon solubilisation by the wound exudate, diffuses through the dressing.

The visibility of the moisture indicator 110 is altered as a result of the physical transformation of a first material 112. The first material acts as a mask, which either conceals or exposes the moisture indicator, based on the type of physical transformation. In certain embodiments the physical transformation affects a change in the appearance of the first material, preferably without changing the composition of the indicator. In certain embodiments the physical transformation is a transformation from a dry material to a wet material, from a solid material to a gel or gel-like material and vice versa, or from a substantially transparent or translucent material to a substantially opaque material and vice versa or a combination thereof. The physical transformation produces a transformed region 114 within the first material 112 and it is this region which affects the visibility of the moisture indicator. In some embodiments, the transformed region 114 functions as a mask which conceals the moisture indicator before the region is physically transformed. Once the region is transformed the mask is disrupted and the moisture indicator becomes visible. In alternative embodiments, the transformed region 114 functions as a mask which conceals the moisture indicator after the region is physically transformed. The transformation of the region results in the formation of the mask and the moisture indicator becomes invisible.

As shown in FIGS. 34A and 34B, the wound dressing comprises a water-soluble coloured moisture indicator for indicating the saturation levels of the dressing. FIG. 34A shows a side cross-sectional view of a wound dressing 200 having a wound contacting layer 202, the lower surface of which is a wound-facing surface 204. The dressing also comprises an absorbent element 206. A first material 212 is located on or adjacent to the surface of the absorbent element which is opposed to the wound-facing surface 204. The first material 212 is of a first colour, preferably white, although it is envisaged that other colours could be utilized. A water-soluble coloured moisture indicator 210, having a second colour, is provided on or within the absorbent layer 206. This second colour is selected to be a contrasting colour to the first colour. For example, if the first colour is white, the second colour is selected to be not white. Suitable water-soluble coloured moisture indicators, for example water-soluble dyes, for use in wound dressings are readily apparent to persons skilled in the art. The absorbent layer has opposing peripheral edges 214 and 216 and although FIGS. 34A and 34B depict the water-soluble coloured moisture indicator 210 as a mark which is centrally located in the absorbent layer, it is envisaged that the indicator 210 can be located anywhere between the opposing peripheral edges and, if desired, additional indicators (of the same or of a different colour) can be provided at different locations between the peripheral edges in order to provide an indication of the horizontal spread of wound exudate within the absorbent layer. For example, as illustrated, an indicator 211 based on a water-soluble dye of the same colour as indicator 210 is provided nearer to an outer peripheral edge.

FIG. 34B, illustrates two stages of wound dressing saturation and the temporal relationship between the solubilisation and subsequent visualisation of the marks 210 and 211. In the upper panels (A) the wound dressing is dry and, from the plan view, it can be seen that the first material is substantially white. This informs the user, for example, the patient or care provider, that the absorbent layer has not been saturated and that the wound dressing does not require changing. As illustrated in the lower panels (B), when wound exudate 208 has saturated the absorbent layer 206, the indicators 210 and 211 become solubilised and diffuse through the first material 212 and become visible as a contrasting coloured mark on the upper surface of the first material. This indicates to the user that the dressing needs to be changed. In some embodiments, the first material 212 forms the uppermost surface of the wound dressing, which is often referred to as the backing layer. In alternative embodiments, the first material 212 is covered by additional layers of the dressing, although such layers are preferably transparent, such that the first material is visible therethrough and the appearance of the coloured mark(s) on the first material is not hampered.

As described above, in some embodiments the coloured moisture indicator appears on the upper surface of the first material, this surface being white or other light colour. The coloured moisture indicator is of a contrasting colour to white, so that the apparent "white to colour" transition provides an unambiguous visual indication as to dressing saturation.

Methods for fabricating wound dressing products are also contemplated. An example includes the following steps for making the dressing illustrated in FIG. 34, as outlined below:

In a first step, a first coating (filler layer) is applied to the upper side of a sheet of conventional copy paper (~80 GSM). Coating I (~100 GSM) may be a dispersion of talc, or other transparent filler, in a water-soluble binder such as carboxymethylcellulose. The dispersion is preferably formulated with a high pigment/binder ratio to provide satisfactory porosity The function of this coating is to mask traces of the underlying coloured moisture indicator.

In a second step, the lower side of the paper is coated with a second coating (barrier layer). An example barrier layer is coating 2 (~5-10 GSM), a thin film of polyvinyl alcohol (PVOH). The function of this coating is to seal the paper, in order to impair or prevent the low viscosity ink from diffusing through the paper upon its application.

In a third step, ink is applied to the surface of the second coating, by inkJet or similar deposition method. An example ink is a low-viscosity ink, based on a water-soluble dye.

The response time of the indicator is typically about 10 minutes, but the response time may vary as a function of the paper porosity, thickness of the barrier film and/or the solubility of the dye. In certain applications although the coated paper may react with liquid water, it is not affected by the high levels of humidity associated with sterilization of the wound dressing (e.g by ethylene oxide).

Methods of fabricating alternative specific embodiments of the structure illustrated in FIG. 34 include;

In a first step, the filler layer is applied to the lower surface of the paper so that it is sandwiched between the paper and the barrier layer.

In a second step, a dispersion of aluminium hydroxide is used to form the filler layer. This compound may cause the mobile ink to instantly gel, so preventing if from diffusing before it is contacted by wound exudate.

In a third step, titanium dioxide is added to the filler dispersion to emphasise the contrast of colour against a white background without significantly reducing the colour strength.

In certain embodiments, the wound dressing comprises a coloured moisture indicator which gradually becomes invisible as the wound dressing becomes saturated. Such a mechanism is shown in FIGS. 35A and 35B.

FIG. 35A shows a side cross-sectional view of a wound dressing 300 having a wound contacting layer 302, the lower surface of which is a wound-facing surface 304. The dressing also comprises an absorbent element 306. Located on the surface of the absorbent element which is opposed to the wound-facing surface 304 is a first material 312 which is made of a material which, upon hydration, transforms from a transparent material to an opaque material having a first colour. Many polymers, such as solutions of polyvinyl acetate (PVA), shellac and latex rubber form transparent films when the carrier solvent evaporates. When the film subsequently comes into contact with water, the polymer re-hydrates to form a white, opaque film. When PYA is bought into contact with water, a relatively high level of opacity develops within a short length of time. This can provide a real-time indication of wound dressing saturation. As illustrated, a coloured moisture indicator 310 having a second colour lies between the absorbent layer and the first material. The second colour is selected to contrast with the colour of the opaque film. For example, if a PVA film is used, which forms a white opaque film upon hydration, the second colour is selected to be non-white and is desirably selected to be a colour that readily contrasts with white. Whilst the material selected for the first material is preferably able to physically transform from a transparent material to an opaque material, it is not a requirement that the first material is colourless i.e clear.

In some embodiments, the coloured moisture indicator 310 is in close contact with, for example, overlies the absorbent layer. In some embodiments the coloured moisture indicator 310 contacts only part of the absorbent layer 306, for example, the central part or a peripheral part For example, the coloured moisture indicator 310 may form a peripheral edge upon the upper surface of the absorbent layer 306, and the subsequent visibility of the coloured indicator indicates full saturation of the dressing to the peripheral edges. In certain embodiments the coloured indicator is a porous coloured substrate, for example a coloured paper. In other embodiments a coloured mark/graphic (e.g a logo) is applied directly onto the upper surface of the absorbent layer. In some embodiments of the invention the first material 312 forms the uppermost surface of the wound dressing, which is often referred to as the backing layer In alternative embodiments, the first material 312 is covered by additional layers of the dressing, although such layers are transparent, such that the first material is visible there through. In certain embodiments the physical transformation is reversible. For example, upon hydration the PVA film forms a white opaque film, but if the wound starts to dry out, which is indicative of suboptimal healing, the opaque film reverts to a transparent film and the coloured moisture indicator becomes visible again.

FIG. 35B illustrates two stages of wound dressing saturation and the temporal relationship between the wound dressing saturation and the visibility of the coloured moisture indicator 310. In the upper panels (A) the wound dressing is dry and from the plan view of the dressing it can be seen that the first material 312 is completely transparent and the coloured moisture indicator 310 is visible through the first material 310. This informs the user, for example the patient or care provider, that the absorbent layer has not been saturated and that the wound dressing does not require changing. As illustrated in the lower panels (B), when the wound exudate saturates the absorbent layer 306, it permeates through the coloured moisture indicator 310 and contacts the first material 312. This contact hydrates the first material 312 and causes the development of an emulsion, turning the transparent first material 312 opaque. The opaqueness conceals the coloured moisture indicator 310, for example a coloured substrate or a coloured mark/graphic (e.g a logo) which is associated with the absorbent layer. When a predetermined amount of the coloured moisture indicator has become concealed, it indicates that it is time to change the dressing. A reference guide can be provided which informs the user of the relationship between the visibility of the coloured moisture indicator and the level of saturation of the dressing, in order that an informed decision about the need to change the dressing can be taken.

In certain embodiments, the wound dressing is a superabsorbent dressing utilized in a Negative Pressure Wound Therapy (NPWT) System, for example the dressing of the PICO® Single Use Negative Pressure Wound Therapy System (Smith & Nephew Inc.). Such dressings are provided with a port into which a vacuum tube is secured. It could be advantageous for the coloured moisture indicator to be associated with this port, with the concealment of the coloured moisture indicator being indicative of a fully saturated dressing, which should be removed.

As described above, in some embodiments the coloured moisture indicator becomes concealed by the development of an opaque film. In embodiments in which the opaque film is white in colour, the coloured moisture indicator may be a contrasting colour to white, so the apparent "colour to white" transition provides an unambiguous visual indication as to dressing saturation.

An Example method for fabricating a specific embodiment of the structure illustrated in FIG. 35 is outlined below:

In a first step, a film of PYA emulsion is deposited onto a thin (e.g 35 micron) a polyester/plastic film, for example Mylar® (Dupont). This prevents the reticulation of the converted PYA. The PYA is preferably a 50% aqueous emulsion, for example Unibond (Henkle) or Cementone Rendabond (Bostik).

In a second step, the wet film is oven-dried (e.g to about 70 degrees Celsius) to provide a transparent PYA film of about 1 00 microns thick. The PYA/Mylar laminate is then bonded to an appropriately coloured material (e.g a, 2-ply paper tissue (35 GSM)) using an adhesive such as polyvinyl alcohol or KS adhesive (Smith & Nephew, Inc).

In a third step, the laminate prepared in step 2 is adhered to the upper surface of the absorbent layer in a wound dressing.

Although PVA film may react with liquid water, it is not necessarily affected by the high levels of humidity associated with the ethylene oxide sterilization of the wound dressing.

Methods of fabricating alternative embodiments of the structure illustrated in FIG. 35 include:

In a first step, the PVA/Mylar layer is bonded directly onto an appropriate coloured piece of fusible interlining, for example based on non-woven rayon.

In a second step, the Mylar film is omitted and instead the layer of PVA emulsion is screen printed, or otherwise directly deposited, onto the porous coloured substrate.

In a third step, the porous coloured tissue paper is omitted and the coloured mark/graphic (e.g a logo) is directly applied onto the upper surface of the absorbent layer of the dressing.

In a fourth step, the use of an adhesive is omitted by instead hot bonding the PVA/Mylar laminate onto the porous coloured substrate.

In a fifth step, the porous coloured substrate is omitted and instead a pattern (e.g a chequerboard) or other graphic element (e.g a logo) is directly applied onto the uppermost transparent film (e.g PYA/Mylar laminate) such that the pattern can be displayed as a more distinctive change signal.

In certain embodiments the wound dressing comprises a coloured moisture indicator which gradually becomes visible as the wound dressing becomes saturated. Such a mechanism is shown in FIGS. 36A and 36B.

FIG. 36A shows a side cross-sectional view of a wound dressing 400 having a wound contacting layer 402, the lower surface of which is the wound-facing surface 404. The dressing also comprises an absorbent element 406. Located on the surface of the absorbent element which is opposed to the wound-facing surface 404 is a first material 412, made of a material which upon hydration transforms from being opaque to a transparent/translucent. A suitable material is a water-soluble paper, which is preferably a polyvinyl alcohol-based. The water-soluble paper has a fibrous structure which upon hydration transforms and disintegrates into a transparent/translucent gel or gel-like material. There are many types of suitable water soluble papers available, including, for example, water-soluble papers based on plant materials such as rice, cornflour and cellulose or based on synthetic polymers, such as polyvinyl alcohol, the base for the Aquasol (Aquasol Corp) range. The water-soluble paper is preferably white. As illustrated, a coloured moisture indicator 410 having a second colour lies between the absorbent layer and the first material. The second colour is selected to contrast with the colour of the opaque water-soluble paper. For example, if the non-hydrated form of the water-soluble paper is white, then the second colour is selected to be non-white and is preferably a colour that readily contrasts with white. In some embodiments, the coloured moisture indicator 410 is in close contact with the absorbent layer, for example, it may overly the absorbent layer. In some embodiments, the coloured moisture indicator 410 contacts only part of the absorbent layer, for example, the central part or a peripheral part. The coloured moisture indicator 410 may form a peripheral edge upon the upper surface of the absorbent layer, such that the subsequent visibility of the coloured indicator indicates of full saturation of the dressing to the peripheral edges. When the practitioner sees that the indication he or she may decide to change the dressing. In certain embodiments the coloured indicator is a porous coloured substrate, for example a coloured paper. In other embodiments a coloured mark/graphic (e.g a logo) is applied directly onto the upper surface of the absorbent layer. In some embodiments, the first material 412 forms the uppermost surface of the wound dressing, which is often referred to as the backing layer. In alternative embodiments, the first material 412 is covered by additional layers of the dressing, although such layers are transparent, such that the first material is visible there through. In some embodiments, an additional coloured element is disposed between the first material 412 and the coloured moisture indicator 410. This additional coloured element has a third colour, which is of a contrasting colour to the second colour. In this embodiment, the first material 412 and the additional coloured element do not necessarily extend completely over the coloured moisture indicator 410, such that when the first material 412 becomes hydrated and dissolves, the third colour becomes visible against the coloured moisture indicator. In certain embodiments, the wound dressing is a superabsorbent dressing utilized in a Negative Pressure Wound Therapy (NPWT) System, for example the dressing of the PICO® Single Use Negative Pressure Wound Therapy System (Smith & Nephew Inc). Such dressings are provided with a port into which a vacuum tube is attached to. If the coloured moisture indicator is associated with this port, the exposure of the coloured moisture indicator may indicate a fully saturated dressing, which should be removed.

FIG. 36B illustrates two stages of wound dressing saturation and illustrates the temporal relationship between the wound dressing saturation and the visibility of a coloured moisture indicator 408. In the upper panels (A) the wound dressing is dry and from the plan view of the dressing it can be seen that the first material 412 is completely opaque and the coloured moisture indicator 410 is invisible through the backing layer. This informs the user, for example the patient or care provider, that the absorbent layer has not been saturated and that the wound dressing does not require changing. As illustrated in the lower panels (B), when the wound exudate 408 has saturated the absorbent layer 406, it permeates through the coloured substrate 410 and contacts the first material 412. This contact hydrates the first material 412, causing the development of a transparent/translucent gel. This transparency exposes the coloured moisture indicator 410 beneath. When a predetermined amount of the second colour has become exposed it is time to change the dressing. A reference guide can be provided which informs the user of the relationship between the visibility of the coloured moisture indicator and the level of saturation of the dressing, in order that an informed decision about the need to change the dressing can be made.

As described above, in some embodiments the coloured moisture indicator becomes exposed by the development of a transparent/translucent film. The coloured moisture indicator may be a contrasting colour to white, so the apparent "white to colour" transition, provides an unambiguous visual indication as to dressing saturation.

An Example method for fabricating an embodiment of the structure illustrated in FIG. 36 is outlined below:

In a first step, a water-soluble paper (~60 GSM) is bonded to an appropriately coloured material (e.g. a 2-ply, paper tissue (~35 GSM)) using an adhesive such as polyvinyl alcohol or KS adhesive (Smith & Nephew, Inc), to form a laminate.

In a second step, the laminate prepared in Step I is adhered to the upper surface of an absorbent layer in a wound dressing.

Although the laminate reacts with liquid water, it not necessarily affected by the high levels of humidity associated with sterilization of the wound dressing (e.g by ethylene oxide).

Methods of fabricating alternative embodiments of the structure illustrated in FIG. 36 include:

In a first step, the water-soluble paper is bonded directly onto an appropriate coloured piece of fusible interlining, for example based on non-woven rayon.

In a second step, the use of an adhesive is omitted and instead an adherent water-soluble paper is used.

In certain embodiments, the wound dressing includes a coloured moisture indicator associated with each layer of the dressing, such that the user is visually informed of the vertical progression of the wound exudate and therefore the saturation state of each dressing layers. An example of this design of dressing is illustrated in FIGS. 37A and 37B in which the wound dressing comprises a water-soluble coloured moisture indicator associated with each layer of the dressing.

FIG. 37A shows a side cross-sectional view of a wound dressing 500 having a wound contacting layer 502, the lower surface of which is a wound-facing surface 504. A first material 512 is located on or adjacent to the surface of the wound contacting layer 502 which is opposed to the wound-facing surface 204. The wound contacting layer 502 and the first material 512 are preferably of the same diameter. The dressing also comprises an absorbent element 506. A second material 516 is located on or adjacent to the surface of the absorbent element 506 which is opposed to the wound-facing surface 504. The absorbent element 506 and the second material 516 are preferably of the same diameter, with this diameter being selected to be smaller than the diameter of the wound contacting layer 502 and the first material 512. As a result of this selection, a border or flange of the wound contacting layer 502/first material 512 extends outwardly from below the perimeter edges of the absorbent element 506/second material 516. The first material 512 and the second material 516 are of a first colour, preferably white, although it is envisaged that other colours could be utilized. A water-soluble coloured moisture indicator 510, having a second colour, is provided on or within the wound contacting layer 502. A water-soluble coloured moisture indicator 511, having a third colour, is provided on or within the absorbent layer 506. The second and third colours are selected to be a contrasting colour to the first colour. For example, if the first colour is white, the second and third colours are selected to be not white. Suitable water-soluble coloured moisture indicators, for example water-soluble dyes, for use in wound dressings are readily apparent to persons skilled in the art.

FIG. 37B, illustrates two stages of wound dressing saturation and the temporal relationship between the solubilisation and subsequent visualisation of the marks 510 and 511. In the upper panels (A) the wound dressing is dry and, from the plan view, it can be seen that the first material and the second material are substantially white. This informs the user, for example, the patient or care provider, that neither the wound contacting layer, nor the absorbent layer, has been saturated by wound exudate. As illustrated in the middle panels (B), when wound exudate 508 has saturated the wound contacting layer 502 the indicator 510 is solubilised and diffuses through the first material 512 and becomes visible as a contrasting coloured mark on the upper surface of the first material 512. In some embodiments, the first material 512 forms the uppermost surface of the wound contacting layer. The visibility of the indicator 510 indicates to the user that the wound contacting layer 502 has become saturated. This may not necessarily indicate that a dressing change is required, but it may be a useful indication to the user of the rate of wound exudate secretion from the wound. As illustrated in the lower panels (C), when wound exudate 508 has saturated the absorbent layer 506, the indicator 511 is solubilised and diffuses through the second material 516 to become visible as a contrasting coloured mark on the upper surface of the second material 516. In some embodiments, the second material 516 forms the uppermost surface of the wound contacting layer. In alternative embodiments, the second material 516 is covered by additional layers of the dressing, although such layers are preferably transparent, such that the second material is visible there through and the appearance of the coloured mark(s) on the second material is not hampered. The visibility of the indicator 511 indicates to the user that the absorbent layer of the dressing has become saturated and that the dressing may require changing.

As described in relation to FIGS. 37A and 37B, in certain embodiments, the wound dressing includes a coloured moisture indicator associated with each layer of the dressing, this enables the user to be visually informed as each layer of the dressing becomes saturated by the vertical progression of the wound exudate. Whilst FIGS. 37A and 37B disclose the use of water-soluble dyes as the moisture indicator, in alternative embodiments, it is envisaged that the moisture indicators disclosed in reference to FIGS. 35 and 36 may be utilized within a similar design of dressing, as described below.

In embodiments, the first and second materials 512, 516 that are associated with the wound contacting layer 502 and the absorbent layer 506, respectively, are made of a material which, upon hydration, transforms from a transparent material to an opaque material having a first colour, as disclosed above in reference to FIG. 35. The first colour is preferably white. A first coloured moisture indicator, for example a coloured substrate or a coloured mark/graphic (e.g a logo), is placed between the wound contacting layer and the first material. The first coloured moisture indicator is of a colour that is contrasting to white. A second coloured moisture indicator, for example a coloured substrate or a coloured mark/graphic (e.g a logo), is placed between the absorbent layer and the second material. The second coloured moisture indicator is also of a colour that is contrasting to white and further is discernable from the colour of the first coloured moisture indicator. Within the dry dressing, both the first and second coloured moisture indicators are visible to the user. When the wound contacting layer becomes saturated the first material becomes hydrated and turns opaque, concealing the first coloured moisture indicator. When the absorbent layer becomes saturated the second material becomes hydrated and turns opaque, concealing the second coloured moisture indicator. The fully hydrated dressing will appear white to the user.

In embodiments, the first and second materials 512, 516 that are associated with the wound contacting layer 502 and the absorbent layer 506, respectively, are made of a material which, upon hydration, transforms from an opaque material having a first colour to a transparent material, as disclosed above in reference to FIG. 35. The first colour is preferably white. A first coloured moisture indicator, for example a coloured substrate or a coloured mark/graphic (e.g a logo), is placed between the wound contacting layer and the first material. The first coloured moisture indicator is of a colour that is contrasting to white. A second coloured moisture indicator, for example a coloured substrate or a coloured mark/graphic (e.g a logo), is placed between the absorbent layer and the second material. The second coloured moisture indicator is also of a colour that is contrasting to white and further is discernable from the colour of the first coloured moisture indicator. Within the dry dressing, both the first and second coloured moisture indicators are invisible to the user. When the wound contacting layer becomes saturated the first material becomes hydrated and turns transparent, exposing the first coloured moisture indicator. When the absorbent layer becomes saturated the second material becomes hydrated and turns transparent, exposing the second coloured moisture indicator. The fully hydrated dressing will have a central first colour and a ring of a second colour extending thereabouts.

DETAILED DESCRIPTION SECTION 5

Reference numbers cited in Section 5 correspond to the reference numbers used in FIGS. 38-50.

An automated wound dressing image processing system provides a physician or patient with an effective and reliance approach to monitoring a wound, such as when negative pressure wound therapy is applied to the wound. FIG. 38 shows a wound monitoring method 100 that informs the patient or physician of wound status indicated by a color-coded pH indicator wound dressing. The method 100 automates the determination of bandage color to provide accurate readings of wound pH. Rather than relying on a user's judgment in discerning the color of a wound pH indicator and relating the discerned color to a pH scale, the method 100 allows the user to capture a digital image of the wound dressing and applies image processing techniques to determine the indicated pH. The resulting monitoring method thus improves the reliability of pH readings that may be used to apply or change the treatment regimen applied to the healing wound. The illustrated method can be implemented by a user device alone or in combination with one or more computing devices, such as a server.

The wound monitoring method 100 begins when an image of a color-coded wound pH indicator is captured at step 102. The indicator is disposed on a patient's wound dressing and includes one or more pH-sensitive dyes or compounds that change color as the pH of the wound to which the dressing is applied changes. For example, a particular dye may exhibit a spectrum of colors, from lighter yellow and orange colors to darker red or purple colors, when exposed to different pH values over the range from 0 to 14. Particular dyes and compounds disposed on such bandages may vary, and any suitable wound pH indicators, exhibiting any suitable known spectrum of colors, may be employed in the systems and methods of the present disclosure.

The image captured at step 102 of method 100 is taken on a user device, for example, by a physician during a patient visit or by the patient away from the doctor's office. With the advancements in smartphones and mobile technology, the range of user devices suitable for use in method 100 is quite broad. Any user device having a camera for image capture and circuitry either to process the image locally or transmit the image for remote processing is suitable for the method. For example, smartphones, tablet computers, laptop computers, digital cameras, web-enabled cameras, or any other user devices with image capturing and processing or communication circuitry could be used at step 102. The portability of many of these devices provides an advantage by allowing the user to capture the image at step 102 in virtually any location with the user device. Thus, the method 100 provides a patient with wound monitoring and feedback without requiring constant check-ups with a doctor or visits to the doctor's office to obtain a reading.

The image captured at step 102 is processed at step 104 to determine the pH of the wound that is indicated by the color of the wound dressing. In some embodiments, the image is captured on a mobile device, for example using an app on a smartphone, and the mobile device itself performs the processing at step 104 to calculate the indicated pH. In other embodiments, the user device transmits the captured image to a remote location, for example to a server, where the image is processed to calculate the pH. The server may then transmit the calculated pH back to the user device for display and use in evaluating the wound status. The server, the user device, or both can also store a record of the pH readings for trend and progress analyses.

The image processing at step 104 automatically characterizes the color of the wound dressing in the captured image. This may be done, for example, by determining where the color of the dressing lies in the RGB color model (or any other suitable color model such as CMYK, Lab colour space, and the like). The processing applied to the image determines the red, blue, and green components of the overall dressing color and uses the relative presence of the three colors to characterize the color. The RGB characterization values are then compared to standardized pH RGB values to calculate the pH indicated by the wound dressing. Further details on this processing and pH calculation are discussed below, for example in relation to FIG. 39.

After the pH of the wound is determined at step 104, the calculated pH value is relayed to the patient or physician at step 106. The pH is displayed either on the user device used to capture the image or on another device in communication with the user device or with a server in the system. In addition to the calculated value, the pH may be displayed at step 106 with one or more accessory features, such as a graph showing past pH readings for the patient, a list of pH readings, an indication of wound health based on the reading, a suggested mode of treatment for the wound, or any other suitable information for the patient or physician. In addition, the display may provide the user with various options for storing or identifying the pH reading. For example, step 106 may include displaying an option to the user to accept or reject the pH reading, and may prompt the user to capture a new image if the pH reading is rejected. The display may also provide the user with an option to identify the patient for record keeping, where the calculated pH value is associated with either an already stored patient or a newly identified patient for tracking the progress of the wound. In some embodiments, the patient may be automatically identified by a barcode or a QR code on the bandage in the image.

The method 100 provides prompt feedback and an accurate pH reading, by implementing automated image processing and analysis at step 104. The color extraction and pH calculation performed at step 104 can provide improved accuracy in the pH reading, and thus in the treatment decisions that are based on the pH. The processing applied to the image first automates the determination of wound dressing color, and then applies processing to provide a pH read out from the detected color.

FIG. 39 shows a method 110 for processing a wound dressing image to provide a patient or physician with a pH readout, which may be the method performed at step 104 in FIG. 38. The illustrated method can be implemented by a user device alone or in combination with one or more computing devices, such as a server. After an image is captured or received, system implementing the method 110 defines or identifies a region of interest in the wound dressing captured in the image at step 112. The region of interest defines the area of the image that is determined to be an adequate representation of the wound dressing for color and pH determinations. The region may have any suitable shape and size, for example a circle or a square having a radius or area defined by a predetermined number of pixels. In some embodiments, the region is defined as the pixels that form a particular shape of a particular size around a determined center point of the wound dressing image. In such embodiments, the center of the dressing image is first defined at step 112, and the region of interest is defined based on the shape and size settings around the defined center point. A circular region around the center point can be defined having a radius of any suitable number of pixels, for example five pixels, ten pixels, twenty pixels, fifty pixels, one hundred pixels, or any other suitable radius. The shape and size of the region may be an oval, rectangle, square, triangle, trapezoid, or any suitable shape of a suitable size. The shape and size of the region may also be defined based on the resolution settings of the camera used to capture the image, or on the size of the captured image. In certain implementations, the method 110 defines or identifies multiple regions of interest. Any suitable number and dimensions of the multiple regions can be selected. For example, the multiple regions can be five circles as depicted in FIG.

47 (namely one circular region in the middle or the dressing surrounded by four circular regions in each of the four corners of the dressing).

When the region of interest for analysis has been defined, a system implementing the method 110 characterizes the color of the dressing, as determined from the region of interest, at step 114. Each pixel lying within the defined region of interest is analyzed to extract the RGB values for the pixel color from the image. Particularly for cases in which the region of interest is larger, there may be variation of the exact color of the wound dressing over the pixels included in the region. Thus, it may be preferable to define the region of interest large enough to capture pixels that will provide an accurate representation of the dressing color. Including too few pixels in the region may result in one pixel or small area of the dressing, for example a pixel or area that is artificially dark due to poor imaging, skewing the overall RGB characterization and affecting the accuracy of the pH value calculated from the characterization. If the region is defined broadly enough, the extraction of RGB values at step 114 will include enough accurate pixel readings to dilute the effect of any artificial pixels or areas. Alternatively, a filter may be applied to remove these artificially light or dark pixels from the analysis. For example, individual pixels that exhibit RGB values that lie a certain distance from the average RGB values of the pixels in the region of interest may be designated as outliers and removed from the analysis.

After the individual pixel RGB values within the region of interest are extracted from the image, the values are averaged at step 116 to determine the RGB value characterization for the overall dressing in the image. By averaging the pixel values at step 116, the method 110 provides an accurate automated reading of the color of the dressing, as determined by the color or colors present within the defined region of interest. The averaged RGB values determined at step 116 are the values that are then used in calculating a pH value indicated by the imaged wound dressing indicator.

In order to provide accurate pH calculations from the values determined at step 116, the method 110 includes performing color determinations for calibration color squares. The calibration colors can provide readings of standardized colors that are used to normalize the dressing RGB values. This normalization can account for variation in captured images, for example caused by variations in the image capture device, positioning of the wound dressing, lighting when the image is captured, type of wound dressing, pH-sensitive dye included in the dressing, or other factors that may affect captured dressing images. The calibration colors that are analyzed may be included in the same image as the dressing image, for example as a strip provided on the dressing itself or a strip placed in this image window with the dressing, or may be captured in a separate image under the same or similar conditions as the dressing image. Providing the strip on the dressing itself may be convenient for the user as a separate strip does not need to be included in each image. Using a separate strip may also be advantageous for reproducing, for example, for a doctor who uses the same strip for all patients. The separate strip may also ensure the color blocks do not become discolored from blood in the wound under the bandage.

The calibration colors that are captured for normalization exhibit the expected color of the wound dressing at a range of pH values. The colors may be provided as a series of color blocks, for example as three, five, seven, or more blocks, in a strip on the wound dressing. The color blocks may show the expected colors at set pH increments, for example at one or more of pH values 4.0, 5.0, 6.0, 7.0, 8.0, 9.0, intermediate values between those pH values, or pH values above 9.0 or below 4.0. Whether these color blocks are included as a color calibration strip on the wound dressing or as a separate component by an image, the standardized colors are processed beginning at step 118 of method 110 to normalize the dressing RGB values determined at step 116 and reduce the effect of image variation.

At step 118, similar to step 112 for the dressing, a region of interest is defined for each calibration color block included in the captured color calibration strip. As with the dressing, each region of interest may be defined as a set shape of a set number of pixels surrounding the center of the color block. The shape and size of each color block region of interest may be the same as the shape and size of the dressing region of interest, or may be a different shape or size. For example, in an embodiment where the color calibration strip is provided at the bottom of the wound dressing, the color blocks may be smaller than the dressing area, and the regions of interest may also be defined as smaller pixel areas.

The defined region of interest in each color block is analyzed at step 120 to extract RGB value characterizations of the calibration colors. Though the colors in the strip may be the same between different dressings or different images of the same dressings, variations in lighting and image capture condition can cause different RGB value determinations at step 120 between readings. The purpose of the color calibration strip is to identify, and correct for, this variation in readings of identical colors between images. As with the dressing RGB values, the individual pixel RGB values extracted for each color block at step 120 are averaged at step 122 to provide a single set of RGB values for each standardized color block in the calibration strip.

After the individual calibration pixel RGB values are averaged at step 122, the image has been processed to determine a first set of RGB values that characterizes the dressing color and a series of RGB value sets, one for each color block, each of which characterizes a standardized color in the color calibration strip. The dressing RGB values and the calibration RGB values are combined at step 124, and a single pH value for the wound dressing is calculated and provided to the user. While the exact processing that is applied at step 124 may vary, an illustrative process is shown visually in FIG. 40.

FIG. 40 depicts a process that treats each RGB value in an extracted wound dressing RGB value set and three extracted calibration RGB value sets as point locations in a three-dimensional space represented by RGB axis 130. The illustrated process can be implemented by a user device alone or in combination with one or more computing devices, such as a server. The dressing RGB value set is depicted as point 132, labeled $RGB_{SAMP}$, in the three-dimensional space. The three calibration RGB value sets are depicted as points 134, 136, and 138, labeled $RGB_{CAL1}$, $RGB_{CAL2}$, and $RGB_{CAL3}$, respectively. While three calibration RGB points are shown in FIG. 40 for illustration, any suitable number of calibration points, corresponding to the number of color blocks in the imaged color calibration strip, may be used to determine pH value.

From the plotted points, the process determines the distances between the dressing RGB point 132 and each of the calibration RGB points 134 ($d_3$), 136 ($d_1$), and 138 ($d_2$). These distances graphically represent the similarity between the color of the wound dressing, as defined by the $RGB_{SAMP}$ values, and each of the calibration colors, represented by the $RGB_{CAL}$ values. A relatively small distance between the dressing RGB values and a given set of calibration RGB values indicates similarity between the dressing and particular calibration color, while relatively larger distances indicate different colors. For example, in FIG. 40, each of $d_1$ and $d_2$ are shorter than distance $d_3$. This indicates that the color of the wound dressing from which the $RGB_{SAMP}$ values were extracted is more similar to the color of the color blocks from which the $RGB_{CAL2}$ and $RGB_{CAL3}$ values were extracted than it is to the color of the color block from which the $RGB_{CAL1}$ values were extracted.

Once all distances between the dressing RGB value and each set of calibration RGB values are determined. The process selects the two smallest determined distances to identify the two calibration colors, and corresponding standardized pH values associated with these two calibrated colors, that are most similar to the dressing color and wound pH value. For example, in the visualization in FIG. 40 distances $d_1$ and $d_2$, with corresponding RGB values $RGB_{CAL2}$ and $RGB_{CAL3}$, are selected as most similar to the dressing RGB values. $RGB_{SAMP}$. Thus, it is determined that the pH value indicated by the colored wound dressing is closer to the standardized pH values $pH_{CAL2}$ and $pH_{CAL3}$ associated with $RGB_{CAL2}$ and $RGB_{CAL3}$, respectively, than it is to any other standardized pH values, such as $pH_{CAL2}$ associated with $RGB_{CAL1}$.

In order to calculate an estimate for the dressing pH, which falls between the selected two closest standardized pH values, the dressing RGB values are normalized to a line segment defined by the two selected calibration RGB values. In FIG. 40, this line segment is shown as a line between $RGB_{CAL2}$ and $RGB_{CAL3}$, which includes a point $RGB_{NORM}$ that is the normalized RGB value for the wound dressing. The value $RGB_{NORM}$ is defined by projecting the dressing RGB values $RGB_{SAMP}$ perpendicularly (or in any other suitable way) onto the line defined by the two calibration RGB values. The location of the $RGB_{NORM}$ point 140 along this line is then used to calculate the final pH estimation for the wound dressing. While selection of two calibration and smallest distances is described, the illustrated process can select less or more than two calibration values and/or smallest distances. In addition, in certain implementations, one or more distances other than the smallest can be utilized.

The distance between the normalized point 140 and each of the calibration RGB points 136 (distance $a_1$) and 138 (distance $b_1$) are determined and used to calculated the pH estimation. The proportions of the line between the calibration RGB points made up of these distances indicates where the $pH_{SAMP}$ value lies between the $pH_{CAL2}$ and $pH_{CAL3}$ standardized values. For example, if $a_1$ is equal to $b_1$, then $pH_{SAMP}$ is halfway between $pH_{CAL2}$ and $pH_{CAL3}$. Thus, if $pH_{CAL2}$ is 6.5 and $pH_{CAL3}$ is 7.0, then $pH_{SAMP}$ is calculated as 6.75. If, on the other hand, $a_1$ is equal to 75% of the line between $RGB_{CAL2}$ and $RGB_{CAL3}$, then the $pH_{SAMP}$ is closer to $pH_{CAL3}$ than to $pH_{CAL2}$. In that case, if $pH_{CAL2}$ is 6.5 and $pH_{CAL3}$ is 7.0, then $pH_{SAMP}$ is calculated as 6.875. The process returns the calculated $pH_{SAMP}$ value for display to the user and storage in a patient record.

In some implementations, the analysis methods shown in FIGS. 38-40 employ a pH-sensitive wound dressing, and images captured of that dressing, to provide the user with pH readings and wound status feedback. A wound dressing 150 suitable for use in such methods is shown in FIG. 41. The wound dressing 150 includes a pH indicator 152 and a color calibration strip 154. The pH indicator 152 is the pH-sensitive component of the wound dressing 150 and includes one or more dyes or compounds that exhibit different colors under different pH conditions. When the wound dressing

150 is visualized, or images of the dressing are captured, the color of the indicator 152 is used to determine a pH level for the wound to which the dressing 150 is applied.

The color calibration strip 154 is provided on the wound dressing 150 to facilitate interpretation of the indicator 152 to determine pH level. The color calibration strip 154 includes five color blocks 156*a-e*, each of which indicate the known color of the dye or compound in indicator 152 at a given pH level. While only five color blocks are shown on the dressing 150, more or fewer color blocks could be included on the dressing. As an alternative to providing the strip 154 directly on the dressing, the strip may be a separate component that is placed on the dressing during image capture. The color blocks 156*a-e* are selected to span the range of expected pH values that the dressing 150 will contact, and may be indicative of pH values spaced either at even or uneven increments over that expected range. For example, color block 156*a* may indicate the expected color of indicator 152 at a pH value of 5.0, and each of color block 156*b-e* may indicate the expected color of indicator 152 at pH values incremented by 1.0, up to a value of 9.0 for color block 156*e*. Other ranges and increments, varied and constant, may be used, and more or fewer than five calibration pH levels may be used for dressings having more or fewer color blocks.

The dressing 150 includes orientation indicators for automated image processing. Calibration strip location indicators 158*a* and 158*b* are provided at each end of the color calibration strip 154. These indicators 158*a* and 158*b* can be used for image processing to automatically detect the color blocks 156*a-e*. A processing system may locate the indicators 158*a* and 158*b* in a received image and draw a line between the two indicators. The system may then identify each of color blocks 156*a-e* along the drawn line. This approach may facilitate identification of the color blocks in images in which the dressing 150 is not optimally aligned, for example when the calibration color strip is not straight relative to an alignment frame in a captured image.

The dressing 150 also includes corner indicators 160*a-d* for automated image processing to identify the location of the pH indicator 152. As with the indicators 158*a* and 158*b*, the corner indicators 160*a-d* can be detected by an image processing system and used to re-orient an image of the dressing 150 that is not optimally aligned during image capture. In some implementations, it may be preferable to identify a particular region of interest within the pH indicator 152 that is used for color analysis, and the corner indicators 1 60*a-d* may be used to identify that region. For example, the image process system may define an X 162 extending between the corner indicators 160*a-d*. The intersection of the two lines that form the X 162 may then be processed to define center point 164 that identifies the center of the pH indicator 152. From this center point 164, the region of interest for analysis can be defined.

Various implementations of devices that are usable for the methods and wound systems described above for providing pH reading and monitoring are envisioned, including both local user devices and processing systems as well as remote server systems in communication with local devices over a network. For ease of illustration, embodiments of these devices are described below with respect to illustrative user devices, servers, and networks. The systems, devices, and methods disclosed herein, however, may be adapted to other implementations and other embodiments of such devices and networks.

As used herein, "user device" includes, without limitation, any suitable combination of one or more devices configured with hardware, firmware, and software to carry out one or more of the computerized techniques described herein. A user device can be any computing device that is capable of receiving user input, for example receiving images, and providing responsive analysis, for example providing calculated pH values or trends, to a user either as a stand-alone device or in communication with an external processing system, such as a server, over a communication network. For example, a user device may include a mobile computing device (e.g., a laptop computer, a tablet computer, a personal digital assistant (PDA), a mobile telephone (such as a smartphone), or a camera) or a stationary computing device (e.g., a personal computer, stationary telephone, or other computing device). A user device is preferably capable of wireless communications for interfacing with external systems. However, devices without wireless communication capabilities may be used without departing from the scope of this disclosure. A user device may include one or more cameras, including both front-facing and rear-facing cameras, for capturing images of wound dressings. In some implementations, a user device is a device worn by a user such as augmented reality glasses. A user device may also include software for generating or editing images.

As used herein, the terms "processor," "processing circuitry," or "computing device" refers to one or more computers, microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. It may also refer to other devices configured with hardware that includes logic circuitry, firmware, and software to carry out one or more of the computerized techniques described herein. Processors and processing devices may also include one or more memory devices for storing inputs, outputs, and data that is currently being processed. An illustrative computing device, which may be used to implement any of the processing circuitry and servers described herein, is described in detail below with reference to FIG. 44.

As used herein, "user interface" includes, without limitation, any suitable combination of one or more input devices (e.g., keypads, a mouse, touch screens, trackballs, voice recognition systems, gesture recognition systems, accelerometers, RFID and wireless sensors, optical sensors, solid-state compasses, gyroscopes, stylus input, joystick, etc.) and/or one or more output devices (e.g, visual displays, speakers, tactile displays, printing devices, etc.) For example, user interfaces can include a display (which may be a touch-sensitive color display, optical projection system, or other display) for graphically receiving and providing information to the user.

FIGS. 42 and 43 depict embodiments of device, a computing device, such as a server, and network structures that may be used to implement the systems and methods disclosed herein. FIG. 42 is a block diagram of a computerized system 170 for providing automated reading and monitoring of wound pH status and trends. Generally, in system 170, a user device 172 and server 180 are connected over a communications network 178. The user device 172 includes processing circuitry 174 and a user interface 176. The server 180 includes processing circuitry 182 and memory 184.

During wound evaluation and monitoring, an image of a wound dressing having a pH color indicator, such as the dressing 150 discussed above, is captured by the user device 172 and transmitted to the server 180 over network 178 in transmission 186. The processing circuitry 182 at the server 180 analyzes the received image and provides feedback, for example a calculated pH value, over the network 178 in transmission 188. In addition to images and pH values, the transmission 186 and 188 may include any other information provided by the user or sent by the server 180, for example any additional user input or requests may be provided in transmission 186 and any additional information such as patient pH trends and diagnoses may be provided in transmission 188.

The network 178 couples the user device 172 and server 180 and carries transmissions, such as transmissions 186 and 188, between the two components. Communications network 178 may be any suitable network for exchanging information between user device 172 and server 180. For example, communications network 178 can include the Internet, a mobile phone network, mobile voice or data network (e.g., a 3G, 4G, or LTE network), cable network, public switched telephone network, a satellite network, or other type of communications network or combinations of communications networks. The user device 172 and server 180 can communicate using one or more communications paths, such as a satellite path, a fiber-optic path, a cable path, a path that supports Internet communications, free-space connections (e.g., for broadcast or other wireless signals), or any other suitable wired or wireless communications path or combination of such paths. The transmissions sent over the communications may be encrypted to provide secure data transmissions. The secure transmission is preferable for the sensitive patient and medical information sent by the devices.

Only one server 180 and one user device 172 are shown in FIG. 42 to avoid complicating the drawing, but the system 170 can support multiple servers and multiple user devices. For example, rather than being located in the single server 180, processor 182 may be located in a first server to provide image processing and analysis, while memory 184 may be located in a second server to provide data storage and retrieval. Multiple servers may operate together as a cluster or as a distributed computing network.

In some implementations, the system 170 is implemented in a cloud computing environment in which one or more of the components are provided by different processing and storage services connected via the Internet or other communications system. In a cloud computing environment, various types of computing services for content sharing, storage, or distribution are provided by a collection of network-accessible computing and storage resources. For example, the cloud can include a collection of server computing devices, which may be located centrally or at distributed locations that provide cloud-based services to various types of users and devices connected via a network such as the Internet via communications network 178. These cloud resources may include one or more content sources and one or more data sources.

In addition or in the alternative, the remote computing sites may include other user devices, such as user medical devices, user computer devices, and wireless user communications devices. For example, the other user devices may provide access to stored copies of data or images. The user devices may operate in a peer-to-peer manner without communication with the server 180. The cloud provides access to services, such as content storage, content sharing, or social networking services, among other examples, as well as access to any content described below. Services can be provided in the cloud through cloud computing service providers, or through other providers of online services. For example, the cloud-based services can include a content storage service, a content sharing site, a social networking site, or other services via which user-sourced content is distributed for viewing by others on connected devices. These cloud-based services may allow a user device to store content to the cloud and to receive content from the cloud rather than storing content locally and accessing locally-stored content. Cloud resources may be accessed by user device 172 using, for example, a web browser, a desktop application, a mobile application, and/or any combination of access applications. In some implementations, a user device receives content from multiple cloud resources simultaneously. For example, a user device can access data and information from one cloud resource while downloading or uploading content to or from a second cloud resource. A user device may also download or upload content to or from multiple cloud resources for more efficient downloading or uploading.

While FIG. 42 depicts a network-based system for providing wound monitoring and wound pH determinations, the functional components of the system 170 may be implemented as one or more components included within or local to a user device. For example, FIG. 43 depicts a user device 190 that includes processing circuitry 192, a user interface 194, and memory 196. The processing circuitry 194 may be configured to perform any or all of the functions of processing circuitry 174 and 182 of FIG. 42, the memory 196 may be configured to store any or all of the data stored in memory 184 of FIG. 42, and the user interface 194 may be configured to perform any of the input and output functions described herein for the user interface 176 of FIG. 42. In some implementations, the user device 190 is configured to perform all of the functions described herein for image capture, image analysis, pH calculation, patient and pH data storage, and user interaction described herein for wound monitoring. The data stored in memory 196 can be encrypted and require password authorization for access to protect sensitive patient and medical information.

FIG. 44 shows a block diagram of an illustrative computing device 200, which may be any of the computerized components of the systems in FIGS. 42 and 43, for performing any of the processes described herein. Each of the components of the systems 170 or 190 described in FIGS. 42 and 43 may be implemented on one or more computing device 200. In certain aspects, a plurality of the components of these systems may be included within one computing device 200. In certain implementations, a component and a storage device may be implemented across several computing devices 200. The computing device 200 includes at least one communications interface 208, an input/output controller 210, system memory 201, and one or more data storage device 211. The system memory 201 includes at least one random access memory (RAM 202) and at least one read-only memory (ROM 204). These elements are in communication with a central processing unit (CPU 206) to facilitate the operation of the computing device 200.

The computing device 200 may be configured in many different ways. For example, the computing device 200 may be a conventional standalone computer or alternatively, the functions of computing device 200 may be distributed across multiple computer system and architectures. In FIG. 44, the computing device 200 is linked, via network or local network, to other servers or systems. The computing device 200 may be configured in a distributed architecture, wherein databases and processing circuitry is housed in separate units or locations. Some units perform primary processing functions and contain at a minimum a general controller or a processing circuitry and a system memory. In distributed architecture implementations, each of these units may be attached via the communications interface 208 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to, Ethernet, SAP, SAS™, ATP, BLU-ETOOTH™, GSM, DICOM and TCP/IP.

Communications interface 208 is any suitable combination of hardware, firmware, or software for exchanging information with external devices. Communications interface 208 may exchange information with external systems using one or more of a cable modem, an integrated services digital network (ISDN) modem, a digital subscriber line (DSL) modem, a telephone modem, an Ethernet card, or a wireless modem for communications with other devices, or any other suitable communications interface. Such communications may involve the Internet or any other suitable communications networks 178 as discussed in relation to FIG. 42. In addition, the communications interface 208 may include circuitry that enables peer-to-peer communication, or communication between user devices in locations remote from each other.

The CPU 206 comprises a processor, such as one or more conventional microprocessors and one or more supplementary co-processors such as math co-processors for offloading workload from the CPU 206. The CPU 206 is in communication with the communications interface 208 and the input/output controller 210, through which the CPU 206 communicates with other devices such as other servers, user terminals, or devices. The communications interface 208 and the input/output controller 210 may include multiple communication channels for simultaneous communication with, for example, other processors, servers or client terminals.

The CPU 206 is also in communication with the data storage device 211 and system memory 201. The data storage device 211 and system memory 201 may comprise an appropriate combination of magnetic, optical or semiconductor memory, and may include, for example, RAM 202, ROM 204, flash drive, an optical disc such as a compact disc or a hard disk or drive. The system memory 201 may be any suitable combination of fixed and/or removable memory, and may include any suitable combination of volatile or non-volatile storage. The memory 201 may be physically located inside a user device or server or may be physically located outside of the user device (e.g., as part of cloud-based storage) and accessed by the user device over a communications network. The CPU 206 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 206 may be connected to the data storage device via the communications interface 208. The CPU 206 may be configured to perform one or more particular processing functions.

The data storage device 211 may store, for example, (i) an operating system 212 for the computing device 200; (ii) one or more applications 214 (e.g., computer program code or a computer program product) adapted to direct the CPU 206 in accordance with the systems and methods described here, and particularly in accordance with the processes described in detail with regard to the CPU 206; and/or (iii) database(s) 216 adapted to store information that may be utilized by the program.

The operating system 212 and applications 214 may be stored, for example, in a compressed, an uncompiled and an encrypted format, and may include computer program code. The instructions of the program may be read into a main memory of the processing circuitry from a computer-readable medium other than the data storage device, such as from the ROM 204 or from the RAM 202. While execution of sequences of instructions in the program causes the CPU 206 to perform the process steps described herein, hardwired circuitry may be used in place of, or in combination with, software instructions for implementation of the processes of systems and methods described in this application. Thus, the systems and methods described are not limited to any specific combination of hardware and software.

Suitable computer program code may be provided for performing one or more functions as described herein. The program also may include program elements such as an operating system 212, a database management system and "device drivers" that allow the processing circuitry to interface with computer peripheral devices (e.g., a video display, a keyboard, a computer mouse, etc.) via the input/output controller 210.

The term "computer-readable medium" as used herein refers to any non-transitory medium that provides or participates in providing instructions to the processing circuitry of the computing device 200 (or any other processing circuitry of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 206 (or any other processing circuitry of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 200 (e.g., a server) can receive the data on the respective communications line and place the data on a system bus for the processor. The system bus carries the data to main memory, from which the processing circuitry retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

The implementation of the methods and systems discussed above provides prompt and accurate wound status and progression feedback to a patient or physician for monitoring or adjusting wound care. Whether the image processing, pH calculation, and data storage is provided locally at a user's device or remotely at one or more server or cloud components, a local device provides an interface to the user for providing and receiving data and information that is used in or results from such processing and data storage. The series of screenshots discussed below and shown in FIGS. 45-50 demonstrate data and information that may be transmitted to or received from a user, either on a local user device or on an accessory device in communication with a user device. It will be understood that the screens, fields, and data shown in the displays in FIGS. 45-50 may be modified or omitted as desired, and the display descriptions below do not limit or exclude the displays and data that may be relayed to a user.

Figure 45:
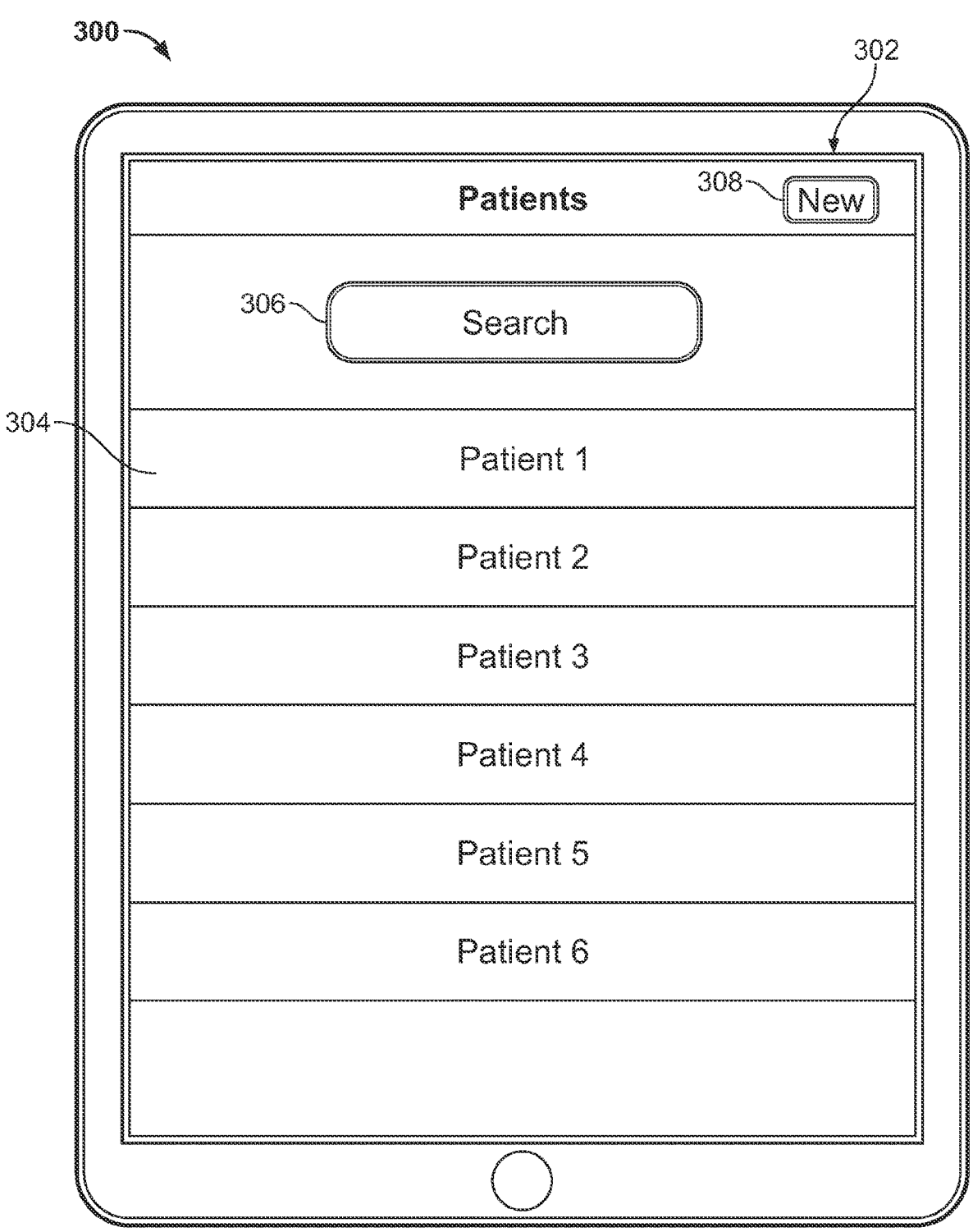

FIG. 45 shows an illustrative display 302 on a user device 300 for identifying patients and receiving user selections of a patient. Such selection may be used, for example, to identify a particular patient being monitored for current pH value readings from a plurality of patients who use the same device 300 or who visit the same doctor who uses the device 300 for patient monitoring. The display 302 facilitates identification and tracking of the patients in such situation, when multiple records are accessed from the same device. Depending on the system in which the user device 300 is implemented, the list of patients may provide access to locally-stored data and information specific to each patient, or may provide access to data and information stored locally. In response to user selection of a patient when data is stored locally, the user device 300 accesses the locally stored data to display to the user or to update a stored record with a new pH reading. In response to user selection of a patient when data is stored remotely, the user device 300 transmits a request to the remote storage device to send the data for user display or transmits a new pH reading to be added to the remotely-stored record.

Wound monitoring systems may also provide automated patient identification that determines the patient from the wound dressing image. A wound dressing may include a name, number, barcode, QR code, or other unique identifier that is related with a particular patient. The identifier may be included on a wound dressing, such as dressing, 150 in FIG. 41, and a box of bandages can all include the same identifier. Alternatively, the identifier may be provided separate from a dressing, for example, as a sticker, and the patient or physician may transfer the identifier to a new dressing each time the wound bandage is changed. When the bandage and identifier are imaged for the first time, the device alerts the user that the identifier has not been associated with a patient and provides the display 302 for the user to select the patient. On subsequent readings, the patient is automatically determined from the identifier, and the display 302 is bypassed.

The screen 302 includes a list of patients each identified by name, for example "Patient 1" for identifier 304 in the list. From this list, a user can select one of the identifiers to access records for the patient; begin a new wound pH reading for the patient, view or edit identifying information for the patient, or perform any other desired function for that particular patient. In situations where the list of patients is quite long, a search query box 306 may be included to facilitate patient selection without requiring a user to scroll through the long list of patients to find the desired identifier. The list of patient identifiers may automatically update in real time as a user types in the query box 306 to filter the list and eliminate any patient identifiers that do not contain the query being entered.

Figure 46:
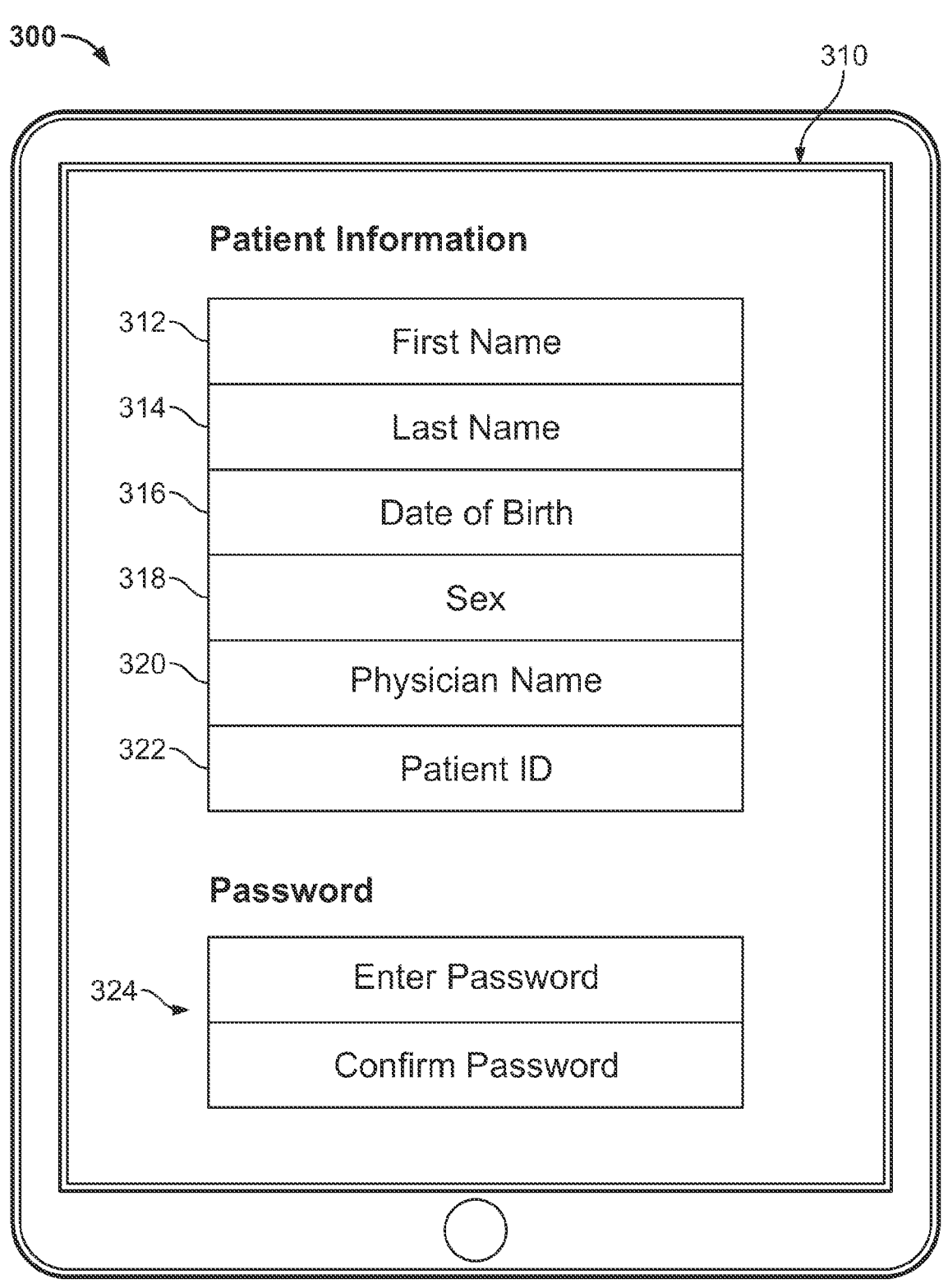

If a new patient is being monitored, the patient or the patient's physician may select the new patient option 308 to add a new record to the database of stored patient information and data. When a user selects the new patient option 308, a prompt screen is displayed to the user for identification information to be used for the new patient's record. The display 310 on user device 300 shown in FIG. 46 depicts an illustrative example of such a new patient prompt screen. The display 310 includes fields for patient identification and information that can be used to identify the particular patient and associate any records kept from pH monitoring with the particular patient to which they relate. While the display 310 includes particular information fields, some of the fields shown may be omitted, or additional information fields may be included in the display 310, depending on the information desired for patient record keeping in a particular implementation.

The display 310 includes a first name field 312, last name field 314, date of birth field 316, and sex field 318 for identifying the specific patient. These standard identifying fields can be stored in patient records for each patient in a given system, and can be used to sort the patients or filter the patients as desired. The first name field 312 and last name field 314 in particular can be used to efficiently identify or find patients, for example by searching for patients in a list of records using a search like the search query box 306 shown in FIG. 45.

The display 310 also includes a physician name field 320 and a patient ID field 322 that may be used to connect physicians and patients in certain implementations. The physician name field 320 may be used, for example, in systems that store patient records for many patients and for patients of different physicians. For example, a cloud computing system may be maintained by a provider of the pH monitoring application running on user device 300, or by the provider of wound dressings used to monitor pH. The cloud system may use the physician field 320 to group patient records by physician and provide a given physician with access to the records for only his or her patients. In such implementations, the patient ID field 322 may be used to facilitate record keeping for physicians. Each physician may assign ID numbers to each patient for easier record keeping, and the pH monitoring readings for each patient may be stored by ID number in addition to patient name. For security purposes, the display 310 may also include password fields 324 for setting and confirming a password for each new patient that is later required to access any records or take new readings for the particular patient.

Figure 47:
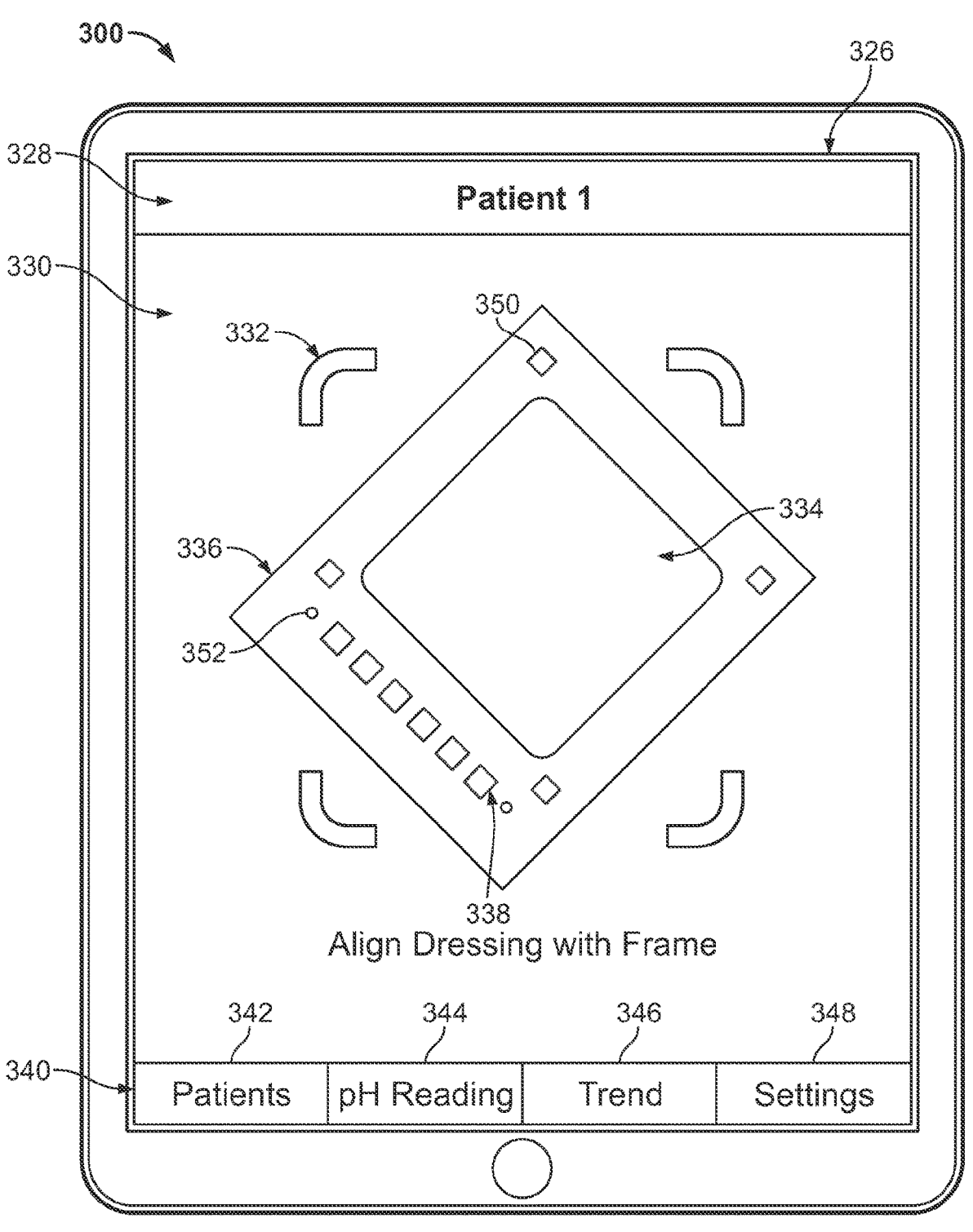

The pH readings that are stored for individual patients are obtained from images captured by the user device 300. The device 300, preferably through an application running on the device, provides a user with image capture cues to facilitate capturing quality images that will result in reliable pH readings for a wound dressing. Display 326 on user device 300 in FIG. 47 shows an embodiment of such an image capture screen. The display 326 includes a patient identifier 328, image capture screen 330, and tabs menu 340. The patient identifier 328 displays a selected patient for whom a reading is being taken for implementations in which the patient is selected before pH readings are obtained. In implementations where images and pH readings can be obtained and the associated patient identified after the readings, the patient identifier 328 may be blank or may be omitted from the display 326.

The tabs menu 340 facilitates navigation between the various screens provided on user device 300, and may be included or omitted from any of the displays discussed herein as desired. The menu 340 includes a patients tab 342 for accessing a list of patients for whom records are stored and accessible, a pH reading tab 344 to access the image capture display 326 and take readings, a trend tab 346 to access a list or graph of past readings for a particular patient, and a settings tab 348 to access general configurable application and image capture settings.

The image capture screen 330 of display 326 helps a user take quality images of wound dressings, for example dressing 336 in FIG. 47, to provide reliable and repeatable pH readings. The screen 330 displays a guiding frame 332 for a user to indicate the optimal orientation of dressing 336 for image capture. The guiding frame 332 gives the user a visual cue to align the dressing 336 before causing the user device 300 to capture an image of the dressing 336 for pH reading. In addition to providing the guiding frame 332, the user device 300 may monitor the orientation of the dressing 336, for example by detecting the location of corner indicators 350 or calibration strip indicators 352, and automatically capture an image for processing when the dressing 336 is adequately aligned with the guiding frame 332. Once the pH indicator 334, color calibration strip 338, corner indicators 350, and calibration strip indicators 352 are all positioned within the guiding frame 332, the user is provided with visual confirmation that a suitable image of the dressing 336 can be captured, whether done manually by pressing a capture button or automatically by the user device 300.

Figure 48:
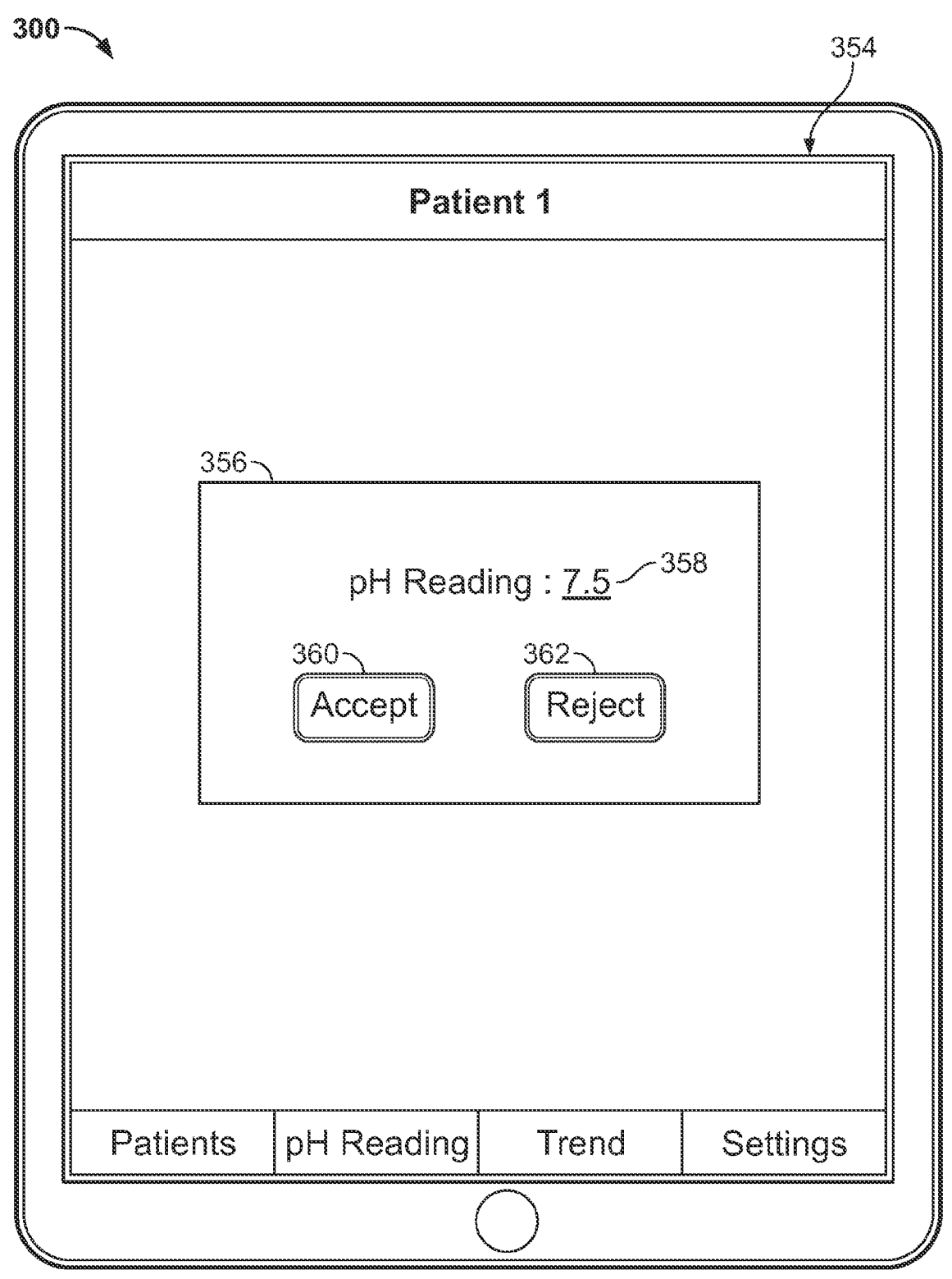

An image that is captured in the image capture screen 330 is processed, either locally at user device 300 or remotely at a processor in communication with user device 300 over a network, to return a calculated pH value for the wound dressing 336. Display 354 in FIG. 48 shows an illustrative screen that displays the calculated value to a patient or physician. The display 354 includes a reading window 356 that provides the user with the calculated pH 358 for the dressing image that was captured. The window 356 also presents the user with an accept option 360 and a reject option 362 that a user can use to indicate whether or not the calculated pH 358 is reasonable or acceptable. If a user determines that the calculated pH 358 is reasonable, he or she may select the accept option 360, and the calculated pH 358 can be added to the patient's record. If a user determines that the calculated pH 358 is not reasonable, for example if it is nonsensical or seems either inconsistent or too high or low, the user can select the reject option 362. If the reject option 362 is selected, the calculated pH 358 may not be stored in a patient's record, or may be stored in the record with a special flag to indicate the calculated pH 358 was marked as unreliable or wrong. Optionally, the user device 300 may provide the user with a prompt or additional option to capture another dressing image if the reject option 362 is selected.

The user device 300 also provides a user with screens that allow a patient or physician to review patient data either after a reading is accepted from display 354 in FIG. 48, after a patient is selected from display 302 in FIG. 45, after trend tab 346 is selected from display 326, or when patient records are accessed from any other screens. The displays of user device 300 shown in FIGS. 49 and 50 show screens that may be implemented to provide a patient or physician with a data record review interface.

Figure 49:
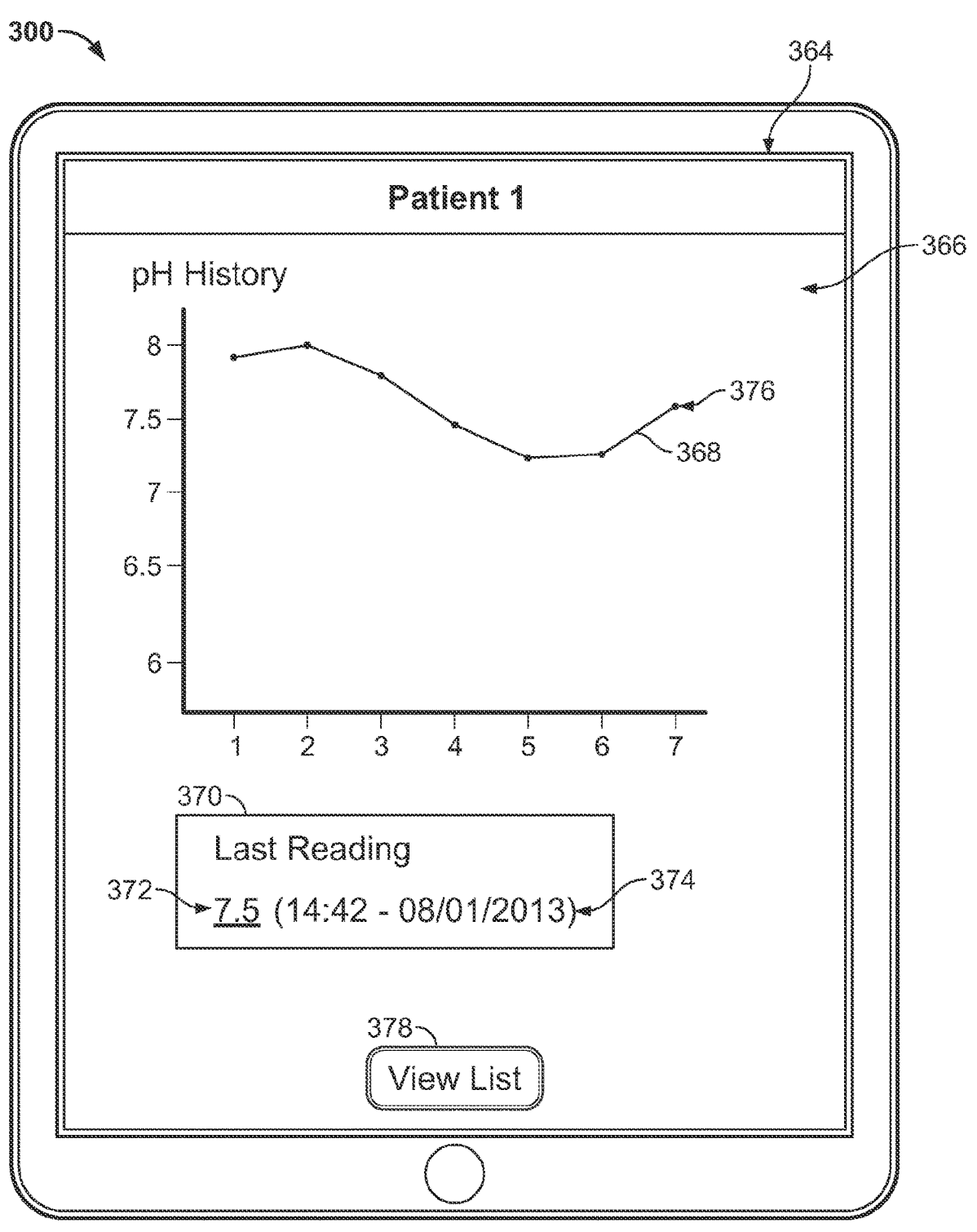

FIG. 49 shows a display 364 on user device 300 that provides a graphical representation of pH reading history for a particular patient. The display 364 includes a graph 366 showing a trend 368 in calculated pH values over time for an identified patient "Patient 1." The trend 368 plots the last seven pH values that were obtained for the patient in the graph 366. More or fewer than seven pH values may be displayed in the graph 366, and the size and spacing of the graph may be scaled as appropriate for showing more of fewer pH data points.

The display 364 also shows a last reading window 370 that identifies the last calculated pH value 372 to the user. This calculated pH value 372 corresponds to the last point 376 plotted in trend 368 of graph 366. The window 370 also identifies the date and time 374 at which the calculated pH value 372 was obtained for the patient. At the bottom of display 364, a list option 378 is provided. If a user selects the list option 378, the user device 364 displays a list of all of the calculated pH values plotted in the graph 366, along with date and time information and any other desired identification information for each point.

Figure 50:
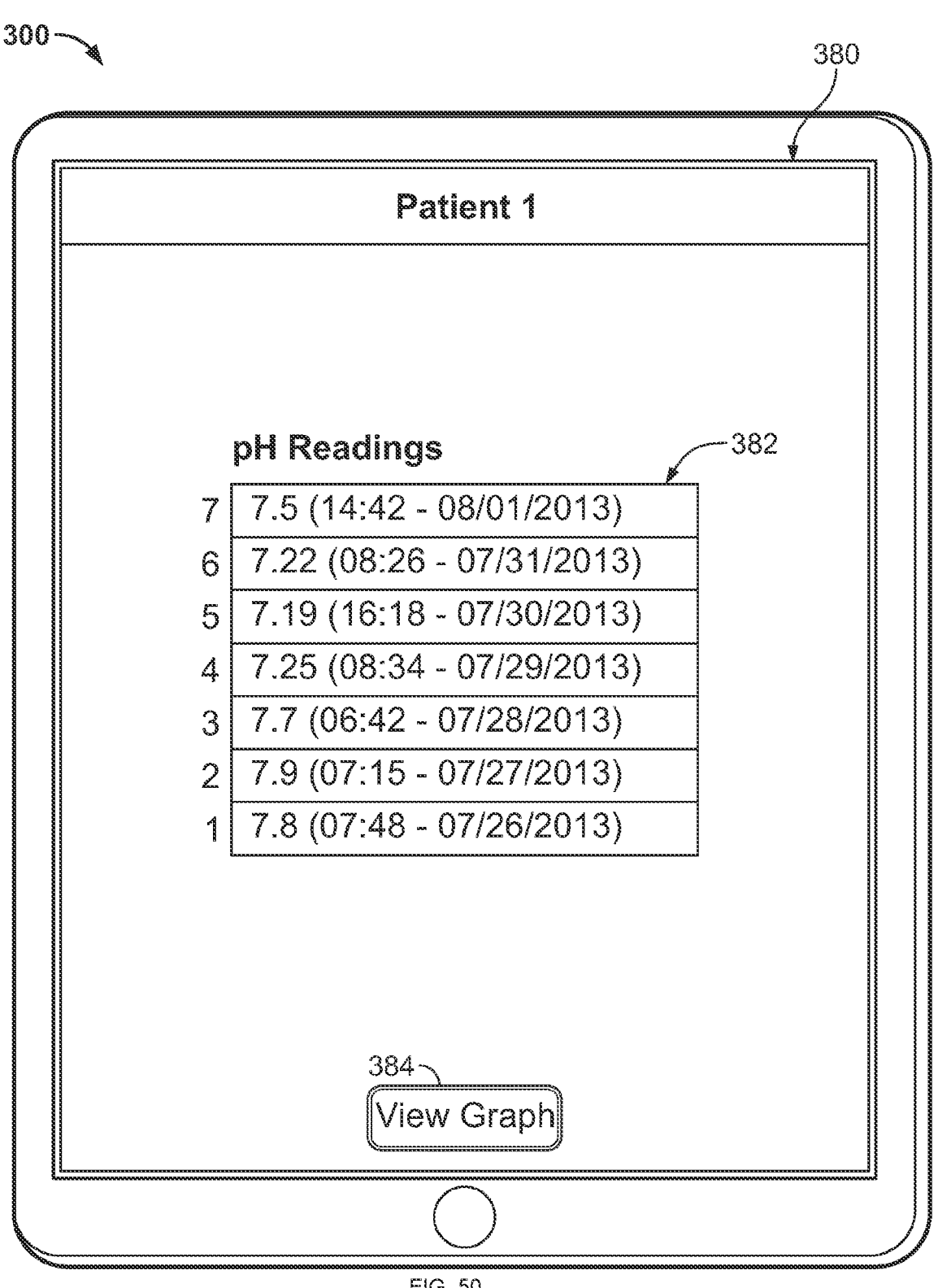

FIG. 50 shows a list display 380 that may be displayed in response to a user selection of the list option 378 of display 364. The display 380 includes a data list 382 that shows the calculated pH value and corresponding date and time for each data point plotted in the graph 366 of FIG. 49. While seven data points are shown in the list 382, any number of data points can be displayed, and the list 382 can be scaled accordingly to fit the desired number of points. If there are too many points to fit on the display 380, the list 382 may be scrollable to allow the user to go backwards and forwards through the serial data points. In addition to the list 382, the display 380 includes a view graph option 384 that allows the user to toggle the user device 300 to a graphical display of the data in the list 382, for example by returning to the screen 364 of FIG. 49 if the graph option 384 is selected.

EXAMPLE EMBODIMENTS

Group A

A1. A method of monitoring a wound, comprising:
  capturing, with a user device, an image of a wound dressing;
  determining the color of a pH indicator on the wound dressing, wherein determining the color comprises extracting RGB values from the captured image;
  calculating a pH value for the wound dressing from the dressing RGB values; and
  displaying, on the user device, an indication of the calculated pH value.

A2. The method of A1, further comprising displaying, on the user device, a guiding frame during image capture, wherein the guiding frame provides an indication of proper wound dressing alignment to a user.

A3. The method of A2, further comprising detecting, with the user device, the alignment of the wound dressing relative to the displayed guide frame, wherein the image is automatically captured by the user device when the wound dressing is properly aligned with the guiding frame.

A4. The method of any of the preceding embodiments, further comprising:
  rejecting, with the user device, an image having inadequate light or excessive shadow; and
  displaying, on the user device, a request to a user to capture a new image.

A5. The method of any of the preceding embodiments, further comprising displaying, on the user device, an option to accept or reject the calculated pH value when the calculated pH value is displayed.

A6. The method of any of the preceding embodiments, further comprising storing, in memory on the user device, the calculated pH value in a record of pH values.

A7. The method of A6, further comprising receiving, with the user device, user input identifying a particular patient, wherein the stored record is associated with the particular patient.

A8. The method of A7, wherein the user input comprises a selection of the particular patient from a list of stored patients.

A9. The method of A7, wherein the user input comprises identification information for a new patient.

A10. The method of any of A6-A9, further comprising displaying, on the user device, a trend of pH values for the particular patient.

A11. The method of A10, wherein the displayed trend comprises at least one of a graph and a list of pH values.

A12. The method of any of the preceding embodiments, wherein extracting dressing RGB values from the captured image comprises determining individual pixel RGB values for each one of a plurality of pixels in the image and averaging the individual pixel RGB values for the plurality of pixels to determine the dressing RGB values.

A13. The method of A12, further comprising defining a center point of the captured image.

A14. The method of A13, further comprising defining a dressing circle region around the center point of the captured image, wherein the dressing circle region comprises the plurality of pixels for which the individual pixel RGB values are determined.

A15. The method of A14, wherein the dressing circle region has a radius between about 5 and about 100 pixels.

A16. The method of A15, wherein the dressing circle region has a radius between about 10 and about 50 pixels.

A17. The method of A16, wherein the dressing circle region has a radius between about 20 and about 30 pixels.

A18. The method of any of the preceding embodiments, further comprising capturing, with the user device, an image of a color calibration strip.

A19. The method of A18, wherein the color calibration strip is captured in the same image as the wound dressing.

A20. The method of A18 or A19, further comprising extracting calibration RGB values from the image of the color calibration strip for each of a plurality of color blocks in the color calibration strip.

A21. The method of A20, wherein:
  each color block is associated with a standardized pH value; and
  the pH value for the wound dressing is calculated using the dressing RGB values and the calibration RGB values.

A22. The method of A20 or A21, wherein extracting calibration RGB values for each of the plurality of color blocks comprises determining individual pixel RGB values for each one of a plurality of pixels in a color block and averaging the individual pixel RGB values for the plurality of pixels in the color block to determine the calibration RGB values for the color block.

A23. The method of A22, further comprising defining a center point of each of the plurality of color blocks.

A24. The method of A23, wherein the center points are defined from alignment indicators positioned on either side of the color calibration strip.

A25. The method of A23 or A24, further comprising defining a calibration circle region around the center point of each color block, wherein each of the calibration circle regions comprises the plurality of pixels for which the individual pixel RGB values are determined in each color block.

A26. The method of A25, wherein each of the calibration circle regions has a radius between about 3 and about 10 pixels.

A27. The method of A26, wherein each of the calibration circle regions has a radius of about 5 pixels.

A28. The method of any of A18-A27, further comprising calculating a distance between the dressing RGB values and each of the calibration RGB values in a three-dimensional space.

A29. The method of A28, further comprising:
determining the two smallest calculated distances; and
calculating the pH value for the wound dressing based on the RGB calibration values and standardized pH values associated with the two smallest distances.

A30. The method of A29, further comprising:
normalizing the dressing RGB values to a line defined by the two RGB calibration values associated with the two shortest distances; and
calculating the pH value for the wound dressing from the normalized position of the dressing RGB values on the line.

Group B

B1. A method of monitoring a wound, comprising:
receiving, at a server, an image of a wound dressing;
determining the color of a pH indicator on the wound dressing, wherein determining the color comprises extracting dressing RGB values from the received image;
calculating a pH value for the wound dressing from the dressing RGB values; and
transmitting, from the server, an indication of the calculated pH value.

B2. The method of B1, further comprising:
rejecting, at the server, an image having inadequate light or excessive shadow; and
transmitting, from the server, a request to a user to capture a new image.

B3. The method of B1 or B2, further comprising displaying, on a user device in communication with the server, the calculated pH value with an option to accept or reject the calculated pH value.

B4. The method of any of the preceding embodiments, further comprising storing, in memory on the server, the calculated pH value in a record of pH values.

B5. The method of B4, further comprising receiving, at the server, user input identifying a particular patient, wherein the stored record is associated with the particular patient.

B6. The method of B5, wherein the user input comprises a selection of the particular patient from a list of stored patients.

B7. The method of B6, wherein the user input comprises identification information for a new patient.

B8. The method of any of B4-B7, further comprising transmitting, from the server, a trend of pH values for the particular patient for display on a user device in communication with the server.

B9. The method of B8, wherein the trend comprises at least one of a graph and a list of pH values.

B10. The method of any of the preceding embodiments, wherein extracting dressing RGB values from the received image comprises determining individual pixel RGB values for each one of a plurality of pixels in the image and averaging the individual pixel RGB values for the plurality of pixels to determine the dressing RGB values.

B11. The method of B10, further comprising defining a center point of the received image.

B12. The method of B11, further comprising defining a dressing circle region around the center point of the received image, wherein the dressing circle region comprises the plurality of pixels for which the individual pixel RGB values are determined.

B13. The method of B12, wherein the dressing circle region has a radius between about 5 and about 100 pixels.

B14. The method of B13, wherein the dressing circle region has a radius between about 10 and about 50 pixels.

B15. The method of B14, wherein the dressing circle region has a radius between about 20 and about 30 pixels.

B16. The method of any of the preceding embodiments, further comprising receiving, at the server, an image of a color calibration strip.

B17. The method of B17, wherein the color calibration strip is in the same received image as the wound dressing.

B18. The method of B16 or B17, further comprising extracting calibration RGB values from the image of the color calibration strip for each of a plurality of color blocks in the color calibration strip.

B19. The method of B18, wherein:
each color block is associated with a standardized pH value; and
the pH value for the wound dressing is calculated using the dressing RGB values and the calibration RGB values.

B20. The method of B18 or B19, wherein extracting calibration RGB values for each of the plurality of color blocks comprises determining individual pixel RGB values for each one of a plurality of pixels in a color block and averaging the individual pixel RGB values for the plurality of pixels in the color block to determine the calibration RGB values for the color block.

B21. The method of B20, further comprising defining a center point of each of the plurality of color blocks.

B22. The method of B21, wherein the center points are defined from alignment indicators positioned on either side of the color calibration strip.

B23. The method of B21 or B22, further comprising defining a calibration circle region around the center point of each color block, wherein each of the calibration circle regions comprises the plurality of pixels for which the individual pixel RGB values are determined in each color block.

B24. The method of B23, wherein each of the calibration circle regions has a radius between about 3 and about 10 pixels.

B25. The method of B24, wherein each of the calibration circle regions has a radius of about 5 pixels.

B26. The method of any of B16-B25, further comprising calculating a distance between the dressing RGB values and each of the calibration RGB values in a three-dimensional space.

B27. The method of B26, further comprising:
determining the two smallest calculated distances; and
calculating the pH value for the wound dressing based on the RGB calibration values and standardized pH values associated with the two smallest distances.

B28. The method of B27, further comprising:
normalizing the dressing RGB values to a line defined by the two RGB calibration values associated with the two shortest distances; and calculating the pH value for the wound dressing from the normalized position of the dressing RGB values on the line.

Group C

C1. A method of monitoring a wound, comprising:

capturing, with a user device, an image of a wound dressing having a pH indicator;

transmitting, from the user device, the captured image;

receiving, at the user device, a pH value for the wound dressing in the captured image; and displaying, on the user device, an indication of the received pH value.

C2. The method of C1, further comprising displaying, on the user device, a guiding frame during image capture, wherein the guiding frame provides an indication of proper wound dressing alignment to a user.

C3. The method of C2, further comprising detecting, with the user device, the alignment of the wound dressing relative to the displayed guide frame, wherein the image is automatically captured by the user device when the wound dressing is properly aligned with the guiding frame.

C4. The method of any of the preceding embodiments, further comprising:

rejecting, with the user device, an image having inadequate light or excessive shadow; and displaying, on the user device, a request to a user to capture a new image.

C5. The method of any of the preceding embodiments, further comprising displaying, on the user device, an option to accept or reject the received pH value when the received pH value is displayed.

C6. The method of any of the preceding embodiments, further comprising storing, in memory on the user device, the received pH value in a record of pH values.

C7. The method of C6, further comprising receiving, with the user device, user input identifying a particular patient, wherein the stored record is associated with the particular patient.

C8. The method of C7, wherein the user input comprises a selection of the particular patient from a list of stored patients.

C9. The method of C7, wherein the user input comprises identification information for a new patient.

C10. The method of any of C6-C9, further comprising displaying, on the user device, a trend of pH values for the particular patient.

C11. The method of C10, wherein the displayed trend comprises at least one of a graph and a list of pH values.

C12. The method of any of the preceding embodiments, further comprising:

determining, at a server in communication with the user device, individual pixel RGB values for each one of a plurality of pixels in the captured image;

averaging, at the server, the individual pixel RGB values for the plurality of pixels to determine dressing RGB values; and calculating, at the server, the pH value for the wound dressing from the dressing RGB values.

C13. The method of C12, further comprising defining a center point of the captured image.

C14. The method of C13, further comprising defining a dressing circle region around the center point of the captured image, wherein the dressing circle region comprises the plurality of pixels for which the individual pixel RGB values are determined.

C15. The method of C14, wherein the dressing circle region has a radius between about S and about 100 pixels.

C16. The method of C15, wherein the dressing circle region has a radius between about 10 and about 50 pixels.

C17. The method of C16, wherein the dressing circle region has a radius between about 20 and about 30 pixels.

C18. The method of any of C12-C17, further comprising capturing, with the user device, an image of a color calibration strip.

C19. The method of C18, wherein the color calibration strip is captured in the same image as the wound dressing.

C20. The method of C18 or C19, further comprising extracting, at a server in communication with the user device, calibration RGB values from the image of the color calibration strip for each of a plurality of color blocks in the color calibration strip.

C21. The method of C20, wherein:

each color block is associated with a standardized pH value; and the pH value for the wound dressing is calculated at the server using the calibration RGB values.

C22. The method of C20 or C21, wherein extracting calibration RGB values for each of the plurality of color blocks comprises determining, at the server, individual pixel RGB values for each one of a plurality of pixels in a color block and averaging, at the server, the individual pixel RGB values for the plurality of pixels in the color block to determine the calibration RGB values for the color block.

C23. The method of C22, further comprising defining a center point of each of the plurality of color blocks.

C24. The method of C23, wherein the center points are defined from alignment indicators positioned on either side of the color calibration strip.

C25. The method of C23 or C24, further comprising defining a calibration circle region around the center point of each color block, wherein each of the calibration circle regions comprises the plurality of pixels for which the individual pixel RGB values are determined in each color block.

C26. The method of C25, wherein each of the calibration circle regions has a radius between about 3 and about 10 pixels.

C27. The method of C26, wherein each of the calibration circle regions has a radius of about 5 pixels.

C28. The method of any of C18-C27, further comprising calculating, at the server, a distance between the dressing RGB values and each of the calibration RGB values in a three dimensional space.

C29. The method of C28, further comprising:

determining the two smallest calculated distances; and calculating the pH value for the wound dressing based on the RGB calibration values and standardized pH values associated with the two smallest distances.

C30. The method of C29, further comprising:

normalizing the dressing RGB values to a line defined by the two RGB calibration values associated with the two shortest distances; and calculating the pH value for the wound dressing from the normalized position of the dressing RGB values on the line.

Group D

D1. A non-transitory computer-readable medium for monitoring a wound, wherein the computer-readable medium is encoded with machine-readable instructions for performing the method according to any of A1-A30, B1-B28, or C1-C30.

Group E

E1. A device for monitoring a wound, comprising:
memory;
a display; and
processing circuitry in communication with the memory and the display, the processing circuitry being configured to perform any of the methods of A1-A30.

Group F

F1. A server for monitoring a wound, comprising:
memory;
communications circuitry coupled to a network for transmitting and receiving communications over the network; and
processing circuitry associated with the communications circuitry and the memory, the processing circuitry being configured to perform any of the methods of B1-B28.

Group G

G1. A device for monitoring a wound, comprising:
memory;
communications circuitry coupled to a network for transmitting and receiving communications over the network; and
processing circuitry associated with the communications circuitry and the memory, the processing circuitry being configured to perform any of the methods of C1-C30.

Group H

H1. A system for monitoring a wound, comprising:
the server of F1; and
the device of G1.

Group I

I1. A system for monitoring a wound, comprising:
means for capturing an image of a wound dressing;
means for determining the color of a pH indicator on the wound dressing, wherein the means for determining the color comprises means for extracting RGD values from the captured image;
means for calculating a pH value for the wound dressing from the dressing RGB values; and
means for displaying an indication of the calculated pH value.

I2. The system of I1, further comprising means for displaying a guiding frame during image capture, wherein the guiding frame provides an indication of proper wound dressing alignment to a user.

I3. The system of I2, further comprising means for detecting the alignment of the wound dressing relative to the displayed guide frame, wherein the image is automatically captured by the means for capturing when the wound dressing is properly aligned with the guiding frame.

I4. The system of any of the preceding embodiments, further comprising:
means for rejecting an image having inadequate light or excessive shadow; and
means for displaying a request to a user to capture a new image.

I5. The system of any of the preceding embodiments, further comprising means for displaying an option to accept or reject the calculated pH value when the calculated pH value is displayed.

I6. The system of any of the preceding embodiments, further comprising means for storing the calculated pH value in a record of pH values.

I7. The system of I6, further comprising means for receiving user input identifying a particular patient, wherein the stored record is associated with the particular patient.

I8. The system of I7, wherein the user input comprises a selection of the particular patient from a list of stored patients.

I9. The system of I7, wherein the user input comprises identification information for a new patient.

I10. The system of any of I6-I9, further comprising means for displaying a trend of pH values for the particular patient.

I11. The system of A10, wherein the displayed trend comprises at least one of a graph and a list of pH values.

I12. The system of any of the preceding embodiments, wherein means for extracting dressing RGB values from the captured image comprises means for determining individual pixel RGB values for each one of a plurality of pixels in the image and means for averaging the individual pixel RGB values for the plurality of pixels to determine the dressing RGB values.

I13. The system of I12, further comprising means for defining a center point of the captured image.

I14. The system of I13, further comprising means for defining a dressing circle region around the center point of the captured image, wherein the dressing circle region comprises the plurality of pixels for which the individual pixel RGB values are determined.

I15. The system of I14, wherein the dressing circle region has a radius between about 5 and about 100 pixels.

I16. The system of I15, wherein the dressing circle region has a radius between about 10 and about 50 pixels.

I17. The system of I16, wherein the dressing circle region has a radius between about 20 and about 30 pixels.

I18. The system of any of the preceding embodiments, further comprising means for capturing an image of a color calibration strip.

I19. The system of A18, wherein the color calibration strip is captured in the same image as the wound dressing.

I20. The system of I18 or I19, further comprising means for extracting calibration RGB values from the image of the color calibration strip for each of a plurality of color blocks in the color calibration strip.

I21. The system of I20, wherein:
each color block is associated with a standardized pH value; and
the pH value for the wound dressing is calculated using the dressing RGB values and the calibration RGB values.

I22. The system of I20 or I21, wherein the means for extracting calibration RGB values for each of the plurality of color blocks comprises means for determining individual pixel RGB values for each one of a plurality of pixels in a color block and means for averaging the individual pixel RGB values for the plurality of pixels in the color block to determine the calibration RGB values for the color block.

I23. The system of I22, further comprising means for defining a center point of each of the plurality of color blocks.

I24. The system of I23, wherein the center points are defined from alignment indicators positioned on either side of the color calibration strip.

I25. The system of I23 or I24, further comprising means for defining a calibration circle region around the center point of each color block, wherein each of the calibration circle regions comprises the plurality of pixels for which the individual pixel RGB values are determined in each color block.

I26. The system of I25, wherein each of the calibration circle regions has a radius between about 3 and about 10 pixels.

I27. The system of I26, wherein each of the calibration circle regions has a radius of about 5 pixels.

I28. The system of any of I18-I27, further comprising means for calculating a distance between the dressing RGB values and each of the calibration RGB values in a three-dimensional space.

I29. The system of I28, further comprising:
means for determining the two smallest calculated distances; and
means for calculating the pH value for the wound dressing based on the RGB calibration values and standardized pH values associated with the two smallest distances.

I30. The system of I29, further comprising:
means for normalizing the dressing RGB values to a line defined by the two RGB calibration values associated with the two shortest distances; and
means for calculating the pH value for the wound dressing from the normalized position of the dressing RGB values on the line.

Group J

J1. A system for monitoring a wound, comprising:
means for receiving an image of a wound dressing;
means for determining the color of a pH indicator on the wound dressing, wherein the means for determining the color comprises means for extracting dressing RGB values from the received image;
means for calculating a pH value for the wound dressing from the dressing RGB values; and
means for transmitting an indication of the calculated pH value.

J2. The system of J1, further comprising:
means for rejecting an image having inadequate light or excessive shadow; and
means for transmitting a request to a user to capture a new image.

J3. The system of J1 or J2, further comprising means for displaying the calculated pH value with an option to accept or reject the calculated pH value.

J4. The system of any of the preceding embodiments, further comprising means for storing the calculated pH value in a record of pH values.

J5. The system of J4, further comprising means for receiving user input identifying a particular patient, wherein the stored record is associated with the particular patient.

J6. The system of J5, wherein the user input comprises a selection of the particular patient from a list of stored patients.

J7. The system of J6, wherein the user input comprises identification information for a new patient.

J8. The system of any of J4-J7, further comprising means for transmitting a trend of pH values for the particular patient for display on a user device in communication with the means for transmitting.

J9. The system of J8, wherein the trend comprises at least one of a graph and a list of pH values.

J10. The system of any of the preceding embodiments, wherein the means for extracting dressing RGB values from the received image comprises means for determining individual pixel RGD values for each one of a plurality of pixels in the image and means for averaging the individual pixel RGB values for the plurality of pixels to determine the dressing RGB values.

J11. The system of J10, further comprising means for defining a center point of the received image.

J12. The system of J11, further comprising means for defining a dressing circle region around the center point of the received image, wherein the dressing circle region comprises the plurality of pixels for which the individual pixel RGB values are determined.

J13. The system of J12, wherein the dressing circle region has a radius between about 5 and about 100 pixels.

J14. The system of J13, wherein the dressing circle region has a radius between about 10 and about 50 pixels.

J15. The system of J14, wherein the dressing circle region has a radius between about 20 and about 30 pixels.

J16. The system of any of the preceding embodiments, further comprising means for receiving an image of a color calibration strip.

J17. The system of J17, wherein the color calibration strip is in the same received image as the wound dressing.

J18. The system of J16 or J17, further comprising means for extracting calibration RGB values from the image of the color calibration strip for each of a plurality of color blocks in the color calibration strip.

J19. The system of J18, wherein:
each color block is associated with a standardized pH value; and
the pH value for the wound dressing is calculated using the dressing RGB values and the calibration RGB values.

J20. The system of J18 or J19, wherein the means for extracting calibration RGB values for each of the plurality of color blocks comprises means for determining individual pixel RGB values for each one of a plurality of pixels in a color block and means for averaging the individual pixel RGB values for the plurality of pixels in the color block to determine the calibration RGB values for the color block.

J21. The system of J20, further comprising means for defining a center point of each of the plurality of color blocks.

J22. The system of J21, wherein the center points are defined from alignment indicators positioned on either side of the color calibration strip.

J23. The system of J21 or J22, further comprising means for defining a calibration circle region around the center point of each color block, wherein each of the calibration circle regions comprises the plurality of pixels for which the individual pixel RGB values are determined in each color block.

J24. The system of J23, wherein each of the calibration circle regions has a radius between about 3 and about 10 pixels.

J25. The system of J24, wherein each of the calibration circle regions has a radius of about 5 pixels.

J26. The system of any of J16-J25, further comprising means for calculating a distance between the dressing RGB values and each of the calibration RGB values in a three-dimensional space.

J27. The system of J26, further comprising:
means for determining the two smallest calculated distances; and
means for calculating the pH value for the wound dressing based on the RGB calibration values and standardized pH values associated with the two smallest distances.

J28. The system of J27, further comprising:
means for normalizing the dressing RGB values to a line defined by the two RGB calibration values associated with the two shortest distances; and
means for calculating the pH value for the wound dressing from the normalized position of the dressing RGB values on the line.

Group K

K1. A system for monitoring a wound, comprising:

means for capturing an image of a wound dressing having a pH indicator;

means for transmitting the captured image;

means for receiving a pH value for the wound dressing in the captured image; and means for displaying an indication of the received pH value.

K2. The system of K1, further comprising means for displaying a guiding frame during image capture, wherein the guiding frame provides an indication of proper wound dressing alignment to a user.

K3. The system of K2, further comprising means for detecting the alignment of the wound dressing relative to the displayed guide frame, wherein the image is automatically captured by the means for capturing when the wound dressing is properly aligned with the guiding frame.

K4. The system of any of the preceding embodiments, further comprising:

means for rejecting an image having inadequate light or excessive shadow; and means for displaying a request to a user to capture a new image.

K5. The system of any of the preceding embodiments, further comprising means for displaying an option to accept or reject the received pH value when the received pH value is displayed.

K6. The system of any of the preceding embodiments, further comprising means for storing the received pH value in a record of pH values.

K7. The system of K6, further comprising means for receiving user input identifying a particular patient, wherein the stored record is associated with the particular patient.

K8. The system of K7, wherein the user input comprises a selection of the particular patient from a list of stored patients.

K9. The system of K7, wherein the user input comprises identification information for a new patient.

K10. The system of any of K6-K9, further comprising means for displaying a trend of pH values for the particular patient.

K11. The system of K10, wherein the displayed trend comprises at least one of a graph and a list of pH values.

K12. The system of any of the preceding embodiments, further comprising:

means for determining individual pixel RGB values for each one of a plurality of pixels in the captured image;

means for averaging the individual pixel RGB values for the plurality of pixels to determine dressing RGB values; and means for calculating the pH value for the wound dressing from the dressing RGB values.

K13. The system of K12, further comprising means for defining a center point of the captured image.

K14. The system of K13, further comprising means for defining a dressing circle region around the center point of the captured image, wherein the dressing circle region comprises the plurality of pixels for which the individual pixel RGB values are determined.

K15. The system of K14, wherein the dressing circle region has a radius between about 5 and about 100 pixels.

K16. The system of K15, wherein the dressing circle region has a radius between about 10 and about 50 pixels.

K17. The system of K16, wherein the dressing circle region has a radius between about 20 and about 30 pixels.

K18. The system of any of K12-K17, further comprising means for capturing an image of a color calibration strip.

K19. The system of K18, wherein the color calibration strip is captured in the same image as the wound dressing.

K20. The system of K18 or K19, further comprising means for extracting calibration RGB values from the image of the color calibration strip for each of a plurality of color blocks in the color calibration strip.

K21. The system of K20, wherein:

each color block is associated with a standardized pH value; and the pH value for the wound dressing is calculated using the calibration RGB values.

K22. The system of K20 or K21, wherein the means for extracting calibration RGB values for each of the plurality of color blocks comprises means for determining individual pixel RGB values for each one of a plurality of pixels in a color block and means for averaging the individual pixel RGB values for the plurality of pixels in the color block to determine the calibration RGB values for the color block.

K23. The system of K22, further comprising means for defining a center point of each of the plurality of color blocks.

K24. The system of K23, wherein the center points are defined from alignment indicators positioned on either side of the color calibration strip.

K25. The system of K23 or K24, further comprising means for defining a calibration circle region around the center point of each color block, wherein each of the calibration circle regions comprises the plurality of pixels for which the individual pixel RGB values are determined in each color block.

K26. The system of K25, wherein each of the calibration circle regions has a radius between about 3 and about 10 pixels.

K27. The system of K26, wherein each of the calibration circle regions has a radius of about 5 pixels.

K28. The system of any of K18-K27, further comprising means for calculating a distance between the dressing RGB values and each of the calibration RGB values in a three dimensional space.

K29. The system of K28, further comprising:

means for determining the two smallest calculated distances; and means for calculating the pH value for the wound dressing based on the RGB calibration values and standardized pH values associated with the two smallest distances.

K30. The system of K29, further comprising:

means for normalizing the dressing RGB values to a line defined by the two RGB calibration values associated with the two shortest distances; and means for calculating the pH value for the wound dressing from the normalized position of the dressing RGB values on the line.

Group L

L1. A system for monitoring a wound, comprising:

the system of any of J1-J28; and the system of any of K1-K30.

With respect to all of Sections 1, 2, 3, 4 and 5 of the application, the foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in wound monitoring approaches using wound dressing having color pH indicators, user devices, and servers, may be applied to systems, devices, and methods to be used in other approaches for wound monitoring using pH tracking or tracking of other wound indicators using color bandages.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made pact of this application.

The invention claimed is:

1. A wound dressing configured to indicate wound exudate loading, comprising:

an absorbent layer comprising a wound-facing side and a non-wound-facing side, the absorbent layer configured to absorb wound exudate and allow wound exudate to migrate through the absorbent layer to an indicator, the indicator positioned to be in contact with the non-wound-facing side of the absorbent layer, comprising:

a first composition configured to transform from a first state to a second state, each state having a different color; and a second composition configured to dissolve upon contact with wound exudate and release ions to alter analyte levels within a portion of the wound exudate, the portion configured to transform the first composition from the first state to the second state upon contact, the transformation from the first state to the second state comprising a color change from a first color to a second color, wherein the second composition is encapsulated in a soluble barrier configured to dissolve upon contact with wound exudate such that the second composition does not interact with the first composition until the soluble barrier is contacted by wound exudate; and a spacer layer comprising a 3-D knitted spacer fabric material comprising a differential filament count configured to vertically transport wound exudate, the spacer layer positioned between the first composition and the second composition such that the spacer layer physically separates the first composition and the second composition such that the first and second compositions do not interact until wound exudate passes through the spacer layer.

2. The wound dressing of claim 1, wherein the ions comprise hydrogen or hydroxide ions.

3. The wound dressing of claim 2, wherein the ions comprise hydrogen ions.

4. The wound dressing of claim 2, wherein the ions comprise hydroxide ions.

5. The wound dressing of claim 1, wherein the first and second compositions are impregnated into different carrier materials within the wound dressing.

6. The wound dressing of claim 1, wherein the first and second compositions are impregnated into a single carrier material within the device.

7. The wound dressing of claim 1, wherein the absorbent layer has a peripheral edge and wherein the indicator extends outwardly from the peripheral edge.

8. A wound dressing according to claim 7, wherein the indicator extends from the peripheral edge to form an annular ring.

9. The wound dressing of claim 1, wherein the spacer layer is coated in a hydrophilic material.

10. The wound dressing of claim 1, wherein the spacer layer is configured to promote wound exudate transport between the carrier layers.

\* \* \* \* \*